US008980952B2

(12) United States Patent
Simard et al.

(10) Patent No.: US 8,980,952 B2
(45) **Date of Patent: *Mar. 17, 2015**

(54) METHODS FOR TREATING BRAIN SWELLING WITH A COMPOUND THAT BLOCKS A NON-SELECTIVE CATION CHANNEL

(75) Inventors: J. Marc Simard, Baltimore, MD (US); Mingkui Chen, Baltimore, MD (US)

(73) Assignees: University of Maryland, Baltimore, Baltimore, MD (US); The United States of America as represented by the Dept. of Veterans Affairs, Washington, DC (US)

( * ) Notice: Subject to any disclaimer, the term of this patent is extended or adjusted under 35 U.S.C. 154(b) by 884 days.

This patent is subject to a terminal disclaimer.

(21) Appl. No.: 11/359,946

(22) Filed: Feb. 22, 2006

(65) Prior Publication Data

US 2006/0276411 A1 Dec. 7, 2006

Related U.S. Application Data

(63) Continuation-in-part of application No. 10/391,561, filed on Mar. 20, 2003, now abandoned, and a continuation-in-part of application No. 11/229,236, filed on Sep. 16, 2005, now Pat. No. 7,872,048.

(60) Provisional application No. 60/365,933, filed on Mar. 20, 2002, provisional application No. 60/698,272, filed on Jul. 11, 2005, provisional application No. 60/610,758, filed on Sep. 18, 2004.

(51) Int. Cl.

| | |
|---|---|
| ***A61K 31/18*** | (2006.01) |
| ***A61K 31/64*** | (2006.01) |
| ***A61K 31/435*** | (2006.01) |
| ***A61K 31/198*** | (2006.01) |
| ***A61K 31/415*** | (2006.01) |
| ***A61K 31/17*** | (2006.01) |
| ***A61K 31/00*** | (2006.01) |
| ***A61K 31/175*** | (2006.01) |
| ***A61K 31/365*** | (2006.01) |
| ***A61K 31/426*** | (2006.01) |
| ***A61K 31/4439*** | (2006.01) |
| ***A61K 31/56*** | (2006.01) |
| ***A61K 31/70*** | (2006.01) |
| ***A61K 31/7048*** | (2006.01) |
| ***B01J 19/00*** | (2006.01) |
| ***B32B 37/12*** | (2006.01) |
| ***C07K 14/705*** | (2006.01) |
| ***G01N 27/447*** | (2006.01) |
| ***G01N 33/68*** | (2006.01) |
| *B29L 31/00* | (2006.01) |

(52) U.S. Cl.

CPC ................ *A61K 31/17* (2013.01); *A61K 31/00* (2013.01); *A61K 31/175* (2013.01); *A61K 31/365* (2013.01); *A61K 31/426* (2013.01); *A61K 31/4439* (2013.01); *A61K 31/56* (2013.01); *A61K 31/64* (2013.01); *A61K 31/70* (2013.01); *A61K 31/7048* (2013.01); *B01J 19/0093* (2013.01); *B32B 37/1292* (2013.01); *C07K 14/705* (2013.01); *G01N 27/44791* (2013.01); *G01N 33/6872* (2013.01); *B29L 2031/756* (2013.01); *G01N 2500/04* (2013.01); *Y10S 514/87* (2013.01)

USPC .......... 514/592; 514/317; 514/563; 514/593; 514/604; 514/870; 514/401

(58) Field of Classification Search

None

See application file for complete search history.

(56) References Cited

U.S. PATENT DOCUMENTS

| | | | |
|---|---|---|---|
| 5,047,429 | A | 9/1991 | Nye et al. |
| 5,166,162 | A | 11/1992 | Masereel et al. |

(Continued)

FOREIGN PATENT DOCUMENTS

| | | | |
|---|---|---|---|
| EP | 0338415 | A2 | 3/1991 |
| EP | 0 467 709 | | 1/1992 |

(Continued)

OTHER PUBLICATIONS

Pfeiffer et al (1972. Diabetologia. 8: 41-47).*

(Continued)

*Primary Examiner* — Zachary Howard

(74) *Attorney, Agent, or Firm* — Norton Rose Fulbright US LLP

(57) ABSTRACT

The present invention is directed to therapeutic compounds, treatment methods, and kits affecting the $NC_{Ca-ATP}$ channel of neural tissue, including neurons, glia and blood vessels within the nervous system, and methods of using same. The $NC_{Ca-ATP}$ channel is newly expressed in neural tissue following injury such as ischemia, and is regulated by the sulfonylurea receptor SUR1, being inhibited by sulfonylurea compounds, e.g., glibenclamide and tolbutamide, and opened by diazoxide. Antagonists of the $NC_{Ca-ATP}$ channel, including SUR1 antagonists, are useful in the prevention, diminution, and treatment of injured or diseased neural tissue, including astrocytes, neurons and capillary endothelial cells, that is due to ischemia, tissue trauma, brain swelling and increased tissue pressure, or other forms of brain or spinal cord disease or injury. Agonists of the $NC_{Ca-ATP}$ channel may be are useful in the treatment neural tissue where damage or destruction of the tissue, such as a gliotic capsule, is desired.

32 Claims, 54 Drawing Sheets

(56) References Cited

U.S. PATENT DOCUMENTS 5,215,985 A 6/1993 Murphy et al.
5,236,932 A 8/1993 Greenfield et al.
5,281,599 A 1/1994 Murphy et al.
5,451,580 A 9/1995 Murphy et al.
5,545,656 A 8/1996 Loose et al.
5,677,344 A 10/1997 Greenfield et al.
5,811,393 A 9/1998 Klagsbrun et al.
5,849,796 A 12/1998 Gericke et al.
5,916,871 A 6/1999 Johnson
5,929,082 A 7/1999 Chambers et al.
5,962,645 A 10/1999 Keay et al.
6,043,224 A 3/2000 Lee et al.
6,056,977 A 5/2000 Bhagwat et al.
6,100,047 A 8/2000 Wilkison et al.
6,156,522 A 12/2000 Keay et al.
6,180,671 B1 1/2001 Freedman et al.
6,184,248 B1 2/2001 Lee et al.
6,187,756 B1 2/2001 Lee et al.
6,232,289 B1 5/2001 Keay et al.
6,242,200 B1 6/2001 Wilkison et al.
6,365,577 B1 4/2002 Iversen .......................... 514/44
6,372,743 B1 4/2002 Darrow et al.
6,376,197 B1 4/2002 Keay et al.
6,469,055 B2 10/2002 Lee et al.
6,492,130 B1 12/2002 Wilkison et al.
6,492,339 B1 12/2002 Sleevi et al.
6,511,989 B2 1/2003 Heitsch et al.
6,569,633 B1 5/2003 Wilkison et al.
6,569,845 B1 5/2003 Futamura et al.
6,596,751 B2 7/2003 Fujita et al.
6,610,746 B2 8/2003 Fryburg et al.
6,613,785 B2 9/2003 Bril et al.
6,679,859 B1 1/2004 Keipert et al.
7,285,574 B2 10/2007 Simard et al.
7,877,048 B2 1/2011 Kitagawa
8,318,810 B2 * 11/2012 Simard et al. ................ 514/592
2001/0003751 A1 6/2001 Terashita et al.
2001/0016586 A1 8/2001 Guitard et al.
2002/0013268 A1 1/2002 Fryburg et al.
2002/0016443 A1 2/2002 Keay et al.
2002/0037928 A1 3/2002 Jaen et al.
2002/0065315 A1 5/2002 Jensen et al.
2002/0081306 A1 6/2002 Elliott et al.
2002/0094977 A1 7/2002 Robl et al.
2003/0215889 A1 11/2003 Simard et al.
2003/0216294 A1 11/2003 Fryburg et al.
2005/0009733 A1 1/2005 Stephenson et al.
2005/0054659 A1 3/2005 Ellsworth et al.
2006/0100183 A1 5/2006 Simard ........................ 514/171
2006/0276411 A1 12/2006 Simard et al.
2007/0203239 A1 8/2007 Gehenne et al.
2009/0130083 A1 5/2009 Simard et al.
2010/0092469 A1 4/2010 Simard et al.
2010/0311639 A1 12/2010 Simard
2011/0026347 A1 2/2011 Fort et al.
2012/0237449 A1 9/2012 Simard et al.

FOREIGN PATENT DOCUMENTS

EP 0467709 A3 7/1992
EP 1 782 815 1/2006
JP H09208562 A 8/1997
JP 2004-516236 6/2004
WO WO-97/41857 A1 11/1997
WO WO 01/10430 2/2001
WO WO-01/54771 8/2001
WO WO 02/070499 9/2002
WO 03057843 A2 7/2003
WO 03075933 9/2003
WO WO-03/075933 A1 9/2003
WO 03079987 10/2003
WO WO-03/079987 10/2003
WO 2005/041877 A2 5/2005
WO 2006/000608 A1 1/2006
WO WO-/2006/000608 1/2006
WO 2006/034048 A2 3/2006
WO 2007011926 A2 1/2007
WO WO 2007/011595 1/2007
WO 2007058902 5/2007
WO WO-2006/036278 A2 5/2007
WO WO-2007 058902 5/2007
WO WO 2008/089103 7/2008
WO WO-2008/098160 A1 8/2008
WO WO 2009/002832 12/2008

OTHER PUBLICATIONS

Haider et al, 2007. The EMBO Journal. 26: 3749-3759.*

Rosenberg, Gary A.; Ischemic Brain Edema; Progress in Cardiovascular Diseases, vol. 42, No. 3 (Nov./Dec.), 1999: pp. 209-216.

Corrected International Search Report issued Sep. 18, 2008 during the prosecution of International Application No. PCT/US07/62392.

International Preliminary Report on Patentability issued Oct. 21, 2008 during the prosecution of International Application No. PCT/US07/62392.

Slikker et al., "Session IV: Models of Neurotoxicity and Neuroprotection, Questions for Dr. Banik", Ann NY Acad Sci; 2003; 993; 159-160.

Sribnick et al., "Estrogen as a Neuroprotective Agent in the Treatment of Spinal Cord Injury", Ann. N.Y. Acad. Sci., vol. 993;. 2003;125-133.

Supplementary European Search Report issued during the prosecution of European Application EP 05 81 1299. Date: Aug. 27, 2008.

Written Opinion issued Sep. 18, 2008 during the prosecution of International Application No. PCT/US07/62392.

Yune et al., "Systemic Administration of 17ÿ-Estradiol Reduces Apoptotic Cell Death and Improves Functional Recovery following Traumatic Spinal Cord Injury in Rats", Journal of Neurotrauma. Mar. 1, 2004, 21(3): 293-306.

Annex to Form PCT/ISA/206, Communication Relating to the Results of the Partial International Search, regarding International Application No. PCT/US2005/026455, Date Oct. 12, 2006.

Simard et al., "Endothelial sulfonylurea receptor 1-regulated NC Ca-ATP channels mediate progressive hemorrhagic necrosis following spinal cord injury," J Clin Invest. Aug. 2007;117(8):2105-13.

Medline Plus® Merriam Webster Medical Dictionary, main entry: par.en.ter.al, online <http://www2.merriam-webster.com/cgi-bin/mwmednlm>; 2005; 1 page.

Supplementary European Search Report issued Jun. 19, 2008 during the prosecution of European Application No. 03 71 8003.

Rothstein et al, "Neuroprotective strategies in a model of chronic glutamate-mediated motor neuron toxicity," J Neurochem. Aug. 1995;65(2):643-51.

Communication pursuant to Article 94(3) EP issued Dec. 10, 2008, during the prosecution of European Application No. 05 812 199.7-2123.

European Patent Office Communication Pursuant to Article 94(3) EPC issued Jan. 16, 2009, regarding EP Application No. 05 805 849.6-2123.

Canadian Office Action issued Nov. 4, 2009 during the prosecution of Canadian Patent Application No. 2,477,812.

Crepel et al., "Glibenclamide depresses the slowly inactivating outward current ($I_D$) in hippocampal neurons," *Canadian Journal of Physiology and Pharmacology*, 70(2):306-307, 1992.

Gribble et al., "Sulfonylurea sensitivity of adenosine triphosphate-sensitive potassium channels from β cells and extrapancreatic tissues," *Metabolism*, 49(10:2):3-6, 2000.

Grijalva et al., "Efficacy and safety of 4-aminopyridine in patients with long-term spinal cord injury: a randomized, double-blind, placebo-controlled trial," *Pharmacotherapy*, 23(7):823-834, 2003.

Liu et al., "Suppression of hippocampus fos expression and activator protein-1 (AP-1) activity during focal cerebral ischemia using antisense strategy," *Stroke*, 26(1):182, 1995.

Office Action issued in Japanese Application No. 2007-532507, mailed Jun. 20, 2011 (and English language translation thereof).

Partial European Search Report issued in European Application No. 10010753.1, mailed Jul. 22, 2011.

(56) References Cited

OTHER PUBLICATIONS

Wickelgren, "Animal studies raise hopes for spinal cord repair," *Science*, 297(5579):178-181, 2002.
Yokoshiki et al, "Antisense oligodeoxynucleotides of sulfonylurea receptors inhibit ATP-sensitive $K^+$channels in cultured neonatal rat ventricular cells," *Eur. J. Physiol*., 437:400-408, 1999.
Extended European Search Report issued in European Application No. 10010753.1, mailed Oct. 26, 2011.
Hozumi at al., "Biochemical and immunocytochemical changes in glial fibrillary acidic protein after stab wounds," *Brain Research*, 524:64-71, 1990.
Sang et al., "ATP sensitive potassium channels are involved in the protective effect of ischemic preconditioning on spinal cord in rabbits"; Chinese Pharmacological Bulletin, 2003, Issue 12, 1362-1365.
Notification of the First Office Action issued Jan. 22, 2010 during prosecution of Chinese Patent Aplication No. 200580036055.7 (English Translation).
Khan Hussein Hamed, et al.; "Comparison of Therapeutic Effects by K+ Channel Opener Minoxidil and Blocker Glyburide on Cerebral Ischemia Produced by MCAO and Levo-thyroxine in Rats"; Journal of China Pharmaceutical University; Jan. 2000; vol. 31(4); pp. 289-293.
Second Office Action, issued Jul. 30, 2010 (published Jul. 30, 2010) during the prosecution of Chinese Application No. 200580036055.7.
Japanese Office Action, issued in Japanese Patent Application No. 2007-532321, mailed Apr. 22, 2011.
PCT International Preliminary Report on Patentability, issued in International application No. PCT/US2009/057111, dated Mar. 31, 2011.
Launary et al., "TRPM4 Regulates Calcium Oscillations After T Cell Activation", Science, 306(5700):1374-1377, 2004.
Definition of "infusion" from www.merriam-webster.com, printed on Apr. 10, 2013, 1 pages as printed.
Heurteaux et al., "Alpha-Linolenic Acid and Riluzole Treatment Confer Cerebral Protection and Improce Survival After Focal Brain Ischemia", Neuroscience, 137:241-251, 2006.
Simard et al., Comparative effects of glibenclamide and riluzole in a rat model of severe cervical spinal cord injury', Experimental Neurology, 233:566-574, 2012.
Demion et al., "TRPM4, a Ca2+—activated nonselective cation channel in mouse sino-atrial nod cells ", Cardiovasuclar Research, 73:531-538, 2007.
Khansari, "An investigation of the neuroprotective properties of fenamate NSAIDs, against experimental models of ischemic stroke", Dissertation Abstracts International, 68:11B, 197 pages, 2007.
Khansari and Halliwell, "Evidence for neuroprotection by the fenamate NSAID, mefenamic acid", Neurochemistry International, 55:683-688, 2009.
Klose et al., "Fenamates as TRP channel blockers: mefenamic acid selectively blocks TrPM3", British Journal of Pharmacology, 162:1757-1769, 2011.
Pirollo and Chang, "Targeted Delivery of Small Interfering RNA: Approaching Effetive Cancer Therapies", Cancer Res., 68(5):1247-1250, 2008.
Hausmann, "Post-traumatic inflammation following spinal cord injury", Spinal Cord, 41:369-378, 2003.
Woodcock, "The role of markers of inflammation in traumatic brain injury", Frontiers in Neurology, 4:1-18, 2013.
Hugelshofer, "Neuroinflammation after Subarachnoid Hemorrhage: The Role of Microglia", UniversitatsSpital Zurich Institut fur Neuropathologie & Klinik fur Neurochirurgie, p. 1-18, 2013.
Hallevi, "Inflammatory response to intraventricular hemorrage: Time course, magnitude and effect of t-PA," Journal of the Nurological Science, 315:93-95, 2012.
Kunte et al., "Sulfonylureas Improve Outcome in Patients With Type 2 Diabetes and Acute Ischemic Stroke", Stroke, 38(9):2526-2530, 2007.
Liang et al., Neurosurg Focus, 22(5):E2, ppg. 1-16, 2007.
Gavin, "Management of Diabetes Mellitus During Surgery", West J M. 151:525-529, 1989.
Vestergaard et al., "Relative fracture risk in patients with diabetes melitus, and the impact of insulin and oral antidiabetic medication on relative fracture risk", Diabetologia, 48:1292-1299, 2005.
Inder and Volpe, "Mechanisms of Perinatal Brain Injury", 5 Semin, Neonatol. 3, 2000.
Wright et al., Evidence from Multicenter Networks on the Current Use and Effectiveness of Antenantal Corticosteroids in Low Birth Weight Infants, Am. J Obstet. Gynecol., 173:263, 1995.
Egarter et al., "Antibiotic Treatment in Preterm Premature Rupture of Membranes and Neonatal Morbidity: A Metaanalysis", Am. J. Obstet. Gynecol., 174:589, 1996.
Huss et al., "Differentiation of canine bone marrow cells with hemopoietic characteristics from an adherent stromal cell precursor", Proc natl. Acad. Sci USA, 92:748-752, 1995.
Simard, J., et. al., "Molecular pathophysiology of brains edema in focal ischemia—a focused review" (Apr. 8, 2006) pp. 1-483.
Walaas et al., PCPP-260, A Purkinje Cell-Specific Cyclic AMP-Regulated Membrane Phosphoprotein of Mr 260,000, J Neurosci. Apr. 1986;6(4):954-61.
Rosenberg, "Ischemic brain edema." Prog Cardiovasc Dis. Nov.-Dec. 1999; vol. 42(3):209-16.
Apo-Glibenclamide Data Sheet, Medsafe (New Zealand Medicines and Medical Devices Safety Authority), published Jun. 16, 1999, 6 pages; online http://www.medsafe.govt.nz/Profs/DataSheet/a/Apoglibenclamidetab.htm.
Weih et al., "Sulfonylurea Drugs Do Not Influence Initial Stroke Severity and In-Hospital Outcome in Stroke Patients With Diabetes", Stroke. 2001; vol. 32(9):2029-2032.
Lee et al., "In vitro Antitumor Activity of Cromakalim in Human Brain Tumor Cells," Pharmacology 1994; vol. 49:69-74.
Yune et al., "Systemic Administration of 17?—Estradiol Reduces Apoptotic Cell Death and Improves Functional Recovery following Traumatic Spinal Cord Injury in Rats", Journal of Neurotrauma. Mar. 1, 2004, 21(3): 293-306.
Gagliardino, J.J. et al.; Inhibitory effect of sulfonylureas on protein phosphatase activity in rat pancreatic islets; Acta Diabetol (1997) 34:6-9; Springer-Verlang 1997.
Medline Plus® Merriam Webster Medical Dictionary, main entry: par.en.ter.al, online <http://www2.merriam-webstercom/cgi-bin/mwmednlm>; 2005; 1 page.
Maybaur, D.M., et al, "The ATP-sensitive Potassium-channel Inhibitor Glibenclamide Improves Outcome in an Ovine Model of Hemorragic Shock," Shock, vol. 22(4), 2004, pp. 387-391.
Simard, J. M., et al.; "Glibenclamide Reduces Inflammation, Vasogenic Edema, and Caspase-3 Activation After Subarachnoid Hemorrhage"; Journal of Cerebral Blood Flow & Metabolism (2008), 29(2) pp. 317-330.
Simard, J. M., et al.; "Sulfonylurea Receptor 1 in the Germinal Matrix of Premature Infants"; Pediatr Res.; Dec. 2008; 64(6), pp. 648-52.
Wang, H., et al., "Targeting Ischemic Stroke with a Novel Opener of ATP-Sensitive Potassium Channels in the Brain", Molecular Pharmacology, vol. 66(5), 2004, pp. 1160-1168.
Koltz, Michael T., et al; "Tandem Insults of Prenatal Ischemia Plus Postnatal Raised Intrathoracic Pressure in a Novel Rat Model of Encephalopathy of Prematurity"; J. Neurosurg. Pediatrics, Dec. 2011, vol. 8, pp. 628-639.
Kraemer, Jennifer, et al; "Perfusion Studies of Glyburide Transfer Across the Human Placenta: Implications for Fetal Safety"; American Journal of Obstetrics and Gynecology, 2006, vol. 195, pp. 270-274.
Elliott, Byron D., et al; "Comparative Placental Transport of Oral Hypoglycemic Agents in Humans: A Model of Human Placental Drug Transfer"; Am. J. Obstet. Gynecol., Sep. 1994, vol. 171, No. 3, pp. 653-660.
Elliott, Byron D., et al; "Insignificant Transfer of Glyburide Occurs Across the Human Placenta"; Oct. 1991; Am. J. Obstet. Gynecol., vol. 165, No. 4, Part 1, pp. 807-812.
Koren, Gideon; "Glyburide and Fetal Safety; Transplacental Pharmacokinetic Considerations"; Reproductive Toxicology, 2001, vol. 15, pp. 227-229.
Tosun, Cigdem, et al; "The Protective Effect of Glibenclamide in a Model of Hemorrhagic Encephalopathy of Prematurity"; Brain Sciences, 2013, vol. 3, pp. 215-238.

(56) References Cited

OTHER PUBLICATIONS

Mizognchi et al., "Inhibition of Carbonic Anydrases Enhanced the Recovery from Acute Experimental colitis by Controlling Epithelial Registration", Abstract in: Elsevier Health Journals, p. 821, 2003.
Kawaguchi et al., "A case of hemorrhagic colitis associated with flufenamic acid aluminium", Japanese Journal of National Medical Services, 47(12):999-1003, 1993.
Gunal et al., "Estradiol Treatment Ameliorates Acetic Acid-Induced Gastric and Colonic Injuries in Rats", Inflammation, 27(6):351-359, 2003.
Jin et al., "Altered gene expression and increased bursting activity of colonic smooth muscle ATP—sensitive K+ channels in experimental colitis", Am. J. Physiol. Gastrointest. Liver Physiol., 287:G274-G285, 2004.
Daneshmand et al., "Chronic lithium administration ameliorates 2,4,6-trinitrobenzene sulfonic acid-induced colitis in rats; potential role for adenosine triphosphate sensitive potassium channels", Gastroenterology and Hepatology, 26:1174-1181, 2011.
Nieuwenhuijs et al., "Hepatic ischemia-reperfusion injury: roles of Ca2+ and other intracellular mediators of impaired bile flow and hepatocyte damage"; Digestive Diseases and Sciences, Jun. 2006, vol. 51(6); 1087-102.
Pompermayer et al.; "The ATP-sensitive potassium channel blocker glibenclamide prevents renal ischemia/reperfusion injury in rats"; Kidney International, May 2005, vol. 67(5); 1785-96.
Kim, H.J., et al.; "Anthocyanins from soybean seed coat inhibit the expression of TNF-alpha-induced genes associated with ischemia/reperfusion in endothelial cell by NF-kappaB-dependent pathway and reduce rat myocardial damages incurred by ischemia and reperfusion in vivo"; FEBS Letters 580, Jan. 20, 2006; pp. 1391-1397.
Fagan et al., "Targets for vascular protection after acute ischemic stroke"; Stroke. Sep. 2004;35(9):2220-5. Epub Jul. 29, 2004.
Gürsoy-Özdemir et al., "Role of Endothelial Nitric Oxide Generation and Peroxynitrite Formation in Reperfusion Injury After Focal Cerebral Ischemia"; Stroke. 2000;31:1974.
Manley et al., "Aquaporin-4 deletion in mice reduces brain edema after acute water intoxication and ischemic stroke"; Nature Medicine 6, 159-163 (2000).
Morris et al., "Extension of the Therapeutic Window for Recombinant Tissue Plasminogen Activator With Argatroban in a Rat Model of Embolic Stroke"; Stroke. 2001;32:2635-2640.
Nilius et al., "Transient Receptor Potential Cation Channels in Disease"; Physiol. Rev. 87: 165-217, 2007.
Pisano et al., "Undersulfated, low-molecular-weight glycol-split heparin as an antiangiogenic VEGF antagonist"; Glycobiology 2005 15(2):1C-6C.
Rosenberg et al., "TIMP-2 reduces proteolytic opening of blood-brain barrier by type IV collagenase" Brain Res—Apr. 3, 1992; 576(2): 203-7.
Ullrich et al., "Comparison of functional properties of the Ca2+-activated cation channels TRPM4 and TRPM5 from mice"; Cell Calcium. Mar. 2005; 37(3):267-78.
Grand, T., et al; "9-Phenanthrol Inhibits Human TRPM4 But Not TRPM5 Cationic Channels"; British Journal of Pharmacology; 2008, vol. 153, vol. 1697-1705.
Matsuo, Michinori, et al; "Different Binding Properties and Affinities for ATP and ADP Among Sulfonylurea Receptor Subtypes, SUR1, SUR2A, and SUR2B"; The Journal of Biological Chemistry; Sep. 15, 2000; vol. 275, No. 37, pp. 28757-28763.
Nilius, Bernd, et al; "Intracellular Nucleotides and Polyamines Inhibit the Ca2+-Activated Cation Channel TRPM4b"; Pfulgers Arch—Eur. J. Physiol., 2004, vol. 448; pp. 70-75.
Babenko; Audrey P., et al; "Pharmaco-topology of Sulfonylurea Receptors"; The Journal of Biological Chemistry (Accelerated Publication); vol. 275, No. 2, Jan. 14, 2000, pp. 717-720.
Earley, Scott, et al; "Protein Kinase C Regulates Vascular Myogenic Tone Through Activation of TRPM4"; American Physiological Society; Feb. 9, 2007; vol. 292; pp. H2613-H2622.
Woo, Seung Kyoon, et al; "The Sulfonylurea Receptor 1 (Sur1)—Transcient Receptor Potential Melastatin 4 (Trpm4) Channel"; The Journal of Biological Chemistry, Feb. 1, 2013, vol. 288, No. 5, pp. 3655-3667.
Pfeiffer et al., "Controlled extension of oral antidiabetic therapy on former insulin dependent diabetics by means of the combined i.v . . . Glibenclamide-glucose-response test", Diabetologia, 8:41-47, 1972.
Wise, "New clinical guidelines for stroke published", BMJ, 320:823, 2000.
Bereczki et al., "Mannitol for acute stroke (Review)", Cochrane Database of Systematic Reviews, Issue 3, p. 1-20, 2009.
Chen et al., "Fenamates protect neurons against ischemic and exitotoxic injury in chick embryo retina", Neuroscience Letters, 242(3):163-166, 1998.
Riddle, "Editorial: sulfonylureas differ in effects on ischemic preconditioning—is it time to retire glyburide?", The Journal of Clincial Endocrinology & Metabolism, 2003, 88(2):528-530.
Gurke et al., "Mechanisms of ischemic preconditionin in skeletal muscle", Journal of Surgical Research, 2000, 94:18-27.
Greenwood et al., "Comparison of the effects of fenamates on Ca-activated chloride and potassium currents in rabbit portal vein smooth muscle cells" Biritish Journal of Pharmacology, 116:2939-2948, 1995.
Schmidt et al., "Endocrine and metabolic consequences of spinal injuries", Chapter 18, Sprinal Coard Medicine; Principles and Practices, pp. 221-235, 2002.
Aguilar-Bryan et al., "Cloning of the beta cell high-affinity sulfonylurea receptor: a regulator of insulin secretion," *Science*, 268: 423-426, 1995.
Ahmad et al., "Mouse cortical collecting duct cells show nonselective cation channel activity and express a gene related to the cGMP-gated rod photoreceptor channel," *Proc. Natl. Acad. Sci USA*, 89: 10262-10266, 1992.
Angel et al., "The binding site for [3H]glibenclamide in the rat cerebral cortex does not recognize K-channel agonists or antagonists other than sulphonylureas," *Fundam. Clin. Pharmacol*, 5(2): 107-15, 1991 (abstract only).
Apo-Glibenclamide Data Sheet, Medsafe (New Zealand Medicine and Medical Device Safety Authority), Jun. 16, 1999.
Armijo, "Advances in the physiopathology of epilegtogenesis: molecular aspects," *Rev. Neuro*., 34(5): 409-29, 2002 (abstract only).
Auger, G. et al; Purification and Partial Characterization of a Hepatocyte Antiproliferative Glycopeptide, Journal of Cellular Biochemistry, (1989) vol. 40, pp. 439-451.
Ballerini, "Glial cells express multiple ATP binding cassette proteins which are involved in ATP release," *Neuroreport*, 13(14): 1789-92, 2002 (abstract only).
Bareyre et al., "Inflammation, degeneration and regeneration in the injured spinal cord: insights from DNA microarrays," *Trends Neurosci*., 26(10): 555-563, 2003.
Bartholdi et al., "Expression of pro-inflammatory cytokine and chemokine mRNA upon experimental spinal cord injury in mouse: an in situ hybridization study," *Eur. J. Neurosci*., 9(7): 1422-1438, 1997.
Baudelet et al., "Evidence for a Neuroprotective Effect of Pyrid-3-yl-sulphonyl-urea in Photochemically Induced Focal Ischaemia in Rats: Magnetic Resonance Imaging Evaluation," *J. Pharm. Pharmacol*., 51: 967-970, 1999.
Beier-Holgersne, R., "The in vitro cytotoxicity of urine from patients with interstitial cystitis", Journal of Urology (Jan. 1994), vol. 151, pp. 206-207.
Benos, "Methods to study CFTR protein in vitro", Journal of Cystic Fibrosis; 2004; 79-83; vol. 3.
Bevan et al, "Voltage Gasted Ionic Channels in Rat Cultured Astrocytes, Reactive Astrocytes and an Astrocyte-oligodendrocyte Progenitor Cell, " J. Physiol vol. 82, 1987, pp. 327-335.
Biochimica et Biophysica ACTA, Biomembranes, vol. 508 (1978) pp. 155-164.
Champigny et al., "A voltage, calcium, and ATP sensitive non selective cation channel in human colonic tumor cells," *Biochem. Biophys. Res. Commun*., 176: 1196-1203, 1991.

(56) References Cited

OTHER PUBLICATIONS

Chen et al, "Cell Swelling and a Nonselective Cation Channel Regulated by Internal CA2+ and ATP in Native Reactive Astrocytes from Adult Rat Brain," The Journal of Neuroscience vol. 21 No. 17, Sep. 1, 2001, pp. 6512-6521.
Chen et al., "A Calcium-Activated Nonspecific Cation Channel in Reactive Astrocytes from Adult Rat Brain," Society for Neuroscience Abstracts, vol. 26, No. 1-2, Abstract No. 791.1, 2000 [abstract].
Chen et al., "Functional coupling between sulfonylurea receptor type 1 and a nonselective cation channel in reactive astrocytes from adult rat brain," *J. Neurosci*., 23: 8568-8577, 2003.
Chen, M., et al., "Glial and Other Non-Neuronal Cell Specification and Differentiation IV", Society for Neuroscience, (2000) vol. 26, pp. 791.1.
Copin et al., "70-kDa heat shock protein expression in cultured rat astrocytes after hypoxia: regulatory effect of almitrine," *Neurochem. Res*., 20(1): 11-15, 1995.
Csanady et al., "Ca(2+)—and voltage-dependent gating of Ca(2+)—and ATP-sensitive cationic channels in brain capillary endothelium," *Biophys. J*., 85: 313-327, 2003.
Currie et al., "Benign focal ischemic preconditioning induces neuronal Hsp70 and prolonged astrogliosis with expression of Hsp27," *Brain Res*., 863(1-2): 169-181, 2000.
Davies, "Insulin secretagogues," *Curr. Med. Res. Opin. 18 Suppl*., 1: ss22-30, 2002 (abstract only).
Dubyak, "Ion homeostasis, channels, and transporters: an update on cellular mechanisms", Adv Physiol Educ; 2004; 143-154, vol. 28.
Eben-Brunnen, J., et al., "Lentil Lectin Enriched Microsomes from the Plasma Membrane of the Human B-Lymphocyte Cell Line H2LCL Carry a Heavy Load of Type-1 Porin", Biol. Chem., vol. 379, (1998) pp. 1419-1426.
Eriksson, "Preparation of liver microsomes with high recovery of endoplasmic reticulum and a low grade of contamination", Biochim Biophys Acta; 1978; 155-64; vol. 508(1).
Favre, I., et al., "Reconstitution of Native and Cloned Channels into Planar Bilayers", Methods in Enzymology, (1999) vol. 294, pp. 287-304.
Fujita et al., "Molecular aspects of ATP-sensitive K+ channels in the cardiovascular system and K+ channel openers," *Pharmacol. Ther*., 85: 39-53, 2000.
Garcia, Ann Maria, et al., "Channel-mediated monovalent cation fluxes in isolated sarcoplasmic reticulum vesicles," J. Gen. Physiol., vol. 83, (Jun. 1984) pp. 819-839.
Garty, H. et al, "A simple and sensitive procedure for measuring isotope fluxes through ion-specific channels in heterogenous populations of membrane vesicles," The Jol. of Bio. Chem., vol. 256, No. 21 (1983) pp. 13094-13099.
Gopalakrishnan et al., "Pharmacological characterization of a 1,4-dihydropyridine analogue, 9- (3,4-dichorophenyl)-3,3,6,6-tetramethyl-3,4,6,7,9,10-hexahydro-1,8(2H,5H)-acridinedione (A-184209) as a novelK(ATP) channel inhibitor," *Br. J. Pharmacol*., 138(2): 393-99, 2003 (abstract only).
Gray et al., "Non-selective cation channel on pancreatic duct cells," *Biochem. Biophys. Acta*, 1029:33-42, 1990.
Gribble et al., "Differential selectivity of insulin secretagogues. Mechanisms, clinical implications, and drug interactions," *J. Diabetes Complications*, 17(2 Suppl): 11-5, 2003 (abstract only).
Gribble et al., "The interaction of nucleotides with the tolbutamide block of cloned ATP-sensitive K+ channel currents expressed in Xenopus oocytes: a reinterpretation", J Physiol.; 1 997; 35-45; vol. 504(Pt 1).
Gribble et al., "Tissue Specificity of Sulfonylureas: Studies on Cloned Cardiac and B-Cells K-ATP Channels," *Diabetes*, 47: 1412-1418, 1998.
Gribble, "Sulphonylurea action revisited: the post-cloning era", Diabetologia, 2003; 875-91. vol. 46(7).
Hambrock et al., "Four novel splice variants of sulfonylurea receptor 1," *Am. J. Physiol. Cell Physiol*., 283: C587-C598, 2002.
Hambrock, A., et al., "$Mg^{2+}$and ATP dependence of $K_{ATP}$ channel modulator binding to the recombinant sulphonylurea receptor, SUR2B", British Journal of Pharm.), vol. 125, pp. 577-583. Date of Publication: 1998.
Heinemann et al., "Frontiers in Bioscience 3, d483-493", May 1, 1998, printed out from the bioscience.org website as pp. 1-24.
Hernandez-Sanchez et al., "Mice transgenically overexpressing sulfonylurea receptor 1 in forebrain resist seizure induction and excitotoxic neuron death," *PNAS*, 98(6): 3549-3554, 2001.
Inagaki et al., "A family of sulfonylurea receptors determines the pharmacological properties of ATP-sensitive K+ channels," *Neuron*, 16: 1011-1017, 1996.
Isomoto et al., "A novel sulfonylurea receptor forms with BIR (Kir6. 2) a smooth muscle type ATP-sensitive K+ channel," *J. Biol. Chem*., 271: 24321-24324, 1996.
Jamme et al., Focal cerebral ischaemia induces a decrease in activity and a shift in ouabain affinity of Na+, K+-ATPase isoforms without modifications in mRNA and protein expression', Brain Res.; 1999; 132-42; vol. 819(1-2).
Jarvis et al., "Purinergic Mechanisms in the Nervous System Function and Disease States," Psychopharmacology: The Fourth Generation of Progress, (Kupfer, David J. et al., Lippincott 2000), found at www.acnp.org/g4/GN401000063/CH.html.
Kaal et al., "The management of brain edema in brain tumors", Curr. Opin. Oncol.; 2004; 593-600; vol. 16.
Kakimura et al., "Microglial activation and amyloid-beta clearance induced by exogenous heat-shock proteins," *FASEB J*., 16(6): 601-603, 2002.
Keay, S., et al.; Bladder Epithelial Cells from Patients with Interstitial Cystitis Produce an Inhibitor of Heparin-Binding Epidermal Growth Factor-Like Growth Factor Production, The Journal of Urology (Dec. 2000) vol. 164, pp. 2112-2118.
Keay, S., et al.; Changes in human bladder epithelial cell gene expression associated with interstitial cystitis or antiproliferative factor treatment, Physiol. Genomics (2003) vol. 14, pp. 107-115.
Keay, S., et al.; Current and future directions in diagnostic markers in interstitial cystitis, Inter'l J. of Urology (2003) vol. 10, pp. S27-230.
Keay, S., et al.; Decreased in Vitro Proliferation of Bladder Epithelial Cells from Patients with Interstitial Cystitis, The Journal of Urology (2003) vol. 61, pp. 1278-1284.
Kempski, "Cerebral edema", Semin Nephol; 2001; 303-307; vol. 21 (3); abstract only.
Kimelberg et al., "Astrocytic swelling in traumatic-hypoxic brain injury. Beneficial effects of an inhibitor of anion exchange transport and glutamate uptake in glial cells," *Mol. Chem. Neuropathol*., 11(1): 1-31, 1989 (abstract only).
Koch et al., "Mechanism of shrinkage activation of nonselective cation channels in M-1 mouse cortical collecting duct cells," *J Membr. Biol*., 177(3): 231-42, 2000 (abstract only).
Koch et al., "Osmotic shrinkage activates nonselective cation (NSC) channels in various cell types," *J. Membr. Biol*., 168(2): 131-39, 1999 (abstract only).
Lauritzen et al., "The potassium channel opener (-)—cromakalim prevents glutamate-induced cell death in hippocampal neurons," *J. Neurochem*., 69(4): 1570-79, 1997 (abstract only).
Lee et al, "Upregulation of Phospolipase D in Astrocytes in Response to Transient Forebrain Ischemia," GLIA vol. 30, 2000, pp. 311-317.
Lee et al., "Differential neuroprotection from human heat shock protein 70 overexpression in in vitro and in vivo models of ischemia and ischemia-like conditions," *Exp. Neurol*., 170(1): 129-139, 2001.
Lee et al., "Direct demonstration of sulphonylurea-sensitive KATP channels on nerve terminals of the rat motor cortex," *Br. J. Pharmacol*., 115(3): 385-87, 1995 (abstract only).
Lee et al., "In vitro Antitumor Activity of Cromakalim in Human Brain Tumor Cells," *Pharmacology*, 49: 69-74, 1994.
Lee et al., "The high-affinity sulphonylurea receptor regulates KATP channels in nerve terminals of the rat motor cortex," *J. Neurochem*., 66(6): 2562-71, 1996 (abstract only).
Liu et al., "Tenidap, a novel anti-inflammatory agent, is an opener of the inwardly rectifying K+ channel hKir2.3," *Eur. J. Pharmacol*., 435(2-3): 153-60, 2002 (abstract only).

(56) References Cited

OTHER PUBLICATIONS

Loffler-Walz et al., "Interaction of the diuretics torasemide and U-37883A with the K(ATP) channel in rat isolated aorta", Naunyn Schmiedebergs Arch Pharmacol.; 1998; 230-7; vol. 358(2).
Matz et al., "Heme-oxygenase-1 induction in glia throughout rat brain following experimental subarachnoid hemorrhage," *Brain Res.*, 713(1-2): 211-222. Date of Publication: 1996.
Mautes et al., "Co-induction of HSP70 and heme oxygenase-1 in macrophages and glia after spinal cord contusion in the rat," *Brain Res.*, 883(2): 233-237, 2000.
Mautes et al., "Sustained induction of heme oxygenase-1 in the traumatized spinal cord," *Exp. Neurol.*, 166(2): 254-265, 2000.
Mersel et al., "Plasma membrane isolated from astrocytes in primary cultures. Its acceptor oxidoreductase properties", Biochim Biophys Acta, 1984; 144-54; vol. 778(1).
Mest et al., "Glucose-induced insulin secretion is potentiated by a new imidazoline compound," *Naunyn Schmledebergs Arch. Pharmacol.*, 364(1): 47-52, 2001 (abstract only).
Nelson, N., et al., "Reconstitution of purified acetylcholine receptors with functional ion channels in planar lipid bilayers", Proc. Natl. Acad. Sci., Sci. USA, vol. 77, No. 5 (May 1990) pp. 3057-3061.
Nichols et al., "Adenosine diphosphate as an intracellular regulator of insulin secretion," *Science*, 272: 1785-1787, 1996.
Nishimura, M., et al., "Cerebral ATM-Sensitive Potassium Channels During Acute Reduction of Carotid Blood Flow", American Heart Assoc., (1995), vol. 25, 1069-1074.
Ono et al., "ATP and calcium modulation of nonselective cation channels in IMCD cells," *Am. J. Physiol.*, 267: F558-F565, 1994.
Papadopoulos et al., "Over-expression of HSP-70 protects astrocytes from combined oxygen-glucose deprivation," *Neuroreport*, 7(2): 429-432, 1996.
Parson, C.L., et al., "Role of Toxic Urine in Interstitial Cystitis", Journal of Urology (1990) vol. 143, p. 373A.
Perillan et al., "Inward Rectifier K+ Channel Kir2.3 (IRK3) in Reactive Astrocytes from Adult Rat Brain," *GLIA*, 31: 181-192, 2000.
Perillan et al., "K+ Inward Rectifier Currents in Reactive Astrocytes from Adult Rat Brain," *GLIA*, 27: 213:225, 1999.
Perillan et al., "Transforming Growth Factor-B1 Regulates Kir2.3 Inward Rectifier K+ Channels via Phospholipase C and Protein Kinase C-d in Reactive Astrocytes from Adult Rat Brain," *J. Biol. Chem.*, 277: 1974-1980, 2002.
Phillips, "The challenge of gene therapy and DNA delivery", Journal of Pharmacy and Pharmacology; 2001; 1169-1174; vol. 53(9).
Plangger, "Effect of torasemide on intracranial pressure, mean systemic arterial pressure, and cerebral perfusion pressure in experimental brain edema of the rat", Acta Neurochir Suppl (Wien), 1994; 519-20; vol. 60.
Popp et al, "A Calcium and ATP Sensitive Nonselective Cation Channel in the Antiluminal Membrane of Rat Cerebral Capillary Endothelial Cells," Biochimica et Niophysica Acta vol. 1108, 1992, pp. 59-66.
Proks et al., "Sulfonylurea stimulation of insulin secretion," *Diabetes*, 51(Suppl. 3): S368-76, 2002 (abstract only).
Proks ey al., "Inhibition of recombinant K(ATP) channels by the antidiabetic agents midaglizole, LY397364 and LY389382", Eur. J. Pharmacol.; 2002; 11-9, vol. 452(1).
Rae et al., "A non-selective Cation Channel in Rabbit Corneal Endothelium Activated by Internal Calcium and Inhibited by Internal ATP," *Exp. Eye. Res.*, 50: 373-384, 1990.
Rashid, H., et al; Interstitial cystitis antiproliferative factor (APF) as a cell-cycle modulator, BMC Urology (2004) 4:3, pp. 1-5.
Regan et al., "Heme oxygenase-1 induction protects murine cortical astrocytes from hemoglobin toxicity," *Neurosci. Lett.*, 282(1-2): 1-4, 2000.
Ren, Y., et. al. "Altered mRNA Expression of ATP-Sensitive and Inward Rectifier Potassium Channel Subunits in Streptozotocin-Induced Diabetics Rat Herat and Aorta", J. Pharmacol Sci., 2003, vol. 93, pp. 478-483.
Salvail, Dany, et al., "Direct modulation of tracheal C1—channel activity by 5,6- and 11, 12- EET," Amer. Physio. Soc. (1998) pp. L432-L441.
Schindler, H. et al., "Functional acetylcholine receptor from *Torpedo* marmorata in planar membranes," Proc. Nat'l. Acad. Sci. USA, vol. 77, No. 5, (May 1980) pp. 3052-3056.
Schroder et al., "AMPA receptor-mediated modulation of inward rectifier K+ channels in astrocytes of couse hippocampus," *Mol. Cell Neurosci.*, 19(3): 447-8, 2002 (abstract only).
Schubert et al., "Cascading glia reactions: a common pathomechanism and its differentiated control by cyclic nucleotide signaling," *Ann. N.Y. Acad. Sci.*, 903: 24-33, 2000 (abstract only).
Sharma, R.V., et al., "Isolation and characterization of plasma membranes from bovine carotid arteries." Amer. Physio. Soci. (1996) pp. C65-C75.
Shyng et al., "Regulation of KATP channel activity by diazoxide and MgADP. Distinct functions of the two nucleotide binding folds of the sulfonylurea receptor," *J. Gen. Physiol.*, 110: 643-654, 1997.
Simard et al., "Newly expressed SUR1-regulated NCCa-ATP channel mediates cerebral edema after ischemic stroke", Nature Medicine; 2006; 433-440, vol. 12(4).
Simard et al., "Regulation by sulfanylurea receptor type 1 of a non-selective cation channel involved in cytotoxic edema of reactive astrocytes," *J. Neurosurg. Anesthesiol.*, 16(1): 98-9, 2004.
Song et al., "GeneChip analysis after acute spinal cord injury in rat," *J. Neurochem.*, 79(4): 804-815, 2001.
Sturgess et al., "Calcium and ATP regulate the activity of a non-selective cation channel in a rat insulinoma cell line," *Pflugers Arch.*, 409: 607-615, 1987.
Suarez-Isla, B., et al, "Single calcium channels in native sarcoplasmic reticulum membranes from skeletal muscle." Proc. Nat'l. Acad. Sci., USA, vol. 83, (Oct. 1986) pp. 7741-7745.
Suarez-Isla, B., et al. "Single-Channel Recordings from Purified Acetylcholine Receptors Reconstitute in Bilayers Formed at the Tip of Patch Pipets, " American Chemical Society (1983) pp. 2319-2323.
Submitted: Simard, J., et. al., "Molecular pathophysiology of brains edema in focal ischemia—a focused review" (Apr. 8, 2006) pp. 1-483.
Tank, D., et al. "Isolated-patch recording from liposomes containing functionally reconstituted chloride channels from *Torpedo* electroplax," Proc. Nat'l. Acad. Sci. USA vol. 79, (Dec. 1982) pp. 7749-7753.
Torsemide advanced consumer drug information, pp. 1-10. http://www.drugs.com/MMX/Torsemide.html. (May 2006).
Torsemide Tablets Package Insert, pp. 1-2. Date of Publication: Oct. 2004.
Unterberg et al., "Edema and Brain Trauma", Neuroscience, 2004; 1021-1029; vol. 129.
Verkhratsky et al., "Ion channels in glial cells," *Brain Res. Rev.*, 32: 380-412, 2000.
Vidal, "Making sense of antisense", Eur. J. Cancer, 2005; 2812-8; vol. 41(18).
Walaas, S. I., et al., "PCPP-260, A Purkinje Cell-Specific Cyclic AMP-Regulated Membrane Phosphoprotein of $M_r$ 260,000", The Jol. of Neuroscience (Apr. 1986), No. 6(4); pp. 954-961.
Weith et al., "Stroke", 2001; 2029-3032; vol. 32.
Xu et al., "HSP70 protects murine astrocytes from glucose deprivation injury," *Neurosci. Lett.*, 224(1): 9-12, 1997.
Zhang, C., et al; Comparison of APF Activity and Epithelial Growth Factor Levels in Urine from Chinese, African-American, and White American Patients with Intestitial Cystitis, Urology (2003) vol. 61, pp. 897-901.
Zhu, Q., et al., "Modulation by Nucleotides of Binding Sites for [$^3$H] Glibenclamide in Rat Aorta and Cardiac Ventricular Membranes", J. of Cardivascular Pharm., (2001), vol. 37, pp. 522-531.
Kawanabe Yoshifumi; Masaki Tomoh; Hashimoto Nobuo: "Effects of the Ca++-permeable nonselective cation channel blocker LOE 908 on subarachnoid hemorrhoage-induced vasospasm in the basilar artery in rabbits.", Mar. 2003, XP008150600.
Lin et al: "17b-Estradiol Inhibits Endothelin-1 Production and Attenuates Cerebral Vasospasm After Experimental Subarachnoid Hemorrhage", Experimental Biology and Medicine, Jun. 1, 2006, pp. 1054-1057, XP55024011, Retrieved from the intemet: URL:http://ebm.rsmjournals.com/content/231/6/1054.full.pdf#page=1&view=FitH [retrieved on Apr. 5, 2012].

(56) References Cited

OTHER PUBLICATIONS

Maeda Yoshihisa et al: "Endothelial dysfunction and altered bradykinin response due to oxidative stress induced by serum deprivation in the bovine cerebral artery", European Journal of Pharmacology, Elsevier Science, NL, vol. 491, No. 1, Apr. 26, 2004, pp. 53-60, XP008150602, ISSN: 0014-2999, DOI: 10.1016/J.EJPHAR.2004.03.019 [retrieved on Apr. 15, 2004].

Shao-Hua Yang: "17-beta estradiol can reduce secondary ischemic damage and mortality of subarachnoid hemorrhage" pp. 174-181, XP055024012. Date of Publication: 2001.

White, R.P., et al: "Cerebral arterial contractions induced by human and bovine thrombin", Stroke, vol. 11, No. 4, Jul. 1, 1980, pp. 363-368, XP55024008, ISSN: 0039-2499, DOI: 10.1161-01.STR.11.4.363.

White, R.P., et al.: "Comparison of Piroxicam, Meclofenamate, Ibuprofen, Aspirin, and Prostcyclin Efficacy in a Chronic Model of Cerebral Vasospasm", Neurosurgery, Williams & Wilkins, Baltimore, MD, US, vol. 12, No. 1, Jan. 1, 1983, pp. 40-46, XP000614038, ISSN: 0148-396X.

* cited by examiner 1 2 3 4 5 6

Use of Sulfonylurea Compounds as Treatment for Brain Swelling $PIP_2$ 50 μM

A. CTR
SP1 100 μM

B stroke
SP1

C
SP1 10 μM

FIG. 41 tPA + Glibenclamide at 6 hr

VWF

100 μM

SUR1

FIG. 48

METHODS FOR TREATING BRAIN SWELLING WITH A COMPOUND THAT BLOCKS A NON-SELECTIVE CATION CHANNEL

CROSS-REFERENCE TO RELATED APPLICATIONS

This application claims priority under 35 U.S.C. §119(e) to U.S. Provisional Patent Application Ser. No. 60/365,933 filed on Mar. 20, 2002, to U.S. Provisional Application Ser. No. 60/610,758 filed Sep. 18, 2004, and to U.S. Provisional Patent Application Ser. No. 60/698,272 filed on Jul. 11, 2005, and is a continuation-in part of, and claims priority under 35 U.S.C. §120, to U.S. Non-Provisional application Ser. No. 10/391,561, now abandoned, filed on Mar. 20, 2003, and U.S. Non-Provisional application Ser. No. 11/229,236, filed Sep. 16, 2005, all of which provisional and non-provisional applications are hereby incorporated herein by reference in their entirety.

STATEMENT REGARDING FEDERALLY SPONSORED RESEARCH OR DEVELOPMENT

This invention was made with government support under Grant No. NS048260 awarded by the National Institutes of Health, a grant awarded by the Heart Lung and Blood Institute (HL082517), and a Merit Review grant from the United States Department of Veterans Affairs. The United States Government has certain rights in the invention.

FIELD OF THE INVENTION

The present invention generally regards the fields of cell biology, neurophysiology, and medicine. In particular, the present invention relates to a novel non-selective monovalent cationic ATP sensitive ion channel (hereinafter referred to as the $NC_{Ca-ATP}$ channel) that is coupled to sulfonylurea receptor type 1 in neural cells, including astrocytes, neurons and neural endothelial cells, to compounds and treatments that may modulate $NC_{Ca-ATP}$ channel activity, and to kits including compounds useful for treatment of disease or injury conditions such as stroke or brain trauma.

BACKGROUND OF THE INVENTION

Injury to the nervous system has serious consequences. Following traumatic brain injury and stroke, the normal response of the surrounding brain is to mount a cellular response that includes formation of reactive astrocytes that are believed to be important to "contain" and "clean-up" the injury site. Swelling of neural cells is part of the cytotoxic or cell swelling response that characterizes brain damage in cerebral ischemia and traumatic brain injury, and is a major cause of morbidity and mortality. See, Staub et al., 1993; Kimelberg et al., 1995. A number of mediators have been identified that initiate swelling of neural cells, including elevation of extracellular $K^+$, acidosis, release of neurotransmitters and free fatty acids. See, Kempski et al., 1991; Rutledge and Kimelberg, 1996; Mongin et al., 1999. Cytotoxic edema is a well-recognized phenomenon clinically that causes brain swelling, which worsens outcome and increases morbidity and mortality in brain injury and stroke.

Mechanisms underlying apoptotic death of reactive astrocytes and other cells have been studied. See, Tanaka et al., 2000; Yu et al., 2001. The mechanisms responsible for necrotic cell death of astrocytes, neurons and neural endothelial cells have not been characterized. Apoptotic cell death is preceded by cell shrinkage and net loss of $K^+$. See, Yu et al., 1997; Yu et al., 1999. By contrast, in necrotic cell death, the plasma membrane is ruptured, causing cytosolic contents to be released and thereby triggering tissue inflammation. See, Leist and Nicotera, 1997. Necrotic cell death may be more deleterious to nearby viable tissues, given the secondary inflammatory damage that is initiated.

Necrotic cell death is initiated by osmotic swelling following influx of $Na^+$, the major extracellular osmolyte. In most cell types, accumulation of $Na^+$ intracellularly is regarded as a passive process that does not require activation of specific effectors but that is due instead to defective outward Na' pumping under conditions of low intracellular adenosine triphosphate concentration ([ATP]i). See, Leist and Nicotera, 1997; Trump et al., 1997. Cell blebbing or swelling, an indication of intracellular Na' overload, is generally regarded as an early sign of necrotic cell death. See, Leist and Nicotera, 1997; Majno and Joris, 1995.

Inhibition of ATP synthesis or ATP depletion also causes neural cell swelling, blebbing and, if sufficiently severe, plasma membrane disruption and cell death. See, Jurkowitz-Alexander et al., 1993. The mechanisms of neural cell swelling associated with ATP-depletion remained incompletely characterized. See, Lomneth and Gruenstein, 1989; Juurlink et al., 1992; Rose et al., 1998.

One potential mechanism would be changes in $Na^+$ and $K^+$ concentration due to inhibition of the $Na^+/K^+$-ATPase pump. However, an equivalent degree of osmotic swelling induced by ouabain-mediated inhibition of the $Na^+/K^+$-ATPase pump in neural cells does not produce large depolarization, blebbing or cell death. See, Jurkowitz-Alexander et al., 1992; Brismar and Collins, 1993. Failure of the $Na^+/K^+$-ATPase pump, therefore, is not the mechanism critical to swelling of neural cells. None of these studies have identified the cellular mechanism instrumental in the cell swelling that is associated with brain damage in cerebral ischemia and traumatic brain injury and spinal cord injury.

One subtype of ATP sensitive cation channel is a non-selective cation channel, that is sensitive to $Ca^{2+}$ and ATP. More specifically, some non-selective cation channels are activated by intracellular $Ca^{2+}$ ($[Ca^{2+}]_i$) and inhibited by intracellular ATP ($[ATP]_i$). Although $Ca^{2+}$- and ATP-sensitive cation channels had been identified in a number of non-neural cell types, they have not been identified in astrocytes or any other neural cells. See, Sturgess et al., 1987; Gray and Argent, 1990; Rae et al., 1990; Champigny et al., 1991; Popp and Gogelein, 1992; Ono et al., 1994, each of which is hereby incorporated by reference in its entirety. These non-astrocyte channels comprise a heterogeneous group with incompletely defined characteristics. They exhibit single-channel conductances in the range of 25-35 pS, discriminate poorly between $Na^+$ and $K^+$, are impermeable to anions, for the most part impermeable to divalent cations, and they are blocked by similar concentrations of the adenine nucleotides ATP, ADP and AMP on the cytoplasmic side. The function of these non-selective ATP sensitive cation channels in these non-neural cell types remains enigmatic, in part because unphysiological concentrations of $Ca^{2+}$ are generally required for channel activation.

Another subtype of ATP sensitive cation channel is the ATP-sensitive potassium channel ($K_{ATP}$ channels) in pancreatic β cells. One class of insulin secretagogues, the antidiabetic sulfonylureas, is used to inhibit these $K_{ATP}$ channels and stimulate insulin release in diabetes mellitus. See, Lebovitz, 1985. Antidiabetic sulfonylureas mediate their effect on $K_{ATP}$ channels via a high affinity sulfonylurea receptor (SUR). See, Panten et. al., 1989; Aguilar-Bryan et. al., 1995. Several isoforms of the SUR, termed SUR1, SUR2A, SUR2B, and SUR2C, have been identified and cloned. See, Aguilar-Bryan et. al., 1995; Inagaki et. al., 1996; Isomoto et. al., 1996; Lawson, 2000. These receptors belong to the ATP-binding cassette (ABC) transporter family, of which the cystic fibrosis transmembrane conductance regulator (CFTR), another ion channel modulator, is also a member. See, Higgins, 1992; Aguilar-Bryan et. al., 1995. Notably, the CFTR has major therapeutic importance, since its genetic absence causes cystic fibrosis, a fatal disease.

The sulfonylurea receptor imparts sensitivity to antidiabetic sulfonylureas such as glibenclamide and tolbutamide. Also, SUR is responsible for activation of the potassium channel by a chemically diverse group of agents termed $K^+$ channel openers (SUR-activators), such as diazoxide, pinacidil, and cromakalin. See, Aguilar-Bryan et. al., 1995; Inagaki et. al., 1996; Isomoto et. al., 1996; Nichols et. al., 1996; Shyng et. al., 1997b. In various tissues, molecularly distinct SURs are coupled to distinct channel moieties to form different $K_{ATP}$ channels with distinguishable physiological and pharmacological characteristics. The $K_{ATP}$ channel in pancreatic β cells is formed from SUR1 linked with a $K^+$ channel, whereas the cardiac and smooth muscle $K_{ATP}$ channels are formed from SUR2A and SUR2B, respectively, linked to $K^+$ channels. See, Fujita and Kurachi, 2000.

Gliotic Capsule

The gliotic capsule that forms around a "foreign body" in the brain is an important, albeit neglected, biological system. On the one hand, the gliotic capsule represents the response of the brain to an injurious stimulus—an attempt by the brain to wall off, isolate, dispose of, and otherwise protect itself from the foreign body. On the other hand, the gliotic capsule forms a potentially harmful mass of tissue from which originates edema fluid that contributes to brain swelling, and whose constituent cells undergo cytotoxic edema, which adds further to brain swelling. Also, the gliotic capsule protects foreign cells from immunologic surveillance.

The essential elements involved in formation of a gliotic capsule appear to be uniform in many types of CNS pathology, be it a traumatically implanted foreign body, a metastatic tumor, a brain abscess, or infarcted necrotic tissue following a stroke. First, microglia and astrocytes become activated near the site of injury, with large, stellate-shaped GFAP-positive reactive astrocytes forming the most prominent cellular component of the response. Secondly, the foreign nature of the entity is recognized, and the response is initiated to surround and contain it. Although the concept of "foreign body" encompasses a large variety of pathological conditions, the responses in most cases bear a great deal of similarity to one another.

The interface between the foreign body and the gliotic capsule, referred to as the inner zone of the gliotic capsule, appears to be of great importance in determining the overall response to injury.

Thus, a need exists for a physiological target instrumental in the cell swelling that is associated with brain damage in cerebral ischemia and traumatic brain injury and in the consequent morbidity and mortality. There is also a need for specific treatments for the cytotoxic edema that causes brain swelling, which worsens outcome and increases morbidity and mortality in brain injury and stroke. Other and further objects, features, and advantages will be apparent from the following description of the presently preferred embodiments of the invention, which are given for the purpose of disclosure.

SUMMARY OF THE INVENTION

The present invention is based, in part, on the discovery of a specific channel, the $NC_{Ca\text{-}ATP}$ channel, which, for example, is expressed in neurons, glia and neural endothelial cells after brain trauma. This unique non-selective cation channel is activated by intracellular calcium and blocked by intracellular ATP ($NC_{Ca\text{-}ATP}$ channel), and can be expressed in neuronal cells, neuroglia cells (also termed glia, or glial cells, e.g., astrocyte, ependymal cell, oligodentrocyte and microglia) or neural endothelial cells (e.g., capillary endothelial cells) in which the cells have been or are exposed to a traumatic insult, for example, an acute neuronal insult (e.g., hypoxia, ischemia, tissue compression, mechanical distortion, cerebral edema or cell swelling), toxic compounds or metabolites, an acute injury, cancer, brain abscess, etc.

More specifically, the $NC_{Ca\text{-}ATP}$ channel of the present invention has a single-channel conductance to potassium ion ($K^+$) between 20 and 50 pS. The $NC_{Ca\text{-}ATP}$ channel is also stimulated by $Ca^{2+}$ on the cytoplasmic side of the cell membrane in a physiological concentration range, where concentration range is from $10^{-8}$ to $10^{-5}$ M. The $NC_{Ca\text{-}ATP}$ channel is also inhibited by cytoplasmic ATP in a physiological concentration range, where the concentration range is from $10^{-1}$ to 10 M. The $NC_{Ca\text{-}ATP}$ channel is also permeable to the following cations; $K^+$, $Cs^+$, $Li^+$, $Na^+$; to the extent that the permeability ratio between any two of the cations is greater than 0.5 and less than 2.

More particularly, the present invention relates to the regulation and/or modulation of this $NC_{Ca\text{-}ATP}$ channel and how its modulation can be used to treat various diseases and/or conditions, for example acute neuronal insults (e.g., stroke, an ischemic/hypoxic insult, a traumatic or mechanical injury) and diseases or conditions leading to formation of a gliotic capsule. Yet further, the present invention relates to the regulation and/or modulation of this $NC_{Ca\text{-}ATP}$ channel and its role in maintaining or disrupting the integrity of the gliotic capsule. The modulation and/or regulation of the channel results from administration of an activator or agonist of the channel or an antagonist or inhibitor of the channel. Thus, depending upon the disease, a composition (an antagonist or inhibitor) is administered to block or inhibit the channel to prevent cell death, for example to treat cerebral edema that results from ischemia due to tissue trauma or to increased tissue pressure. In these instances the channel is blocked to prevent or reduce or modulate depolarization of the cells. Alternatively, in order to treat or disrupt a gliotic capsule, it is desirable to open or activate the channel by administering an agonist or activator compound to cause cell depolarization resulting in cell death of diseased target cells.

In one aspect, the present invention provides novel methods of treating a patient comprising administering a therapeutic compound that targets a unique non-selective cation channel activated by intracellular calcium and blocked by intracellular ATP ($NC_{Ca\text{-}ATP}$ channel). In specific embodiments, the therapeutic compound may be an antagonist, and uses thereof in therapies, such as treatment of cerebral ischemia or edema, benefiting from blocking and/or inhibiting the $NC_{Ca\text{-}ATP}$ channel. In further embodiments, where death of cells expressing the $NC_{Ca\text{-}ATP}$ channel is desired for therapeutic purposes, the therapeutic compound may be an agonist. Compositions comprising agonists and/or antagonists of the $NC_{Ca\text{-}ATP}$ channel are also contemplated.

The invention also encompasses the use of such compounds and compositions that modulate $NC_{Ca\text{-}ATP}$ channel activity to treat brain swelling. For example, the present invention relates to methods for the treatment of brain swelling that results from brain trauma or cerebral ischemia, resulting in neural cell swelling, cell death, and an increase in transcapillary formation of ionic and vasogenic edema. Further provided is a method of preventing brain swelling and the resulting brain damage through the therapeutic use of antagonists to the $NC_{Ca-ATP}$ channel. In one embodiment, the therapeutic antagonist can be administered to or into the brain. Such administration to the brain includes injection directly into the brain, particularly in the case where the brain has been rendered accessible to injection due to trauma to the skull, for example. The invention further provides the therapeutic use of sulfonylurea compounds as antagonists to the $NC_{Ca-ATP}$ channel to prevent cell swelling in brain. In one embodiment the sulfonylurea compound is glibenclamide. In another embodiment, the sulfonylurea compound is tolbutamide, or any of the other compounds that have been found to promote insulin secretion by acting on KATP channels in pancreatic β cells, as listed elsewhere herein.

The invention also encompasses agonists and antagonists of the $NC_{Ca-ATP}$ channel, including small molecules, large molecules, and antibodies, as well as nucleotide sequences that can be used to inhibit $NC_{Ca-ATP}$ channel gene expression (e.g., antisense and ribozyme molecules). An antagonist of the $NC_{Ca-ATP}$ channel includes one or more compounds capable of (1) blocking the channel; (2) preventing channel opening; (3) reducing the magnitude of membrane current through the channel; (4) inhibiting transcriptional expression of the channel; and/or (5) inhibiting post-translational assembly and/or trafficking of channel subunits.

The invention relates to assays designed to screen for compounds or compositions that modulate the $NC_{Ca-ATP}$ channel, particularly compounds or compositions that act as antagonists of the channel, and thereby modulate neural cell swelling and the concomitant brain swelling. To this end, cell-based assays or non-cell based assays can be used to detect compounds that interact with, e.g., bind to, the outside (i.e., extracellular domain) of the $NC_{Ca-ATP}$ channel and/or its associated SUR1 regulatory subunit. The cell-based assays have the advantage in that they can be used to identify compounds that affect $NC_{Ca-ATP}$ channel biological activity (i.e., depolarization). The invention also provides a method of screening for and identifying antagonists of the $NC_{Ca-ATP}$ channel, by contacting neural cells with a test compound and determining whether the test compound inhibits the activity of the $NC_{Ca-ATP}$ channel. In one embodiment, methods for identifying compounds that are antagonists of the $NC_{Ca-ATP}$ are provided. In one embodiment, therapeutic compounds of the present invention, including $NC_{Ca-ATP}$ antagonists, are identified by the compound's ability to block the open channel or to prevent channel opening, such as by quantifying channel function using electrophysiological techniques to measure membrane current through the channel, for example. $NC_{Ca-ATP}$ antagonists include compounds that are $NC_{Ca-ATP}$ channel inhibitors, $NC_{Ca-ATP}$ channel blockers, SUR1 antagonists, SUR1 inhibitors, and/or compounds that reduce the magnitude of membrane current through the channel, for example. In this embodiment, channel function can be measured in a preparation of neural cells from a human or animal, and the test compound can be brought into contact with the cell preparation by washing it over the cell preparation in solution. The invention further provides a method of screening for sulfonylurea compounds that may act as antagonists of the $NC_{Ca-ATP}$ channel.

The present invention relates to drug screening assays to identify compounds for the treatment of brain swelling, such as the swelling that occurs after brain injury or cerebral ischemia by using the $NC_{Ca-ATP}$ channel as a target. The invention also relates to compounds that modulate neural cell swelling via the $NC_{Ca-ATP}$ channel. The present invention also relates to the treatment of brain swelling by targeting the $NC_{Ca-ATP}$ channel.

The present invention is also directed to purified compositions comprising a novel $Ca^{2+}$-activated, $[ATP]_i$-sensitive nonspecific cation channel. In a preferred embodiment of the present invention, the compositions comprise mammalian neural cells or membrane preparations expressing the $NC_{Ca-ATP}$ channel, most preferably wherein the mammalian neural cells are freshly isolated reactive astrocytes, neurons or neural endothelial cells. A preferred example of such a purified composition comprising the $NC_{Ca-ATP}$ channel is a membrane preparation derived from native reactive astrocytes. As demonstrated herein, when neural cells expressing the $NC_{Ca-ATP}$ channel are depleted of intracellular ATP, the $NC_{Ca-ATP}$ channel opens and the cells swell and die. However, if the $NC_{Ca-ATP}$ channel is blocked on such cells, the cells do not swell and die. The invention is also based, in part, on the discovery that the $NC_{Ca-ATP}$ channel is regulated by a type 1 sulfonylurea receptor, and that antagonists of this receptor are capable of blocking the $NC_{Ca-ATP}$ channel and inhibit neural cell swelling.

The composition(s) of the present invention may be delivered alimentarily or parenterally. Examples of alimentary administration include, but are not limited to orally, buccally, rectally, or sublingually. Parenteral administration can include, but are not limited to intramuscularly, subcutaneously, intraperitoneally, intravenously, intratumorally, intraarterially, intraventricularly, intracavity, intravesical, intrathecal, or intrapleural. Other modes of administration may also include topically, mucosally, transdermally, direct injection into the brain parenchyma.

An effective amount of an agonist or antagonist of $NC_{Ca-ATP}$ channel that may be administered to a cell includes a dose of about 0.0001 nM to about 2000 μM, for example. More specifically, doses of an agonist to be administered are from about 0.01 nM to about 2000 μM; about 0.01 μM to about 0.05 μM; about 0.05 μM to about 1.0 μM; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM and about 1500 μM to about 2000 μM, for example. Of course, all of these amounts are exemplary, and any amount in-between these points is also expected to be of use in the invention.

An effective amount of an agonist or antagonist of the $NC_{Ca-ATP}$ channel or related-compounds thereof as a treatment varies depending upon the host treated and the particular mode of administration. In one embodiment of the invention the dose range of the agonist or antagonist of the $NC_{Ca-ATP}$ channel or related-compounds thereof will be about 0.01 μg/kg body weight to about 20,000 μg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 μg/kg body weight to 20,000 μg/kg body weight, 0.02 μg/kg body weight to 15,000 μg/kg body weight, 0.03 μg/kg body weight to 10,000 μg/kg body weight, 0.04 μg/kg body weight to 5,000 μg/kg body weight, 0.05 μg/kg body weight to 2,500 μg/kg body weight, 0.06 μg/kg body weight to 1,000 μg/kg body weight, 0.07 μg/kg body weight to 500 μg/kg body weight, 0.08 μg/kg body weight to 400 μg/kg body weight, 0.09 μg/kg body weight to 200 μg/kg body weight or 0.1 μg/kg body weight to 100 μg/kg body weight. Further, those of skill will recognize that a variety of different dosage levels will be of use, for example, 0.0001 μg/kg, 0.0002 μg/kg, 0.0003 μg/kg, 0.0004 μg/kg, 0.005 μg/kg, 0.0007 μg/kg, 0.001 μg/kg, 0.1 μg/kg, 1.0 μg/kg, 1.5 μg/kg, 2.0 μg/kg, 5.0 μg/kg, 10.0 μg/kg, 15.0 μg/kg, 30.0 μg/kg, 50 μg/kg, 75 μg/kg, 80 μg/kg, 90 μg/kg, 100 μg/kg, 120 μg/kg, 140 μg/kg, 150 μg/kg, 160 μg/kg, 180 μg/kg, 200 μg/kg, 225 μg/kg, 250 μg/kg, 275 μg/kg, 300 μg/kg, 325 μg/kg, 350 μg/kg, 375 μg/kg, 400 μg/kg, 450 μg/kg, 500 μg/kg, 550 μg/kg, 600 μg/kg, 700 μg/kg, 750 μg/kg, 800 μg/kg, 900 μg/kg, 1 mg/kg, 5 mg/kg, 10 mg/kg, 12 mg/kg, 15 mg/kg, 20 mg/kg, and/or 30 mg/kg. In particular embodiments, there may be dosing of from very low ranges (e.g. 1 mg/kg/day or less; 5 mg/kg bolus; or 1 mg/kg/day) to moderate doses (e.g. 2 mg bolus, 15 mg/day) to high doses (e.g. 5 mg bolus, 30-40 mg/day; and even higher). Of course, all of these dosages are exemplary, and any dosage in-between these points is also expected to be of use in the invention. Any of the above dosage ranges or dosage levels may be employed for an agonist or antagonist, or both, of $NC_{Ca-ATP}$ channel or related-compounds thereof.

The $NC_{Ca-ATP}$ channel is blocked by antagonists of type 1 sulfonylurea receptor (SUR1) and is opened by SUR1 activators. More specifically, the antagonists of type 1 sulfonylurea receptor (SUR1) include blockers of $K_{ATP}$ channels and the SUR1 activators include activators of $K_{ATP}$ channels. The channel can be inhibited by an $NC_{Ca-ATP}$ channel inhibitor, an $NC_{CaATP}$ channel blocker, a type 1 sulfonylurea receptor (SUR1) antagonist, SUR1 inhibitor, or a compound capable of reducing the magnitude of membrane current through the channel. More specifically, the SUR1 antagonist may be selected from the group consisting of glibenclamide, tolbutamide, repaglinide, nateglinide, meglitinide, midaglizole, LY397364, LY389382, gliclazide (also known in the art as glyclazide), glimepiride, estrogen, estrogen related-compounds (estradiol, estrone, estriol, genistein, non-steroidal estrogen (e.g., diethystilbestrol), phytoestrogen (e.g., coumestrol), zearalenone, etc.), and compounds known to inhibit or block $K_{ATP}$ channels. MgADP can also be used to inhibit the channel. Other compounds that can be used to block or inhibit $K_{ATP}$ channels include, but are not limited to tolbutamide, glyburide (1[p-2[5-chloro-O-anisamido)ethyl] phenyl]sulfonyl]-3-cyclohexyl-3-urea); chlopropamide (1-[[(p-chlorophenyl)sulfonyl]-3-propylurea; glipizide (1-cyclohexyl-3[[p-[2(5-methylpyrazine carboxamido)ethyl] phenyl]sulfonyl]urea); or tolazamide(benzenesulfonamide-N-[[(hexahydro-1H-azepin-1yl)amino]carbonyl]-4-methyl). In additional embodiments, non-sulfonyl urea compounds, such as 2,3-butanedione and 5-hydroxydecanoic acid, quinine, and therapeutically equivalent salts and derivatives thereof, may be employed in the invention.

The channel is expressed on neuronal cells, neuroglia cells, neural epithelial cells, neural endothelial cells, or a combination thereof, for example. The inhibitor blocks the influx of $Na^+$ into the cells thereby preventing depolarization of the cells. Inhibition of the influx of $Na^+$ into the cells thereby at least prevents or reduces cytotoxic edema and/or ionic edema, and prevents or reduces hemorrhagic conversion. Thus, this treatment reduces cell death or necrotic death of neuronal and/or neural endothelial cells.

In certain embodiments, the amount of the SUR1 antagonist administered to the subject is in the range of about 0.0001 μg/kg/day to about 20 mg/kg/day, about 0.01 μg/kg/day to about 100 μg/kg/day, or about 100 μg/kg/day to about 20 mg/kg/day. Still further, the SUR1 antagonist may be administered to the subject in the from of a treatment in which the treatment may comprise the amount of the SUR1 antagonist or the dose of the SUR1 antagonist that is administered per day (1, 2, 3, 4, etc.), week (1, 2, 3, 4, 5, etc.), month (1, 2, 3, 4, 5, etc.), etc. Treatments may be administered such that the amount of SUR1 antagonist administered to the subject is in the range of about 0.0001 μg/kg/treatment to about 20 mg/kg/treatment, about 0.01 μg/kg/treatment to about 100 μg/kg/treatment, or about 100 μg/kg/treatment to about 20 mg/kg/treatment.

Another embodiment of the present invention comprises a method of reducing mortality of a subject suffering from a stroke comprising administering to the subject a compound effective to inhibit $NC_{Ca-ATP}$ channels in a neuronal cell, a neuroglia cell, a neural endothelial cell or a combination thereof. The compound reduces stroke size and reduces edema located in the peri-infarct tissue. The compound can be administered alimentary (e.g., orally, buccally, rectally or sublingually) or parenterally (e.g., intravenously, intradermally, intramuscularly, intraarterially, intrathecally, subcutaneously, intraperitoneally, intraventricularly) and/or topically (e.g., transdermally), mucosally, or by direct injection into the brain parenchyma.

Still further, another embodiment comprises a method of reducing edema in a peri-infarct tissue area of a subject comprising administering to the subject a compound effective to inhibit $NC_{Ca-ATP}$ channels in a neuronal cell, a neuroglial cell, a neural endothelial cell, or a combination thereof.

Further embodiments comprises a method of treating a subject at risk for developing a stroke comprising administering to the subject a compound effective to inhibit a $NC_{Ca-ATP}$ channel in neuronal cell, a neuroglia cell, a neural endothelial cell or a combination thereof.

In certain embodiments, the subject is undergoing treatment for a cardiac condition, thus the condition increases the subjects risk for developing a stroke. The treatment, for example, may comprise the use of thrombolytic agents to treat myocardial infarctions. Still further, the subject may be at risk for developing a stroke because the subject suffers from atrial fibrillation or a clotting disorder. Other subjects that are at risk for developing a stroke include subjects that are at risk of developing pulmonary emboli, subjects undergoing surgery (e.g., vascular surgery or neurological surgery), or subjects undergoing treatments that increase their risk for developing a stroke, for example, the treatment may comprise cerebral/endovascular treatment, angiography or stent placement. In other embodiments, the subject may be undergoing treatment for vascular disease that could place the spinal cord at risk for ischemia, such as surgery requiring aortic cross-clamping, surgery for abdominal aortic aneurysm, etc. In other embodiments, the patient may be undergoing surgery for a spinal or spinal cord condition, including discectomy, fusion, laminectomy, extradural or intradural surgery for tumor or mass etc., that would place the spinal cord at risk of injury. In some embodiments of the invention, the subject has a chronic condition, whereas in other embodiments of the invention, the subject does not have a chronic condition, such as a short-term condition.

Another embodiment of the present invention comprises a method of treating a subject at risk for developing cerebral edema comprising administering to the subject a compound effective to inhibit a $NC_{Ca-ATP}$ channel in a neuronal cell, a neuroglia cell, a neural endothelial cell or a combination thereof. The subject at risk may be suffering from an arteriorvenous malformation, or a mass-occupying lesion (e.g., hematoma) or may be involved in activities that have an increased risk of brain trauma.

Another embodiment of the present invention comprises a composition comprising a membrane preparation derived from a neural endothelial cell expressing a $NC_{Ca-ATP}$ channel, wherein channel is blocked by antagonists of type 1 sulfonylurea receptor (SUR1) and opened by SUR1 activators. More specifically, the channel has the following characteristics: (a) it is a 35 pS type channel; (b) it is stimulated by cytoplasmic $Ca^{2+}$ in the concentration range from about $10^{-8}$ to about $10^{-5}$ M; (c) it opens when cytoplasmic ATP is less than about 0.8 μM; and (d) it is permeable to the monovalent cations $K^+$, $Cs^+$, $Li^+$ and $Na^+$.

In further embodiments, the compound that inhibits the $NC_{Ca-ATP}$ channel can be administered in combination with a thrombolytic agent (e.g., tissue plasminogen activator (tPA), urokinase, prourokinase, streptokinase, anistreplase, reteplase, tenecteplase), an anticoagulant or antiplatelet (e.g., aspirin, warfarin or coumadin), statins, diuretics, vasodilators (e.g., nitroglycerin), mannitol, diazoxide or similar compounds that stimulate or promote ischemic precondition.

Yet further, another embodiment of the present invention comprises a pharmaceutical composition comprising a thrombolytic agent (e.g., tissue plasminogen activator (tPA), urokinase, prourokinase, streptokinase, anistreplase, reteplase, tenecteplase), an anticoagulant or antiplatelet (e.g., aspirin, warfarin or coumadin), statins, diuretics, vasodilators, mannitol, diazoxide or similar compounds that stimulate or promote ischemic precondition or a pharmaceutically acceptable salt thereof and a compound that inhibits a $NC_{Ca-ATP}$ channel or a pharmaceutically acceptable salt thereof. This pharmaceutical composition can be considered neuroprotective, in specific embodiments. For example, the pharmaceutical composition comprising a combination of the thrombolytic agent and a compound that inhibits a $NC_{Ca-ATP}$ channel is neuroprotective because it increases the therapeutic window for the administration of the thrombolytic agent by several hours; for example the therapeutic window for administration of thrombolytic agents may be increased by several hours (e.g. about 4-about 8 hrs) by co-administering antagonist of the $NC_{Ca-ATP}$ channel.

Still further, another embodiment comprises a method of treating acute cerebral ischemia in a subject comprising administering to a subject an amount of a thrombolytic agent or a pharmaceutically acceptable salt thereof in combination with an amount of a compound that inhibits a $NC_{Ca-ATP}$ channel or a pharmaceutically acceptable salt thereof. In certain embodiments, the thrombolytic agent is a tissue plasminogen activator (tPA), urokinase, prourokinase, streptokinase, anistreplase, reteplase, tenecteplase or any combination thereof. The SUR1 antagonist can be administered by any standard parenteral or alimentary route, for example the SUR1 antagonist may be administered as a bolus injection or as an infusion or a combination thereof.

Another embodiment of the present invention comprises a method of disrupting a gliotic capsule, such as to disrupt the integrity of the tumor-brain barrier surrounding a tumor in the brain of a subject comprising administering to the subject a compound effective to activate a $NC_{Ca-ATP}$ channel in a neuronal cell, or a neuroglia cell, a neural endothelial cell or a combination thereof.

Where destruction of cells expressing the $NC_{Ca-ATP}$ channel is desired, an SUR1 activator or agonist may be administered, for example, to reduce or remove a gliotic capsule. The activator compound or agonist can be a type 1 sulfonylurea receptor agonist. For example, agonists that can be used in the present invention include, but are not limited to agonist of SUR1, for example, diazoxide, pinacidil, P1075, cromakalin, or combinations thereof. Other agonists can include, but are not limited to diazoxide derivatives, for example 3-isopropylamino-7-methoxy-4H-1,2,4-benzothiadiazine 1,1-dioxide (NNC 55-9216), 6,7-dichloro-3-isopropylamino-4H-1,2,4-benzothiadiazine 1,1-dioxide (BPDZ 154), 7-chloro-3-isopropylamino-4H-1,2,4-benzothiadiazine 1,1-dioxide (BPDZ 73), 6-Chloro-3-isopropylamino-4H-thieno[3,2-e]-1,2,4-thiadiazine 1,1-dioxide (NNC 55-0118) 4,6-chloro-3-(1-methylcyclopropyl)amino-4H-thieno[3,2-e]-1,2,4-thiadiazine 1,1-dioxide (NN414), 3-(3-methyl-2-butylamino)-4H-pyrido[4,3-e]-1,2,4-thiadiazine 1,1-dioxide (BPDZ 44), 3-(1',2',2'-trimethylpropyl)amino-4H-pyrido(4,3-e)-1,2,4-thiadiazine 1,1-dioxide (BPDZ 62), 3-(1',2',2'-trimethylpropyl) amine-4H-pyrido (2,3-e)-1,2,4-thiadiazine, 1,1-dioxide (BPDZ 79), 2-alkyl-3-alkylamino-2H-benzo- and 2-alkyl-3-alkylamino-2H-pyrido[4,3-e]-1,2,4-thiadiazine 1,1-dioxides, 6-Chloro-3-alkylamino-4H-thieno[3,2-e]-1,2,4-thiadiazine 1,1-dioxide derivatives, 4-N-Substituted and -unsubstituted 3-alkyl- and 3-(alkylamino)-4H-pyrido[4,3-e]-1,2,4-thiadiazine 1,1-dioxides, or combinations thereof. In addition, other compounds, including 6-chloro-2-methylquinolin-4(1H)-one (HEI 713) and LN 533021, as well as the class of drugs, arylcyanoguanidines, are known activators or agonist of SUR1. Other compounds that can be used include compounds known to activate $K_{ATP}$ channels.

Still further, another embodiment of the present invention comprises a method of inducing cell death of one or more of a neuronal or a neuroglia cell or a neural endothelial cell comprising administering to the cell a compound effective to activate a $NC_{Ca-ATP}$ channel in the cell. Activation of the $NC_{Ca-ATP}$ channel results in an influx of sodium ions ($Na^+$) causing depolarization of the cell. The influx of $Na^+$ alters the osmotic gradient causing an influx of water into the cell that leads to cytotoxic edema ultimately resulting in necrotic cell death.

Yet further, another embodiment of the present invention comprises a method of maintaining the integrity of the gliotic capsule surrounding brain abscess of a subject comprising administering to the subject a compound effective to inhibit and/or block at least one $NC_{Ca-ATP}$ channel in a neuronal cell, a neuroglia cell, a neural endothelial cell or a combination thereof.

Still further, another method of the present invention comprises a method of diagnosing neuronal cell edema and/or cytotoxic damage in the brain comprising: labeling an antagonist of SUR1; administering the labeled antagonist of SUR1 to a subject; measuring the levels of labeled antagonist of SUR1 in the brain of the subject, wherein the presence of labeled antagonist of SUR1 indicates neuronal cell edema and/or cytotoxic damage in the brain.

In further embodiments, the methods can comprise a method of determining the penumbra following a stroke comprising: labeling an antagonist of SUR1; administering the labeled antagonist of SUR1 to a subject; visualizing the labeled antagonist of SUR1 in the brain of the subject, wherein the presence of labeled antagonist of SUR1 indicates the penumbra.

Yet further, the present invention comprises a method monitoring stroke neural disease comprising: labeling an antagonist of SUR1; administering the labeled antagonist of SUR1 to a subject; visualizing the labeled antagonist of SUR1 in the brain of the subject, wherein the presence of labeled antagonist of SUR1 indicates the progression of the disease. In certain embodiments, the step of visualizing is performed daily to monitor the progression of the stroke.

Another embodiment comprises a neuroprotective infusion kit comprising a compound that inhibits a $NC_{Ca-ATP}$ channel in a neuronal cell, a neuroglia cell, a neural endothelial cell or a combination thereof and an IV solution. The compound and solution are contained within the same container or within different containers. More specifically, the compound is contained within the container of solution.

The kit may further comprise a neuroprotective bolus kit, wherein the bolus kit comprises a pre-loaded syringe of a compound inhibits a $NC_{Ca-ATP}$ channel in a neuronal cell, a neuroglia cell, a neural endothelial cell or a combination thereof.

Still further, another embodiment comprises a neuroprotective kit comprising a compound that inhibits $NC_{Ca-ATP}$ channel in a neuronal cell, a neuroglia cell, an endothelium cell or a combination thereof and a thrombolytic agent (e.g., tPA), an anticoagulant (e.g., warfarin or coumadin), an antiplatelet (e.g., aspirin), a diuretic (e.g., mannitol), a statin, or a vasodilator (e.g., nitroglycerin).

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 1 (comprised of FIGS. 1A, 1B, 1C, 1D, 1E and 1F)

FIG. 2 (comprised of FIGS. 2A and 2B)

FIG. 3 (comprised of FIGS. 3A, 3B, 3C and 3D)

FIG. 4 (comprised of FIGS. 4A and 4B)

FIG. 5 (comprised of FIGS. 5A and 5B)

FIG. 9 (comprised of FIGS. 9A and 9B) shows that the channel activator diazoxide can elicit channel activities under outside-out patch recording configuration.

FIG. 10C show a plot of mean single channel amplitudes at the different potentials studied; the slope of the data indicates 35 pS conductance of the glibenclamide-sensitive channel.

FIG. 11 (comprised of FIGS. 11A and 11B) shows that sulfonylurea compounds inhibit channel activities.

FIG. 12 (comprised of FIGS. 12A, 12B, 12C, 12D, 12E, 12F, 12G, 12H and 12I)

FIG. 13 (comprised of FIGS. 13A, 13B and 13C)

FIG. 14A shows the cells when formaldehyde-glutaraldehyde fixation was initiated under control conditions; FIG. 14B shows the cells fixed 5 min after exposure to 1 mM $NaN_3$. FIG. 14C shows the cells fixed 25 min after exposure to 1 mM $NaN_3$. Bar, 12 μm.

FIG. 15 (comprised of FIGS. 15A, 15B and 15C)

FIG. 16 shows that addition of exogenous phosphatidylinositol-4,5-bisphosphate ($PIP_2$) causes activation of the $NC_{Ca\text{-}ATP}$ channel, despite the presence of ATP in the bath solution. Initially, channel activity was recorded in an inside-out patch of membrane from an R1 astrocyte, with a bath solution containing 1 μM $Ca^{2+}$ and 10 μM ATP, which was sufficient to block channel activity. Addition of 50 μM $PIP_2$ resulted in channel activation, reflecting an apparent decrease in affinity of the channel for ATP.

FIG. 17 shows that the $NC_{Ca\text{-}ATP}$ channel in an R1 astrocyte is inhibited by estrogen. The initial portion of the record shows brisk activity from a number of superimposed channels, recorded in a cell attached patch of membrane from an R1 astrocyte obtained from a female. Addition of 10 nM estrogen to the bath promptly resulted in strong inhibition of channel activity. The mechanism involved is believed to be related to estrogen receptor mediated activation of phospholipase C (PLC), resulting in depletion of $PIP_2$ from the membrane, and reflecting an apparent increase in affinity for ATP.

FIG. 18A was developed using antibodies directed against estrogen receptors (ER), demonstrating that both ERα and ERβ are expressed in astrocytes from both genders. Western blots showed that SUR1 is also expressed by cells from both genders, with pancreatic tissue used as control (FIG. 18B).

FIG. 20A shows a coronal section of a rat brain sectioned though the site of implantation of a large gelatin sponge; the sponge (innermost dark region) is encapsulated by a gliotic capsule (light area), outside of which is found a region of vasogenic edema (outer dark area), identified by pre-mortem administration of methylene blue. FIGS. 20B and 20C show low power and high power views, respectively, of the gliotic capsule immunolabeled for GFAP. FIG. 20D shows a high power view of GFAP-labeled cells inside of the gelatin sponge implant.

FIGS. 21A, 21C, 21E show freshly-isolated large phase-bright R1 astrocytes immunolabeled for GFAP (FIG. 21C) and vimentin (FIG. 21E). FIGS. 21B,D,F show freshly-isolated small phase-dark R2 astrocytes immunolabeled for GFAP (FIG. 21D) and vimentin (FIG. 21F). FIG. 21G shows primary cultures of astrocytes isolated from a gliotic capsule, with R1 astrocytes developing into large polygonal cells (FIG. 21Gb), and R2 astrocytes developing into small bipolar cells (FIG. 21Ga). FIG. 21H shows that R2 astrocytes, but not R1 astrocytes, are labeled with fluorescein tagged chlorotoxin derived from the scorpion, *Leiurus quinquestriatus.*

FIG. 22D shown RT-PCR for SUR1 in control insulinoma cells (lane 2) and in isolated R1 astrocytes (lane 3), and for SUR2 in control cardiac cells (lane 4), but not in isolated R1 astrocytes (lane 5).

FIGS. 23G-I show that pimonidazole, HIF1α and occludens all localize to GFAP-positive astrocytes that form the inner zone of the gliotic capsule.

FIG. 28A shows phase contrast images of 4 different freshly isolated R1 astrocytes observed over the course of 30 min each. The cell exposed to vehicle solution alone remained phase bright with no pathological deterioration (control). The cell depleted of ATP by exposure to Na azide (1 mM) developed progressive blebbing consistent with cytotoxic edema. Similarly, the cell exposed to the $NC_{Ca-ATP}$ channel opener, diazoxide, developed progressive blebbing consistent with cytotoxic edema. The cell exposed to Na azide in the presence of glibenclamide remained phase bright with no pathological deterioration. FIGS. 28B and 28C show cell death of isolated R1 astrocytes induced by ATP depletion in vitro. Freshly isolated R1 astrocytes were labeled for necrotic death with propidium iodide (PI) (FIG. 28B), or for apoptotic death with annexin V (FIG. 28C), under control conditions, after exposure to Na azide (1 mM), or after exposure to Na azide in the presence of glibenclamide (1 μM). Exposure to Na azide resulted mostly in necrotic death that was largely prevented by glibenclamide.

FIG. 31A shows phase-contrast image of large neuron-like cells enzymatically isolated from ischemic region 3 hr following MCAO. FIG. 31B shows recording of inside-out patch using $Cs^+$ as the charge carrier; channel activity was blocked by glibenclamide given as indicated (arrow); a and b show expanded records of the portions indicated. FIG. 31C shows recordings at potentials indicated of inside-out patch using $K^+$ as the charge carrier; channel activity was blocked by glibenclamide. FIG. 31D shows a plot of single channel amplitudes at different voltages showing single channel slope conductance of 34 pS.

In FIG. 32A, Mortality was assessed during 7 days after MCA stroke [double occlusion model with malignant cerebral edema (MCE)] in two treatment groups, each comprised of 19 female and 10 male rats, treated with either saline (empty symbols) or glibenclamide (filled symbols); mortality at 7 days was significantly different. Subgroup analyses for males and females showed similar results. In FIG. 32B edema was assessed 8 hr after MCA stroke (MCE model) in two treatment groups, each comprised of 6 male rats treated with either saline or glibenclamide; tissues were first processed with TTC to allow separation into TTC(+) and TTC(−) portions of the involved hemisphere and contralateral hemisphere, prior to determining wet/dry weights; values in TTC(+) regions were statistically different. In FIGS. 32C-32E, stroke size was assessed 48 hr after MCA stroke [thromboembolic (TE) model] in two treatment groups, each comprised of 10 male rats, treated with either saline or glibenclamide; images of TTC-stained coronal sections following MCA stroke (TE model) in an animal treated with saline (FIG. 32C) and another treated with glibenclamide (FIG. 32D), showing cortical sparing often associated with glibenclamide treatment; values of stroke size, expressed as percent of hemisphere volume (FIG. 32E).

In FIG. 33D, immunofluorescence image of a brain section from an animal 6 hr after MCA stroke (MCE model) labeled with anti-SUR1 antibody showing strong labeling in a capillary and in adjacent neuron-like cells.

FIGS. 34A-34D are from animals co-treated with saline; FIGS. 34E-34H are from animals co-treated with glibenclamide. The left column of photographs of coronal sections shows, in rows 1-2 only, intraventricular hemorrhage, plus large areas of hemorrhagic conversion in ischemic cortical/subcortical regions (red areas on the right side of pictures; arrows). The right column of photographs of TTC-processed sections from the same animals show the areas of infarction.

FIG. 35A shows activation of MMP-9 & MMP-2 in stroke tissue compared to control; activity of recombinant MMP-9 & MMP-2 shown at left. FIG. 35B shows gelatinase activity of recombinant enzyme and stroke tissue under control conditions (CTR), in presence of glibenclamide (10 μM), and in presence of MMP inhibitor II (300 nM; Calbiochem).

FIGS. 37A and 37B show superimposed macroscopic currents recorded during 200 ms depolarizing pulses from −120 mV to +120 mV in 20 mV steps in an endothelial cell (FIG. 37A) and in an elongated smooth muscle cell (FIG. 37B); holding potential, −60 mV; nystatin perforated patch technique; bath solution, standard Krebs with 2 mM $Ca^{2+}$; pipette solution, 145 mM $K^+$. FIGS. 37C and 37D show current-voltage curves computed from average (mean±SE) currents at the end of 200-ms test pulses recorded in 9 endothelial cells (FIG. 37C) and 7 smooth muscle cells (FIG. 37D); same holding potential, technique and solutions as in FIGS. 37A and 37B. FIGS. 37E and 37F show current voltage curves recorded during ramp pulses (0.45 mV/ms, holding potential, −60 mV) in an endothelial cell (FIG. 37E) and in a smooth muscle cell (FIG. 37F); same holding potential, technique and bath solution as in FIGS. 37A and 37B, but with pipette solution containing 145 mM $Cs^+$ instead of $K^+$.

FIGS. 39A and 39B show Western blot (FIG. 39A) and quantification of Western blots (FIG. 39B) of R1 cell lysates confirmed knock down of SUR1 expression by antisense. FIGS. 39C-39E show Na azide caused large depolarizations in cells exposed to SCR-ODN (FIGS. 39C, 39E) but little or no depolarization in cells exposed to AS-ODN (FIGS. 39D, 39E).

FIGS. 41A-41C show an increase in nuclear localization of the transcription factor, SP1, and SP1 co-localization with SUR1 in stroke. Immunofluorescence images showing increase of nuclear SP1 labeling in ischemic area 3-hr after MCAO (FIG. 41B), compared to contralateral side (FIG. 41A). FIG. 41C double labeling of large neuron-like cell showing nuclear SP1 (green) and cytoplasmic/plasmalemmal SUR1 (red) in the same cell.

FIGS. 42A and 42C show Western blot analysis of HIF1α protein in R1 astrocytes from gelfoam implant model of control (CTR) and HIF1α knock-down (KD). FIGS. 42B and 42C show SUR1 protein in the same cell lysates.

FIG. 48 shows high power views of previous image (above/right panel), showing SUR1 expression following brain contusion; SUR1 expression was seen in large neuron-like cells (left panel) and in capillaries co-labeled with SUR1 and von Willebrand factor (middle and right panels).

DETAILED DESCRIPTION

Figures 1A, 1B:
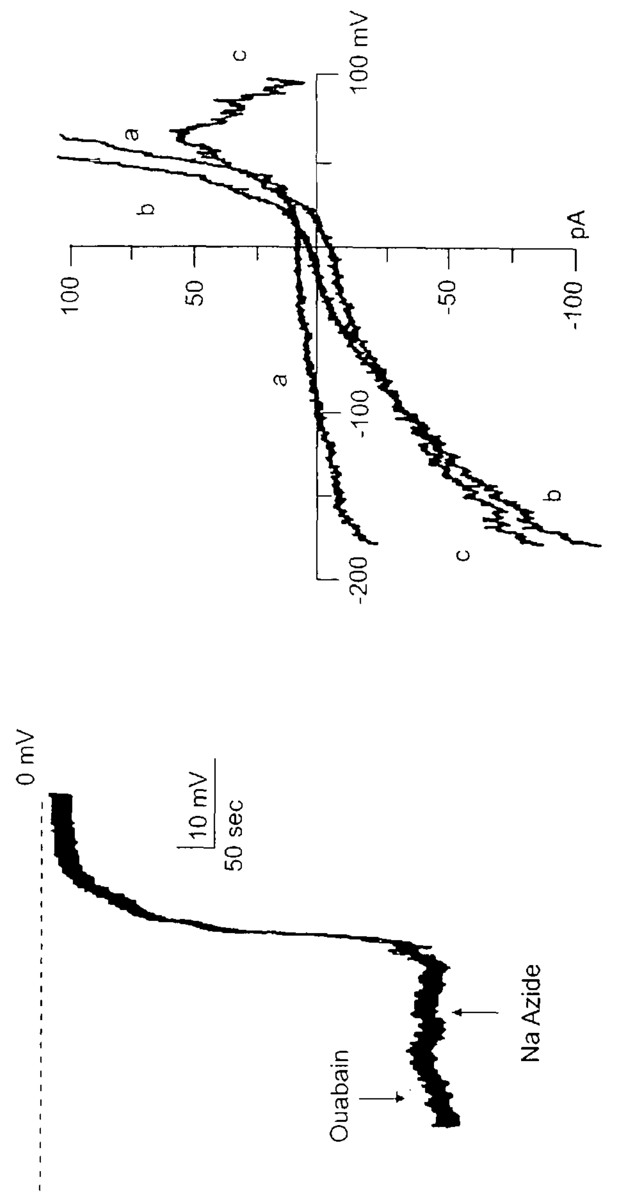
FIG. 1A shows whole cell current clamp recording before and after exposure to ouabain and before and after exposure to $NaN_3$.
FIG. 1B shows whole cell voltage-clamp recordings during ramp pulses (a) before and (b) after exposure to $NaN_3$; (c) is the difference current.

The present invention relates to a novel ion channel whose function underlies the swelling of mammalian neural cells, such as in response to ATP depletion; treatment methods related to diseases, trauma, and conditions that lead to the expression of such channels, including the use of inhibitors of the channel function to prevent this cell swelling response, which characterizes brain damage in cerebral ischemia and traumatic brain injury. The present invention also relates to the use of the channel to screen for channel inhibitors and activators, and other uses.

The $NC_{Ca-ATP}$ channel of the present invention is distinguished by certain functional characteristics, the combination of which distinguishes it from known ion channels. The characteristics that distinguish the $NC_{Ca-ATP}$ channel of the present invention include, but are not necessarily limited to, the following: 1) it is a non-selective cation channel that readily allows passage of Na, K and other monovalent cations; 2) it is activated by an increase in intracellular calcium, and/or by a decrease in intracellular ATP; 3) it is regulated by sulfonylurea receptor type 1 (SUR1), which heretofore had been considered to be associated exclusively with $K_{ATP}$ channels such as those found in pancreatic β cells, for example.

More specifically, the $NC_{Ca-ATP}$ channel of the present invention has a single-channel conductance to potassium ion ($K^+$) between 20 and 50 pS. The $NC_{Ca-ATP}$ channel is also stimulated by $Ca^{2+}$ on the cytoplasmic side of the cell membrane in a physiological concentration range, where said concentration range is from $10^{-8}$ to $10^{-5}$ M. The $NC_{Ca-ATP}$ channel is also inhibited by cytoplasmic ATP in a physiological concentration range, where said concentration range is from about $10^{-1}$ to about 10 μM. The $NC_{Ca-ATP}$ channel is also permeable to the following cations; $K^+$, $Cs^+$, $Li^+$, $Na^+$; to the extent that the permeability ratio between any two of said cations is greater than 0.5 and less than 2.

Some of the preferred embodiments of the present invention will be described in detail with reference to the attached drawings.

This invention may be embodied in many different forms and should not be construed as being limited to the embodiments set forth herein.

I. $NC_{Ca-ATP}$ Channel

A unique non-selective monovalent cationic ATP-sensitive channel ($NC_{Ca-ATP}$ channel) was identified first in native reactive astrocytes (NRAs) and later, as described herein, in neurons and capillary endothelial cells after stroke or traumatic brain or spinal cord injury (See at least International application WO 03/079987 to Simard et al., and Chen and Simard, 2001, each incorporated by reference herein in its entirety). As with the $K_{ATP}$ channel in pancreatic β cells, the $NC_{CaATP}$ channel is thought to be a heteromultimer structure comprised of sulfonylurea receptor type 1 (SUR1) regulatory subunits and pore-forming subunits (Chen et al., 2003). The pore-forming subunits have been characterized biophysically, but have yet to be characterized molecularly.

The invention is based, in part, on the discovery of a specific channel, the $NC_{Ca-ATP}$ channel, defined as a channel on astrocytes in US Application Publication No. 20030215889, which is incorporated herein by reference in its entirety. More specifically, the present invention has further defined that this channel is not only expressed on astrocytes, it is expressed at least on neural cells, neuroglial cells, and/or neural endothelial cells after brain and spinal cord trauma, for example, an hypoxic event, an ischemic event, or other secondary neuronal injuries relating to these events.

The $NC_{Ca-ATP}$ channel is activated by calcium ions ($Ca^{2+}$) and is sensitive to ATP. Thus, this channel is a non-selective cation channel activated by intracellular $Ca^{2+}$ and blocked by intracellular ATP. When opened by depletion of intracellular ATP, this channel is responsible for complete depolarization due to massive $Na^+$ influx, which creates an electrical gradient for $Cl^-$ and an osmotic gradient for $H_2O$, resulting in cytotoxic edema and cell death. When the channel is blocked or inhibited, massive $Na^+$ does not occur, thereby preventing cytotoxic edema.

Certain functional characteristics distinguish the $NC_{Ca-ATP}$ channel from other known ion channels. These characteristics can include, but are not limited to, at least some of the following: 1) it is a non-selective cation channel that readily allows passage of $Na^+$, $K^+$ and other monovalent cations; 2) it is activated by an increase in intracellular calcium, and/or by a decrease in intracellular ATP; 3) it is regulated by sulfonylurea receptor type 1 (SUR1), which heretofore had been considered to be associated exclusively with $K_{ATP}$ channels such as those found in pancreatic β cells.

More specifically, the $NC_{Ca-ATP}$ channel of the present invention has a single-channel conductance to potassium ion ($K^+$) between 20 and 50 pS. The $NC_{Ca-ATP}$ channel is also stimulated by $Ca^{2+}$ on the cytoplasmic side of the cell membrane in a physiological concentration range, where concentration range is from $10^{-8}$ to $10^{-5}$ M. The $NC_{Ca-ATP}$ channel is also inhibited by cytoplasmic ATP in a physiological concentration range, where the concentration range is from $10^{-1}$ to 10 M. The $NC_{Ca-ATP}$ channel is also permeable to the following cations; $K^+$, $Cs^+$, $Li^+$, $Na^+$; to the extent that the permeability ratio between any two of the cations is greater than 0.5 and less than 2.

SUR imparts sensitivity to antidiabetic sulfonylureas such as glibenclamide and tolbutamide and is responsible for activation by a chemically diverse group of agents termed "$K^+$ channel openers" such as diazoxide, pinacidil and cromakalin (Aguilar-Bryan et al., 1995; Inagaki et al., 1996; Isomoto et al., 1996; Nichols et al., 1996; Shyng et al., 1997). In various tissues, molecularly distinct SURs are coupled to distinct pore-forming subunits to form different $K_{ATP}$ channels with distinguishable physiological and pharmacological characteristics. The $K_{ATP}$ channel in pancreatic β cells is formed from SUR1 linked with Kir6.2, whereas the cardiac and smooth muscle $K_{ATP}$ channels are formed from SUR2A and SUR2B linked with Kir6.2 and Kir6.1, respectively (Fujita et al., 2000). Despite being made up of distinctly different pore-forming subunits, the $NC_{Ca-ATP}$ channel is also sensitive to sulfonylurea compounds.

Also, unlike the $K_{ATP}$ channel, the $NC_{Ca-ATP}$ channel conducts sodium ions, potassium ions, cesium ions and other monovalent cations with near equal facility (Chen and Simard, 2001) suggesting further that the characterization, and consequently the affinity to certain compounds, of the $NC_{Ca-ATP}$ channel differs from the $K_{ATP}$ channel.

Other nonselective cation channels that are activated by intracellular $Ca^{2+}$ and inhibited by intracellular ATP have been identified by others but not in astrocytes or neurons as disclosed herein. Further, the $NC_{Ca-ATP}$ channel expressed and found in astrocytes differs physiologically from the other channels with respect to calcium sensitivity and adenine nucleotide sensitivity (Chen et al., 2001).

Summary of $NC_{Ca-ATP}$ Channel Characteristics

At least some of the characteristics of cells expressing and composition comprising the $NC_{Ca-ATP}$ channel of the present invention are summarized in Table 1 (taken from experiments with freshly isolated native reactive astrocytes [NRA]).

TABLE 1

| Properties of cells and membrane compositions containing the $NC_{Ca-ATP}$ Channel of the Present Invention | Reactive Astrocytes | Membrane Preparation derived from freshly isolated native reactive astrocytes |
|---|---|---|
| Monovalent cation permeable? | Yes:<br>$Na^+$<br>$K^+$<br>$Li^+$<br>$Rb^+$<br>$Cs^+$<br>($Na^+ \approx K^+ \approx Li^+ \approx Rb^+$) | Yes:<br>$Na^+$<br>$K^+$<br>$Li^+$<br>$Rb^+$<br>$Cs^+$<br>($NA^+ \approx K^+ \approx Li^+ \approx Rb^+$) |
| Anion permeable? | No | No |
| Divalent cation permeable? | No | No |
| Compounds blocking channel activity | SUR1 antagonists | SUR1 ANTAGONISTS |
| Channel opening Requires: | Intracell. ATP depletion<br>Intracell. $Mg^{2+}$ | Intracell ATP depletion<br>Intracell. $Mg^{2+}$ |
| Single Channel Conductance | ~35 pS | ~35 PS |

TABLE 1-continued

| | | |
|---|---|---|
| Activation $[Ca^{2+}]$ | <1.0 μM | <1.0 μM |
| $[ATP]_1$ $EC_{50}$ (um) | 0.79 μM | 0.79 μM |
| ADP AMP | No channel effect | No channel effect |
| Pore radius (nm) | 0.41 | 0.41 |

II. Gliotic Capsule

The gliotic capsule forms a potentially harmful mass of tissue that contributes to brain swelling and mass effect, and that may shelter foreign cells from surveillance by the immune system. Applicants are the first to determine that, in a variety pathological conditions in both rats and humans, reactive astrocytes (R1 astrocytes) in the inner zone of the gliotic capsule express a novel SUR1-regulated cation channel, the $NC_{Ca-ATP}$ channel, and that this channel directly controls cell viability: opening the channel is associated with necrotic cell death and closing the channel is associated with protection from cell death induced by energy (ATP) depletion.

As described herein, Applicants are the first to determine that the inner zone of the gliotic capsule is populated by R1 astrocytes expressing the $NC_{Ca-ATP}$ channel. Selectively killing the astrocytes expressing the $NC_{Ca-ATP}$ channel may aid in the treatment of conditions that lead to the formation of gliotic capsules. For example, selectively killing the astrocytes expressing the $NC_{Ca-ATP}$ channel disrupts the "tumor brain barrier" (TBB), causing migration of leukocytes across the TBB and aiding in treatment of tumors in the brain.

Also there exists a need for therapeutic compounds capable of modulating the activity of this target in order to prevent brain damage. The present invention is directed to a newly characterized non-selective calcium and ATP sensitive monovalent cation channel, termed the $NC_{Ca-ATP}$ channel, which is present in neural cells and linked to an SUR. The present invention further provides a method to screen for or identify antagonists to $NC_{Ca-ATP}$ channel activity. Further, the present invention provides a method for the therapeutic use of antagonists, such as sulfonylureas and other SUR1 blockers, to inhibit this channel's activity and thereby prevent neural cell swelling and cell death and the concomitant nervous system damage that includes brain swelling and brain damage.

Sodium azide ($NaN_3$) is a metabolic toxin used to induce "chemical hypoxia" by depleting intracellular ATP. See, Swanson, 1992. The morphological and electrophysiological responses of neural cells to $NaN_3$ are examined in a novel cell preparation. Freshly isolated native reactive astrocytes (NRAs) from adult rat brain are used and studied in a native state immediately after their isolation. Reactive astrocytes are astrocytes that have been activated or stimulated in vivo, such as those associated with brain or neural injury. In the post-mortem brains of traumatic brain injury (TBI) patients, reactive astrocytes are found in proximity to the injury. The majority of reactive astrocytes surrounding an injury site in the brain are reactive astrocytes. Type 1 reactive astrocytes comprise >80% of recoverable reactive astrocytes, whereas type 2 reactive astrocytes comprise about 5%. Reactive astrocytes are normally polarized under quiescent conditions.

It is readily apparent to one skilled in the art that various embodiments and modifications can be made to the invention disclosed in this Application without departing from the scope and spirit of the invention.

III. Definitions

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternative are mutually exclusive, although the disclosure supports a definition that refers to only alternatives and "and/or."

As used herein, the term "acute" refers to the onset of a health effect, usually the effect is a rapid onset that is considered brief, not prolonged.

As used herein, the term "acute cerebral ischemia" refers to a cerebral ischemic event that has a rapid onset and is not prolonged. The terms "acute cerebral ischemia" and "stroke" can be used interchangeably."

As used herein, the term "agonist" refers to a biological or chemical agent that combines with a receptor on a cell and initiates the same or equivalent reaction or activity produced by the binding of an endogenous substance. In the present invention, the agonist combines, binds, and/or associates with a $NC_{Ca-ATP}$ channel of a neuronal cell, a neuroglial cell, or a neural endothelial cell, such that the $NC_{Ca-ATP}$ channel is opened (activated). In certain embodiments, the agonist combines, binds and/or associates with a regulatory subunit of the $NC_{Ca-ATP}$ channel, particularly a SUR1. Alternatively, the agonist combines, binds, and/or associates with a pore-forming subunit of the $NC_{Ca-ATP}$ channel, such that the $NC_{Ca-ATP}$ channel is opened (activated). The terms agonist and/or activator can be used interchangeably.

As used herein, the term "antagonist" refers to a biological or chemical agent that acts within the body to reduce the physiological activity of another chemical or biological substance. In the present invention, the antagonist blocks, inhibits, reduces and/or decreases the activity of a $NC_{Ca-ATP}$ channel of a neuronal cell, a neuroglia cell or a neural endothelial cell (e.g., capillary endothelial cells). In the present invention, the antagonist combines, binds, associates with a $NC_{Ca-ATP}$ channel of neuronal cell, a neuroglia cell or a neural endothelial cell (e.g., capillary endothelial cells), such that the $NC_{Ca-ATP}$ channel is closed (deactivated), meaning reduced biological activity with respect to the biological activity in the diseased state. In certain embodiments, the antagonist combines, binds and/or associates with a regulatory subunit of the $NC_{Ca-ATP}$ channel, particularly a SUR1. Alternatively, the antagonist combines, binds, and/or associates with a pore-forming subunit of the $NC_{Ca-ATP}$ channel, such that the $NC_{Ca-ATP}$ channel is closed (deactivated). The terms antagonist or inhibitor can be used interchangeably.

As used herein, the terms "brain abscess" or "cerebral abscess" refer to a circumscribed collection of purulent exudate that is typically associated with swelling.

As used herein, the terms "blood brain barrier" or "BBB" refer the barrier between brain blood vessels and brain tissues whose effect is to restrict what may pass from the blood into the brain.

As used herein, the term "cerebral ischemia" refers to a lack of adequate blood flow to an area, for example a lack of adequate blood flow to the brain or spinal cord, which may be the result of a blood clot, blood vessel constriction, a hemorrhage or tissue compression from an expanding mass.

As used herein, the term "depolarization" refers to an increase in the permeability of the cell membrane to sodium ions wherein the electrical potential difference across the cell membrane is reduced or eliminated.

As used herein, the terms "effective amount" or "therapeutically effective amount" are interchangeable and refer to an amount that results in an improvement or remediation of the symptoms of the disease or condition. Those of skill in the art understand that the effective amount may improve the patient's or subject's condition, but may not be a complete cure of the disease and/or condition.

As used herein, the term "endothelium" refers a layer of cells that line the inside surfaces of body cavities, blood vessels, and lymph vessels or that form capillaries.

As used herein, the term "endothelial cell" refers to a cell of the endothelium or a cell that lines the surfaces of body cavities, for example, blood or lymph vessels or capillaries. In certain embodiments, the term endothelial cell refers to a neural endothelial cell or an endothelial cell that is part of the nervous system, for example the central nervous system or the brain or spinal cord.

As used herein, the term "gliotic capsule" refers to a physical barrier surrounding, in whole or in part, a foreign body, including a metastatic tumor, a cerebral abscess or other mass not normally found in brain except under pathological conditions. In certain embodiments, the gliotic capsule comprises an inner zone comprising neuronal cells, neuroglial cells (e.g., astrocytes) and/or endothelial cells expressing a $NC_{Ca\text{-}ATP}$ channel.

As used herein, the term "ionic edema" in brain or nervous tissue refers to edema arising in tissue in which the blood-brain barrier remains substantially intact, and is associated with the movement of electrolytes (e.g. $Na^+$, $Cl^-$) plus water into brain parenchyma.

As used herein, the term "inhibit" refers to the ability of the compound to block, partially block, interfere, decrease, reduce or deactivate a channel such as the $NC_{Ca\text{-}ATP}$ channel. Thus, one of skill in the art understands that the term inhibit encompasses a complete and/or partial loss of activity of a channel, such as the $NC_{Ca\text{-}ATP}$ channel. Channel activity may be inhibited by channel block (occlusion or closure of the pore region, preventing ionic current flow through the channel), by changes in an opening rate or in the mean open time, changes in a closing rate or in the mean closed time, or by other means. For example, a complete and/or partial loss of activity of the $NC_{Ca\text{-}ATP}$ channel as may be indicated by a reduction in cell depolarization, reduction in sodium ion influx or any other monovalent ion influx, reduction in an influx of water, reduction in extravasation of blood, reduction in cell death, as well as an improvement in cellular survival following an ischemic challenge.

The term "morbidity" as used herein is the state of being diseased. Yet further, morbidity can also refer to the disease rate or the ratio of sick subjects or cases of disease in to a given population.

The term "mortality" as used herein is the state of being mortal or causing death. Yet further, mortality can also refer to the death rate or the ratio of number of deaths to a given population.

As used herein, the term "neuron" refers to a nerve cell, also termed a neuronal cell.

As used herein, the term "neuronal cell" refers to a cell that is a morphologic and functional unit of the nervous system. The cell comprises a nerve cell body, the dendrites, and the axon. The terms neuron, nerve cell, neuronal, neurone, and neurocyte can be used interchangeably. Neuronal cell types can include, but are not limited to a typical nerve cell body showing internal structure, a horizontal cell (of Cajal) from cerebral cortex; Martinottic cell, biopolar cell, unipolar cell, Pukinje cell, and a pyramidal cell of motor area of cerebral cortex.

As used herein, the term "neural" refers to anything associated with the nervous system. As used herein, the term "neural cells" includes neurons and glia, including astrocytes. As used herein, the term "isolated neural cells" means neural cells isolated from brain.

As used herein, the terms "neuroglia" or "neuroglial cell" refers to a cell that is a non-neuronal cellular element of the nervous system. The terms neuroglia, neurogliacyte, and neuroglial cell can be used interchangeably. Neuroglial cells can include, but are not limited to ependymal cells, astrocytes, oligodendrocytes, or microglia.

The term "preventing" as used herein refers to minimizing, reducing or suppressing the risk of developing a disease state or parameters relating to the disease state or progression or other abnormal or deleterious conditions.

The term "reactive astrocytes" means astrocytes found in brain at the site of a lesion or ischemia. The term "native reactive astrocytes" or "NRAs" means reactive astrocytes that are freshly isolated from brain. The term "freshly isolated" as used herein refers to NRAs that have been purified from brain, particularly NRAs that were purified from about 0 to about 72 hours previously. When NRAs are referred to as being "purified from brain" the word "purified" means that the NRAs are isolated from other brain tissue and/or implanted gelatin or sponge and does not refer to a process that simply harvests a population of cells from brain without further isolation of the cells. As described herein, the $NC_{Ca\text{-}ATP}$ channel found in reactive astrocytes is present only in freshly isolated cells; the $NC_{CA\text{-}ATP}$ channel is lost shortly after culturing the cells under typical normoxic conditions. NRAs provide an in vitro model that is more similar to reactive astrocytes as they exist in vivo in the brain, than astrocytes grown in culture. The terms "native" and "freshly isolated" are used synonymously.

As used herein, the term "reduces" refers to a decrease in cell death, inflammatory response, hemorrhagic conversion, extravasation of blood, etc. as compared to no treatment with the compound of the present invention. Thus, one of skill in the art is able to determine the scope of the reduction of any of the symptoms and/or conditions associated with a spinal cord injury in which the subject has received the treatment of the present invention compared to no treatment and/or what would otherwise have occurred without intervention.

As used herein, the term "stroke" refers to any acute, clinical event related to the impairment of cerebral circulation. The terms "acute cerebral ischemia" and "stroke" can be used interchangeably.

The terms "treating" and "treatment" as used herein refer to administering to a subject a therapeutically effective amount of a composition so that the subject has an improvement in the disease or condition. The improvement is any observable or measurable improvement. Thus, one of skill in the art realizes that a treatment may improve the patient's condition, but may not be a complete cure of the disease. Treating may also comprise treating subjects at risk of developing a disease and/or condition.

As used herein, the term "vasogenic edema" in brain or nervous tissue refers to edema arising in tissue in which the blood-brain barrier is not substantially intact, and in which macromolecules plus water enter into brain parenchyma in addition to any movement of electrolytes.

Reactive astrocytes are produced in vivo and harvested from brain according to a method system similar to that described by Perillan. See, Chen et al., 2003; Chen et al., 2001, for example. Harvested cells are then isolated and not cultured; rather, the freshly isolated reactive astrocytes are studied in a native state immediately after their isolation from the brain. As described by Perillan et al. (1999; 2000), cultured astrocytes do not express the $NC_{Ca\text{-}ATP}$ channel.

The Examples described herein reveal that NRAs from adult rat brain express a non-selective cation channel that is activated by depletion of $[ATP]_i$ at physiological concentrations of $[Ca^{2+}]_i$. This $NC_{Ca\text{-}ATP}$ channel of the present invention, which is newly identified in NRAs and present in >90% of membrane patches from such cells, is distinguished from previously reported non-selective calcium and ATP channels by exhibiting significantly different properties. These distinguishing properties of the $NC_{Ca\text{-}ATP}$ of the present invention include: being activated by submicromolar $[Ca^{2+}]$ and exhibiting a different sensitivity to block by various adenine nucleotides. Opening of the $NC_{Ca\text{-}ATP}$ channel of the present invention by ATP depletion causes profound membrane depolarization, which precedes blebbing of the cell membrane. Upon ATP depletion, the $NC_{Ca\text{-}ATP}$ channel opens to allow $Na^+$ influx that leads to cell swelling. This channel is regulated by sulfonylurea receptor type 1 (SUR1). The channel can be blocked by sulfonylurea, such as glibenclamide and tolbutamide; treatment with glibenclamide results in significant reduction in swelling and blebbing and cell death induced by chemical ATP depletion. This channel participates in the cation flux involved in cell swelling and cell death. A method of the present invention includes the use of sulfonylurea compounds to inhibit the flow of current through the $NC_{Ca\text{-}ATP}$ channel and inhibit blebbing related to channel opening. Also, use of sulfonylurea compounds and other compounds that inhibit the flow of current through the $NC_{Ca\text{-}ATP}$ channel, thus can have a therapeutic preventative effect on cell swelling and cell death in the brain and spinal cord.

In some embodiments, the present invention is directed to therapeutic compositions and methods of using the same. In one embodiment, the therapeutic composition is an agonist and/or antagonist of at least one $NC_{Ca\text{-}ATP}$ channel of a neuronal cell, a neuroglial cell, or a neural endothelial cell. Further embodiments of the present invention provide a composition comprising a membrane preparation expressing the $NC_{Ca\text{-}ATP}$ channel. For example, the membrane preparation is derived from neural cells, such as isolated native reactive astrocytes (NRAs), preferably freshly isolated native reactive astrocytes. The $NC_{Ca\text{-}ATP}$ channel in the composition has the following characteristics: (a) it is a 35 pS type channel; (b) it is stimulated by cytoplasmic $Ca^{2+}$; (c) it opens when cytoplasmic ATP is less than about 0.8 μM; and (d) it is permeable to the monovalent cations $K^+$, $Cs^+$, $Li^+$ and $Na^+$ and it can be blocked by antagonists of the type 1 sulfonylurea receptor.

Furthermore, it is an object of the present invention to provide a method of screening for one or more antagonists of the $NC_{Ca\text{-}ATP}$ channel, comprising: (a) contacting a test compound with a composition comprising the $NC_{Ca\text{-}ATP}$ channel; and (b) identifying test compounds that inhibit an activity of said channel by measuring said activity in the presence and absence of said test compound, wherein a test compound that inhibits said activity is identified as an antagonist of the $NC_{Ca\text{-}ATP}$ channel. For example, the composition may contain a preparation of neural cells expressing the $NC_{Ca\text{-}ATP}$ channel or a membrane preparation expressing the $NC_{Ca\text{-}ATP}$ channel, such as a membrane preparation derived from isolated native reactive astrocytes (NRAs) or other cells that express the $NC_{Ca\text{-}ATP}$ channel. The effect of the compound on this channel may include: (a) blocking the $NC_{Ca\text{-}ATP}$ channel; (b) closing the $NC_{Ca\text{-}ATP}$ channel; (c) preventing the $NC_{Ca\text{-}ATP}$ channel from opening; and (d) reducing the magnitude of membrane current through the $NC_{Ca\text{-}ATP}$ channel. It is also an object of the present invention to identify a compound that is an $NC_{Ca\text{-}ATP}$ antagonist, including an $NC_{Ca\text{-}ATP}$ channel inhibitor, an $NC_{Ca\text{-}ATP}$ channel blocker, a SUR1 antagonist, SUR1 inhibitor, and/or a compound capable of reducing the magnitude of membrane current though the channel.

It is a further object of the invention to provide a method for identifying compounds that inhibit neural cell swelling, comprising: (a) contacting a test compound with a composition comprising the $NC_{Ca\text{-}ATP}$ channel, and (b) determining whether the test compound blocks the $NC_{Ca\text{-}ATP}$ channel, wherein a test compound that blocks the $NC_{Ca\text{-}ATP}$ channel is identified as a compound for inhibiting neural cell swelling.

It is a further object of the present invention to provide a method for identifying compounds that inhibit brain swelling, comprising: (a) contacting a test compound with a composition comprising the $NC_{Ca\text{-}ATP}$ channel, and (b) determining whether the test compound blocks the $NC_{Ca\text{-}ATP}$ channel, wherein a test compound that blocks the $NC_{Ca\text{-}ATP}$ channel is identified as a compound for inhibiting brain swelling.

Yet another object of the present invention is to provide a method for identifying compounds that inhibit brain swelling, comprising: (a) contacting a test compound with a composition comprising the $NC_{Ca\text{-}ATP}$ channel, and (b) determining whether the test compound inhibits neural cell swelling, wherein a test compound that inhibits neural cell swelling is identified as a compound for inhibiting brain swelling.

A further object of the present invention provides a method for identifying compounds that inhibit neural cell swelling in an animal, comprising: (a) contacting a test compound with a composition comprising the $NC_{Ca\text{-}ATP}$ channel and determining whether the test compound blocks the channel, and (b) administering the test compound to an animal having a brain injury or cerebral ischemia, and determining whether the test compound that inhibits brain swelling of the treated animal, wherein test compounds that inhibit brain swelling are identified as compounds that inhibit neural cell swelling in an animal.

It is a further object of the present invention to provide a method for identifying compounds that inhibit brain swelling, comprising: (a) contacting a test compound with a composition comprising the $NC_{Ca\text{-}ATP}$ channel, and determining whether the test compound blocks the channel, and (b) administering the test compound to an animal having a brain injury or cerebral ischemia, and determining whether the test compound inhibits brain swelling of the treated animal, wherein test compounds that block the $NC_{Ca\text{-}ATP}$ channel are identified as compounds that inhibit brain swelling.

In each of these objects of the present invention, the composition preferably comprises a preparation of neural cells expressing the $NC_{Ca\text{-}ATP}$ channel or a membrane preparation expressing the $NC_{Ca\text{-}ATP}$ channel, which preferably is derived from isolated native reactive astrocytes (NRAs). It is a further object of the present invention to provide the above methods using a compound that is an antagonist of a type 1 sulfonylurea receptor, such as a sulfonylurea compound, a benzamido derivative or an imidazoline derivative.

It is a further object of the present invention to provide these methods in which the determining step include, but are not limited to, detecting or identifying swelling of the native reactive astrocytes, such as by microscopic observation of cell appearance (normal, blebbing, swelling); measuring channel currents; measuring membrane potential; detecting expression of annexin V; detecting expression of propidium iodide; in vitro binding assays; and combinations thereof.

It is a further object of the present invention to provide a method of preventing neural cell swelling in the brain of a subject, said method comprising administering to the subject a formulation containing an effective amount of a compound that blocks the $NC_{Ca-ATP}$ channel and a pharmaceutically acceptable carrier.

It is a further object of the present invention to provide a method of alleviating the negative effects of traumatic brain injury or cerebral ischemia stemming from neural cell swelling in a subject, comprising administering to the subject a formulation comprising an effective amount of a compound that blocks the $NC_{Ca-ATP}$ channel and a pharmaceutically acceptable carrier. Such administration may be delivery directly to the brain, intravenous, subcutaneous, intramuscular, intracutaneous, intragastric and oral administration. Examples of such compounds include antagonist of a type 1 sulfonylurea receptor, such as sulfonylureas like glibenclamide and tolbutamide, as well as other insulin secretagogues such as repaglinide, nateglinide, meglitinide, midaglizole, LY397364, LY389382, gliclazide, glimepiride, MgADP, and combinations thereof.

It is yet another object of the present invention to provide a formulation for preventing or inhibiting neural cell swelling in the brain of a subject, using a formulation that includes a compound that blocks the $NC_{Ca-ATP}$ channel and a pharmaceutically acceptable carrier, wherein the quantity of said compound is less than the quantity of said compound in formulations for treating diabetes. It is a further object of the present invention to provide a formulation for preventing or inhibiting neural cell swelling in the brain of a subject, using a formulation that includes a compound that blocks the $NC_{Ca-ATP}$ channel and a pharmaceutically acceptable carrier, wherein the quantity of said compound is at least 2 times less than the quantity of said compound in formulations for treating diabetes. It is a further object of the present invention to provide a formulation for preventing or inhibiting neural cell swelling in the brain of a subject, using a formulation that includes a compound that blocks the $NC_{Ca-ATP}$ channel and a pharmaceutically acceptable carrier, wherein the quantity of said compound is at least 5 times less than the quantity of said compound in formulations for treating diabetes. It is yet, another object of the present invention to provide a formulation for preventing or inhibiting neural cell swelling in the brain of a subject, using a formulation that includes a compound that blocks the $NC_{Ca-ATP}$ channel and a pharmaceutically acceptable carrier, wherein the quantity of said compound is at least 10 times less than the quantity of said compound in formulations for treating diabetes.

It is therefore another object of the present invention to provide a method for identifying compounds that inhibit neural cell swelling, comprising: (a) contacting a test compound with a composition comprising the Kir2.3 channel, and (b) determining whether the test compound opens the Kir2.3 channel, wherein a test compound that opens the Kir2.3 channel is identified as a compound for inhibiting neural cell swelling.

It is yet another object of the present invention to provide a method for a method for identifying compounds that inhibit brain swelling, comprising: (a) contacting a test compound with a composition comprising the Kir2.3 channel, and (b) determining whether the test compound opens the Kir2.3 channel, wherein a test compound that opens the Kir2.3 channel is identified as a compound for inhibiting brain swelling.

It is yet another object of the present invention to provide a method for a method for identifying compounds that inhibit neural cell swelling and/or brain swelling in an animal, comprising: (a) contacting a test compound with a composition comprising the Kir2.3 channel, and (b) determining whether the test compound opens the Kir2.3 channel, wherein a test compound that opens the Kir2.3 channel is identified as a compound for inhibiting neural cell swelling and/or brain swelling in an animal.

It is a further object of the present invention to provide a method for identifying compounds that prevent, inhibit and/or alleviate brain swelling in a subject, comprising: (a) contacting a test compound with a composition comprising the Kir2.3 channel, and determining whether the test compound opens the Kir2.3 channel, and (b) administering the test compound to a subject having a brain injury or cerebral ischemia, and determining whether the test compound prevents, inhibits and/or alleviates brain swelling in the subject, wherein test compounds that open the Kir2.3 channel are identified as compounds that inhibit brain swelling.

It is a further object of the present invention to provide a method for identifying compounds that inhibit neural cell swelling in an animal, comprising: (a) contacting a test compound with a composition comprising the Kir2.3 channel, and determining whether the test compound opens the Kir2.3 channel, and (b) administering the test compound to an animal having a brain injury or cerebral ischemia, and determining whether the test compound inhibits brain swelling of the treated animal, wherein test compounds that inhibit brain swelling are identified as compounds that inhibit neural cell swelling in an animal.

It is also an object of the present invention to provide a method of preventing neural cell swelling in the brain of a subject, said method comprising administering to the subject a formulation containing an effective amount of a compound that opens the Kir2.3 channel and a pharmaceutically acceptable carrier.

It is a further objection of the present invention to provide a method of alleviating the negative effects of traumatic brain injury or cerebral ischemia stemming from neural cell swelling in a subject, comprising administering to the subject a formulation comprising an effective amount of a compound that opens the Kir2.3 channel and a pharmaceutically acceptable carrier. In the object of the present invention that provide methods assessing the effect of a compound on the Kir2.3 channel, a preferred compound is Tenidap (5-chloro-2,3-dihydro-3-(hydroxy-2-thienylmethylene)-2-oxo-1H-indole-1-carboxamide). For example the formulation may provide a daily dose of Tenidap that is from about 10 mg/day to about 500 mg/day, or, when administered directly to the brain the daily dose of Tenidap is from about 500 mg/day to 1.5 gms/day or greater.

IV. Exemplary Embodiments of the Present Invention

In addition to the sulfonylurea receptor 1 (SUR1) being expressed in R1 astrocytes as part of the $NC_{Ca-ATP}$ channel, the present invention further describes that the SUR1 regulatory subunit of this channel is up-regulated in neurons and capillary endothelial cells following ischemia, and blocking this receptor reduces stroke size, cerebral edema and mortality. Thus, antagonists of the $NC_{Ca-ATP}$ channel may have an important role in preventing, alleviating, inhibiting and/or abrogating the formation of cytotoxic and ionic edema.

In other embodiments, the therapeutic compound of the present invention comprises an antagonist of a $NC_{Ca-ATP}$ channel of a neuronal cell, a neuroglial cell, a neural endothelial cell or a combination thereof. Antagonists are contemplated for use in treating adverse conditions associated with hypoxia and/or ischemia that result in increased intracranial pressure and/or cytotoxic edema of the central nervous system. Such conditions include trauma, ischemic brain injury, namely secondary neuronal injury, and hemorrhagic infarction. Antagonists protect the cells expressing the $NC_{Ca-ATP}$ channel, which is desirable for clinical treatment in which gliotic capsule integrity is important and must be maintained to prevent the spread of infection, such as with a brain abscess. The protection via inhibition of the $NC_{Ca-ATP}$ channel is associated with a reduction in cerebral edema.

In one aspect, the $NC_{Ca-ATP}$ channel is blocked, inhibited, or otherwise is decreased in activity. In such examples, an antagonist of the $NC_{Ca-ATP}$ channel is administered and/or applied. The antagonist modulates the $NC_{Ca-ATP}$ channel such that flux through the channel is reduced, ceased, decreased and/or stopped. The antagonist may have a reversible or an irreversible activity with respect to the activity of the $NC_{Ca-ATP}$ channel of the neuronal cell, neuroglial cell, endothelial cell or a combination thereof. The antagonist may prevent or lessen the depolarization of the cells thereby lessening cell swelling due to osmotic changes that can result from depolarization of the cells. Thus, inhibition of the $NC_{Ca-ATP}$ channel can reduce cytotoxic edema and death of endothelial cells.

Subjects that can be treated with the therapeutic composition of the present invention include, but are not limited subjects suffering from or at risk of developing conditions associated hypoxia and/or ischemia that result in increased intracranial pressure and/or with cytotoxic edema of the central nervous system (CNS). Such conditions include, but are not limited to trauma (e.g., traumatic brain or spinal cord injury (TBI or SCI), concussion) ischemic brain injury, hemorrhagic infarction, stroke, atrial fibrillations, clotting disorders, pulmonary emboli, arterio-venous malformations, mass-occupying lesions (e.g., hematomas), etc. Still further subjects at risk of developing such conditions can include subjects undergoing treatments that increase the risk of stroke, for example, surgery (vascular or neurological), treatment of myocardial infarction with thrombolytics, cerebral/endovascular treatments, stent placements, angiography, etc.

Another aspect of the present invention for the treatment of ischemia, brain trauma, or other brain injury comprises administration of an effective amount of a SUR1 antagonist and administration of glucose. Glucose administration may be at the time of treatment with an antagonist of the $NC_{Ca-ATP}$ channel, such as a SUR1 antagonist, or may follow treatment with an antagonist of the $NC_{Ca-ATP}$ channel (e.g., at 15 minutes after treatment with an antagonist of the $NC_{Ca-ATP}$ channel, or at one half hour after treatment with an antagonist of the $NC_{Ca-ATP}$ channel, or at one hour after treatment with an antagonist of the $NC_{Ca-ATP}$ channel, or at two hours after treatment with an antagonist of the $NC_{Ca-ATP}$ channel, or at three hours after treatment with an antagonist of the $NC_{Ca-ATP}$ channel). Glucose administration may be by intravenous, or intraperitoneal, or other suitable route and means of delivery. Additional glucose allows administration of higher doses of an antagonist of the $NC_{Ca-ATP}$ channel than might otherwise be possible, so that combined glucose with an antagonist of the $NC_{Ca-ATP}$ channel provides greater protection, and may allow treatment at later times, than with an antagonist of the $NC_{Ca-ATP}$ channel alone. Greater amounts of glucose are administered where larger doses of an antagonist of the $NC_{Ca-ATP}$ channel are administered.

Another aspect of the present invention comprises co-administration of an antagonist of the $NC_{Ca-ATP}$ channel with a thrombolytic agent. Co-administration of these two compound increases the therapeutic window of the thrombolytic agent by reducing hemorrhagic conversion. The therapeutic window for thrombolytic agents may be increased by several (4-8) hours by co-administering antagonist of the $NC_{Ca-ATP}$ channel. In addition to a thrombolytic agent, other agents can be used in combination with the antagonist of the present invention, for example, but not limited to antiplatelets, anticoagulants, vasodilators, statins, diuretics, etc.

Another aspect of the present invention comprises the use of labeled SUR1 antagonists to diagnose, determine or monitor stages of stroke, cerebral edema or visualize the size/boundaries/borders of a tumor and/or the stroke. For example, the penumbra following the stroke may be monitored or visualized using labeled SUR1 antagonists.

Yet further, the compositions of the present invention can be used to produce neuroprotective kits that are used to treat subjects at risk or suffering from conditions that are associated with cytotoxic cerebral edema.

V. Exemplary Methods of the Present Invention

The present invention provides a previously unknown ion channel found in mammalian neural cells that plays a role in cell swelling and brain swelling. The present invention further provides a method of screening for antagonists to the channel and a new use for antagonists to the channel, including sulfonylurea compounds such as glibenclamide and tolbutamide, as a treatment for brain swelling in mammals.

Methods of the present invention for identifying compounds that interact with, (e.g., bind to, open, block) the $NC_{Ca-ATP}$ channel and employ (i) cell based assays and/or (ii) non-cell based assay systems. Such compounds may act as antagonists or agonists of $NC_{Ca-ATP}$ channel activity. In a preferred embodiment of the present invention, antagonists that block and/or inhibit the permeability of the $NC_{Ca-ATP}$ channel are utilized in methods for treating neural cell swelling and/or brain swelling.

The cell based assays use neural cells that express the $NC_{Ca-ATP}$ channel, preferably a functional $NC_{Ca-ATP}$ channel; the preferred cells are NRAs. The non-cell based assay systems include membrane preparations that express the $NC_{Ca-ATP}$ channel, preferably a functional $NC_{Ca-ATP}$ channel. Cell-based assays include, but are not limited to, compound binding assays, microscopic observation of cell status (normal, blebbing, swelling, cell death), and measuring channel currents both before and after exposure to compound. Compositions comprising membrane preparations expressing the $NC_{Ca-ATP}$ channel may be used to identify compounds that interact with, bind to, block or open the $NC_{Ca-ATP}$ channel or SUR1. The term "expressing the $NC_{Ca-ATP}$ channel" or "expresses the $NC_{Ca-ATP}$ channel" means having a functional $NC_{Ca-ATP}$ channel. The term "functional $NC_{Ca-ATP}$ channel" as used herein means an $NC_{Ca-ATP}$ channel capable of being detected. One preferred method of detecting the $NC_{Ca-ATP}$ channel is by determining, in vitro or in vivo, whether the channel is open, closed and/or blocked.

For example, in a typical experiment using a membrane preparation, NRAs that express the $NC_{Ca-ATP}$ channel are used to produce the membrane preparation. Methods for producing membranes from whole cells and tissues are well known in the art. One such method produces purified cell membranes in the form of a purified microsomal fraction isolated from disrupted cells or a tissue sample by discontinuous sucrose gradient centrifugation. Also included are membranes comprised of cell-attached patches, inside-out patches, or outside-out patches. One example of a tissue sample expressing $NC_{Ca-ATP}$ channels is brain tissue adjacent to brain injury.

The membrane preparations are used in a number of assays, including, but not limited to measuring channel currents, both before and after exposure to compound; and in vitro binding assays. The experimental conditions for such assays to determine and quantify the status of the $NC_{Ca-ATP}$ channel are described throughout the instant specification, including binding assay conditions, bath compositions, pipette solutions, concentrations of ATP and $Ca^{2+}$ required, membrane voltage, membrane potentials, compound quantity ranges, controls, etc.

Binding assays and competitive binding assays employ a labeled ligand or antagonist of the $NC_{Ca-ATP}$ channel. In one such experiment, labeled Glibenclamide, such as FITC-conjugated glibenclamide or BODIPY-conjugated glibenclamide or radioactively labeled glibenclamide is bound to the membranes and assayed for specific activity; specific binding is determined by comparison with binding assays performed in the presence of excess unlabelled antagonist.

In one method for identifying $NC_{Ca-ATP}$ channel blockers, membranes are incubated with a labeled compound shown to block this channel, in either the presence or absence of test compound. Compounds that block the $NC_{Ca-ATP}$ channel and compete with the labeled compound for binding to the membranes will have a reduced signal, as compared to the vehicle control samples. In another aspect of the invention the screens may be designed to identify compounds that compete with the interaction between $NC_{Ca-ATP}$ channel and a known (previously identified herein) $NC_{Ca-ATP}$ channel antagonist or SUR1 antagonist, such as glibenclamide. In such screens, the known $NC_{Ca-ATP}$ channel antagonist or SUR1 antagonist is labeled and the test compounds are then assayed for their ability to compete with or antagonize the binding of the labeled antagonist.

The assays described herein can be used to identify compounds that modulate or affect $NC_{Ca-ATP}$ channel activity. For example, compounds that affect $NC_{Ca-ATP}$ channel activity include but are not limited to compounds that bind to the $NC_{Ca-ATP}$ channel or SUR1, inhibit binding of identified blockers or ligands (such as glibenclamide), and either open/activate the channel (agonists) or block/inhibit the channel (antagonists).

Assays described can also identify compounds that modulate neural cell swelling (e.g., compounds which affect other events involved in neural cell swelling that are activated by ligand binding to or blocking of the $NC_{Ca-ATP}$ channel).

VI. Compounds Screened in Accordance with the Invention

The compounds for screening in accordance with the invention include, but are not limited to organic compounds, peptides, antibodies and fragments thereof, peptidomimetics, that bind to the $NC_{Ca-ATP}$ channel and either open the channel (i.e., agonists) or block the channel (i.e., antagonists). For use in the treatment of neural cell swelling or brain swelling, compounds that block the channel are preferred. Agonists that open or maintain the channel in the open state include peptides, antibodies or fragments thereof, and other organic compounds that include the SUR1 subunit of the $NC_{Ca-ATP}$ channel (or a portion thereof) and bind to and "neutralize" circulating ligand for SUR1.

With reference to screening of compounds that affect the $NC_{Ca-ATP}$ channel, libraries of known compounds can be screened, including natural products or synthetic chemicals, and biologically active materials, including proteins, for compounds which are inhibitors or activators. Preferably, such a compound is an $NC_{Ca-ATP}$ antagonist, which includes an $NC_{Ca-ATP}$ channel inhibitor, an $NC_{Ca-ATP}$ channel blocker, a SUR1 antagonist, SUR1 inhibitor, and/or a compound capable of reducing the magnitude of membrane current through the channel.

Compounds may include, but are not limited to, small organic or inorganic molecules, compounds available in compound libraries, peptides such as, for example, soluble peptides, including but not limited to members of random peptide libraries; (see, e.g., Lam, K. S. et al., 1991, Nature 354: 82-84; Houghten, R. et al., 1991, Nature 354: 84-86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72: 767-778), antibodies (including, but not limited to, polyclonal, monoclonal, humanized, anti-idiotypic, chimeric or single chain antibodies, and FAb, F(ab') .sub.2 and FAb expression library fragments, and epitope-binding fragments thereof).

Other compounds which can be screened in accordance with the invention include but are not limited to small organic molecules that may or may not be able to cross the blood-brain barrier, gain entry into an appropriate neural cell and affect the expression of the $NC_{Ca-ATP}$ channel gene or some other gene involved in the $NC_{Ca-ATP}$ channel activity (e.g., by interacting with the regulatory region or transcription factors involved in gene expression); or such compounds that affect the activity of the $NC_{Ca-ATP}$ channel or the activity of some other intracellular factor involved in the $NC_{Ca-ATP}$ channel activity.

Computer modeling and searching technologies permit identification of compounds, or the improvement of already identified compounds, that can modulate $NC_{Ca-ATP}$ channel activity or expression. Having identified such a compound or composition, the active sites or regions are identified. Such active sites might typically be ligand binding sites. The active site can be identified using methods known in the art including, for example, from study of complexes of the relevant compound or composition with other ligands, from the amino acid sequences of peptides, or from the nucleotide sequences of nucleic acids. Chemical or X-ray crystallographic methods can be used to study complexes of the relevant compound to find the active site. The three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential $NC_{Ca\text{-}ATP}$ channel modulating, preferably blocking, compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other. A number of articles review computer modeling of drugs interactive with specific proteins, such as Rotivinen, et al.) 1988, Acta Pharmaceutical Fennica 97: 159-166); Ripka (1988 New Scientist 54-57); McKinaly and Rossmann (1989, Annu. Rev. Pharmacol. Toxicol. 29: 111-122); Perry and Davies, OSAR: Quantitative Structure-Activity Relationships in Drug Design pp. 189-193 Alan R. Liss, Inc. 1989; Lewis and Dean (1989, Proc. R. SOC. Lond. 236: 125-140 and 141-162); and, with respect to a model receptor for nucleic acid components, Askew, et al. (1989, J. Am. Chem. SOC. 111: 1082-1090). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Compounds identified via assays such as those described herein may be useful, for example, in elaborating the biological function of the $NC_{Ca\text{-}ATP}$ channel and for relief of brain swelling.

Assays for testing the efficacy of compounds identified in the cellular screen can be tested in animal model systems for brain or spinal cord swelling. Such animal models may be used as test substrates for the identification of drugs, pharmaceuticals, therapies and interventions which may be effective in treating brain or spinal cord swelling. For example, animal models of brain swelling, such as brain injury, may be exposed to a compound, suspected of exhibiting an ability to inhibit brain swelling, at a sufficient concentration and for a time sufficient to elicit such an inhibition of brain swelling in the exposed animals. The response of the animals to the exposure may be monitored using visual means (e.g., radiological, CAT, MRI), measurement of intracranial pressure, and/or the reversal of symptoms associated with brain swelling. With regard to intervention, any treatments which reverse any aspect of brain swelling-associated symptoms should be considered as candidates for brain swelling therapeutic intervention. Dosages of test agents may be determined by deriving dose-response curves, as discussed herein.

Accordingly, the present invention is useful in the treatment or alleviation of neural cell swelling and death and brain swelling, especially those brain insults related to traumatic brain injury, spinal cord injury, central or peripheral nervous system damage, cerebral ischemia, such as stroke, or complications involving and/or stemming from edema, injury, or trauma. Such damage or complications may be characterized by an apparent brain damage or aberration, the symptoms of which can be reduced by the methods of the present invention including the administration of an effective amount of the active compounds or substances described herein. According to a specific embodiment of the present invention the administration of effective amounts of the active compound can block the channel, which if it remained open would lead to neural cell swelling and cell death. A variety of antagonists to SUR1 are suitable for blocking the channel. Examples of suitable SUR1 antagonists include, but are not limited to glibenclamide, tolbutamide, repaglinide, nateglinide, meglitinide, midaglizole, LY397364, LY389382, gliclazide, glimepiride, MgADP, and combinations thereof. In a preferred embodiment of the invention the SUR1 antagonists is selected from the group consisting of glibenclamide and tolbutamide. Still other therapeutic “strategies” for preventing neural cell swelling and cell death can be adopted including, but not limited to methods that maintain the neural cell in a polarized state and methods that prevent strong depolarization.

A. Modulators of the $NC_{Ca\text{-}ATP}$ Channel

The present invention comprises modulators of the channel, for example one or more agonists and/or one or more antagonists of the channel. Examples of antagonists or agonists of the present invention may encompass respective antagonists and/or agonists identified in US Application Publication No. 20030215889, which is incorporated herein by reference in its entirety. One of skill in the art is aware that the $NC_{Ca\text{-}ATP}$ channel is comprised of at least two subunits: the regulatory subunit, SUR1, and the pore forming subunit.

B. Modulators of SUR1

In certain embodiments, antagonists to sulfonylurea receptor-1 (SUR1) are suitable for blocking the channel. Examples of suitable SUR1 antagonists include, but are not limited to glibenclamide, tolbutamide, repaglinide, nateglinide, meglitinide, midaglizole, LY397364, LY389382, glyclazide, glimepiride, estrogen, estrogen related-compounds estrogen related-compounds (estradiol, estrone, estriol, genistein, non-steroidal estrogen (e.g., diethystilbestrol), phytoestrogen (e.g., coumestrol), zearalenone, etc.) and combinations thereof. In a preferred embodiment of the invention the SUR1 antagonists is selected from the group consisting of glibenclamide and tolbutamide. Yet further, another antagonist can be MgADP. Other antagonist include blockers of $K_{ATP}$ channels, for example, but not limited to tolbutamide, glyburide (1[p-2[5-chloro-O-anisamido)ethyl]phenyl]sulfonyl]-3-cyclohexyl-3-urea); chlopropamide (1-[[(p-chlorophenyl)sulfonyl]-3-propylurea; glipizide (1-cyclohexyl-3[[p-[2(5-methylpyrazine carboxamido)ethyl]phenyl]sulfonyl]urea); or tolazamide(benzenesulfonamide-N-[[(hexahydro-1H-azepin-1yl)amino]carbonyl]-4-methyl).

Agonists that may be used in the present invention include, but are not limited to, one or more agonists of SUR1, for example, diazoxide, pinacidil, P1075, cromakalin or activators of $K_{ATP}$ channels. Other agonists can include, but are not limited to diazoixde derivatives, for example 3-isopropylamino-7-methoxy-4H-1,2,4-benzothiadiazine 1,1-dioxide (NNC 55-9216), 6,7-dichloro-3-isopropylamino-4H-1,2,4-benzothiadiazine 1,1-dioxide (BPDZ 154), 7-chloro-3-isopropylamino-4H-1,2,4-benzothiadiazine 1,1-dioxide (BPDZ 73), 6-Chloro-3-isopropylamino-4H-thieno[3,2-e]-1,2,4-thiadiazine 1,1-dioxide (NNC 55-0118) 4,6-chloro-3-(1-methylcyclopropyl)amino-4H-thieno[3,2-e]-1,2,4-thiadiazine 1,1-dioxide (NN414), 3-(3-methyl-2-butylamino)-4H-pyrido[4,3-e]-1,2,4-thiadiazine 1,1-dioxide (BPDZ 44), 3-(1',2',2'-trimethylpropyl)amino-4H-pyrido(4,3-e)-1,2,4-thiadiazine 1,1-dioxide (BPDZ 62), 3-(1',2',2'-trimethylpropyl)amine-4H-pyrido(2,3-e)-1,2,4-thiadiazine, 1,1-dioxide (BPDZ 79), 2-alkyl-3-alkylamino-2H-benzo- and 2-alkyl-3-alkylamino-2H-pyrido[4,3-e]-1,2,4-thiadiazine 1,1-dioxides, 6-Chloro-3-alkylamino-4H-thieno[3,2-e]-1,2,4-thiadiazine 1,1-dioxide derivatives, 4-N-Substituted and -unsubstituted 3-alkyl- and 3-(alkylamino)-4H-pyrido[4,3-e]-1,2,4-thiadiazine 1,1-dioxides. In addition, other compounds, including 6-chloro-2-methylquinolin-4(1H)-one (HEI 713) and LN 533021, as well as the class of drugs, arylcyanoguanidines, are known activators or agonist of SUR1.

C. Modulators of SUR1 Transcription and/or Translation

In certain embodiments, the modulator can comprise a compound (protein, nucleic acid, siRNA, etc.) that modulates transcription and/or translation of SUR1 (regulatory subunit) and/or the molecular entities that comprise the pore-forming subunit.

D. Transcription Factors

Transcription factors are regulatory proteins that binds to a specific DNA sequence (e.g., promoters and enhancers) and regulate transcription of an encoding DNA region. Thus, transcription factors can be used to modulate the expression of SUR1. Typically, a transcription factor comprises a binding domain that binds to DNA (a DNA-binding domain) and a regulatory domain that controls transcription. Where a regulatory domain activates transcription, that regulatory domain is designated an activation domain. Where that regulatory domain inhibits transcription, that regulatory domain is designated a repression domain. More specifically, transcription factors such as Sp1, HIF1α, and NFκB can be used to modulate expression of SUR1.

In particular embodiments of the invention, a transcription factor may be targeted by a composition of the invention. The transcription factor may be one that is associated with a pathway in which SUR1 is involved. The transcription factor may be targeted with an antagonist of the invention, including siRNA to downregulate the transcription factor. Such antagonists can be identified by standard methods in the art, and in particular embodiments the antagonist is employed for treatment and or prevention of an individual in need thereof. In an additional embodiment, the antagonist is employed in conjunction with an additional compound, such as a composition that modulates the $NC_{CA-ATP}$ channel of the invention. For example, the antagonist may be used in combination with an inhibitor of the channel of the invention. When employed in combination, the antagonist of a transcription factor of a SUR1-related pathway may be administered prior to, during, and/or subsequent to the additional compound.

E. Antisense and Ribozymes

An antisense molecule that binds to a translational or transcriptional start site, or splice junctions, are ideal inhibitors. Antisense, ribozyme, and double-stranded RNA molecules target a particular sequence to achieve a reduction or elimination of a particular polypeptide, such as SUR1. Thus, it is contemplated that antisense, ribozyme, and double-stranded RNA, and RNA interference molecules are constructed and used to modulate SUR1 expression.

F. Antisense Molecules

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

G. RNA Interference

It is also contemplated in the present invention that double-stranded RNA is used as an interference molecule, e.g., RNA interference (RNAi). RNA interference is used to "knock down" or inhibit a particular gene of interest by simply injecting, bathing or feeding to the organism of interest the double-stranded RNA molecule. This technique selectively "knock downs" gene function without requiring transfection or recombinant techniques (Giet, 2001; Hammond, 2001; Stein P, et al., 2002; Svoboda P, et al., 2001; Svoboda P, et al., 2000).

Another type of RNAi is often referred to as small interfering RNA (siRNA), which may also be utilized to inhibit SUR1. A siRNA may comprises a double stranded structure or a single stranded structure, the sequence of which is "substantially identical" to at least a portion of the target gene (See WO 04/046320, which is incorporated herein by reference in its entirety). "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ea., Academic Press, New York, 1993, and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA (Atschul et al.,) and CLUSTAL (Higgins et al., 1992; Thompson, et al., 1994).

Thus, siRNA contains a nucleotide sequence that is essentially identical to at least a portion of the target gene, for example, SUR1, or any other molecular entity associated with the $NC_{Ca-ATP}$ channel such as the pore-forming subunit. One of skill in the art is aware that the nucleic acid sequences for SUR1 are readily available in GenBank, for example, GenBank accession L40624, which is incorporated herein by reference in its entirety. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene (e.g., SUR1), although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

There are several methods for preparing siRNA, such as chemical synthesis, in vitro transcription, siRNA expression vectors, and PCR expression cassettes. Irrespective of which method one uses, the first step in designing an siRNA molecule is to choose the siRNA target site, which can be any site in the target gene. In certain embodiments, one of skill in the art may manually select the target selecting region of the gene, which may be an ORF (open reading frame) as the target selecting region and may preferably be 50-100 nucleotides downstream of the "ATG" start codon. However, there are several readily available programs available to assist with the design of siRNA molecules, for example siRNA Target Designer by Promega, siRNA Target Finder by GenScript Corp., siRNA Retriever Program by Imgenex Corp., EMBOSS siRNA algorithm, siRNA program by Qiagen, Ambion siRNA predictor, Ambion siRNA predictor, Whitehead siRNA prediction, and Sfold. Thus, it is envisioned that any of the above programs may be utilized to produce siRNA molecules that can be used in the present invention.

H. Ribozymes

Ribozymes are RNA-protein complexes that cleave nucleic acids in a site-specific fashion. Ribozymes have specific catalytic domains that possess endonuclease activity (Kim and Cech, 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to therapeutic applications (Scanlon et al., 1991; Sarver et al., 1990; Sioud et al., 1992). Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A,C or U; Perriman, et al., 1992; Thompson, et al., 1995). The frequency of this dinucleotide occurring in any given RNA is statistically 3 out of 16.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in SUR1 targeted ribozymes is simply a matter of preparing and testing a given sequence, and is a routinely practiced screening method known to those of skill in the art.

I. Inhibition of Post-Translational Assembly and Trafficking

Following expression of individual regulatory and pore-forming subunit proteins of the channel, and in particular aspects of the invention, these proteins are modified by glycosylation in the Golgi apparatus of the cell, assembled into functional heteromultimers that comprise the channel, and then transported to the plasmalemmal membrane where they are inserted to form functional channels. The last of these processes is referred to as "trafficking".

In specific embodiments of the invention, molecules that bind to any of the constituent proteins interfere with post-translational assembly and trafficking, and thereby interfere with expression of functional channels. One such example is with glibenclamide binding to SUR1 subunits. In additional embodiments, glibenclamide, which binds with femtomolar affinity to SUR1, interferes with post-translational assembly and trafficking required for functional channel expresson.

VII. Exemplary Methods of Screening for Modulators

Further embodiments of the present invention can include methods for identifying modulators of the $NC_{Ca-ATP}$ channel, for example, agonist or antagonist, that modify the activity and/or expression. These assays may comprise random screening of large libraries of candidate substances; alternatively, the assays may be used to focus on particular classes of compounds selected with an eye towards structural attributes that are believed to make them more likely to modulate the function or activity or expression of the $NC_{Ca-ATP}$ channel.

By function, it is meant that one may assay for mRNA expression, protein expression, protein activity, or channel activity, more specifically, the ability of the modulator to open or inhibit or block the $NC_{Ca-ATP}$ channel. Thus, the compounds for screening in accordance with the invention include, but are not limited to natural or synthetic organic compounds, peptides, antibodies and fragments thereof, peptidomimetics, that bind to the $NC_{Ca-ATP}$ channel and either open the channel (e.g., agonists) or block the channel (e.g., antagonists). For use in the treatment of neural cell swelling or brain swelling, compounds that block the channel are preferred. Agonists that open or maintain the channel in the open state include peptides, antibodies or fragments thereof, and other organic compounds that include the SUR1 subunit of the $NC_{Ca-ATP}$ channel (or a portion thereof) and bind to and "neutralize" circulating ligand for SUR1.

With reference to screening of compounds that affect the $NC_{Ca-ATP}$ channel, libraries of known compounds can be screened, including natural products or synthetic chemicals, and biologically active materials, including proteins, for compounds which are inhibitors or activators. Preferably, such a compound is an $NC_{Ca-ATP}$ antagonist, which includes an $NC_{Ca-ATP}$ channel inhibitor, an $NC_{Ca-ATP}$ channel blocker, a SUR1 antagonist, SUR1 inhibitor, and/or a compound capable of reducing the magnitude of membrane current through the channel.

Compounds may include, but are not limited to, small organic or inorganic molecules, compounds available in compound libraries, peptides such as, for example, soluble peptides, including but not limited to members of random peptide libraries; (see, e.g., Lam, K. S. et al., 1991, Nature 354: 82-84; Houghten, R. et al., 1991, Nature 354: 84-86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72: 767-778), antibodies (including, but not limited to, polyclonal, monoclonal, humanized, anti-idiotypic chimeric or single chain antibodies, and FAb, $F(ab')_2$ and FAb expression library fragments, and epitope-binding fragments thereof).

Other compounds that can be screened in accordance with the invention include but are not limited to small organic molecules that may or may not cross the blood-brain barrier, gain entry into an appropriate neural or endothelial cell and affect the expression of the $NC_{Ca-ATP}$ channel gene or some other gene involved in the $NC_{Ca-ATP}$ channel activity (e.g., by interacting with the regulatory region or transcription factors involved in gene expression, or by interfering with post-translational channel assembly or trafficking); or such compounds that affect the activity of the $NC_{Ca-ATP}$ channel or the activity of some other intracellular factor involved in the $NC_{Ca-ATP}$ channel activity.

To identify, make, generate, provide, manufacture or obtain modulator, one generally will determine the activity of the $NC_{Ca-ATP}$ channel in the presence, absence, or both of the candidate substance, wherein an inhibitor or antagonist is defined as any substance that down-regulates, reduces, inhibits, blocks or decreases the $NC_{Ca-ATP}$ channel expression or activity, and wherein an activator or agonist is defined as any substance that up-regulates, enhances, activates, increases or opens the $NC_{Ca-ATP}$ channel. For example, a method may generally comprise:

(a) providing a candidate substance suspected of activating or inhibiting the $NC_{Ca-ATP}$ channel expression or activity in vitro or in vivo;

(b) assessing the ability of the candidate substance to activate or inhibit the $NC_{Ca-ATP}$ channel expression or activity in vitro or in vivo;

(c) selecting a modulator; and (d) manufacturing the modulator.

In certain embodiments, an alternative assessing step can be assessing the ability of the candidate substance to bind specifically to the $NC_{Ca-ATP}$ channel in vitro or in vivo;

In further embodiments, the $NC_{Ca-ATP}$ channel may be provided in a cell or a cell free system and the $NC_{Ca-ATP}$ channel may be contacted with the candidate substance. Next, the modulator is selected by assessing the effect of the candidate substance on the $NC_{Ca-ATP}$ channel activity or expression. Upon identification of the modulator, the method may further provide manufacturing of the modulator.

An effective amount of modulator of an $NC_{Ca-ATP}$ channel (which may be an agonist or antagonist, and is preferably an antagonist) that may be administered to a cell includes a dose of about 0.0001 nM to about 2000 μM. More specifically, doses of an agonist to be administered are from about 0.01 nM to about 2000 μM; about 0.01 μM to about 0.05 μM; about 0.05 μM to about 1.0 μM; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM and about 1500 μM to about 2000 μM. Of course, all of these amounts are exemplary, and any amount in-between these points is also expected to be of use in the invention.

The $NC_{Ca\text{-}ATP}$ channel modulator or related-compound thereof can be administered parenterally or alimentarily. Parenteral administrations include, but are not limited to intravenously, intradermally, intramuscularly, intraarterially, intrathecally, intraventricularly, intratumorally, subcutaneous, or intraperitoneally U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

The administration of the therapeutic compounds and/or the therapies of the present invention may include systemic, local and/or regional and may oral, intravenous, and intramuscular. Alternatively, other routes of administration are also contemplated such as, for example, arterial perfusion, intracavitary, intraperitoneal, intrapleural, intraventricular, intratumoral, intraparenchyma and/or intrathecal. If desired the therapeutic compound may be administered by the same route as the chemotherapeutic agent, even if the therapeutic compound and the chemotherapeutic agent are not administered simultaneously. The skilled artisan is aware of determining the appropriate administration route using standard methods and procedures. In one example, where assessment of a response to chemotherapy, both peripherally and centrally is desired, the health care professional may use a systemic administration.

Treatment methods will involve treating an individual with an effective amount of a composition containing an agonist of $NC_{Ca\text{-}ATP}$ channel or related-compound thereof. An effective amount is described, generally, as that amount sufficient to detectably and repeatedly to ameliorate, reduce, minimize or limit the extent of a disease or its symptoms. More specifically, it is envisioned that the treatment with the an antagonist of $NC_{Ca\text{-}ATP}$ channel or related-compounds thereof will reduce cell swelling and brain swelling following stroke, brain trauma, or other brain injury, and will reduce brain damage following stroke, brain trauma or other brain injury or spinal cord injury.

The effective amount of "therapeutically effective amounts" of the an antagonist of $NC_{Ca\text{-}ATP}$ channel or related-compounds thereof to be used are those amounts effective to produce beneficial results, particularly with respect to stroke or brain trauma treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as an antagonist of $NC_{Ca\text{-}ATP}$ channel or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

An effective amount of an antagonist of $NC_{Ca\text{-}ATP}$ channel or related-compounds thereof as a treatment varies depending upon the host treated and the particular mode of administration. In one embodiment of the invention the dose range of the agonist of $NC_{Ca\text{-}ATP}$ channel or related-compounds thereof will be about 0.0001 μg/kg body weight to about 500 mg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.0001 μg/kg body weight to 450 mg/kg body weight, 0.0002 μg/kg body weight to 400 mg/kg body weight, 0.0003 μg/kg body weight to 350 mg/kg body weight, 0.0004 μg/kg body weight to 300 mg/kg body weight, 0.0005 μg/kg body weight to 250 mg/kg body weight, 5.0 μg/kg body weight to 200 mg/kg body weight, 10.0 μg/kg body weight to 150 mg/kg body weight, 100.0 μg/kg body weight to 100 mg/kg body weight, or 1000 μg/kg body weight to 50 mg/kg body weight. Further, those of skill will recognize that a variety of different dosage levels will be of use, for example, up to about 0.0001 μg/kg, up to about 0.0002 μg/kg, up to about 0.0003 μg/kg, less than about 0.0004 μg/kg, less than about 0.005 μg/kg, less than about 0.0007 μg/kg, less than about 0.001 μg/kg, less than about 0.1 μg/kg, less than about 1.0 μg/kg, less than about 1.5 μg/kg, less than about 2.0 μg/kg, less than about 5.0 μg/kg, less than about 10.0 μg/kg, less than about 15.0 μg/kg, less than about 30.0 μg/kg, less than about 50 μg/kg, less than about 75 μg/kg, less than about 80 μg/kg, less than about 90 μg/kg, less than about 100 μg/kg, less than about 200 μg/kg, less than about 300 μg/kg, less than about 400 μg/kg, less than about 500 μg/kg, less than about 1 mg/kg, less than about 2 mg/kg, less than about 3 mg/kg, less than about 5 mg/kg, less than about 10 mg/kg, less than about 100 mg/kg. Further, those of skill will recognize that a variety of different dosage levels will be of use, for example, 0.0001 μg/kg, 0.0002 μg/kg, 0.0003 μg/kg, 0.0004 μg/kg, 0.005 μg/kg, 0.0007 μg/kg, 0.001 μg/kg, 0.1 μg/kg, 1.0 μg/kg, 1.5 μg/kg, 2.0 μg/kg, 5.0 μg/kg, 10.0 μg/kg, 15.0 μg/kg, 30.0 μg/kg, 50 μg/kg, 75 μg/kg, 80 μg/kg, 90 μg/kg, 100 μg/kg, 120 μg/kg, 140 μg/kg, 150 μg/kg, 160 μg/kg, 180 μg/kg, 200 μg/kg, 225 μg/kg, 250 μg/kg, 275 μg/kg, 300 μg/kg, 325 μg/kg, 350 μg/kg, 375 μg/kg, 400 μg/kg, 450 μg/kg, 500 μg/kg, 550 μg/kg, 600 μg/kg, 700 μg/kg, 750 μg/kg, 800 μg/kg, 900 μg/kg, 1 mg/kg, 5 mg/kg, 10 mg/kg, 12 mg/kg, 15 mg/kg, 20 mg/kg, and/or 30 mg/kg. Of course, all of these dosages are exemplary, and any dosage in-between these points is also expected to be of use in the invention. Any of the above dosage ranges or dosage levels may be employed for an agonist of $NC_{Ca\text{-}ATP}$ channel or related-compounds thereof.

Administration of the therapeutic agonist of $NC_{Ca\text{-}ATP}$ channel composition of the present invention to a patient or subject will follow general protocols for the administration of chemotherapeutics, taking into account the toxicity, if any, of the agonist of $NC_{Ca\text{-}ATP}$ channel. It is expected that the treatment cycles would be repeated as necessary. It also is contemplated that various standard therapies, as well as surgical intervention, may be applied in combination with the described therapy.

The treatments may include various "unit doses." Unit dose is defined as containing a predetermined quantity of the therapeutic composition (an agonist of $NC_{Ca-ATP}$ channel or its related-compounds thereof) calculated to produce the desired responses in association with its administration, e.g., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

According to the present invention, one may treat stroke, brain trauma, or other brain or spinal cord injury by systemic administration, such as intravenous, intra-arterial, peritoneal, by administration via pump, or by direct injection into the brain or ventricles with an antagonist of $NC_{Ca-ATP}$ channel or related-compound composition. Alternatively, the brain or spinal cord may be infused or perfused with the composition using any suitable delivery vehicle. Systemic administration or oral administration may be performed, and, in embodiments of the present invention, local or regional administration may be performed. Continuous administration also may be applied where appropriate, for example, where a patient may be monitored on an on-going basis. Delivery via syringe or catheterization is one effective method. Continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. Multiple injections delivered as single dose comprise about 0.1 to about 1 ml volumes. In embodiments, the volume to be administered may be about 4-10 ml (preferably 10 ml), while in further embodiments a volume of about 1-3 ml will be used (preferably 3 ml).

VIII. Methods of Cerebral Ischemia Treatment

Treatment with an Antagonist

In other embodiments, the therapeutic compound of the present invention comprises an antagonist of a $NC_{Ca-ATP}$ channel of a neuronal cell, a neuroglial cell, a neural endothelial cell or a combination thereof. Antagonists are contemplated for use in treating adverse conditions associated with intracranial pressure and/or ionic or cytotoxic edema of the central nervous system. Such conditions include trauma (e.g., traumatic brain or spinal cord injury (TBI or SCI, respectively)), ischemic brain or spinal cord injury, primary and secondary neuronal injury, stroke, arteriovenous malformations (AVM), mass-occupying lesion (e.g., hematoma), and hemorrhagic infarction. Antagonists protect the cells expressing the $NC_{CA-ATP}$ channel, which is desirable for clinical treatment in which ionic or cytotoxic edema is formed, in which capillary integrity is lost following ischemia, and in which gliotic capsule integrity is important and must be maintained to prevent the spread of infection, such as with a brain abscess. Those of skill in the art realize that a brain abscess is a completely enclosed and results in cerebral swelling. The protection via inhibition of the $NC_{Ca-ATP}$ channel is associated with a reduction in cerebral ionic and cytotoxic edema. Thus, the compound that inhibits the $NC_{Ca-ATP}$ channel is neuroprotective.

In one aspect, the $NC_{Ca-ATP}$ channel is blocked, inhibited, or otherwise is decreased in activity. In such examples, an antagonist of the $NC_{Ca-ATP}$ channel is administered and/or applied. The antagonist modulates the $NC_{Ca-ATP}$ channel such that flux (ion and/or water) through the channel is reduced, ceased, decreased and/or stopped. The antagonist may have a reversible or an irreversible activity with respect to the activity of the $NC_{Ca-ATP}$ channel of the neuronal cell, neuroglial cell, a neural endothelial cell or a combination thereof. Thus, inhibition of the $NC_{Ca-ATP}$ channel can reduce cytotoxic edema and death of endothelial cells which are associated with formation of ionic edema and with hemorrhagic conversion.

Accordingly, the present invention is useful in the treatment or alleviation of acute cerebral ischemia. According to a specific embodiment of the present invention the administration of effective amounts of the active compound can block the channel, which if remained open leads to neuronal cell swelling and cell death. A variety of antagonists to SUR1 are suitable for blocking the channel. Examples of suitable SUR1 antagonists include, but are not limited to glibenclamide, tolbutamide, repaglinide, nateglinide, meglitinide, midaglizole, LY397364, LY389382, glyclazide, glimepiride, estrogen, estrogen related-compounds and combinations thereof. In a preferred embodiment of the invention the SUR1 antagonists is selected from the group consisting of glibenclamide and tolbutamide. Another antagonist that can be used is MgADP. Still other therapeutic "strategies" for preventing neural cell swelling and cell death can be adopted including, but not limited to methods that maintain the neural cell in a polarized state and methods that prevent strong depolarization.

In further embodiments, inhibitors or antagonist of the $NC_{Ca-ATP}$ channel can be used to reduce or alleviate or abrogate hemorrhagic conversion. The pathological sequence that takes place in capillaries after ischemia can be divided into 3 stages, based on the principal constituents that move from the intravascular compartment into brain parenchyma (Ayata 2002; Betz, 1996; Betz 1989). The first stage is characterized by formation of "ionic" edema, during which the BBB remains intact, with movement of electrolytes ($Na^+$, $Cl^-$) plus water into brain parenchyma. The second stage is characterized by formation of "vasogenic" edema, due to breakdown of the BBB, during which macromolecules plus water enter into brain parenchyma. The third stage is characterized by hemorrhagic conversion, due to catastrophic failure of capillaries, during which all constituents of blood extravasate into brain parenchyma. In accordance with Starling's law, understanding these phases requires that 2 things be identified: (i) the driving force that "pushes" things into parenchyma; and (ii) the permeability pore that allows passage of these things into parenchyma.

Thus, the use of the antagonist or related-compounds thereof can reduce the mortality of a subject suffering from a stroke and/or rescue the penumbra area or prevent damage in the penumbra area which comprises areas of tissue that are at risk of becoming irreversibly damaged.

With the administration of an antagonist of the $NC_{Ca-ATP}$ channel, endothelial cell depolarization is abrogated, slowed, reduced or inhibited due to the opening of the $NC_{Ca-ATP}$ channel. Thus, abrogation of cell depolarization results in abrogation or inhibition of $Na^+$ influx, which prevents a change in osmotic gradient thereby preventing an influx of water into the endothelial cell and stopping cell swelling, blebbing and cytotoxic edema. Thus, preventing or inhibiting or attenuating endothelial cell depolarization can prevent or reduce hemorrhagic conversion.

Neuronal cells in which the antagonist of the $NC_{Ca-ATP}$ channel may be administered may include any cell that expresses SUR1, for example any neuronal cell, neuroglial cell or a neural endothelia cell.

Subjects that may be treated with the antagonist or related-compound thereof include those that are suffering from or at risk of developing trauma (e.g., traumatic brain or spinal cord injury (TBI or SCI)), ischemic brain or spinal cord injury, primary and secondary neuronal injury, stroke, arteriovenous malformations (AVM), brain abscess, mass-occupying lesion, hemorrhagic infarction, or any other condition associated with cerebral hypoxia or cerebral ischemia resulting in cerebral edema and/or increased intracranial pressure, for example, but not limited to brain mass, brain edema, hematoma, end stage cerebral edema, encephalopathies, etc. Thus, the antagonist can be a therapeutic treatment in which the therapeutic treatment includes prophylaxis or a prophylactic treatment. The antagonist or related-compounds thereof are neuroprotective.

Other subjects that may be treated with the antagonist of the present invention include those subjects that are at risk or predisposed to developing a stroke. Such subjects can include, but are not limited to subjects that suffer from atrial fibrillations, clotting disorders, and/or risk of pulmonary emboli.

In certain embodiments, a subject at risk for developing a stroke may include subjects undergoing treatments, for example, but not limited to cerebral/endovascular treatments, surgery (e.g., craniotomy, cranial surgery, removal of brain tumors (e.g., hematoma), coronary artery bypass grafting (CABG), angiography, stent replacement, other vascular surgeries, and/or other CNS or neurological surgeries), and treatment of myocardial infarction (MI) with thrombolytics, as well as surgeries on aortic abdominal aneurysms and major vessels that provide blood supply to the spinal cord. In such cases, the subject may be treated with the antagonist or related-compound of the present invention prior to the actual treatment. Pretreatment can include administration of the antagonist and/or related-compound months (1, 2, 3, etc.), weeks (1, 2, 3, etc.), days (1, 2, 3, etc.), hours (1, 2, 3, 4, 5, 6, 7, 8, 9, 10, 11, 12), or minutes (15, 30, 60, 90, etc.) prior to the actual treatment or surgery. Treatment of the antagonist and/or related-compound can continue during the treatment and/or surgery and after the treatment and/or surgery until the risk of developing a stroke in the subject is decreased, lessened or alleviated.

In further embodiments, the antagonist of the present invention can be given to a subject at risk of developing head/neck trauma, such as a subject involved in sports or other activities that have an increased risk of head/neck trauma.

An effective amount of an antagonist of the $NC_{Ca-ATP}$ channel that may be administered to a cell includes a dose of about 0.0001 nM to about 2000 μM. More specifically, doses of an agonist to be administered are from about 0.01 nM to about 2000 μM; about 0.01 μM to about 0.05 μM; about 0.05 μM to about 1.0 μM; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM and about 1500 μM to about 2000 μM. Of course, all of these amounts are exemplary, and any amount in-between these points is also expected to be of use in the invention.

The antagonist or related-compound thereof can be administered parenterally or alimentary. Parenteral administrations include, but are not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

The administration of the therapeutic compounds and/or the therapies of the present invention may include systemic, local and/or regional administrations, for example, topically (dermally, transdermally), via catheters, implantable pumps, etc. Alternatively, other routes of administration are also contemplated such as, for example, arterial perfusion, intracavitary, intraperitoneal, intrapleural, intraventricular and/or intrathecal. The skilled artisan is aware of determining the appropriate administration route using standard methods and procedures. Other routes of administration are discussed elsewhere in the specification and are incorporated herein by reference.

Treatment methods will involve treating an individual with an effective amount of a composition containing an antagonist of $NC_{Ca-ATP}$ channel or related-compound thereof. An effective amount is described, generally, as that amount sufficient to detectably and repeatedly to ameliorate, reduce, minimize or limit the extent of a disease or its symptoms. More specifically, it is envisioned that the treatment with the an antagonist of $NC_{Ca-ATP}$ channel or related-compounds thereof will inhibit cell depolarization, inhibit $Na^+$ influx, inhibit an osmotic gradient change, inhibit water influx into the cell, inhibit cytotoxic cell edema, decrease stroke size, inhibit hemorrhagic conversion, and decrease mortality of the subject.

The effective amount of an antagonist of $NC_{Ca-ATP}$ channel or related-compounds thereof to be used are those amounts effective to produce beneficial results, particularly with respect to stroke treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as an antagonist of the $NC_{Ca-ATP}$ channel or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the effective amount of the antagonist or related-compound thereof can be the amount that is required to achieve the desired result: reduction in the risk of stroke, reduction in intracranial pressure, reduction in cell death, reduction in stroke size, reduction in spinal cord injury, etc. This amount also is an amount that maintains a reasonable level of blood glucose in the patient, for example, the amount of the antagonist maintains a blood glucose level of at least 60 mmol/l, more preferably, the blood glucose level is maintain in the range of about 60 mmol/l to about 150 mmol/l. Thus, the amounts prevents the subject from becoming hypoglycemic. If glucose levels are not normal, then one of skill in the art would administer either insulin or glucose, depending upon if the patient is hypoglycemic or hyperglycemic.

Administration of the therapeutic antagonist of $NC_{Ca-ATP}$ channel composition of the present invention to a patient or subject will follow general protocols for the administration of therapies used in stroke treatment, such as thrombolytics, taking into account the toxicity, if any, of the antagonist of the $NC_{Ca-ATP}$ channel. It is expected that the treatment cycles would be repeated as necessary. It also is contemplated that various standard therapies, as well as surgical intervention, may be applied in combination with the described therapy.

IX. Pharmaceutical Formulations and Methods of Treating Neural Cell Swelling and Brain Swelling

A. Compositions of the Present Invention

The present invention also contemplates therapeutic methods employing compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

B. Dose Determinations

By a "therapeutically effective amount" or simply "effective amount" of an active compound, such as glibenclamide or tolbutamide, is meant a sufficient amount of the compound to treat or alleviate the brain swelling at a reasonable benefit/risk ratio applicable to any medical treatment. It will be understood, however, that the total daily usage of the active compounds and compositions of the present invention will be decided by the attending physician within the scope of sound medical judgment. The specific therapeutically effective dose level for any particular patient will depend upon a variety of factors including the disorder being treated and the severity of the brain injury or ischemia; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

Toxicity and therapeutic efficacy of such compounds can be determined by standard pharmaceutical procedures in cell assays or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell based assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

In certain situations, it may be important to maintain a fairly high dose of the active agent in the blood stream of the patient, particularly early in the treatment. Such a fairly high dose may include a dose that is several times greater than its use in other indications. For example, the typical anti-diabetic dose of oral or IV glibenclamide is about 2.5 mg/kg to about 15 mg/kg per day; the typical anti-diabetic dose of oral or IV tolbutamide is about to 0.5 gm/kg to about 2.0 gm/kg per day; the typical anti-diabetic dose for oral gliclazide is about 30 mg/kg to about 120 mg/kg per day; however, much larger doses may be required to block neural cell swelling and brain swelling.

For example, in one embodiment of the present invention directed to a method of preventing neuronal cell swelling in the brain of a subject by administering to the subject a formulation containing an effective amount of a compound that blocks the $NC_{Ca-ATP}$ channel and a pharmaceutically acceptable carrier; such formulations may contain from about 0.1 to about 100 grams of tolbutamide or from about 0.5 to about 150 milligrams of glibenclamide. In another embodiment of the present invention directed to a method of alleviating the negative effects of traumatic brain injury or cerebral ischemia stemming from neural cell swelling in a subject by administering to the subject a formulation containing an effective amount of a compound that blocks the $NC_{Ca-ATP}$ channel and a pharmaceutically acceptable carrier.

In situations of traumatic brain injury or cerebral ischemia (such as stroke), or cerebral hypoxia, it may be important to maintain a fairly high dose of the active agent to ensure delivery to the brain of the patient, particularly early in the treatment. Hence, at least initially, it may be important to keep the dose relatively high and/or at a substantially constant level for a given period of time, preferably, at least about six or more hours, more preferably, at least about twelve or more hours and, most preferably, at least about twenty-four or more hours. In situations of traumatic brain injury or cerebral ischemia (such as stroke), it may be important to maintain a fairly high dose of the active agent to ensure delivery to the brain of the patient, particularly early in the treatment.

When the method of the present invention is employed to treat conditions involving bleeding in the brain, such as traumatic brain injury or cerebral ischemia (such as stroke), delivery via the vascular system is available and the compound is not necessarily required to readily cross the blood-brain barrier.

C. Formulations and Administration

The compounds of the present invention may be administered alone or in combination or in concurrent therapy with other agents which affect the central or peripheral nervous system, particularly selected areas of the brain.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

The method of the present invention employs the compounds identified herein for both in vitro and in vivo applications. For in vivo applications, the invention compounds can be incorporated into a pharmaceutically acceptable formulation for administration. Those of skill in the art can readily determine suitable dosage levels when the invention compounds are so used.

As employed herein, the phrase "suitable dosage levels" refers to levels of compound sufficient to provide circulating concentrations high enough to effectively block the $NC_{Ca-ATP}$ channel and prevent or reduce neural cell swelling in vivo.

In accordance with a particular embodiment of the present invention, compositions comprising at least one SUR1 antagonist compound (as described above), and a pharmaceutically acceptable carrier are contemplated.

Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The treatments may include various "unit doses." Unit dose is defined as containing a predetermined quantity of the therapeutic composition (an antagonist of the $NC_{Ca-ATP}$ channel or its related-compounds thereof) calculated to produce the desired responses in association with its administration, e.g., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

X. Combination Treatments

In the context of the present invention, it is contemplated that an antagonist of the $NC_{Ca-ATP}$ channel or related-compounds thereof may be used in combination with an additional therapeutic agent to more effectively treat a cerebral ischemic event, and/or decrease intracranial pressure. In some embodiments, it is contemplated that a conventional therapy or agent, including but not limited to, a pharmacological therapeutic agent may be combined with the antagonist or related-compound of the present invention.

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an anticholesterol agent, an antiinflammatory agent, an antithrombotic/fibrinolytic agent, anticoagulant, antiplatelet, vasodilator, and/or diuretics. Thromoblytics that are used can include, but are not limited to prourokinase, streptokinase, and tissue plasminogen activator (tPA) Anticholesterol agents include but are not limited to HMG-CoA Reductase inhibitors, cholesterol absorption inhibitors, bile acid sequestrants, nicotinic acid and derivatives thereof, fibric acid and derivatives thereof. HMG-CoA Reductase inhibitors include statins, for example, but not limited to atorvastatin calcium (Lipitor®), cerivastatin sodium (Baycol®), fluvastatin sodium (Lescol®), lovastatin (Advicor®), pravastatin sodium (Pravachol®), and simvastatin (Zocor®). Agents known to reduce the absorption of ingested cholesterol include, for example, Zetia®. Bile acid sequestrants include, but are not limited to cholestryramine, cholestipol and colesevalam. Other anticholesterol agents include fibric acids and derivatives thereof (e.g., gemfibrozil, fenofibrate and clofibrate); nicotinic acids and derivatives thereof (e.g., nician, lovastatin) and agents that extend the release of nicotinic acid, for example niaspan. Antiinflammatory agents include, but are not limited to non-sterodial anti-inflammatory agents (e.g., naproxen, ibuprofen, celeoxib) and sterodial anti-inflammatory agents (e.g., glucocorticoids). Anticoagulants include, but are not limited to heparin, warfarin, and coumadin. Antiplatelets include, but are not limited to aspirin, and aspirin related-compounds, for example acetaminophen. Diuretics include, but are not limited to such as furosemide (Lasix®), bumetanide (Bumex®), torsemide (Demadex®), thiazide & thiazide-like diuretics (e.g., chlorothiazide (Diuril®) and hydrochlorothiazide (Esidrix®), benzthiazide, cyclothiazide, indapamide, chlorthalidone, bendroflumethizide, metolazone), amiloride, triamterene, and spironolacton. Vasodilators include, but are not limited to nitroglycerin.

Thus, in certain embodiments, the present invention comprises co-administration of an antagonist of the $NC_{Ca-ATP}$ channel with a thrombolytic agent. Co-administration of these two compounds will increase the therapeutic window of the thrombolytic agent. Examples of suitable thrombolytic agents that can be employed in the methods and pharmaceutical compositions of this invention are prourokinase, streptokinase, and tissue plasminogen activator (tPA).

In certain embodiments, the present invention comprises co-administration of an antagonist of the $NC_{Ca-ATP}$ channel with glucose or related carbohydrate to maintain appropriate levels of serum glucose. Appropriate levels of blood glucose are within the range of about 60 mmol/l to about 150 mmol/ liter. Thus, glucose or a related carbohydrate is administered in combination to maintain the serum glucose within this range.

When an additional therapeutic agent, as long as the dose of the additional therapeutic agent does not exceed previously quoted toxicity levels, the effective amounts of the additional therapeutic agent may simply be defined as that amount effective to reduce cerebral edema when administered to an animal in combination with an agonist of $NC_{Ca-ATP}$ channel or related-compounds thereof. This may be easily determined by monitoring the animal or patient and measuring those physical and biochemical parameters of health and disease that are indicative of the success of a given treatment. Such methods are routine in animal testing and clinical practice.

To inhibit hemorrhagic conversion, reduce cell swelling, etc., using the methods and compositions of the present invention, one would generally contact a cell with antagonist of $NC_{Ca-ATP}$ channel or related-compounds thereof in combination with an additional therapeutic agent, such as tPA, aspirin, statins, diuretics, warfarin, coumadin, mannitol, etc. These compositions would be provided in a combined amount effective to inhibit hemorrhagic conversion, cell swelling and edema. This process may involve contacting the cells with agonist of $NC_{Ca-ATP}$ channel or related-compounds thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes an antagonist of the $NC_{Ca-ATP}$ channel or derivatives thereof and the other includes the additional agent.

Alternatively, treatment with an antagonist of $NC_{Ca-ATP}$ channel or related-compounds thereof may precede or follow the additional agent treatment by intervals ranging from minutes to hours to weeks to months. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 1-24 hr of each other and, more preferably, within about 6-12 hr of each other.

Typically, for maximum benefit of the thrombolytic agent, or therapy must be started within three hours of the onset of stroke symptoms, making rapid diagnosis and differentiation of stroke and stroke type critical. However, in the present invention, administration of the $NC_{Ca-ATP}$ channel with a thrombolytic agent increases this therapeutic window. The therapeutic window for thrombolytic agents may be increased by several (4-8) hours by co-administering antagonist of the $NC_{Ca-ATP}$ channel.

Further embodiments include treatment with SUR1 antagonist, thrombolytic agent, and glucose. Glucose administration may be at the time of treatment with SUR1 antagonist, or may follow treatment with SUR1 antagonist (e.g., at 15 minutes after treatment with SUR1 antagonist, or at one half hour after treatment with SUR1 antagonist, or at one hour after treatment with SUR1 antagonist, or at two hours after treatment with SUR1 antagonist, or at three hours after treatment with SUR1 antagonist). Glucose administration may be by intravenous, or intraperitoneal, or other suitable route and means of delivery. Additional glucose allows administration of higher doses of SUR1 antagonist than might otherwise be possible. Treatment with glucose in conjunction with treatment with SUR1 antagonist (at the same time as treatment with SUR1 antagonist, or at a later time after treatment with SUR1 antagonist) may further enlarge the time window after stroke, trauma, or other brain injury when thrombolytic treatment may be initiated.

Yet further, the combination of the antagonist and tPA results in a decrease or prevention of hemorrhagic conversion following reperfusion. Hemorrhagic conversion is the transformation of a bland infarct into a hemorrhagic infarct after restoration of circulation. It is generally accepted that these complications of stroke and of reperfusion are attributable to capillary endothelial cell dysfunction that worsens as ischemia progresses. Thus, the present invention is protective of the endothelial cell dysfunction that occurs as a result of an ischemic event.

Endothelial cell dysfunction comprises three phases. Phase one is characterized by formation of ionic edema with the blood brain barrier still intact. The second phase is characterized by formation of vasogenic edema in which the blood brain barrier is no longer intact. Phase three is characterized by hemorrhagic conversion due to failure of capillary integrity during which all constituents of blood, including erythrocytes, extravasate into brain parenchyma. Disruption of BBB involves ischemia-induced activation of endothelial cells that results in expression and release of MMPs, specifically, MMP-2 (gelatinase A) and MMP-9 (gelatinase B).

Since hemorrhagic conversion increases mortality of the patient, it is essential that these patients receive treatment in an urgent manner. For example, it is known that hemorrhagic conversion typically results in patients if reperfusion and tPA treatment is delayed beyond 3 hr or more after thrombotic stroke. Thus, the administration of the antagonist of the present invention will reduce necrotic death of ischemic endothelial cells, and will thereby prolong the therapeutic window for tPA, thereby decreasing mortality of the patient.

XI. Diagnostics

The antagonist or related-compound can be used for diagnosing, monitoring, or prognosis of ischemia or damage to neurons, glial cells or in monitoring neuronal cells in zones of cerebral edema, metastatic tumors, etc.

A. Genetic Diagnosis

One embodiment of the instant invention comprises a method for detecting expression of any portion of a $Na_{Ca-ATP}$ channel, for example, expression of the regulatory unit, SUR1, and/or expression of the pore-forming subunit. This may comprise determining the level of SUR1 expressed and/or the level of the pore-forming subunit expressed. It is understood by the present invention that the up-regulation or increased expression of the $Na_{Ca-ATP}$ channel relates to increased levels of SUR1, which correlates to increased neuronal damage, such as cerebral edema.

Firstly, a biological sample is obtained from a subject. The biological sample may be tissue or fluid. In certain embodiments, the biological sample includes cells from the brain and/or cerebral endothelial cells or microvessels and/or gliotic capsule. For example, in metastatic tumors, glial cells are activated and form a capsule around the tumor.

Nucleic acids used are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA (cDNA). In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given subject with a statistically significant reference group of normal subjects and subjects that have been diagnosed with a stroke, cancer, cerebral edema, etc.

Yet further, it is contemplated that chip-based DNA technologies such as those described by Hacia et al., (1996) and Shoemaker et al., (1996) can be used for diagnosis. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al., (1994); Fodor et al., (1991).

B. Other Types of Diagnosis

In order to increase the efficacy of molecules, for example, compounds and/or proteins and/or antibodies, as diagnostic agents, it is conventional to link or covalently bind or complex at least one desired molecule or moiety.

Certain examples of conjugates are those conjugates in which the molecule (for example, protein, antibody, and/or compound) is linked to a detectable label. "Detectable labels" are compounds and/or elements that can be detected due to their specific functional properties, and/or chemical characteristics, the use of which allows the antibody to which they are attached to be detected, and/or further quantified if desired.

Conjugates are generally preferred for use as diagnostic agents. Diagnostics generally fall within two classes, those for use in in vitro diagnostics, such as in a variety of immunoassays, and/or those for use in vivo diagnostic protocols, generally known as "molecule-directed imaging".

Many appropriate imaging agents are known in the art, as are methods for their attachment to molecules, for example, antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention $^{211}$astatine, $^{11}$carbon, $^{14}$carbon, $^{51}$chromium, $^{36}$chlorine, 57cobalt, $^{58}$cobalt, $^{67}$copper, $^{152}$Eu, $^{67}$gallium, $^{3}$hydrogen, $^{123}$iodine, $^{125}$iodine, $^{131}$iodine, $^{111}$indium, $^{59}$iron, $^{32}$phosphorus, $^{186}$rhenium, $^{188}$rhenium, $^{75}$selenium, $^{35}$sulphur, $^{99m}$technicium and/or $^{90}$yttrium. $^{125}$I is often being preferred for use in certain embodiments, and $^{99m}$ technicium and/or $^{111}$indium are also often preferred due to their low energy and suitability for long range detection.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of conjugates contemplated in the present invention are those intended primarily for use in vitro, where the molecule is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

The steps of various other useful immunodetection methods have been described in the scientific literature, such as, e.g., Nakamura et al., (1987). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

Immunologically-based detection methods for use in conjunction with Western blotting include enzymatically-, radiolabel-, or fluorescently-tagged secondary molecules/antibodies against the SUR1 or regulatory subunit of the $NC_{Ca-ATP}$ channel are considered to be of particular use in this regard. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

In addition to the above imaging techniques, one of skill in the art is also aware that positron emission tomography, PET imaging or a PET scan, can also be used as a diagnostic examination. PET scans involve the acquisition of physiologic images based on the detection of radiation from the emission of positrons. Positrons are tiny particles emitted from a radioactive substance administered to the subject.

Thus, in certain embodiments of the present invention, the antagonist or related-compound thereof is enzymatically-, radiolabel-, or fluorescently-tagged, as described above and used to diagnosis, monitor, and/or stage neuronal damage by cerebral edema. For example, the enzymatically-, radiolabel-, or fluorescently-tagged antagonist or related-compound thereof can be used to determine the size, limits and/or boundaries of tumors. It is difficult to determine the boundaries of certain tumors, for example, metastatic tumors. In metastatic tumors, glial cells are activated and form a capsule or gliotic capsule around the tumor. Thus, the labeled antagonist or related-compound thereof can be used to determine the border of tumor, which can enhance the efficiency of its removal by the surgeon. Still further, the labeled antagonist or related-compound thereof may be used to determine or define the penumbra or the areas at risk for later infarction or damage after a stroke.

C. Formulations and Routes for Administration of Compounds

Pharmaceutical compositions of the present invention comprise an effective amount of one or more modulators of $NC_{Ca\text{-}ATP}$ channel (antagonist and/or agonist) or related-compounds or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one modulators of $NC_{Ca\text{-}ATP}$ channel (antagonist and/or agonist) or related-compounds or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The modulators of $NC_{Ca\text{-}ATP}$ channel (antagonist and/or agonist) or related-compounds may comprise different types of carriers depending on whether it is to be administered in solid, liquid or aerosol form, and whether it need to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The modulators of $NC_{Ca\text{-}ATP}$ channel (antagonist and/or agonist) or related-compounds may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include modulators of $NC_{Ca\text{-}ATP}$ channel (antagonist and/or agonist) or related-compounds, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the modulators of $NC_{Ca\text{-}ATP}$ channel (antagonist and/or agonist) or related-compounds may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylatic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Pharmaceutical formulations may be administered by any suitable route or means, including alimentary, parenteral, topical, mucosal or other route or means of administration. Alimentary routes of administration include administration oral, buccal, rectal and sublingual routes. Parenteral routes of administration include administration include injection into the brain parenchyma, and intravenous, intradermal, intramuscular, intraarterial, intrathecal, subcutaneous, intraperitoneal, and intraventricular routes of administration. Topical routes of administration include transdermal administration.

D. Alimentary Compositions and Formulations

In preferred embodiments of the present invention, the modulators of $NC_{Ca\text{-}ATP}$ channel (antagonist and/or agonist) or related-compounds are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

E. Parenteral Compositions and Formulations

In further embodiments, modulators of $NC_{Ca-ATP}$ channel (antagonist and/or agonist) or related-compounds may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intraventricularly, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, DMSO, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

F. Miscellaneous Pharmaceutical Compositions and Formulations

In other preferred embodiments of the invention, the active compound modulators of $NC_{Ca-ATP}$ channel (antagonist and/or agonist) or related-compounds may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

XII. Diagnostic or Therapeutic Kits

Any of the compositions described herein may be comprised in a kit. In a non-limiting example, it is envisioned that a compound that selectively binds to or identifies SUR1 may be comprised in a diagnositc kit. Such compounds can be referred to as an "SUR1 marker", which may include, but are not limited to antibodies (monoclonal or polyclonal), SUR1 oligonucleotides, SUR1 polypeptides, small molecule or combinations thereof, antagonist, agonist, etc. It is envisioned that any of these SUR1 markers may be linked to a radioactive substance and/or a fluorescent marker and/or a enzymatic tag for quick determination. The kits may also comprise, in suitable container means a lipid, and/or an additional agent, for example a radioactive or enzymatic or florescent marker.

The kits may comprise a suitably aliquoted SUR1 marker, lipid and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the SUR1 marker, lipid, additional agent, and any other reagent containers in close confinement for commercial sale. Such containers may include injection or blow molded plastic containers into which the desired vials are retained.

Therapeutic kits of the present invention are kits comprising an antagonist, agonist or an related-compound thereof. Depending upon the condition and/or disease that is being treated, the kit may comprise an SUR1 antagonist or related-compound thereof to block and/or inhibit the $NC_{Ca\text{-}ATP}$ channel or the kit may comprise an SUR1 agonist or related-compound thereof to open the $NC_{Ca\text{-}ATP}$ channel. Such kits will generally contain, in suitable container means, a pharmaceutically acceptable formulation of SUR1 antagonist, agonist or related-compound thereof. The kit may have a single container means, and/or it may have distinct container means for each compound. For example, the therapeutic compound and solution may be contained within the same container; alternatively, the therapeutic compound and solution may each be contained within different containers. A kit may include a container with the therapeutic compound that is contained within a container of solution.

When the components of the kit are provided in one and/or more liquid solutions, the liquid solution is an aqueous solution, with a sterile aqueous solution being particularly preferred. The SUR1 antagonist, agonist or related-compounds thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

Examples of aqueous solutions include, but are not limited to ethanol, DMSO and/or Ringer's solution. In certain embodiments, the concentration of DMSO or ethanol that is used is no greater than 0.1% or (1 ml/1000 L).

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the SUR1 antagonist, agonist or related-compounds thereof is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the SUR1 antagonist, agonist or related-compounds thereof within the body of an animal. Such an instrument may be a syringe, pipette, forceps, and/or any such medically approved delivery vehicle.

In addition to the SUR1 antagonist, agonist or related-compounds thereof, the kits may also include a second active ingredient. Examples of the second active ingredient include substances to prevent hypoglycemia (e.g., glucose, D5W, glucagon, etc.), thrombolytic agents, anticoagulants, antiplatelets, statins, diuretics, vasodilators, etc. These second active ingredients may be combined in the same vial as the SUR1 antagonist, agonist or related-compounds thereof or they may be contained in a separate vial.

Still further, the kits of the present invention can also include glucose testing kits. Thus, the blood glucose of the patient is measured using the glucose testing kit, then the SUR1 antagonist, agonist or related-compounds thereof can be administered to the subject followed by measuring the blood glucose of the patient.

In addition to the above kits, the therapeutic kits of the present invention can be assembled such that an IV bag comprises a septum or chamber which can be opened or broken to release the compound into the IV bag. Another type of kit may include a bolus kit in which the bolus kit comprises a pre-loaded syringe or similar easy to use, rapidly administrable device. An infusion kit may comprise the vials or ampoules and an IV solution (e.g., Ringer's solution) for the vials or ampoules to be added prior to infusion. The infusion kit may also comprise a bolus kit for a bolus/loading dose to be administered to the subject prior, during or after the infusion.

EXAMPLES

The following examples are provided for further illustration of the present invention, and do not limit the invention. The examples provided herein are for illustrative purposes only, and are in no way intended to limit the scope of the present invention. While the invention has been described in detail, and with reference to specific embodiments thereof, it will be apparent to one with ordinary skill in the art that various changes and modifications can be made in the specific embodiments which are disclosed and still obtain a like or similar result without departing from the spirit and scope of the invention. Experiments and exemplary procedures are described below which provide additional enabling support for the present invention. In particular, in vitro studies using freshly isolated reactive astrocytes and in vivo studies using appropriate animal models are disclosed.

Cell Preparation

Reactive astrocytes are produced in vivo and harvested from adult brain in the following manner: gelatin sponges (Gelfoam®, Upjohn Co., Kalamazoo Mich.) are implanted into a stab wound in the parietal lobe of 8 week old Wistar rats as described herein. Sponge pieces are harvested at 8 days and washed three times in phosphate-buffered saline (PBS, pH 7.4) to remove adherent tissue. Depending on the number of NRAs required for a particular study, the sponge pieces may be harvested earlier or later after implantation into a stab wound, with the preferred harvest being conducted from about 2 days to about 30 days after implantation, and the most preferred range being conducted from about 2 days to about 3 days after implantation.

NRAs are freshly isolated from the sponge pieces in the following manner: washed pieces are placed in an Eppendorf tube containing artificial cerebrospinal fluid (aCSF) composed of (mM): 124 mM NaCl, 5.0 mM, 1.3 mM $MgCl_2$, 2.0 mM $CaCl_2$, 26 mM $NaHCO_3$, and 10 mM D-glucose; at pH 7.4, ≈290 mOsm, wherein the aCSF contains papain 20 U/ml, trypsin inhibitor 10 mg/ml and DNase 0.01% (Worthington, Lakewood, N.J.), the entirety of which is referred to as a "digestion system."

This digestion system is transferred to an incubator (humidified 90%/10% air/C02, 37° C.) for 20 minutes, and is gently triturated every 5 minutes. The cell suspension is centrifuged at 3,000 rpm for 1 minute. The pelleted cells are resuspended in aCSF and stored at 4° C. until studied.

For some studies, prior to resuspension in aCSF, the pelleted cells can be further purified by removing red blood cells (RBCs) using density gradient centrifugation in Histopaque-1077 (Sigma Diagnostics, St. Louis, Mo.). This further purification process can produce a population of cells in which <<1% are RBCs, as determined by phase contrast microscopy.

Scanning Electron Microscopy (SEM)

To study cell blebbing and swelling, freshly isolated cells are exposed at room temperature to $NaN_3$ then, after various time intervals, cells are fixed using iced 4% formaldehyde+1% glutaraldehyde for 24 hours then dehydrated using serial concentrations (35, 50, 75, 95, 100%) of ethanol. Specimens are critical point dried (Tousimis), gold coated (Technics), and viewed using an AMR 1000 scanning electron microscope.

Electrophysiology

Experiments are carried out at room temperature, 22-25° C., using NRAs within 24 hour of cell isolation. An aliquot of these freshly isolated NRAs is placed in the recording chamber filled with extracellular bath solution containing (a): NaCl 130, KCl 10, $CaCl_2$ 1, $MgCl_2$ 1, HEPES 32.5, glucose 12.5, pH 7.4. After viable cells adhere to the surface, flushing with excess solution washes away residual debris not previously removed by centrifugation. Membrane currents are amplified (Axopatch 200A, Axon Instruments, Foster City, Calif.) and sampled on-line at 5 kHz using a microcomputer equipped with a digitizing board (Digidata 1200A, Axon Instruments) and running Clampex software (version 8.0, Axon Instruments). Membrane currents are recorded in intact cells using both the cell-attached and the nystatin-perforated whole-cell configurations, according to methods described in Horn and Marty, 1988. Membrane currents are recorded in cell-free isolated membrane patches, using both the inside-out and outside-out configurations, such as those described in Hamill et al., 1981. Patch clamp pipettes, pulled from borosilicate glass (Kimax, Fisher Scientific, Pittsburgh, Pa.), have resistances of 6-8 MΩ a for single channel recordings and 2-4 MΩ a for experiments using the nystatin-perforated whole-cell technique. The bath electrode is a Ag/AgCl pellet (Clark Electromedical, Reading, England) that is placed directly in the bath except when the bath [Cl−] is altered, in which case an agar bridge made with 3 M KCl is used to connect to the bath.

The terms "intracellular" and "cytoplasmic" are interchangeable, as are the terms "extracellular" and "external". The terms "voltage" and "potential" are interchangeable when referring to membrane voltage or membrane potential. "Clamping" a cell membrane refers to holding the voltage across the cell membrane constant and measuring changes in membrane current as membrane resistance changes due to ion channel opening and closing ("voltage clamp") or holding the current across the cell membrane constant and measuring changes in membrane voltage as membrane resistance changes due to ion channel opening and closing ("current clamp"). When a membrane voltage is imposed on the cell, for example with a "ramp" or "pulse", it is understood that the cell membrane has been voltage-clamped and membrane current is being measured. When membrane "resting potential" is measured, it is understood that the cell membrane has been current-clamped and membrane voltage is being measured.

The "whole-cell" experimental configuration refers to a situation in which a recording pipette penetrates the cell membrane so that the pipette solution is continuous with the cytoplasm or the membrane under the pipette is perforated using nystatin, the external solution is in contact with the extracellular membrane, and current or voltage recordings represent measurements from the entire cell membrane. The "cell-attached patch" experimental configuration refers to a situation in which the pipette contacts the cell so that the patch is still forming part of the intact cell membrane and channels in the patch are recorded. The "outside-out patch" experimental configuration refers to a situation in which an excised patch of cell membrane is sealed to the tip of a recording pipette so that the pipette solution is in contact with the extracellular side of the membrane, the external solution is in contact with the cytoplasmic side of the membrane, and current or voltage recordings represent measurements from the excised patch of membrane. The "inside-out patch" experimental configuration refers to a situation in which an excised patch of cell membrane is sealed to the tip of a recording pipette so that the pipette solution is in contact with the cytoplasmic side of the membrane, the external solution is in contact with the extracellular side of the membrane, and current or voltage recordings represent measurements from the excised patch of membrane.

The term "patches" includes, but is not limited to: inside-out patches, outside-out patches, an excised patch of a cell membrane, or a cell-attached patch. The term "membrane preparation" includes patches as well as cell membranes isolated from mammalian cells or tissues. Isolated mammalian cell membranes are produced by methods well known in the art. One example of such a membrane preparation is a microsomal fraction purified from disrupted cells or a tissue sample by discontinuous sucrose gradient centrifugation.

Patches with seal resistance of <3 GΩ and access resistance of >50 MΩ are discarded. Macroscopic membrane currents are measured during step pulses (600 ms) or during ramp pulses (−140 to +50 mV at 0.32 mV/ms) from a holding potential of −67 mV.

Recording Solutions

For whole cell macroscopic recordings, a nystatin perforated patch technique is used, with a bath solution containing (mM): NaCl 130, KCl 10, $CaCl_2$ 1, $MgCl_2$ 1, HEPES 32.5, glucose 12.5, pH 7.4. The pipette solution contains (mM): KCl 55, $K_2SO4$ 75, $MgCl_2$ 8, and HEPES 10, pH 7.2. Nystatin, 50 mg (Calbiochem) is dissolved in dimethylsulfoxide (DMSO), 1 ml. Working solutions are made before the experiment by adding 16.5 μl nystatin stock solution to 5 ml of the base pipette solution to yield a final concentration of nystatin of 165 μg/ml and DMSO 3.3 μl/ml. This composition of the pipette solution includes $K_2SO_4$ instead of a portion of the KCl that would otherwise be included. The $SO_4^{2-}$ anion, unlike Cl−, is not permeable through the nystatin pore. Reducing the pipette [$Cl^-$] reduces the driving force for Cl− into the cell, thereby minimizing osmotic swelling of the cell that might otherwise occur during electrophysiological recording (Horn and Marty, 1988).

For cell-attached patch recording, a bath solution is used containing (mM): NaCl 130, KCl 10, $CaCl_2$ 1, $MgCl_2$ 1, HEPES 32.5, glucose 12.5, pH 7.4. The pipette contains (mM): KCl 145, $MgCl_2$ 1, $CaCl_2$ 0.2, EGTA 5, HEPES 10, pH 7.28. The measured osmolarity of the extracellular solution is ≈300 mOsm (Precision Systems, Natick, Mass.).

For most inside-out patch recording, a bath solution is used containing (mM): CsCl 145, $CaCl_2$ 4.5, $MgCl_2$ 1, EGTA 5, HEPES 32.5, glucose 12.5, pH 7.4. The pipette contains (a): CsCl 145, $MgCl_2$ 1, $CaCl_2$ 0.2, EGTA 5, HEPES 10, pH 7.28. For other inside-out patch recordings, $Cs^+$ in the above solutions is replaced with equimolar $K^+$.

For the inorganic cation substitution experiments, $Cs^+$ in the pipette is typically replaced by equimolar concentrations of individual test ions (Cook et al., 1990).

For outside-out patch recording, the pipette solution contains (mM): CsCl 145, $MgCl_2$ 1, $CaCl_2$ 0.2, EGTA 5, HEPES 10, pH 7.28. The standard bath solution contains (mM): CsCl 145, CaCl24.5, $MgCl_2$ 1, EGTA 5, HEPES 32.5, glucose 12.5, pH 7.4. For the organic cation substitution experiments, Cs+ in the bath is replaced with equimolar concentrations of test cation.

For experiments requiring low concentration of free $Ca^{2+}$ in bath solution, $Ca^{2+}$-EGTA buffered solution is employed, and free [$Ca^{2+}$] is calculated using the program WEBMAXC v2.10 available through the Stanford University World Wide Web Site). For [$Ca^{2+}$]=1 μM, 5 mM EGTA is used and 4.5 mM $Ca^{2+}$ salt. [$Ca^{2+}$]=1 μM is also used in solutions to test intracellular ATP and $Mg^{2+}$ activities.

Single-channel amplitudes used to calculate slope conductance are obtained by fitting a Gaussian function to an all-points amplitude histogram of records obtained at various potentials. To calculate open channel probability (n•Po) at various potentials and with different test agents, the all-points histogram is fit to a Gaussian function and the area under the fitted curve for the open channel is divided by the area under the fitted curve for the closed plus open channel. Values of n•Po at different concentration of test agents are fit to a standard logistic equation using a least-squares method.

For estimating ionic permeabilities of various cations relative to that for $K^+$, each permeability (Px/PK) is obtained from its reversal potential (Erev) by fitting to the Goldman-Hodgkin-Katz (GHK) equation well known in the art. See Goldman 1943; Hodgkin and Katz, 1949. Current-voltage data are fit to the GHK equation, assuming that both K+ and the test ion are permeant.

To estimate the pore size of the $NC_{Ca\text{-}ATP}$ channel of the present invention, the relative permeabilities of organic cations are evaluated. The Stokes-Einstein radius (rse) is calculated from the limiting conductivities (•) of the ions with the formula: $r_{SE}$•λ=constant. The constant is determined from the behavior of TEA at 25° C., for which λ=44.9 $cm^2\Omega{-1}$, $r_{SE}$=0.204 nm. The Stoke-Einstein radius is then converted to the molecular radius using correction factors read off from FIG. 6.1 in Robinson and Stokes, 1970. The equivalent limiting conductance for ethanolamine is given (ibid.) and those of other ions are calculated from their molecular weight by the formula, MW 0.5•λ=constant. The constant is determined by the value for ethanolamine at 25° C.: MW=62.1 and λ=4.42 $cm^{2\Omega-1}$ equi. Relative permeabilities (Px/PCs) are then plotted against the calculated ionic radii. The effect of solute size on the rate of penetration (permeability) through pores is expressed by the Renkin equation (Renkin, 1955):

$$a/a_0=[1-(r/R)]^{2}\cdot[1-2.104(r/R)+2.09(rR)^3-0.95(r/R)^5] \quad (1)$$

in which a, $a_0$, r, and R are the effective area of the pore, the total cross sectional area of the pore, radius of the solute, and radius of the pore, respectively.

Junction potentials are determined with an electrometer by measuring the diffusion potential established across a dialysis membrane and are subtracted when appropriate. Holding currents are not subtracted from any of the recordings. Difference currents are obtained by simply subtracting current records before and after perfusing $NaN_3$, with no other processing being employed.

Example 1

Morphological Changes with ATP Depletion Using $NaN_3$

Cultured neural cells have been shown to swell upon ATP depletion. See, Jurkowitz-Alexander et al., 1992; Jurkowitz-Alexander et al., 1993. Freshly isolated NRAs depleted of ATP also results in cell swelling. Ischemia or traumatic injury in brain also causes depletion of ATP in brain neural cells.

Figures 14A, 14B, 14C:
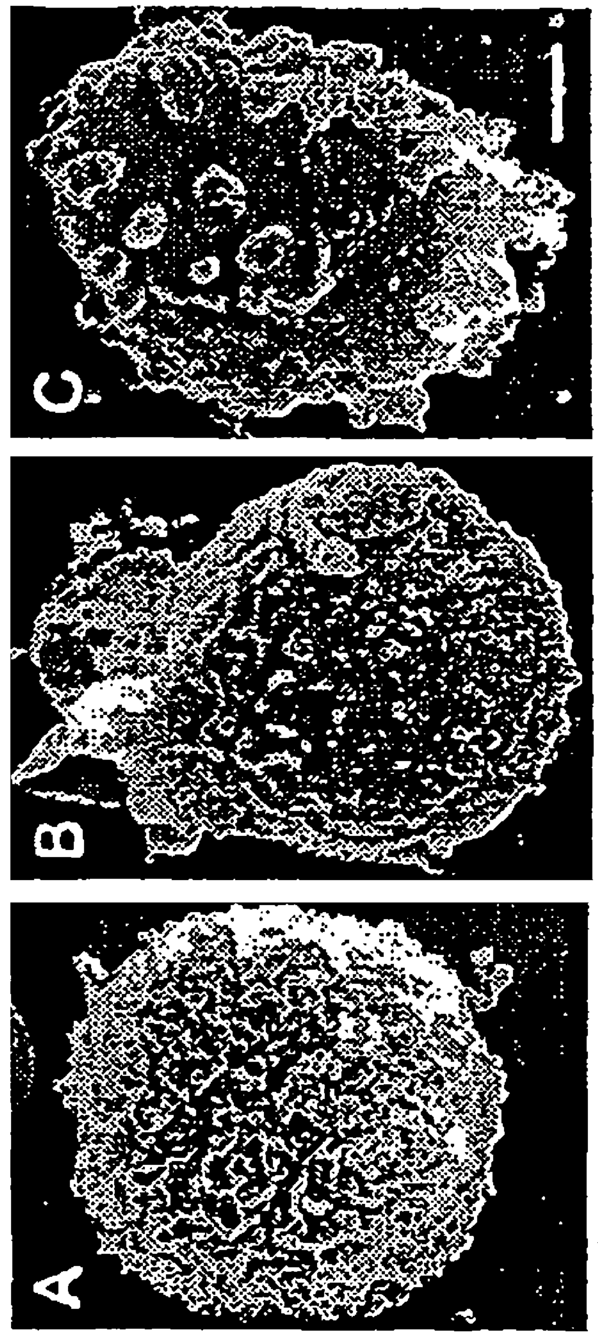
FIGS. 14A, 14B and 14C are scanning electron micrographs of freshly isolated native reactive astrocytes.

The surfaces of freshly isolated NRAs are highly complex, exhibiting small membrane evaginations and fine processes that decorate the entire cell surface, as shown in the scanning electron micrograph in FIG. 14A. Exposure of NRAs to $NaN_3$ (1 mM) causes changes in the surface appearance, characterized early-on by loss of complex structure and development of surface blebs (FIG. 14B), followed later by a grossly swollen appearance with complete loss of fine structure and formation of multiple large blebs (FIG. 14C). Therefore, NRAs undergo blebbing and swelling after $NaN_3$-induced ATP depletion.

Phase contrast microscopy is also useful for assessing this process, although fine structure cannot be resolved. Blebbing is visibly apparent 10-15 minutes after exposure to $NaN_3$. Morphological changes of this sort are attributable to loss of cytoskeletal integrity, combined with action of an osmotic force that causes swelling of the cell.

To assess the contribution of the osmotic gradient to cell swelling, the experiment is repeated in the presence of mannitol, an impermeant oncotic agent. Mannitol (50 mM), at a concentration sufficient to increase osmolarity of the extracellular solution from 300 to 350 mOsm, delays bleb formation >30 minutes after exposure to $NaN_3$. Cellular ATP also can be depleted using exposure to NaCN (2.5 mM) plus 2-deoxyglucose (10 mM). See, Johnson et al., 1994. Similar morphologic changes, including cell membrane blebbing and delay of blebbing by mannitol are obtained following exposure to NaCN and 2-deoxyglucose. This demonstrates that the effect of $NaN_3$ is due in fact to ATP depletion and not to any other non-specific effect of $NaN_3$.

Example 2

General Electrophysiological Properties of NRAs

The macroscopic currents of whole cell preparations of N u s are characterized by small inward currents at negative potentials, large outward currents at positive potentials, and a flat "plateau" region at intermediate potentials. NRAs exhibit macroscopic currents that are consistent with observations in primary cultured cells of the same origin. See, Chen et al., 2003; Chen et al., 2001. The NRAs exhibited inward currents negative to the $K^+$ equilibrium potential ($E_K$) are usually <100 pA, much smaller than values reported in cultured neonatal astrocytes (Ransom and Sontheimer, 1995), but consistent with findings in astrocytes freshly isolated from injured brain (Bordey and Sontheimer, 1998; Schroder et al., 1999). The large outward currents in NRAs are partially blocked by charybdotoxin (100 nM), iberiotoxin (100 nM) and tetraethylammonium chloride (5 mM), consistent with the presence of a large conductance $Ca^{2+}$-activated $K^+$ channel. See, Perillan et al., 1999. The outward current that remains in the presence of charybdotoxin can be further blocked by 4-aminopyridine (5 mM), and exhibits kinetic properties typical of a delayed rectifier $K^+$ channel. Consistent with a previous report (Perillan et al., 1999), fast inward voltage dependent currents attributable to $Na^+$ channels are observed in less that 1% of NRAS.

$NaN_3$ Elicits Depolarizing Inward Current Due to 35 DS Channel

Current clamp recordings are used to investigate the effect of ATP depletion by $NaN_3$ in NRAs. For these experiments, a nystatin-perforated patch method is used to assure that the metabolic disruption comes from drug application and not cell dialysis. Extracellular application of $NaN_3$ (1 mM; room temperature) results in a large and swift depolarization of the cells (FIG. 1A). $NaN_3$ rapidly depolarizes the cells to $E_m \approx 0$ mV (−4.3±0.9 mV). Depolarization usually starts ~1 minute after addition of $NaN_3$, is complete in <3 minutes, and is irreversible on washout of drug. Ouabain is a known $Na^+/K^+$-ATPase blocker. See, Brismar and Collins, 1993. The magnitude of the depolarization observed with $NaN_3$ far exceeds the small reversible depolarization induced by ouabain (1 mM). This indicates that the large depolarization observed after exposure to $NaN_3$ is not caused by $Na^+/K^+$-ATPase pump failure.

The time course of depolarization with $NaN_3$ is appreciably more rapid than the time course for development of cell membrane blebbing observed with the same treatment. Also, neither the time course nor the magnitude of the depolarization is affected by raising the extracellular osmolarity with 50 mM mannitol, a treatment that substantially delays bleb formation. Thus, depolarization is a primary event, not secondary to cell swelling or stretch.

Voltage-clamp recordings show that exposure to $NaN_3$ results in a net increase of inward current in NRAs. Recordings obtained using both ramp (FIG. 1B) and step pulses (FIG. 1C) show significantly larger currents after $NaN_3$ treatment, as shown by comparing the recordings before (a) and after (b) $NaN_3$ treatment. A plot of the "difference currents", obtained by subtracting the current-voltage curve before drug from that after drug (line c in FIG. 1B), indicates that the new current turned on by $NaN_3$ reverses near 0 mV. A reversal potential near 0 mV is indicative that the $NaN_3$-induced current results from a non-specific cation conductance.

Figures 1C, 1D:
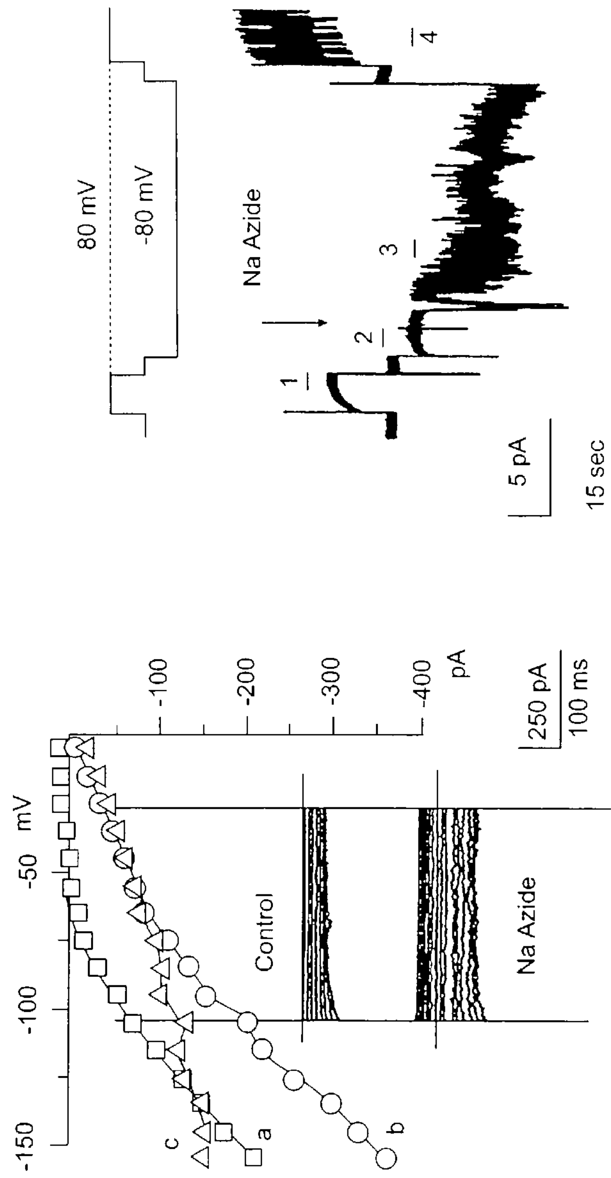
FIG. 1C shows whole cell voltage-clamp recordings during step pulses (a) before and (b) after exposure to $NaN_3$; (c) is the difference current.
FIG. 1D shows cell-attached patch recording of single ion channel openings induced by $NaN_3$ at membrane potentials of (3) −80 mV and (4) 80 mV, compared to control patches at membrane potentials of (1) 80 mV and (2) −80 mV.
Figures 1E, 1F:
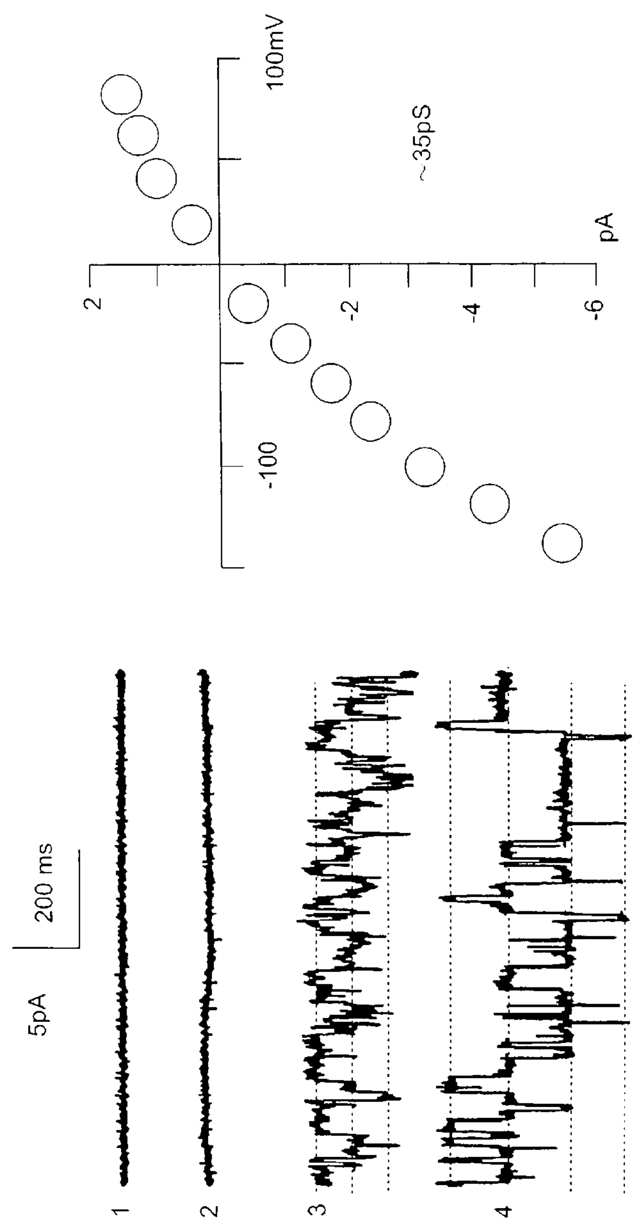
FIG. 1E shows the cell-attached patch currents of FIG. 1D, shown at higher time resolution.
FIG. 1F shows the cell-attached patch single-channel current-voltage relationship.

To further characterize the $NaN_3$-induced current, cell-attached patch recordings are used. Exposure to $NaN_3$ elicits single channel currents in patches that exhibit no single channel currents prior to addition of drug (FIG. 1D). After addition of $NaN_3$, recordings at low temporal resolution reveal a large increase in current variance that, after increasing temporal resolution, is revealed to be due to single channel events (FIG. 1E at 3 and 4). The amplitudes of single-channel events recorded at different membrane potentials are plotted in FIG. 1F, which shows that $NaN_3$ activates a single channel conductance of ≈35 pS that exhibits weak inward rectification when measured in the cell-attached configuration.

Additional experiments are carried out in the cell-attached configuration with the pipette solution supplemented with various drugs. The $NaN_3$-induced single channel currents are not blocked by 10 mM TEA, 5 mM 4-AP, 100 nM iberiotoxin, 100 nM charybdotoxin, or 1 μM tetrodotoxin (4-6 patches for each compound). These experiments indicating that a typical $K^+$ or $Na^+$ channel is not involved. Also, because 0.2 mM $Ca^{2+}$ is included in the pipette solution, these single channel openings are unlikely to be due to monovalent cation influx via an L-type $Ca^{2+}$ channel.

Similar depolarization and activation of a 35 pS channel are obtained when cellular ATP is depleted using exposure to NaCN (2.5 mM) plus 2-deoxyglucose (10 mM). This demonstrates that the effect of $NaN_3$ is caused by ATP depletion and not by any other non-specific effect of $NaN_3$.

Apart from ATP depletion, patch excision is also a highly reliable method for channel activation. Of the more than 120 cells studied in the cell-attached configuration, spontaneous channel activity attributable to a ≈35 pS conductance is detected in only 2 cells. Thus, the $NC_{Ca-ATP}$ channel of the present invention is typically silent in metabolically healthy cells. By contrast, a ≈35-pS channel is present in >90% of inside-out patches formed from NRAs not exposed to $NaN_3$ or other metabolic toxins, thus demonstrating that an intracellular element lost on patch excision normally prevents channel activation.

Another potential mechanism of channel activation other than patch excision is regulatory volume decrease (RVD). Cell swelling is widely recognized as a stimulus that initiates RVD, a phenomenon accompanied by activation of various currents, including a non-selective cation channel in some systems. See, Ono et al., 1994. When membrane patches are studied in a cell-attached configuration, hyposmotic stimulation (210 mosmo/kg$H_2O$) activated single channel events, but none exhibit a ≈35 pS conductance. This finding indicates that the depolarization and channel activation observed with $NaN^3$ are not part of an RVD response secondary to $NaN_3$-induced cell swelling, and accords with the previously noted observation that $NaN_3$-induced depolarization preceded cell swelling. This fact is supported by the observation that the $NC_{Ca-ATP}$ channel is seldom observed in cell attached patches from healthy cells, but becomes evident in >90% of patches after conversion to an inside-out configuration. Also, the $NC_{Ca-ATP}$ channel is lost shortly after culturing reactive astrocytes.

Example 3

Relative Permeabilities and Pore-Size

Figures 2A, 2B:
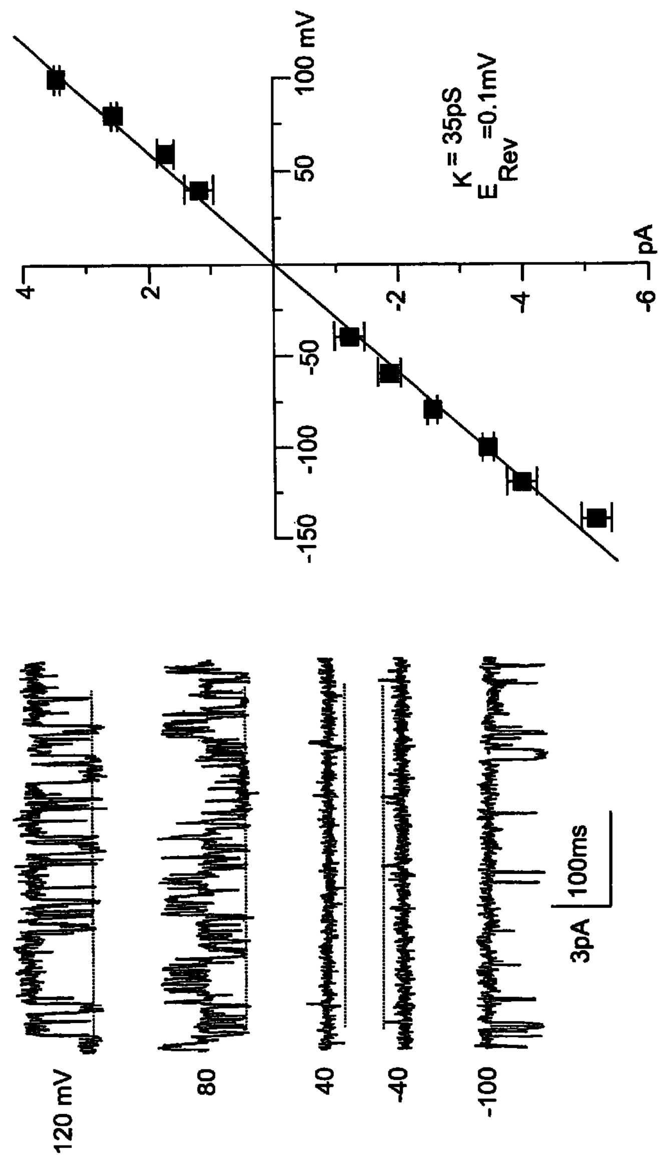
FIG. 2A shows single channel currents recorded in an inside-out patch at different membrane potentials; dotted line indicates channel closing.
FIG. 2B is a plot of inside-out patch single channel amplitude vs. membrane potentials.

The channel is further characterized using membrane patches in the inside-out configuration. Records obtained during test pulses to various potentials with equal $[K^+]$ on both sides of the membrane are shown in FIG. 2A. Amplitude histograms are constructed of events observed at potentials from −140 mV to +100 mV, and values (mean±SE) for 4 patches are plotted and show in FIG. 2B. Fit of the data to a linear equation indicates a slope conductance of 35 pS, with an extrapolated reversal potential ($E_{rev}$) of +0.1 mV, close to the expected $K^+$ reversal potential ($E_K$) of 0 mV.

Figures 3A, 3B:
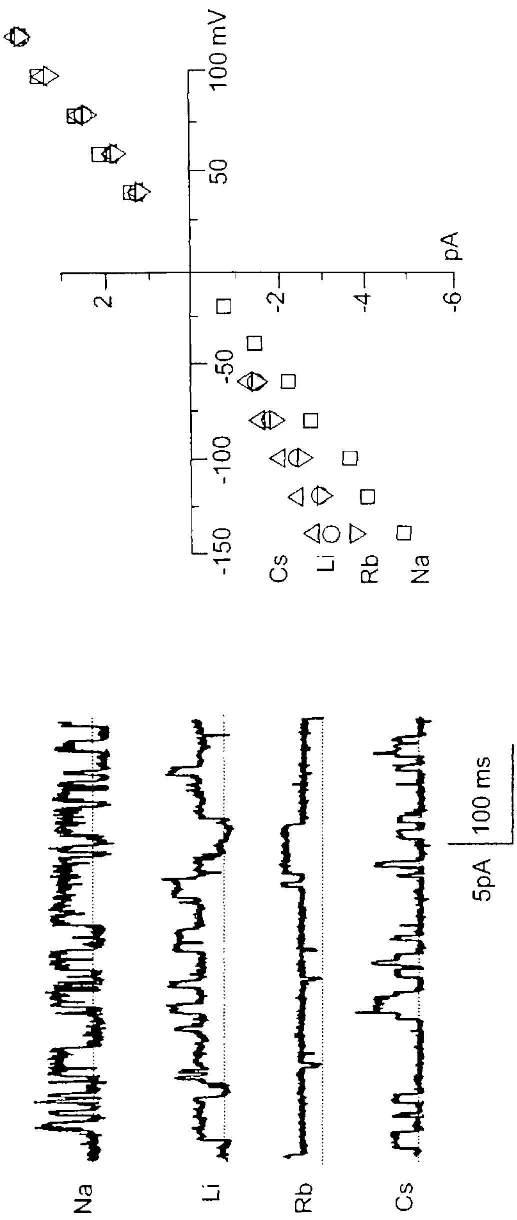
FIG. 3A shows single channel currents recorded in an inside-out patch with various alkaline ions substituting for $K^+$ in the pipette; dotted line indicates channel closing.
FIG. 3B is a plot of channel amplitude vs. membrane potential with various alkaline ions substituting for $K^+$ in the pipette.

In addition to conducting $K^+$, the channel transports a variety of alkaline ions (FIG. 3A), indicating that it is a non-selective cation channel. In inside-out patches, the conductance of the channel is measured with various alkaline ions in the pipette solution, including $Cs^+$, $Na^+$, $Rb^+$, $K^+$, and $Li^+$, always with equimolar $K^+$ in the bath solution. Current-voltage data are fit to the GHK equation. $Na^+$ is shown to have a nearly equal slope conductance (32.6 pS) compared to $K^+$ (35.2 pS), but the slope conductance is reduced with other cations (FIG. 3B). Measurements of $E_{rev}$ are used to estimate relative permeabilities for the series of alkaline ions. Values for relative permeabilities derived from the GHK equation are $P_{Cs}^+/P_K^+=1.06$, $P_{Na}^+/P_K^{30}=1.04$, $P_{Rb}^+/P_K^+=1.02$, and $P_{Li}^+/PK^+=0.96$, indicating that this channel is nearly equally permeable to all monovalent cations.

The permeability of the $NC_{Ca-ATP}$ channel of the present invention to anions, such as $Cl^-$, is also assessed. After measuring single channel current amplitudes at different potentials with 145 mM KCl, the bath solution is changed to equimolar $K^+$ gluconate. When an agar bridge is used, the solution change resulted in a change in $E_{rev}$<O.5 mV, indicating that the $NC_{Ca-ATP}$ channel of the present invention is essentially impermeable to anions.

Figures 3C, 3D:
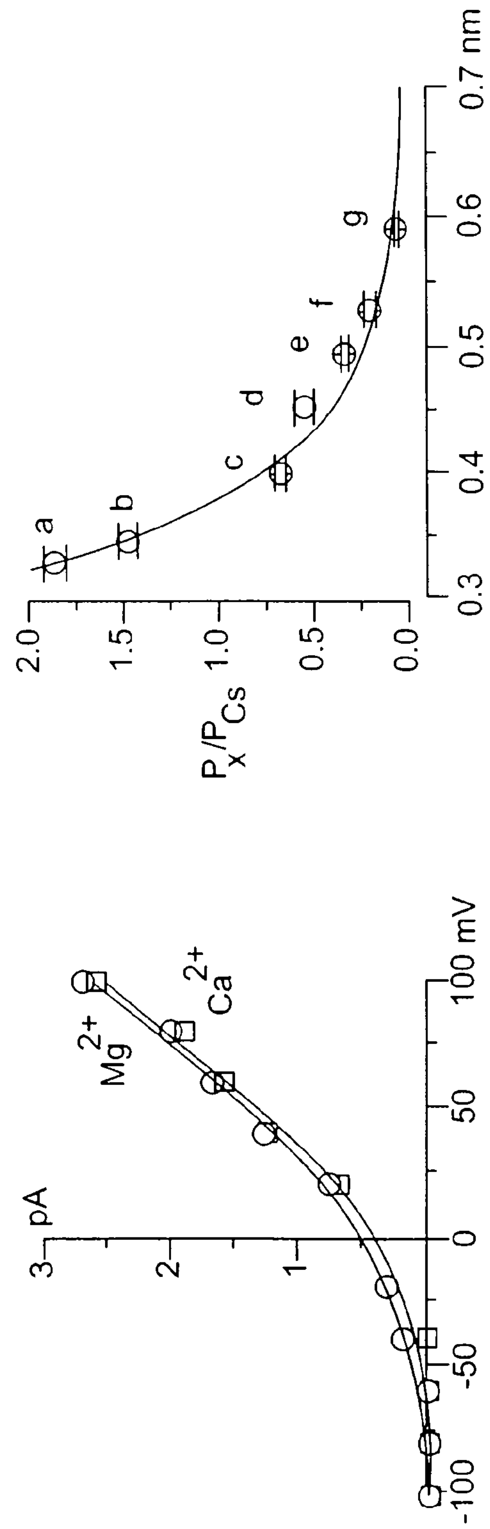
FIG. 3C is a plot of channel amplitude measured in inside-out patches vs. voltage with Ca2$^+$ and $Mg^{2+}$ substituting for $K^+$ in the pipette. To estimate channel pore size.
FIG. 3D is a plot illustrating the relationship between the permeability (relative to $Cs^+$) and the molecular radius of a series of monovalent organic cations, which included: (a) methanolmine, (b) guanidium, (c) ethanolamine, (d) diethylamine, (e) piperazine, (f) Tris, and (g) N-methylglucamine, data indicating an equivalent pore size of 0.67 nm.

The permeability of the instant channel to divalent cations, $Ca^{2+}$ and $Mg^{2+}$, is also investigated (FIG. 3C). When potassium ion in the pipette solution is replaced with 75 mM $Ca^{2+}$ or $Mg^{2+}$, inward currents are not detected. Fit to the GHK equation gives best fit values for $E_{rev}$<<−65 mV for $Ca^{2+}$ and $Mg^{2+}$ respectively, giving relative permeabilities with respect to $K^+$ of <<0.001, indicating that this channel is essentially impermeable to divalent cations.

Because the $NC_{Ca-ATP}$ channel of the present invention discriminates very poorly among monovalent inorganic cations (FIGS. 3A and B), experiments are performed to determine the equivalent pore size of the channel by measuring channel permeability, relative to $Cs^+$, for a wide range of organic cations. Using an outside-out patch configuration, single-channel current-voltage relations are plotted to obtain $E_{rev}$ for a number of organic cations. Permeability ratios are then derived from fits to the GHK equation. For each of the organic cations (a) nethanolamine, (b) guanidium, (c) ethanolamine, (d) diethylamine, (e) piperazine, (f) Tris, and (g) N-methylglucamine, the mean value of relative permeability measured is plotted against its hydrated molecular radius (FIG. 3D, empty circles). The permeability ratios define a smoothly declining series of values that are well fit by the Renkin equation. The Renkin equation describes the permeation of a rigid sphere through a cylindrical pore. Renkin, 1955. Least-squares, fit to the equation, indicates an equivalent pore radius of 0.67 nm for the $NC_{Ca-ATP}$ channel of the present invention. A 0.67 nm pore radius is similar to pore sizes of 6 A, found for the $Ca^{2+}$ channel (McCleskey and Almers, 1985) and 7.4 A, found for the nAChR channel (Adams et al., 1980). Junction potentials determined according to the methods described herein generally did not exceed 5 mV.

Example 4

Inhibition by $[ATP]_i$

The $NC_{Ca-ATP}$ channel is inhibited by intracellular ATP, based on the finding that this channel is turned on after depleting intracellular ATP by exposure to $NaN_3$ (See FIGS. 1B, 1C, 1D and 1E) or to NaCN plus 2-deoxyglucose. This fact is supported by the observation that the $NC_{Ca-ATP}$ channel of the present invention is seldom observed in cell-attached patches from healthy cells, but becomes evident in >90% of patches after conversion to an inside-out configuration.

Figure 4A:
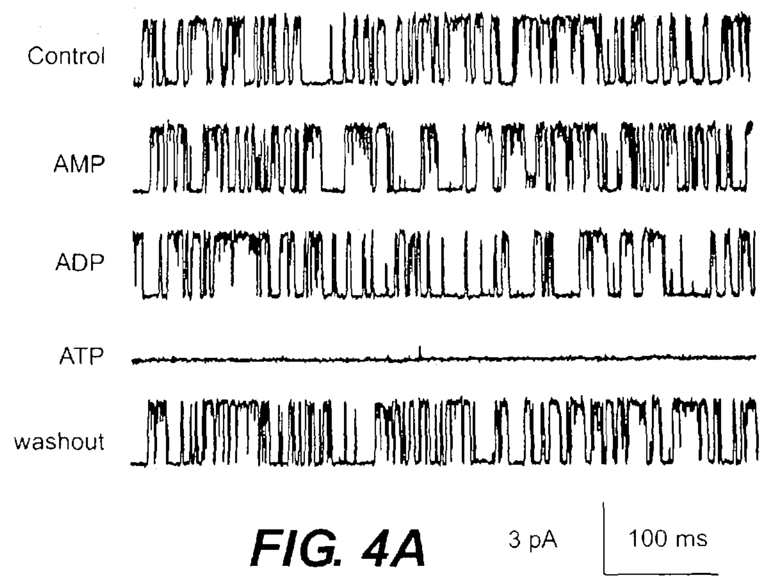
FIG. 4A shows single channel recordings in an inside-out patch in the absence and presence of cytoplasmic ATP.
Figure 4B:
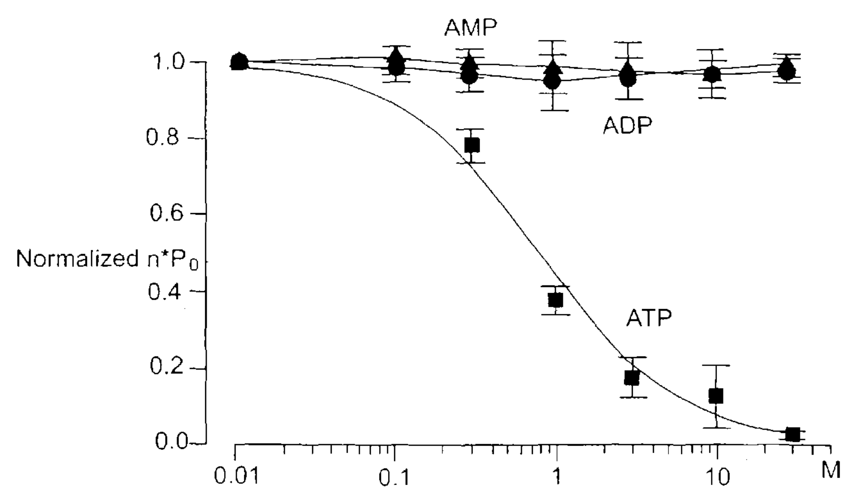
FIG. 4B is a plot of normalized open channel probability (n•Po) vs. concentration of cytoplasmic ATP.

Inside-out patches are used to demonstrate that the channel is sensitive to block by ATP on the cytoplasmic side of the membrane. Patches are studied using $Cs^+$ as the charge carrier, to assure that no $K^+$ channel, such as Kir2.3 or $K_{ATP}$, is contributing to patch activity. With no ATP and 1 μM $Ca^{2+}$ in the bath, the $NC_{Ca-ATP}$ channel exhibits vigorous openings. 1 mM ATP causes profound diminution in channel activity, an effect that is readily reversed on washout (FIG. 4A); however, channel availability is unaffected by 1 mM AMP or ADP. The open channel probability (n•Po) is measured at different $[ATP]_i$, and these values are normalized to that obtained at $[ATP]_i$=0 mM, and fitted to a standard logistic equation. As shown in FIG. 4B, the $NC_{Ca-ATP}$ channel is blocked by $[ATP]_i$ in a dose-dependent manner. Half maximum inhibition ($IC_{50}$) is observed at $[ATP]_i$=0.79 μM with a Hill coefficient of 1, and channel activity is completely abolished at [ATP]i>30 μM. ADP and AMP, have no effect on the $NC_{Ca-ATP}$ channel activity in inside-out patches.

This in vitro assay for determining the concentration of the test compound which achieves a half-maximal inhibition of channel activity (ICSO) may be used to formulate dose in animal models to achieve a circulating plasma concentration range that includes the $IC_{50}$.

Example 5

Activation by $[Ca^{2+}]_i$

Figure 5A:
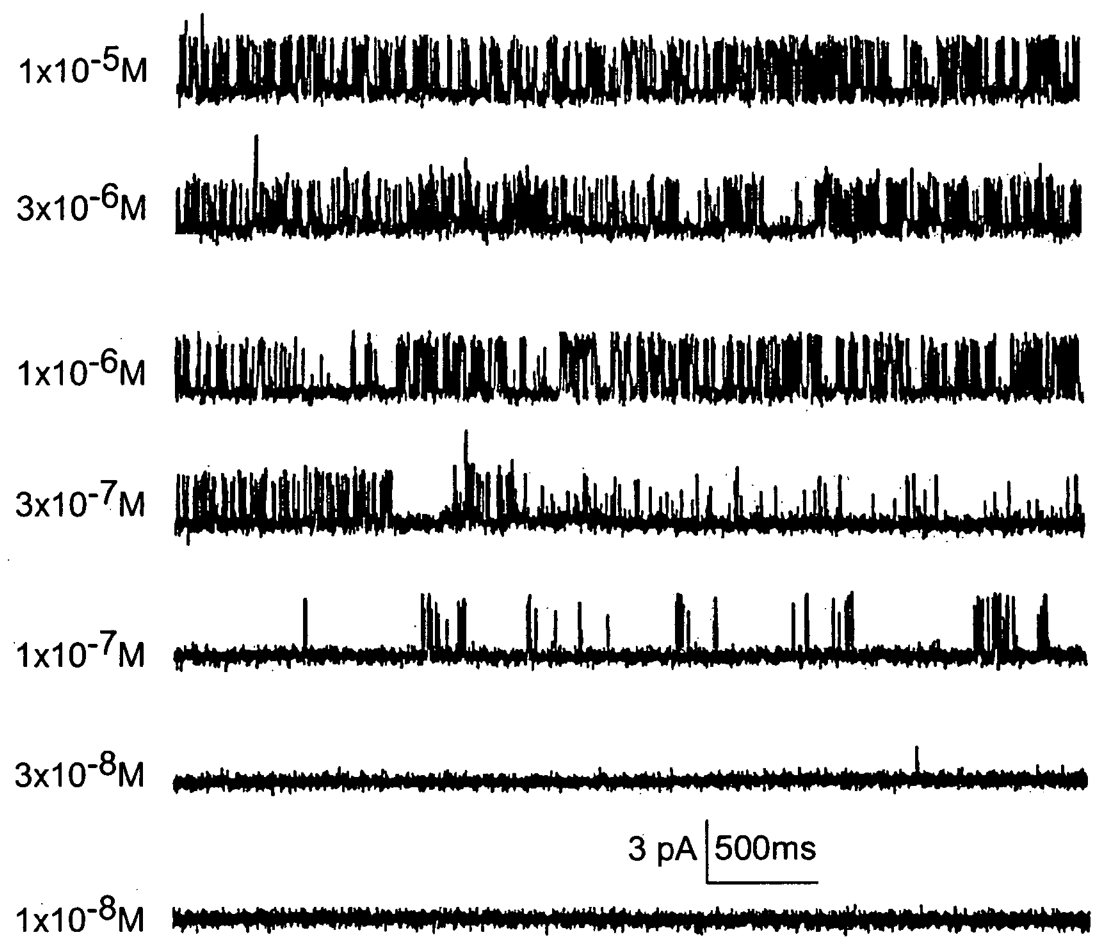
FIG. 5A shows current records from an inside-out patch exposed to different concentrations of $[Ca^{2+}]_i$.
Figure 5B:
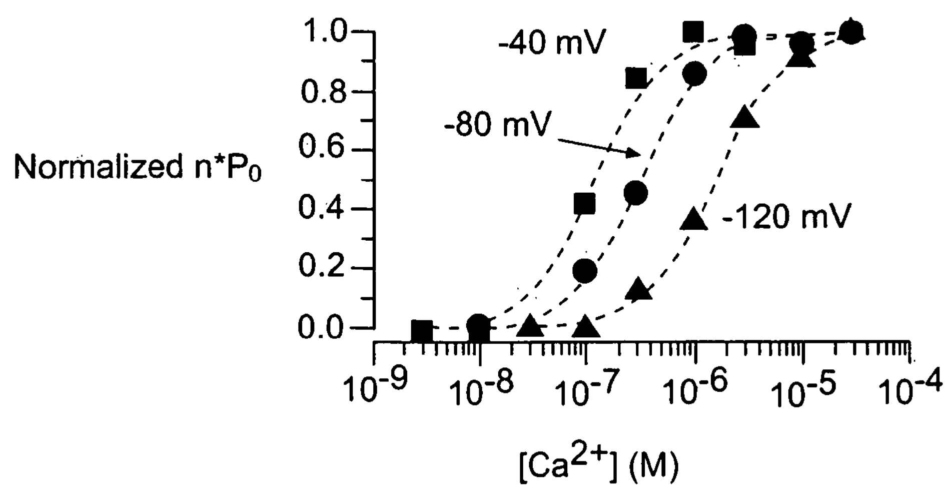
FIG. 5B the values of n•Po measured at the membrane potentials and $[Ca^{2+}]_i$ indicated.

The $Ca^{2+}$ concentration on the cytoplasmic side of the membrane is also found to regulate activity of the $NC_{Ca-ATP}$ channel of the present invention. The relationship between $NC_{Ca-ATP}$ channel activity and $[Ca^{2+]}_i$ is examined using inside-out patches studied at membrane potential (Em)=−80 mV. Changing $[Ca^{2+}]_i$ clearly affects activity of the $NC_{Ca-ATP}$ channel (FIG. 5A). When free $[Ca^{2+}]_i$ is <30 nM, no channel activity is apparent. With $[Ca^{2+}]_i$>30 nM, the open probability (n•Po) increases in accordance with the $[Ca^{2+}]_i$, up to ≈1 μM of $[Ca^{2+}]_i$ at which activity is near maximum. The effect of $Ca^{2+}$ on channel availability is found to depend on membrane voltage. Values of nP•o from 4-9 patches obtained at three different potentials, Em=−40 mV, −80 mV and −120 mV, are normalized to values observed with 3 μM $[Ca^{2+}]_i$. These data are fit to a standard logistic equation using a Hill coefficient of 1.5 and half-maximum values of 0.12 μM, 0.31 μM and 1.5 μM at −40 mV, −80 mV and −120 mV, respectively (FIG. 5B). These data indicate that channel activity is strongly dependent on $[Ca^{2+}]_i$ at physiologically relevant concentrations, and that the effect of $Ca^{2+}$ is voltage dependent, consistent with a $Ca^{2+}$ binding site inside the electric field of the membrane.

Example 6

Internal $Mg^{2+}$ Causes Rectification

Figure 6:
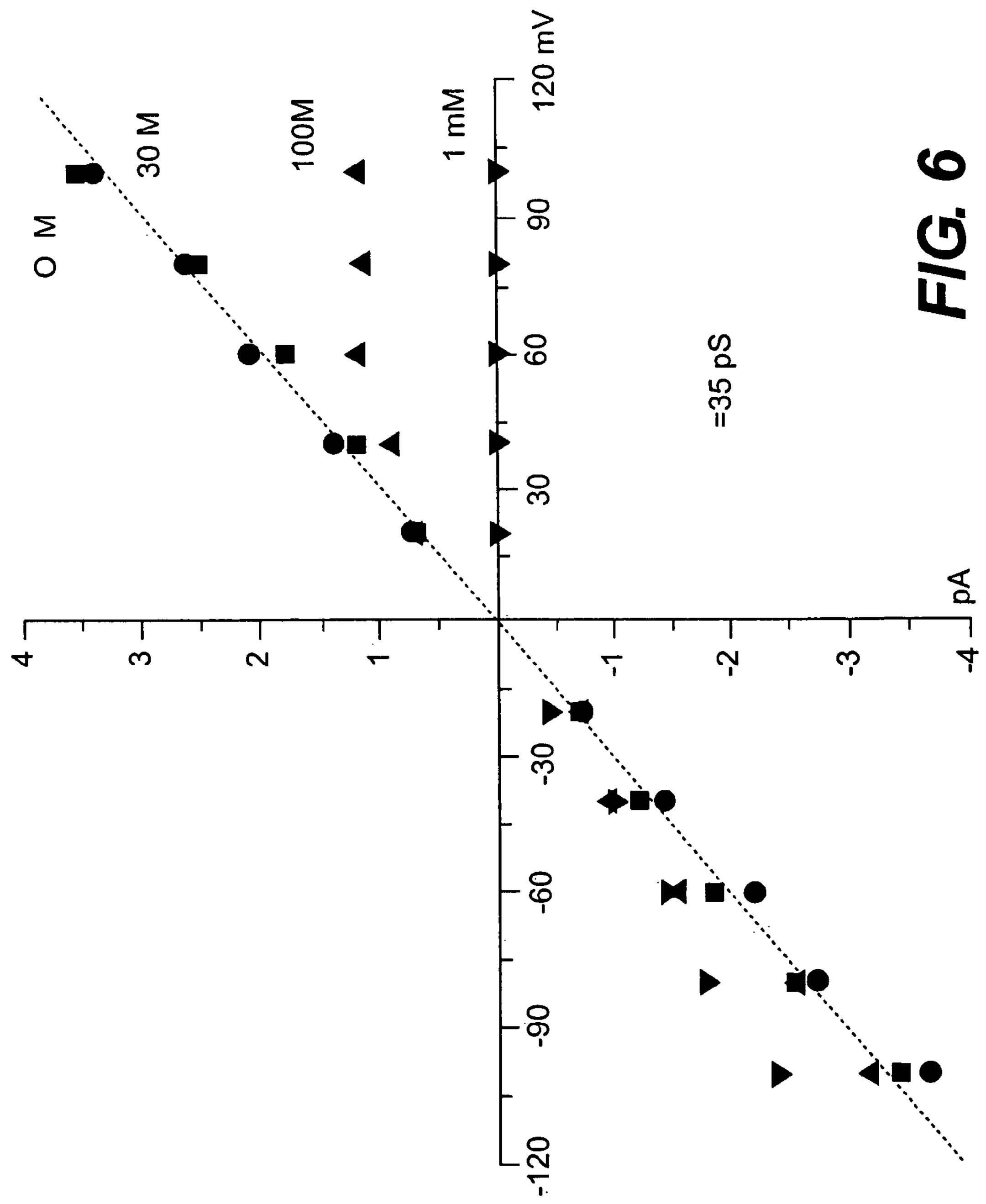
FIG. 6 is a plot of mean single channel amplitudes obtained in an inside-out patch configuration at different potentials studied and with different $[Mg^{2+}]_i$; the dotted line indicates 35 pS conductance.

Because certain channels are sensitive to intracellular $Mg^{2+}$ (Chuang et al., 1997; Perillan et al., 2000), experiments are carried out to determine whether the channel rectification observed in cell-attached patch recordings (see FIG. 1F) might be due to intracellular $Mg^{2+}$. Using inside-out patches studied with equimolar $K^+$ on both sides of the membrane, $[Mg^{2+}]$ is varied on the cytoplasmic side. Single channel records and channel amplitudes observed with different $[Mg^{2+}]_i$ are shown (FIG. 6). No rectification is evident with $[Mg^{2+}]_i$ 30 μM, but at $[Mg^{2+}]_i$≈100 μM, increasingly strong rectification is present. At 100 μM, $Mg^{2+}$ appears to produce a flickery block.

Example 7

Identifying the Presence of SUR in NRAs

To determine if SUR receptors are present in NRAs, the binding of glibenclamide to these cells is assessed by fluorescence microscopy. Eight week old Wistar rats are injured by a stab wound into the subcortical white matter and implantation of a gelatin sponge as previously described herein. Eight days later, tissue sections of formaldehyde-fixed brains from injured animals are incubated for 60 minutes at room temperature with 20 nM FITC-conjugated glibenclamide. A fluorescence image of the gelatin sponge shows labeled cells lining the cavities of the sponge. In brain adjacent to the injury, essentially no glibenclamide binding is apparent. These data indicate that SUR, which are not normally present in subcortical white matter, are expressed in neural cells following traumatic injury.

RT-PCR

Figures 7A, 7B:
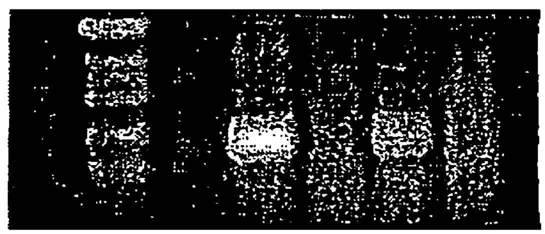
FIG. 7 (comprised of FIGS. 7A and 7B) shows that presence of SUR1 mRNA and absences of Kir6.1 and Kir 6.2 in reactive astrocytes. Lanes 3 and 5 in FIG. 7A show the presence of SUR1 in insulinoma RIN-m5f cells and NRAs, respectively. Lanes 4 and 6 in FIG. 7A show that SUR2 is absent in both cell types. Lanes 3 and 4 in FIG. 7B show that Kir6.1 is present in insulinoma RIN-m5f cells and Kir6.2 is absent from the insulinoma cells, respectively. Lanes 5 and 6 in FIG. 7B show that neither Kir6.1 nor Kir6.2 is present in NRAs, respectively.

Total RNA is extracted from cells and used to synthesize cDNA, which is amplified from reactive astrocytes is analyzed by RT-PCR on an agarose gel stained with ethidium bromide. FIG. 7A is a photograph of the gel showing the RT-PCR for SUR1 and SUR2. FIG. 7B is a photograph of a gel showing the RT-PCR for Kir6.1 and Kir6.2. Lanes 3 and 4 in FIGS. 7A and 7B show the RT-PCR for insulinoma cells. Lanes 5 and 6 show the RT-PCR for reactive astrocytes. Lane 1 in FIGS. 7A and 7B represents ladder size markers; Lane 2 in FIGS. 7A and 7B is a blank control. In FIG. 7A, lanes 3 and 4 show the SUR1 and SUR2 experiments, respectively, in insulinoma cells. Insulinoma cells are known to express SUR1, but not SUR2. Lanes 5 and 6 in FIG. 7A show the SUR1 and SUR2 experiments in reactive astrocytes, respectively. FIG. 7A shows that SUR1 mRNA is present in reactive astrocytes, as well as in the control insulinoma cells. SUR2 is absent in both cell types. In FIG. 7B, lanes 3 and 4 show the Kir6.1 and Kir6.2 experiments in insulinoma cells, respectively. Kir6.1 is present in insulinoma cells, but Kir6.2 is not. Kir6 is the potassium channel associated with SUR1 in insulinoma cells. Lane 5 and 6 in FIG. 7B show that neither Kir6.1 nor Kir6.2 is present in reactive astrocytes. Therefore, reactive astrocytes express SUR1 mRNA, but Kir6.1 and Kir6.2 mRNA is absent from the cells.

The presence of SUR1 in reactive astrocytes combined with the regulation of the $NC_{Ca\text{-}ATP}$ channel in astrocytes by SUR antagonists indicates that SUR regulates the $NC_{Ca\text{-}ATP}$ channel of the present invention.

Example 8

Tryptic Digests

Figure 8:
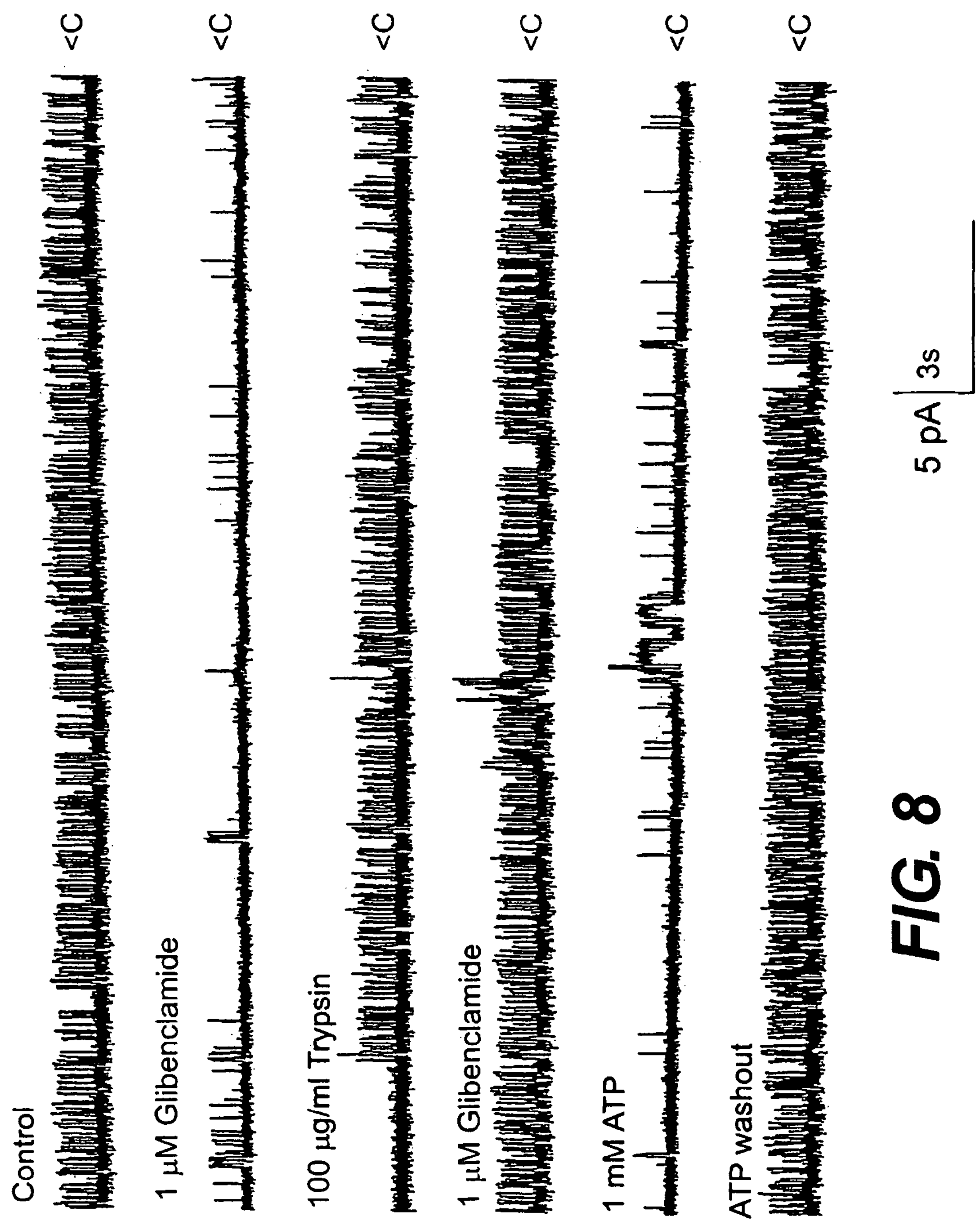
FIG. 8 shows current recordings in an inside-out patch to illustrate the effects of tryptic digestion on channel sensitivity to glibenclamide and ATP.

A characteristic feature of SUR-regulated $K_{ATP}$ function is that tryptic digestion of the cytoplasmic face of the channel, but not its extracellular face causes loss of inhibition by sulfonylureas, without altering sensitivity to ATP and without changing the biophysical properties of the channel. The effect of trypsin on $NC_{Ca\text{-}ATP}$ function is shown in FIG. 8. Under control conditions, channel activity in the inside-out patch configuration is strongly inhibited by 1 μM glibenclamide. Exposure to 100 pg/ml trypsin on the cytoplasmic side of the membrane for 3 minutes yields a patch that still exhibits strong channel activity, but that channel activity is completely unaffected by glibenclamide. After such trypsin treatment of the cytoplasmic side, the biophysical properties of the channel, including open channel conductance, open channel times, $Ca^{2+}$-mediated activation are unchanged, and the channel still maintains its typical sensitivity to ATP. By contrast, exposure of the extracellular side of the membrane has no effect on glibenclamide inhibition. These trypsin digest data on the $NC_{Ca\text{-}ATP}$ channel of the present invention provide additional supporting evidence that SUR1 is involved in regulation of the $NC_{Ca\text{-}ATP}$ channel, because the results compare to previous findings from SUR1-regulated $K_{ATP}$ channels. Linkage of a SUR to a non-selective ATP sensitive cation channel, has not been shown previously.

Assays for Compounds or Compositions that Block $NC_{Ca\text{-}ATP}$ Channel and Inhibit Neural Cell Swelling Example 9

Effects of Sulfonylurea Compounds

Figure 9A:
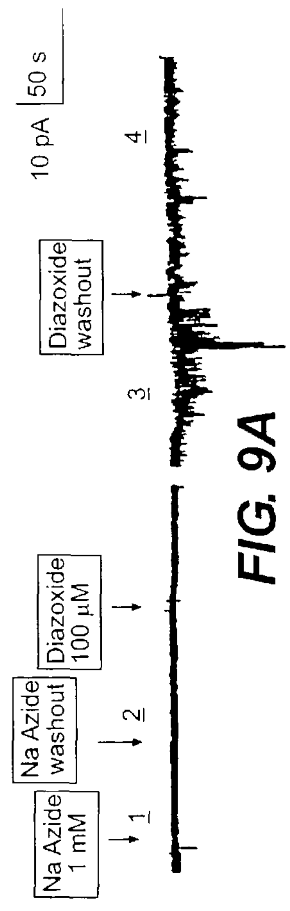
FIG. 9A shows the outside-out patch recordings with Na azide and diazoxide applied to the extracellular side of the membrane.
Figure 9B:
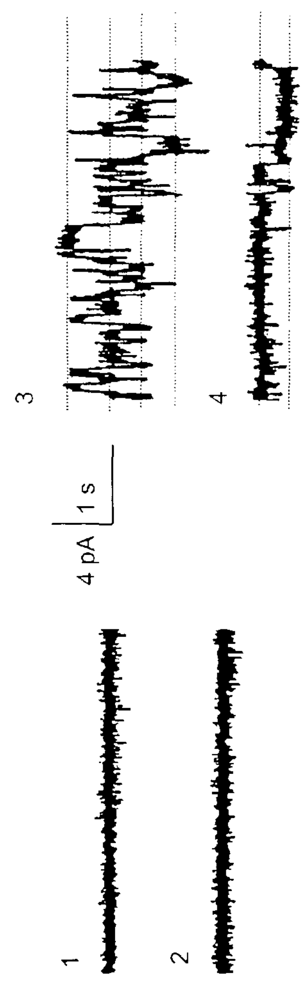
FIG. 9B shows the current records obtained from the segments marked with the corresponding numbers in FIG. 9A, at higher temporal resolution.

Sulfonylurea compounds are known to modulate the sulfonylurea receptor. A sulfonylurea receptor is generally associated with $K_{ATP}$ channels as a regulatory component, and is found in various tissues, including rat NRAs. Notably, the $K_{ATP}$ channels Kir6.1 and Kir6.2 are not present in rat NRAs (FIG. 7B). It is possible to activate the $NC_{Ca\text{-}ATP}$ channel with SUR ligand diazoxide in outside-out patches (FIGS. 9A and 9B). $NaN_3$ does not elicit channel activity in isolated membrane patches, indicating that it works via ATP depletion rather than any direct effect on the channel.

Example 10

Figure 10A:
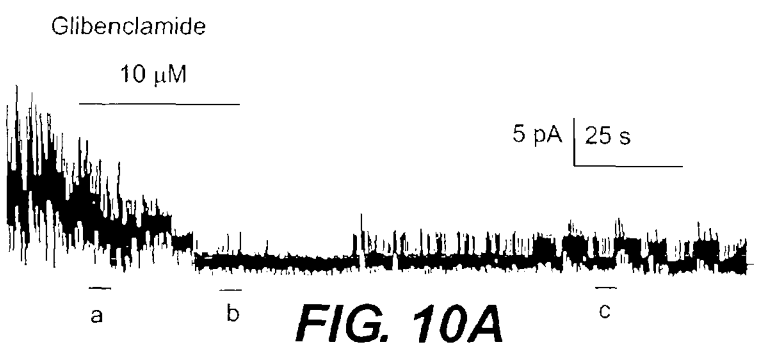
FIG. 10A shows outside-out patch recordings (a) before, (b) during, and (c) after application of glibenclamide to the extracellular side of the membrane.
Figure 10B:
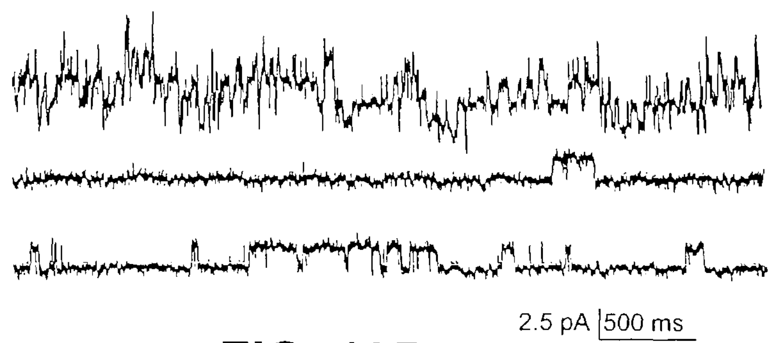
FIG. 10B shows the current records of FIG. 10A at higher temporal resolution.
Figure 10:
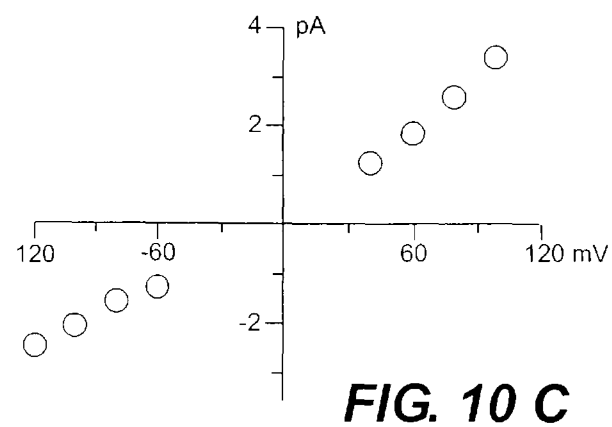
FIG. 10 (comprised of FIGS. 10A, 10B and 10C)
Figure 11A:
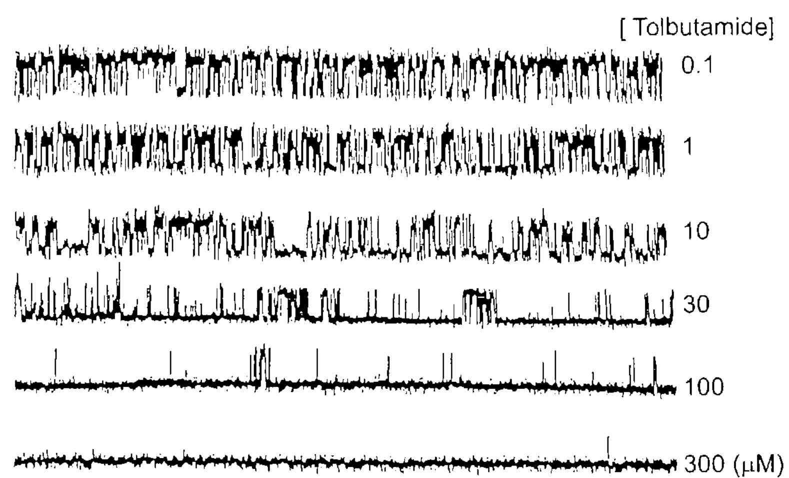
FIG. 11A shows the outside-out patch recordings with various concentrations of tolbutamide applied to the extracellular side of the membrane.
Figure 11B:
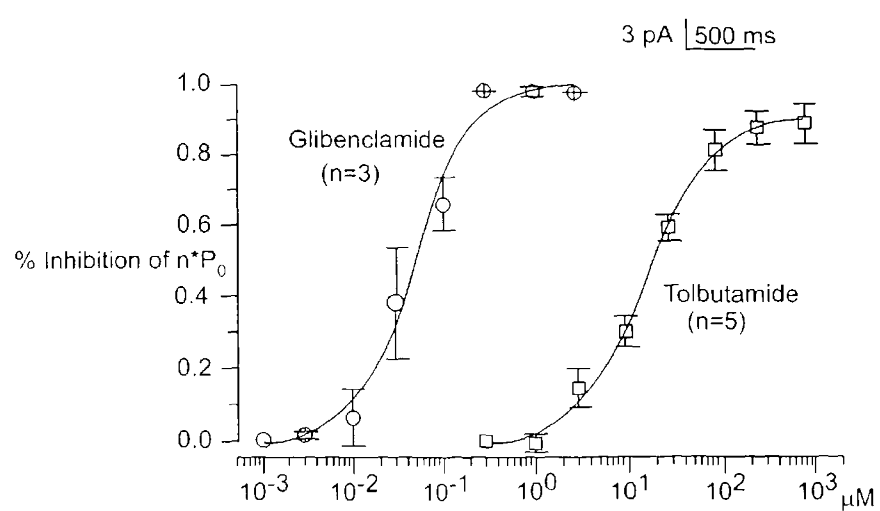
FIG. 11B shows the dose-response curves for inhibition of open channel probability by glibenclamide and tolbutamide to provide a normalized open channel probability (n•Po); data were fit to a standard logistic equation, with a Hill coefficient of 1 and half-maximum inhibition of 48 nM and 16.1 μM; values plotted are means (±SE) from 3 and 5 patches for Glibenclamide and Tolbutamide, respectively.

In vitro Assays for Determining Dose-Dependent Blockage of the $Nc_{ca\text{-}Atp}$ Channel SUR1 blocking compounds, such as glibenclamide and tolbutamide, are known to have an inhibitory effect on $K_{ATP}$ channels. In one embodiment, the present invention arrives at the objects of the invention by providing a method in which the direct inhibitory effect of glibenclamide and tolbutamide on $NC_{Ca\text{-}ATP}$ channels is determined (FIGS. 10 and 11). Inside-out patches are used to show the inhibitory effect of sulfonylureas. To ensure that no $K^+$ channel, particularly $K_{ATP}$ is contributing to patch current, $Cs^+$ is used as the charge carrier. Channel activity is profoundly diminished by the addition of 10 μM glibenclamide (FIG. 10A at b), and the activity is shown to be due to a 35 pS cation channel, which is consistent with the $NC_{Ca\text{-}ATP}$ channel of the present invention (FIG. 10C). Another sulfonylurea, tolbutamide, is also shown to inhibit $NC_{Ca\text{-}ATP}$ channel activity (FIGS. 11A and 11B). As shown in FIG. 11B, the $NC_{Ca\text{-}ATP}$ channel is blocked by the sulfonylureas in a dose-dependent manner. With tolbutamide, half maximum inhibition ($EC_{50}$) is observed at 16.1 μM with a Hill coefficient of 1.3, and channel activity is completely lost at concentrations >300 μM. With glibenclamide, $EC_{50}$ is observed at 48 μM with a Hill coefficient of 1.2. The sensitivity of the $NC_{Ca\text{-}ATP}$ channel of the present invention to blocking in NRAs with both of these sulfonylurea compounds corresponds closely to that reported in pancreatic β cells and in expression systems with SUR1, but not SUR2.

This in vitro assay for determining the concentration of the test compound which achieves a half-maximal inhibition of channel activity may be used to formulate dose in animal models to achieve. a circulating plasma concentration range.

Example 11

Mechanism of Channel Regulation by Sulfonylureas

Figures 12A, 12B, 12C:
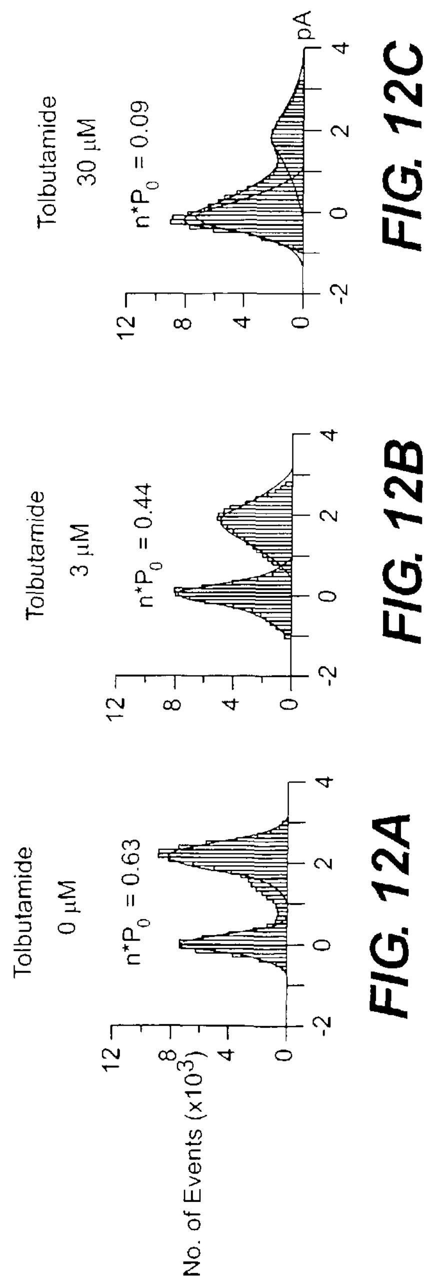
FIGS. 12A, 12B and 12C show the probability of channel opening in the presence of 0 μM, 3 μM, and 30 μM tolbutamide, respectively.
Figures 12D, 12E, 12F:
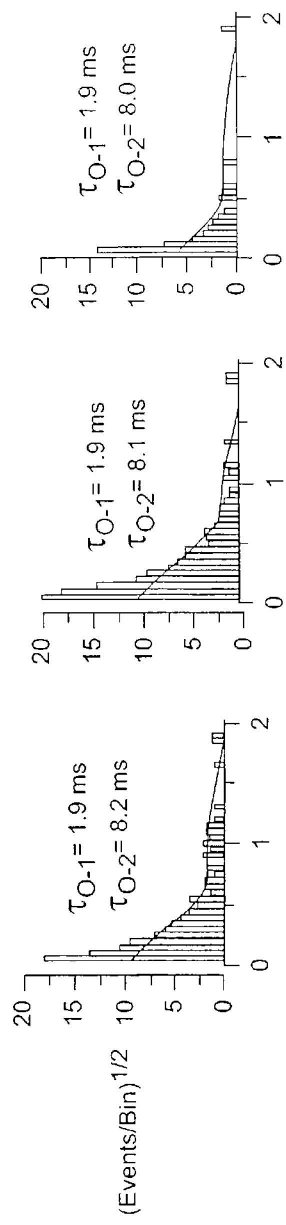
FIGS. 12D, 12E and 12F show the distribution of open channel dwell times in the presence of 0 μM, 3 μM, and 30 μM tolbutamide, respectively.
Figures 12G, 12H, 12I:
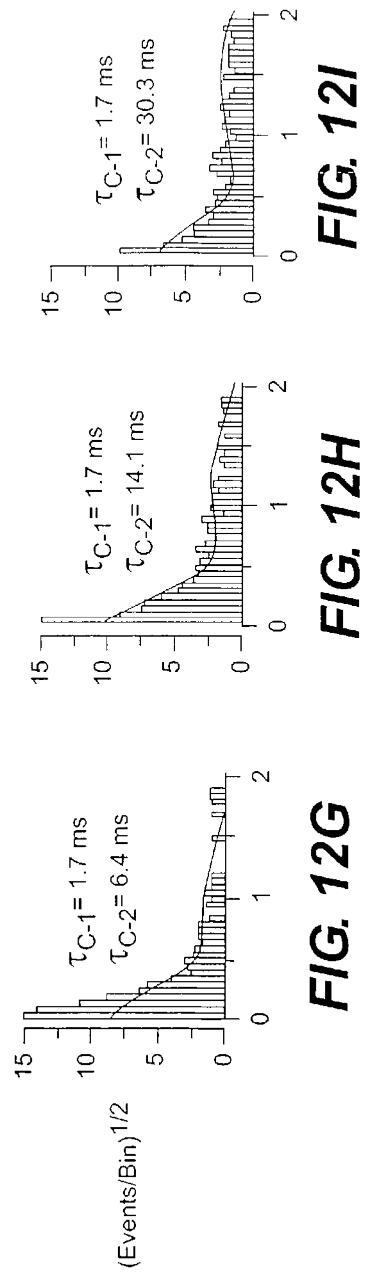
FIGS. 12G, 12H and 12I show the distribution of closed channel dwell times in the presence of 0 μM, 3 μM, and 30 μM tolbutamide, respectively.

The $NC_{Ca\text{-}ATP}$ channel of the present invention exhibits two open states, with a shorter and a longer dwell time, each less than 10 ms. FIG. 12 shows data from a patch exhibiting an open channel probability (n•Po) of 0.63, with open dwell time values $\tau_{0-1}$ $\tau_{0-2}$ and of 1.9 and 8.2 ms. After successive application of 3 μM tolbutamide (FIGS. 12B and 12E) and 30 μM tolbutamide (FIGS. 12C and 12F), n•Po decreased to 0.44 and 0.09, respectively, but the open dwell time values are not appreciably affected by the drug. Closed channel dwell times are increased in duration and frequency by tolbutamide (FIGS. 12H and 12I). Thus, the channel of the present inventions exhibits a form of channel inhibition in which the blocking compound had no effect on open channel dwell times and a progressive increase in long closures. This form of channel inhibition is similar to that produced by sulfonylureas acting on the $K_{ATP}$ channel in pancreatic β cells. See, Gillis et al., 1989; Babeenko et al., 1999).

Example 12

Figures 13A, 13B, 13C:
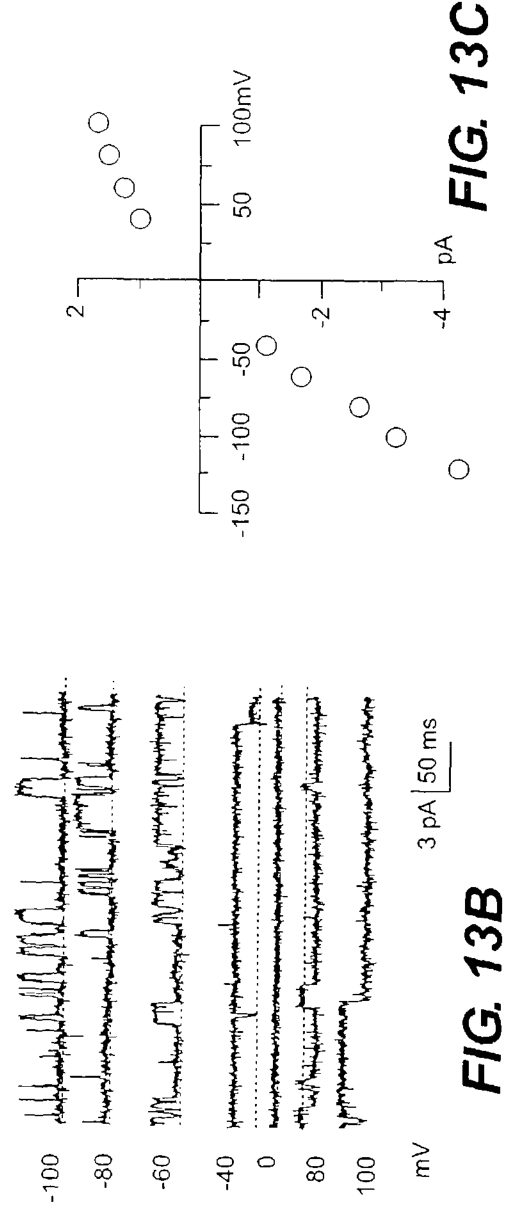
FIG. 13A shows outside-out patch recordings with diazoxide applied to the extracellular side of the membrane.
FIG. 13B shows current records at higher temporal resolution after application of diazoxide and at different membrane potentials.
FIG. 13C shows a plot of mean single channel amplitudes at the different potentials studied; the slope indicates 35 pS conductance of glibenclamide-sensitive channel.

Application of 100 μM of the SUR-activator diazoxide activates the 35 pS channel of the present invention, causing weak inward rectification in cell-attached patches (FIGS. 13A, 13B and 13C). To determine the type of SUR affecting activation of the $NC_{Ca-ATP}$ channel of the present invention, experiments are conducted using sulfonylurea compounds that preferentially activate SUR2 over SUR1, namely cromakalin, and pinacidil. Both cromakalin and pinacidil had no effect on the $NC_{Ca-ATP}$ channel of the present invention, which is consistent with other data described herein indicating that SUR1 is associated with the $NC_{Ca-ATP}$ channel of the present invention, and activation of the channel is not mediated by SUR2.

Example 13

Sur-Mediated Cell Swelling

After addition of $NaN_3$ to deplete ATP in cells, cell blebbing typically becomes apparent in 7-10 minutes. Diazoxide is an SUR1 agonist or SUR1 activator. When diazoxide alone is added to the cells, blebbing occurs even without ATP depletion, Diazoxide, therefore, opens the channel directly without ATP depletion by activating SUR1. However, when cells are pretreated with glibenclamide, addition of $NaN_3$ does not cause blebbing, even after 30 minutes. Thus, activation of $NC_{Ca-ATP}$ channel by ATP depletion or by the channel opener, diazoxide, can result in blebbing and swelling of NRAs, and that swelling can be prevented by blocking the channel with glibenclamide. ATP depletion by Na azide can result in necrotic cell death of NRAs. These findings accord with the data described herein that glibenclamide protects from the opening of the $NC_{Ca-ATP}$ channel following ATP depletion, and that opening of this channel is responsible for cell blebbing.

The antagonist used in the methods of the present invention includes a compound that interferes with $NC_{Ca-ATP}$ function. Typically, the effect of an antagonist is observed as a blocking of $NC_{Ca-ATP}$ current in conditions under which the channel has been activated and current can be measured in the absence of the antagonist.

In addition to SUR1 specific sulfonylurea compounds, agents that block SUR1, also include compounds that are structurally unrelated to sulfonylureas. Such SUR1 blockers include a class of insulin secretagogues compounds that bind to the SUR, which were identified and developed for the treatment of type 2 diabetes. The benzamido derivatives: repaglinide, nateglinide, and meglitinide represent one such class of insulin secretagogues, that bind to the SUR. Nateglinide is an amino acid derivative. Also, imidazoline derivatives have been identified that interact with the sulfonylurea receptor (SUR) 1 subunit such as midaglizole (KAD-1229), LY397364 and LY389382.

In one preferred embodiment of the present invention, compounds that preferentially block SUR1, but not SUR2, are used in the method of the present invention. Such compounds include tolbutamide and gliclazide. The following compounds block both SUR1 and SUR2: glibenclamide, glimepiride, repaglinide, and meglitinide. In yet another embodiment of the method of the present invention, administration is combined with MgADP, which has been show to produce an apparent increase of sulfonylurea efficacy on channels containing SUR1, but not SUR2.

Example 14

To determine whether $NC_{Ca-ATP}$ activation by ATP depletion initiates necrosis of reactive astrocytes that express this channel, studies are conducted to determine if glibenclamide is capable of protecting reactive astrocytes from cell death by inhibiting $NC_{Ca-ATP}$ channel activity via its action on SUR1. Two types of cell death, apoptosis and necrosis, are assessed following ATP depletion.

Thus, activation of $NC_{Ca-ATP}$ channel is responsible for necrotic death of NRAs following ATP depletion, and that glibenclamide can prevent this form of cell death.

In this Example, the preparation of freshly isolated NRAs was further purified by removal of RBCs, as described herein to provide a cell population having <1% RBCs. Over 95% of cells had resting potentials near $E_K$, suggesting that the enzymatic dissociation method had not appreciably harmed the cells. Over 95% of cells are positive for the astrocyte marker, glial fibrillary acidic protein (GFAP) as determined by immunofluorescence. When examined by phase microscopy, the NRAs are of various sizes, ranging from 11-45 μm in diameter, some of which are phase bright and others are phase dark. A subgroup of phase bright cells had multiple short but distinct cell processes that are shorter than the cell soma. In this Example, only larger (≈30 μm diameter), phase bright cells with short processes (<1 cell length) are studied. This population of NRAs reliably express $NC_{Ca-ATP}$ channels.

Experiments are conducted at room temperature (22-25° C.) within 24 hr of cell isolation. An aliquot of cells is placed on a chamber slide (LAB-TEK, Naperville, Ill.) filled with extracellular bath solution containing (a): NaCl 130, KCl 10, $CaCl_2$ 1, $MgCl_2$ 1, HEPES 32.5, glucose 12.5, pH 7.4. After viable cells adhered to the surface, any residual debris not previously removed by centrifugation is washed away by flushing with excess solution. Cells are subjected to ATP depletion by 1 mM Na azide to activate (open) the $NC_{Ca-ATP}$ channels, and then incubated with glibenclamide (1 μM).

Thereafter, the cells are examined by propidium iodide (PI) staining for evidence of cellular membrane permeabilization, an indication of early oncotic or necrotic cell death. See, Barros et al., 2001. The cells are also examined by fluorescein-tagged annexin V binding for evidence of externalization of the phosphoaminolipid phosphotidylserine from the inner face of the plasma membrane to the outer surface, an early indication of apoptosis. See, Clodi et al., 2000; Rucker-Martin et al., 1999. Staining procedure are conducting according to manufacture directions (Vybrant Apoptosis Assay Kit 2, Molecular Probes). Slides are mounted using ProLong antifade mounting medium (Molecular Probes). Signals are visualized using a Nikon Diaphot epifluorescent microscope (Leitz Wetzlar). Images are captured and stored using a SenSys digital camera (Roper Scientific Inc.) and IPLab software (version 3.0; Scanalytics Inc.). Annexin V-positive cells or PI-positive cells are counted in 20 individual fields using a 20× objective lens. Mean values of positive cells in 20 fields for various treatment groups are compared using ANOVA Pairwise multiple comparisons, with $p<0.05$ being considered as indicating a significant difference.

Figure 15A:
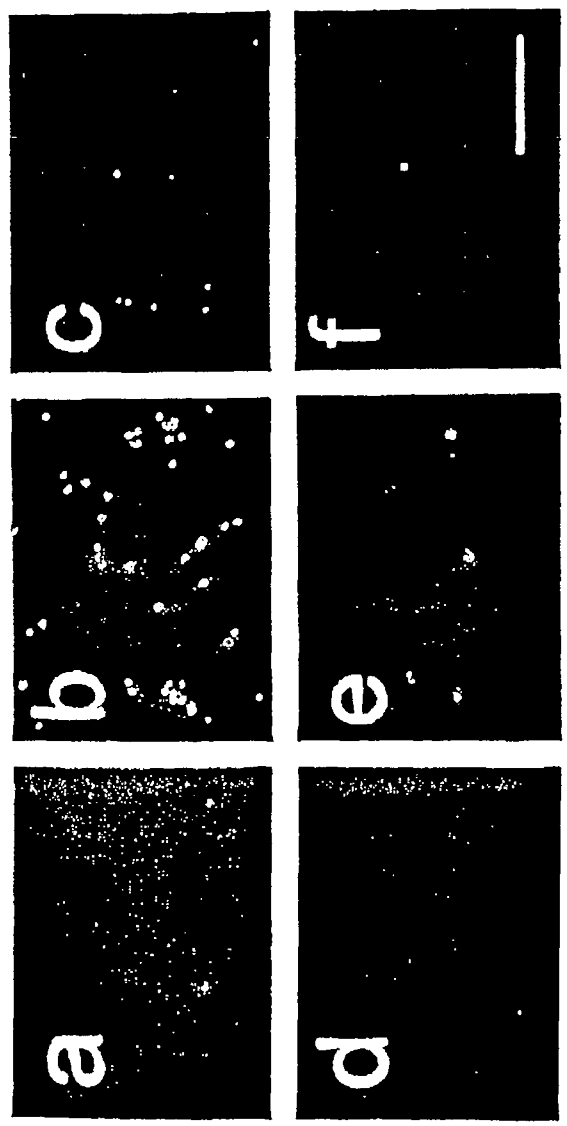
FIG. 15A has photomicrographs of the epifluorescence images of cells exposed to different compounds and labeled with propidium iodide (upper panel a, b and c) or annexin V (lower panel d, e and f). The compounds were: control (a & d), 1 mM Na azide (b & e), 1 mM Na azide plus 1 μM glibenclamide (c & f).
Figure 15B:
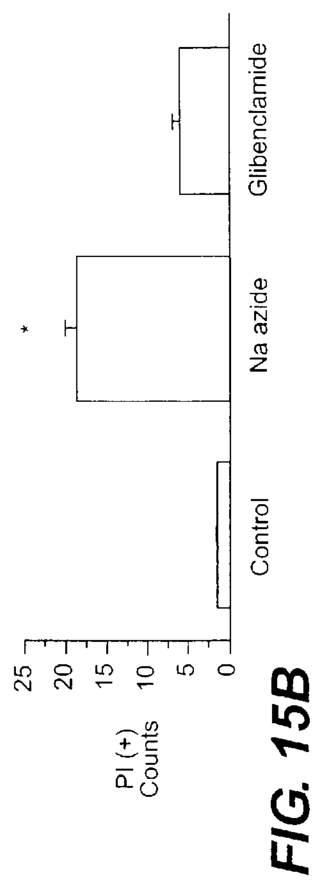
FIG. 15B has bar graphs showing cell-counts for propidium iodide labeling; pairwise multiple comparisons indicated a significant difference ($p<0.05$) with Na azide treatment.
Figure 15C:
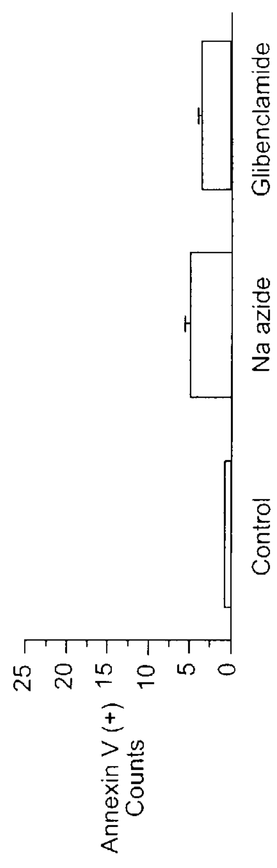
FIG. 15C has bar graphs showing cell-counts for annexin V staining; pairwise multiple comparisons indicated no significant difference with any treatment.

The fluorescence microscopy photos shown in FIG. 15A show that under baseline (control) conditions, both annexin V-positive and PI-positive cells (photos a and d, respectively) are rare in the cell isolates. After a 10-min incubation with Na azide (1 mM), the number of PI-positive cells increased substantially ($p<0.05$) (FIG. 15A at photo b and FIG. 15B). This indicates that ATP depletion triggers necrotic death in these cells. By contrast, Na azide treatment caused the number of annexin V-positive cells to increase slightly; the increase not being statically significant ($p>0.05$) (FIG. 15A at photo e and FIG. 15C). This indicates that apoptotic death was not a major endpoint of ATP depletion in these cells.

Pretreatment of cells with glibenclamide (1 μM) at the time of administration of Na aide dramatically decreased the number of PI-positive cells ($p<0.05$; FIG. 15A at photo c and FIG. 15B), indicating significant protection from necrotic death following ATP depletion. The number of NRAs undergoing apoptotic death also decreased with glibenclamide, as indicated by annexin V labeling (FIG. 15A at photo f and FIG. 15C), but values for this group were not significantly different.

This data indicate that the $NC_{Ca\text{-}ATP}$ channel is involved in the mechanism of the necrotic cell death of reactive astrocytes. This Example shows that necrotic, rather than apoptotic, cell death is the principal endpoint of ATP depletion in these cells. Therefore, ATP depletion by Na azide initiates cell death by removal of the ATP block of the $NC_{Ca\text{-}ATP}$ channel, thus initiating oncotic cell swelling. Involvement of this channel in oncotic cell swelling is confirmed by showing that necrotic death can also be induced by diazoxide, the channel opener that activates the $NC_{Ca\text{-}ATP}$ channel in these cells, and could be blocked by glibenclamide, which prevents opening of the $NC_{Ca\text{-}ATP}$ channel. The involvement of the $NC_{Ca\text{-}ATP}$ channel in cell death of reactive astrocytes provides a mechanism and target of death in these cells, as well as the importance of blocking the $NC_{Ca\text{-}ATP}$ channel to prevent the death of reactive astrocytes, which occurs in traumatic brain injury.

Example 15

In vitro Assays for Determining the Ability of a Test Compound to Provide Dose-Dependent Blockage of the $Nc_{ca\text{-}Atp}$ Channel $NC_{Ca\text{-}ATP}$ channels blocking compounds can be identified by a method in which the direct inhibitory effect of the test compound on $NC_{Ca\text{-}ATP}$ channels is determined. Inside-out patches are used to show the inhibitory effect of the compound. To ensure that no $K^+$ channel, particularly $K_{ATP}$ is contributing to patch current, $Cs^+$ is used as the charge carrier. Compounds that profoundly diminish channel activity, and the activity is shown to be due to a 35 pS cation channel, such a compound is identified as a compound that blocks the $NC_{Ca\text{-}ATP}$ channels and is capable of inhibiting neuronal cell swelling and brain swelling. Varying concentrations of the compound are used to determine whether the $NC_{Ca\text{-}ATP}$ channel is blocked by the compound in a dose-dependent manner. The concentration at which half maximum inhibition ($EC_{50}$) is observed and the concentration at which channel activity is completely lost are determined. The sensitivity of the $NC_{Ca\text{-}ATP}$ channel of the present invention to blocking in NRAs with the test compound can be compared. This in vitro assay for determining the concentration of the test compound which achieves a half-maximal inhibition of channel activity may be used to formulate dose in animal models to achieve a circulating plasma concentration range.

Example 16

In vivo Assays for Determining Dose-Dependent Blockage of the $Nc_{ca\text{-}Atp}$ Channel The concentration of the test compound which achieves a half-maximal inhibition of channel activity is used to formulate dose in animal models to achieve a circulating plasma concentration range. The dose of test compound that achieves a circulating plasma concentration range calculated by methods known in the art is administered to an animal having brain injury or cerebral ischemia. To determine whether the test compound prevents, inhibits or diminishes brain swelling, the epidural pressure and/or intracranial pressure of the animal is measured, such as by using a microballoon, to quantitatively monitor brain swelling. Also, the swelling can be monitored by magnetic resonance (MR) imaging. Three different studies start administration prior to, at the time of, or after the brain injury. A compound that provided diminishes brain swelling, as compared to controls, is identified as a compound capable of inhibiting neuronal cell swelling and brain swelling. Varying concentrations of the compound are used to determine whether the compound delivers efficacy in a dose-dependent manner. The dose at which half maximum inhibition is observed and the concentration at which brain swelling is most quickly alleviated are determined. Formulations are produced comprising the optimal effective dose of the test compound for preventing, inhibiting, or diminishing brain swelling, along with a pharmaceutically acceptable carrier.

Example 17

Additional Mechanisms for Maintaining NRAs in a Polarized State

When reactive astrocytes are strongly depolarized due to opening of the $NC_{Ca\text{-}ATP}$ channel, they undergo blebbing and swelling and eventually sustain necrotic cell death. As stated above, when reactive astrocytes are strongly depolarized due to opening of a non-selective channel that is sensitive to $Ca^{2+}$ and ATP ($NC_{Ca\text{-}ATP}$ channel), they undergo blebbing and swelling and eventually sustain necrotic cell death. The death of these reactive astrocytes can be prevented if strong depolarization can be prevented, in other words, if the cells can be maintained in a polarized state.

One potential way of maintaining the NRAs in a polarized state is to open the Kir2.3 channel. NRAs are exposed to the Kir2.3 channel opener, Tenidap (5-chloro-2,3-dihydro-3-(hydroxy-2-thienylmethylene)-2-oxo-1H-indole-1-carboxamide), to maintain Kir2.3 channels open. Native reactive astrocytes freshly harvested from adult rat brains after injury are exposed to Tenidap to evaluate the drug's ability to open the Kir2.3 channel in these cells. Preferably, type 1 reactive (R1) astrocytes are harvested and used in this assay. One of the subtypes of reactive astrocytes is the type R1 astrocyte. Type R1 astrocytes comprise the largest population of recoverable astrocytes at the site of brain injury. They are characteristically located in the region of tissue surrounding the injury site, many of which are found to have migrated into the injury site itself. See, Perillan, et al., 1999.

The reactive astrocytes that are part of the cellular response to TBI and stroke are comprised of at least two subtypes. One of the subtypes of reactive astrocytes is the type R1 astrocyte. Type R1 astrocytes comprise the largest population of recoverable astrocytes at the site of brain injury. They are characteristically located in the region of tissue surrounding the injury site, with many of these cells also being found to have migrated into the injury site itself. See, Perillan, et al. 1999.

Type R1 astrocytes are the predominant type of reactive astrocyte in the NRA preparations. Type R1 astrocytes express two critically important ion channels in their cell membrane: (a) the Kir2.3 channel, which is present in cultured as well as freshly isolated cells; and (b) the $NC_{Ca\text{-}ATP}$ channel, which is present only in freshly isolated reactive astrocytes and lost shortly after culturing. The Kir2.3 is an inward rectifier channel that is critically important for maintaining the cell polarized to a normal resting potential near the potassium reversal potential (≈−75 mV). When this channel is inactivated or inhibited, the cell depolarizes to a potential near the chloride reversal potential (≈−25 mV). Characteristic features of the $NC_{Ca\text{-}ATP}$ channel are: 1) it is a non-selective cation channels that allows passage of Na+, $K^+$, and other monovalent cations quite readily; 2) it is activated by an increase in intracellular calcium, and/or by a decrease in intracellular ATP; and 3) it is regulated by sulfonylurea receptor type 1 (SUR1). SUR1 had been considered to be associated exclusively with $K_{ATP}$ channels, such as those found in pancreatic β cells.

Opening of the $NC_{Ca\text{-}ATP}$ channel following ATP depletion, as with ischemia or hypoxia, causes depolarization of the cell due to influx of $Na^+$. This influx of $Na^+$ increases the osmotic load within the cell, and as a result, $H_2O$ enters the cell to equilibrate the osmotic load. The result is an excess of $Na^+$ and $H_2O$ intracellularly, a pathological response that produces cell blebbing and cell swelling and that is known as cytotoxic edema. Left unchecked, this pathological response eventually leads to cell death. As disclosed herein, this cell death is mostly necrotic cell death but to a lesser extent, apoptotic cell death as well.

A number of approaches may be used to meliorate brain swelling due to cytotoxic edema. One currently used treatment for treating patients in relevant clinical situations is based on increasing extracellular osmolarity to reduce the driving force for influx of $H_2O$. This strategy also reduces blebbing in isolated cells.

A more specific strategy to reduce cytotoxic edema is inactivating or blocking the $NC_{Ca\text{-}ATP}$ channel that is primarily responsible for the influx of $Na^+$ that draws $H_2O$ into the cell and that actually causes cytotoxic edema. One highly selective approach to inactivating this channel is to exploit the unique relationship between the channel and the controlling regulatory subunit, SUR1. A variety of drugs have been developed that interact with SUR1 in pancreatic β cells to block the $K_{ATP}$ channel in those cells and thereby treat diabetes. Some of these drugs belong to the class of agents called sulfonylureas. As described herein, drugs that block the $K_{ATP}$ channel, such as glibenclamide and tolbutamide, are highly effective at blocking the $NC_{Ca\text{-}ATP}$ channel in type R1 astrocytes. Drugs capable $NC_{Ca\text{-}ATP}$ channel blocking in NRAs (a) prevents cell blebbing in response to ATP depletion, (b) significantly reduces cell death following ATP depletion. Also, the use of glibenclamide to treat brain swelling in an animal suffering from stroke or brain injury is described herein.

Yet another strategy to oppose the effect of the $NC_{Ca\text{-}ATP}$ channel and reduce cytotoxic edema would be to counteract depolarization of the cell that accompanies opening of the $NC_{Ca\text{-}ATP}$ channel. One way to accomplish this is to enhance opening of the Kir2.3 channels that are also present in these cells. An anti-inflammatory compound, Tenidap (5-chloro-2, 3-dihydro-3-(hydroxy-2-thienylmethylene)-2-oxo-1H-indole-1-carboxamide), is an opener of Kir2.3 channels. See, Popp et al., 1992; Liu et al., 2002. Tenidap is evaluated for its ability to reduce cell blebbing and swelling and necrotic cell death in response to ATP depletion in the isolated cells as well as in situ in injured rat brain. To assess whether Tenidap opens the Kir2.3 channels in type R1 astrocytes, using methods similar to those described herein for evaluating the status of the $NC_{Ca\text{-}ATP}$ channel. Results from such experiments that show Tenidap to open Kir2.3 channels in type R1 astrocytes, and reduce cell blebbing and cell death in response to ATP depletion would indicate the usefulness of Tenidap in treating brain swelling and cytotoxic edema resulting from TBI or cerebral ischemia. The effective amount of Tenidap is that amount capable of reducing brain swelling or cerebral ischemia due to the drug's ability to inhibit neural cell swelling and necrotic cell death.

SUR1 blockers are believed to be the most specific, reliable blockers and to provide the fewest untoward side effects. Further, a combination of treatments including use of two to more of osmotic diuretics, $NC_{Ca\text{-}ATP}$ channel blockers such as glibenclamide and Kir2.3 channel openers such as Tenidap may provide excellent efficacy in ameliorating cytotoxic edema and reducing morbidity and mortality in brain injury and stroke. Thus, comcomitant or successive administration of an $NC_{Ca\text{-}ATP}$ channel blocker and a Kir2.3 channel opener is expected to provide excellent efficacy in ameliorating cytotoxic edema and reducing morbidity and mortality in brain injury and stroke. For example, administration of glibenclamide and Tenidap would be useful for ameliorating cytotoxic edema and reducing morbidity and mortality in brain injury and stroke.

Example 18

Modulation by Estrogen

A characteristic feature of $K_{ATP}$ channels (Kir6.1, Kir6.2) is that channel affinity for ATP is modulated by the presence of the membrane lipid, $PIP_2$. The open-state stability of $K_{ATP}$ channels is increased by application of $PIP_2$ to the cytoplasmic side of the membrane (Ashcroft, 1998; Baukrowitz et al., 1998; Rohacs et al., 1999). An increase in the open-state stability is manifested as an increase in the channel open probability in the absence of ATP, and in a corresponding decrease in sensitivity to inhibition by ATP (Enkvetchakul et al., 2000; Haruna et al., 2000; Koster et al., 1999; and Larsson et al., 2000).

Figure 16:
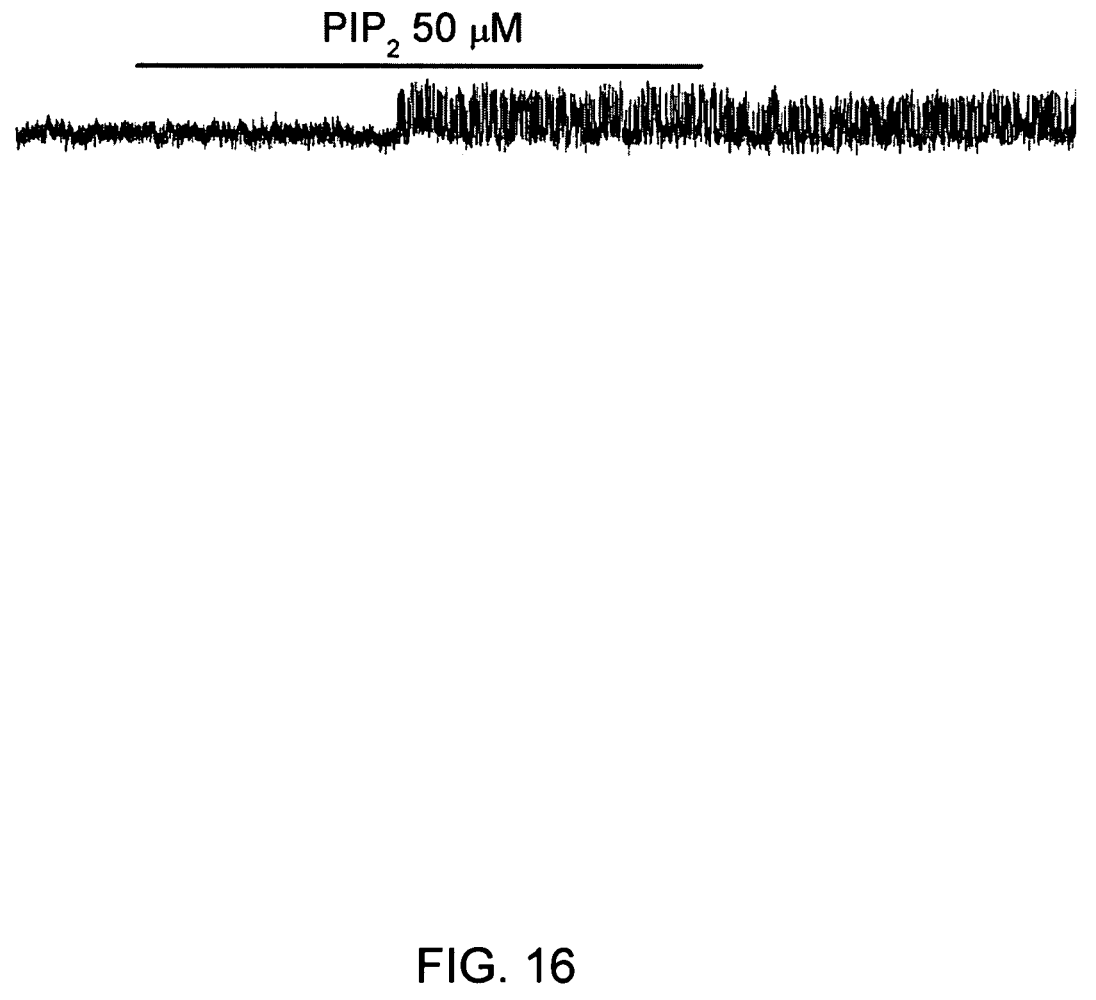

Given the numerous similarities between the $K_{ATP}$ channel and the $NC_{Ca\text{-}ATP}$ channel, the inventors postulated that ATP-sensitivity of the $NC_{Ca\text{-}ATP}$ channel would respond to $PIP_2$ in the same way. This was tested by studying $NC_{Ca\text{-}ATP}$ channels in inside out patches with $Cs^+$ as the charge carrier, and with 1 μM $Ca^{2+}$ and 10 μM ATP in the bath, with the latter expected to fully block the channel. Under these conditions, only the $NC_{Ca\text{-}ATP}$ channel was recorded in R1 astrocytes. When $PIP_2$ (50 μM) was added to the bath, channel activity became prominent (FIG. 16), as predicted by analogy to the effect of $PIP_2$ on $K_{ATP}$ channels. This channel activity was blocked by glibenclamide, confirming identity of the channel.

To determine if a receptor-mediated mechanism was involved in the modulation of $NC_{Ca\text{-}ATP}$ channel activity, a well known phospholipase C (PLC) was used to study if PLC activation would cause degradation and consumption of $PIP_2$ and thereby increase affinity for ATP, e.g., reduce channel opening. Estrogen is a well known PLC activator in brain as well as elsewhere (Beyer et al., 2002; Le Mellay et al., 1999; Qui et al., 2003). For this experiment, cell attached patches were studied to prevent alteration of intracellular signaling machinery. $NC_{Ca-ATP}$ channel activity was produced by exposure to Na azide to cause depletion of cellular ATP (FIG. 2, initial part of the record).

Figure 17:
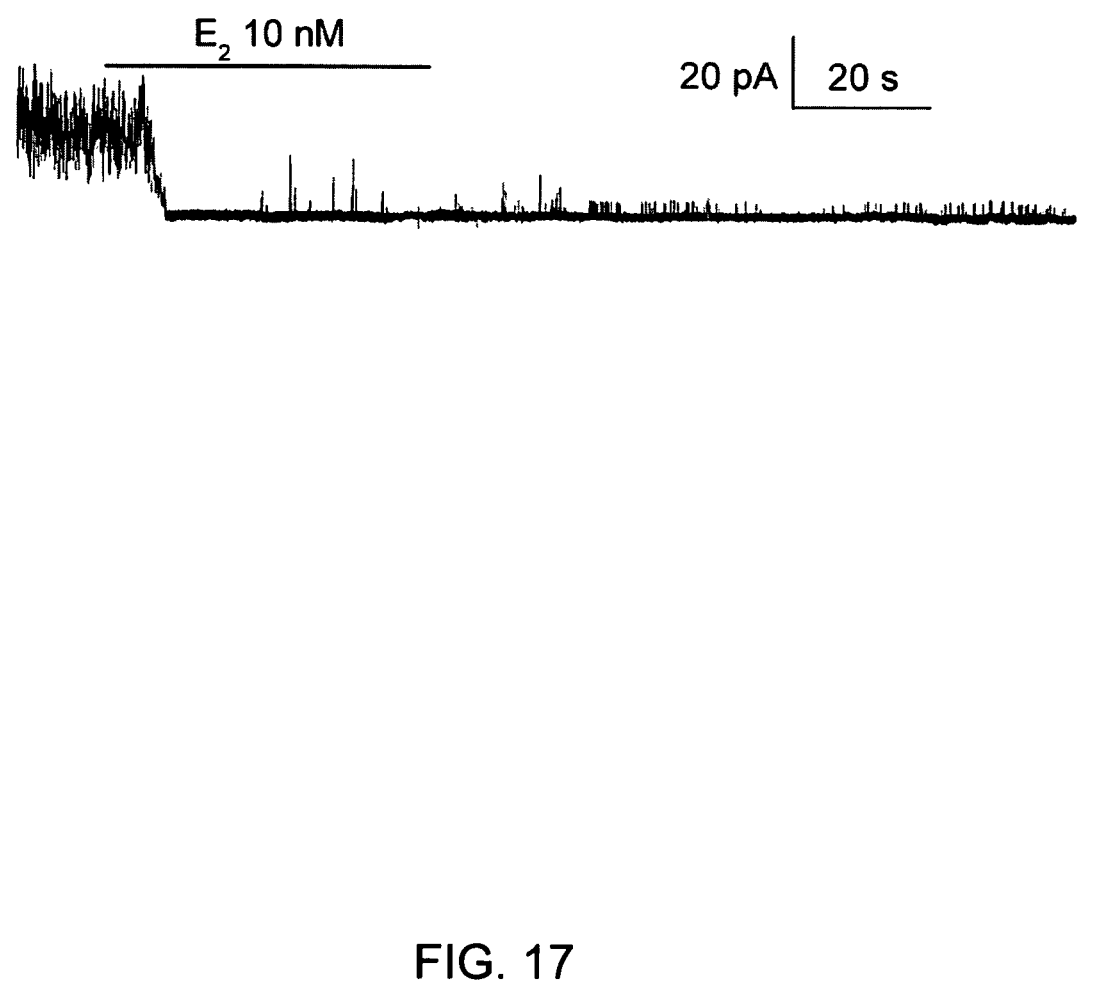

When estrogen (E2; 10 nM) was applied to the bath, activity due to the $NC_{Ca-ATP}$ channel was soon terminated (FIG. 17). This suggested that estrogen exerted regulatory control over the $NC_{Ca-ATP}$ channel, and suggested that an estrogen receptor capable of rapid (non-genomic) activation of signaling cascades was present on these cells.

Figure 18:
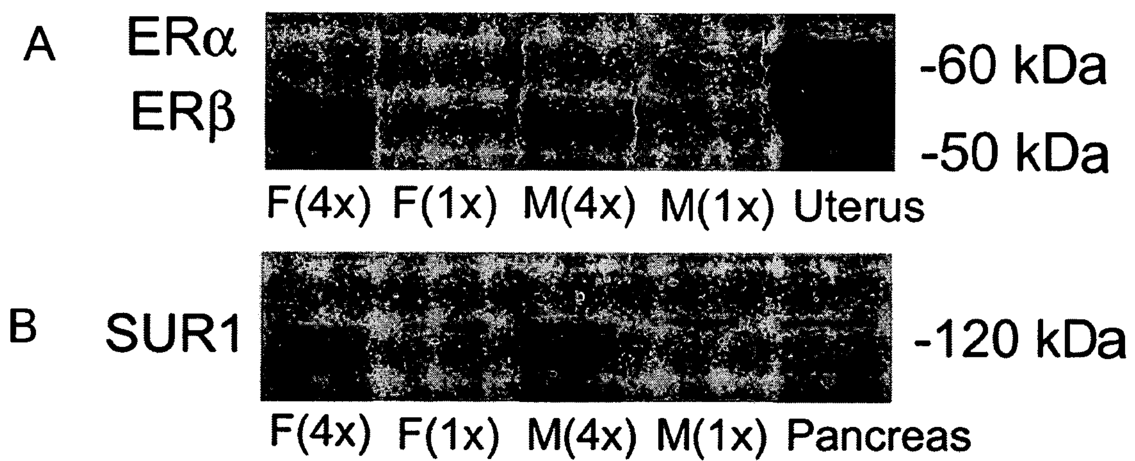
FIGS. 18A-18B show Western blots demonstrating that R1 astrocytes from both males and females express estrogen receptors and SUR1, a marker of the $NC_{Ca\text{-}ATP}$ channel. Cell lysates were obtained from gelatin sponge implants from males (M) and females (F) and studied at two dilutions (4× and 1×), with lysates from uterus used as controls.

Next, to determine whether estrogen receptors could be detected in R1 astrocytes from males and females. Gelatin sponge implants were harvested 7 days after implantation in a group of 3 female rats (F) and another group of 3 male rats (M). Pooled protein from each group was analyzed at 2 dilutions (4×=50 μg total protein; 1×=12.5 μg total protein) by Western blotting, with protein from uterus being used as a control (FIG. 18A). Membranes were blotted with an antibody that recognized both α and β estrogen receptors. Both males and females showed prominent bands at the appropriate molecular weights for the α (66 kDa) and β (55 kDa) receptors (FIG. 18) (Hiroi et al., 1999). The same samples of protein from males and females were also used to confirm presence of SUR1, with protein from pancreas used as a positive control (FIG. 18B). Notably, estrogen receptors have previously been reported in astrocytes from males and females (Choi et al., 2001). In cerebral cortex, the β isoform is reportedly more abundant (Guo et al., 2001) as suggested by theWestern blot.

Figure 19:
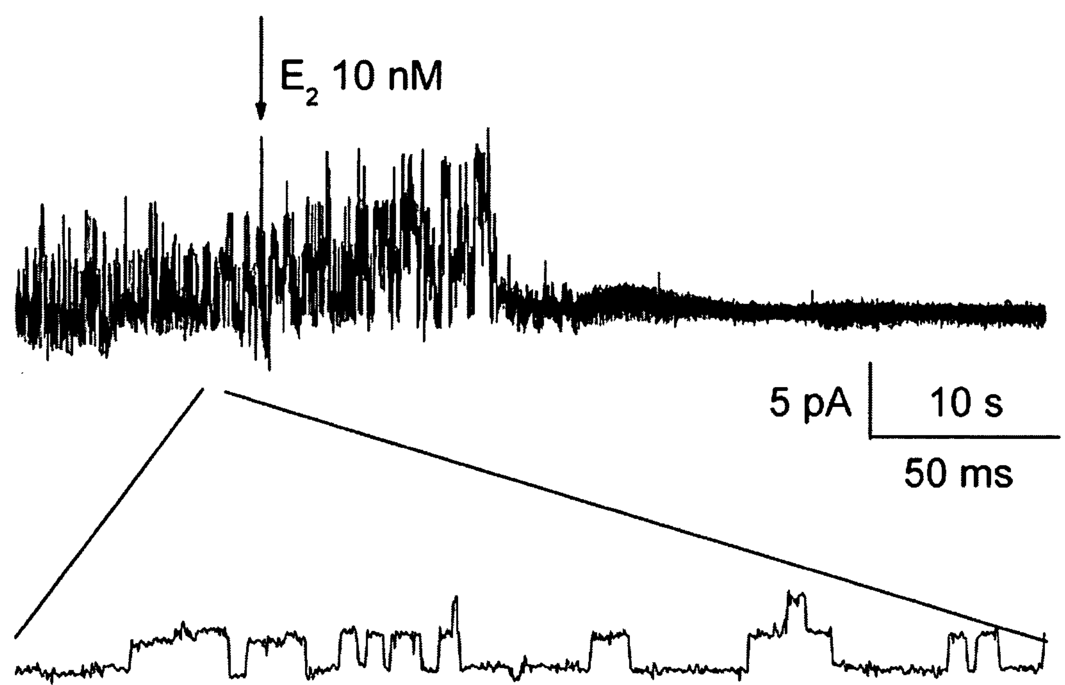
FIG. 19 shows that the $NC_{Ca\text{-}ATP}$ channel in an R1 astrocyte from a male is inhibited by estrogen. The initial portion of the record shows brisk activity from a number of superimposed channels, recorded in a cell attached patch of membrane from an R1 astrocyte obtained from a male. Addition of 10 nM estrogen to the bath promptly resulted in strong inhibition of channel activity.

Next, the electrophysiological experiment of FIG. 17 was repeated using R1 astrocytes harvested from male rats. As above, cell attached patches were studied in which $NC_{Ca-ATP}$ channel activity was activated by depletion of intracellular ATP following exposure to Na azide (FIG. 4A). Examination of the record at higher temporal resolution confirmed activity of a well defined channel of the appropriate conductance for the $NC_{Ca-ATP}$ channel (FIG. 4B). When estrogen was applied to the bath (FIG. 4, E2, 10 nM, arrow), activity due to the $NC_{Ca-ATP}$ channel was quickly terminated (FIG. 19). These data provided further evidence that estrogen exerted regulatory control over the $NC_{Ca-ATP}$ channel, and suggested, in addition, that this response was equally robust in R1 astrocytes from males and females.

By analogy to the effects of estrogen, other mechanisms that deplete $PIP_2$, including other receptor-mediated mechanism as well as more direct activators of PLC such as G-proteins etc., would be expected to have a similar inhibitory effect on activity of the $NC_{Ca-ATP}$ channel and thereby exert a protective effect.

Example 19

The Gliotic Capsule

The standard model involved placing a stab injury into the parietal lobe of an anesthetized rat and implanting a sterile foreign body (gelatin sponge; Gelfoam®) into the stab wound. Variants of the standard model included impregnating the sponge with a substance (e.g., lipopolysaccharide, LPS) or infusing a substance continuously in vivo using an osmotic mini-pump with the delivery catheter placed directly into the sponge. The injury procedure was well tolerated by the animals, with virtually no morbidity or mortality and minimal pain. After an appropriate time in vivo, the whole brain was harvested for histological or immunohistochemical study of tissue sections. Alternatively, if the sponge itself was gently removed from the brain, the inner zone of the gliotic capsule adheres to the sponge and was excised along with it. Thus, the sponge was assayed for protein (e.g., Western) or mRNA (RT-PCR), or it was enzymatically dissociated to yield constituent cells for electrophysiological or other single-cell measurements.

Figure 20:
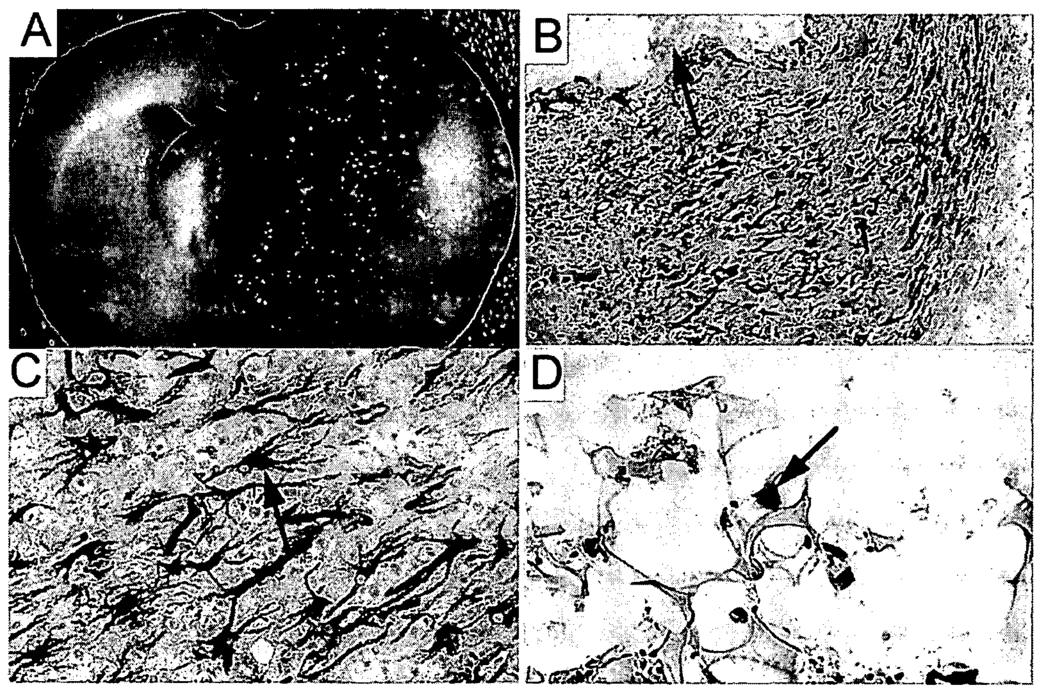
FIGS. 20A-20D shows the gliotic capsule.

The gliotic capsule was well developed 7-10 days after injury. The gliotic capsule was visualized in coronal sections by perfusing the animal with Evans Blue prior to perfusion-fixation of the brain (FIG. 20A). A region of edema (dark) was seen to outline the avascular gliotic capsule (light) that surrounded the gelatin sponge (dark). Immunohistochemical examination with anti-GFAP antibodies showed that the brain parenchyma in the vicinity of the sponge harbors many GFAP-positive reactive astrocytes (FIG. 20B; arrow showed where the gelatin sponge was). At higher power, these intraparenchymal GFAP-positive cells were shown to be large and to bear many prominent cell processes (FIG. 20C, arrow). Examining the gelatin sponge itself showed GFAP-positive reactive astrocytes that migrated into the interstices of the sponge (FIG. 20D, arrow).

Example 20

Isolation of Cells from the Gliotic Capsule

Figure 21:
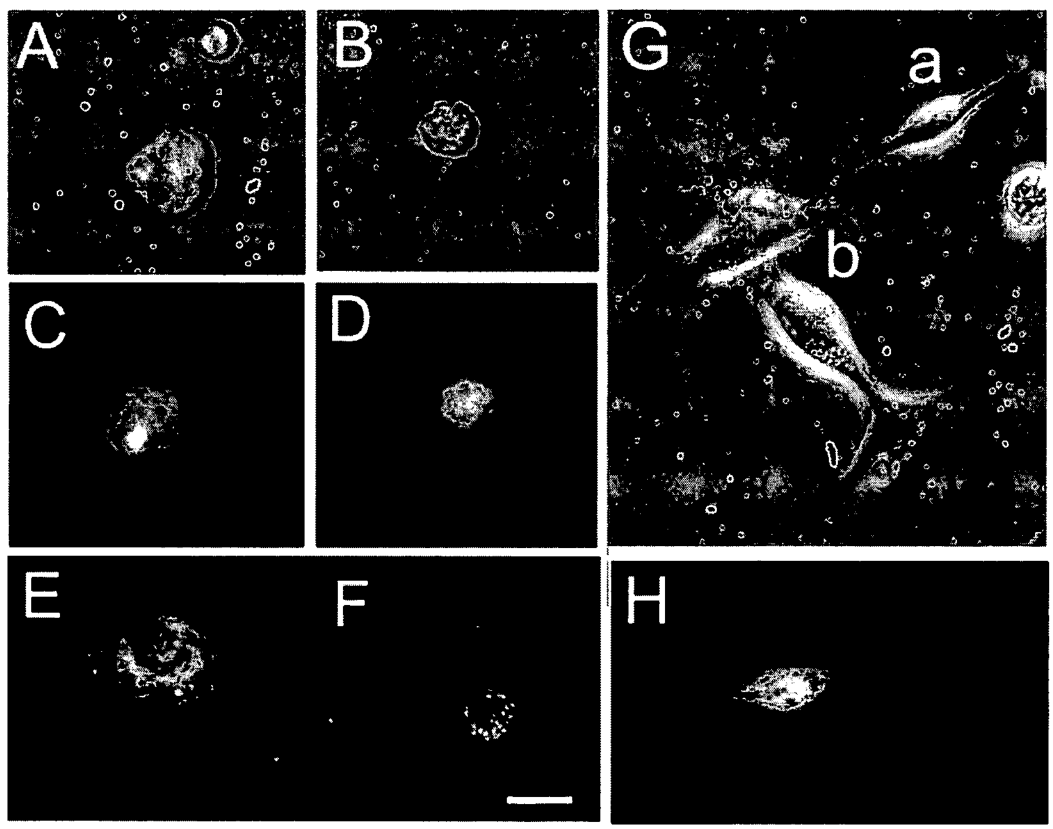
FIGS. 21A-21H show immunolabeled astrocytes.

Phase contrast microscopy of cells freshly isolated by papain digestion of the inner zone of the gliotic capsule and gelatin sponge revealed three types of cells. Most of the cells (>90%) were large, round, have no cell processes and were phase-bright (FIG. 21A). A number of cells (3-5%) were small, round, have no cell processes and were phase-dark (FIG. 21B). Occasionally, a cell was found that was intermediate in size, was phase-bright and had multiple processes that were more than one cell diameter in length (Chen et al., 2003). Immunofluorescence study showed that all of these cells were strongly positive for typical astrocyte markers, including GFAP (FIGS. 21C,D) and vimentin (FIGS. 21E,F). Microglia were not prominent in the inner zone of the gliotic capsule itself, as indicated by sparse labeling for OX-42. Cells of the inner zone of the gliotic capsule were negative for the O2A progenitor marker, A2B5, and the fibroblast marker, prolyl 4-hydroxylase (Dalton et al., 2003).

As with freshly isolated cells, three morphologically distinct types of cells were observed in primary culture. Most cells (>90%) were large polygonal cells (FIG. 21Gb), a few (3-5%) were small bipolar cells (FIG. 21Ga), and only occasionally were process-bearing stellate-shaped cells observed (Perillan et al., 2000). All of these cells were strongly labeled with anti-GFAP antibodies (FIG. 21H). Experiments in which cells obtained by enzymatic digestion were followed individually in primary culture showed that the large phase-bright cells develop into large polygonal cells (FIG. 21Gb), and the small phase-dark cells developed into small bipolar cells (FIG. 21Ga) (Dalton et al., 2003).

The three morphologically distinguishable types of GFAP-positive astrocytes from the inner zone of the gliotic capsule exhibited very different macroscopic whole cell electrophysiological profiles:

(i) Electrophysiological studies on stellate astrocytes showed that they expressed Kir2.3 and Kir4.1 inward rectifier channels, and immunolabeling experiments suggested that they also expressed $K_{ATP}$ channels comprised of SUR1 and Kir6.1 subunits (Chen et al., 2003; Perillan et al., 2000);

(ii) Electrophysiological studies on R2 astrocytes showed that they expressed a novel $Ca^{2+}$-activated Cl− channel that was sensitive to the polypeptide toxin from the scorpion, *Leiurus quinquestriatus* (Dalton et al., 2003). Only the R2 astrocyte expressed this channel.

(iii) Electrophysiological studies on R1 astrocytes showed that they express Kir2.3 inward rectifier channels that are regulated by TGFβ1 via PKCδ (Perillan et al., 2002; Perillan et al., 2000). When freshly isolated but not after culturing, R1 astrocytes also expressd a novel SUR1-regulated $NC_{Ca-ATP}$ channel (Chen et al., 2003; Chen et al., 2001).

Example 21

Expression of SUR1

Figure 22:
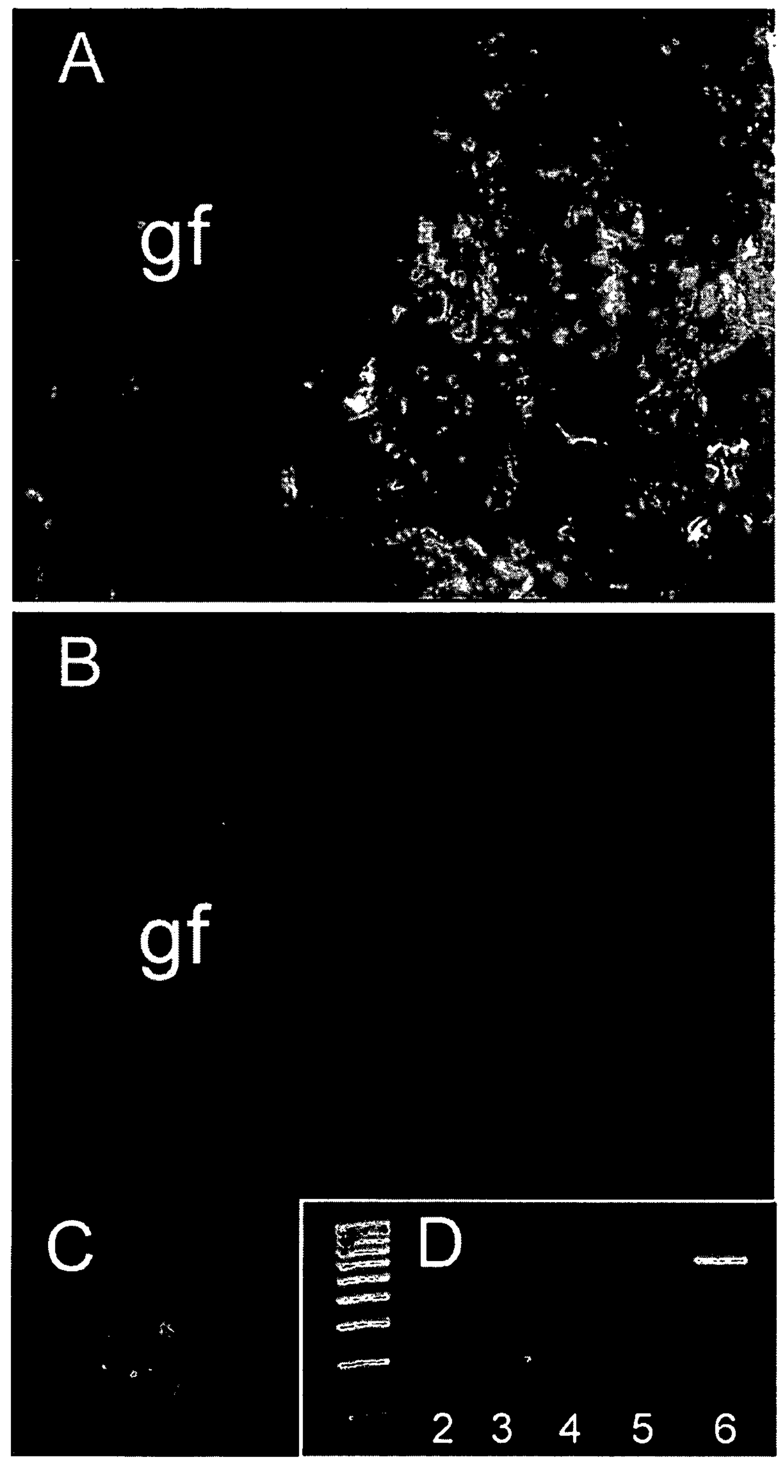
FIGS. 22A-22D show that the inner zone of the gliotic capsule expresses SUR1 but not SUR2. Immunolabling for SUR1 (FIG. 22A) showed prominent expression in cells adjacent to the gelatin sponge (gf), whereas immunolabeling for SUR2 showed no expression (FIG. 22B). A single cell enzymatically isolated from a gelatin sponge implant and immunolabeled for SUR1 is shown (FIG. 22C).

Glibenclamide binds to sulfonylurea receptors, SUR1 and SUR2, with higher affinity for SUR1. Immunofluorescence studies were performed using anti-SURx antibodies. The inner zone of the gliotic capsule immediately outside of the gelatin sponge (gf in FIG. 22) was strongly labeled with anti-SUR1 antibody (FIG. 22A) but not with anti-SUR2 antibody (FIG. 22B). Although individual cells were not discerned at low magnification, higher magnification showed that SUR1 label was uniformly distributed in individual cells after isolation (FIG. 22C).

Evidence for transcription of SUR1, but not SUR2 was also found in RT-PCR experiments run on mRNA from gelatin sponges isolated 7 days after implantation. The signal observed in astrocytes (FIG. 22D, lane 3) was present at the appropriate position on the gel, similar to that from control insulinoma RIN-m5f cells (FIG. 22D, lane 2). By contrast, mRNA for SUR2 is not transcribed in reactive astrocytes (FIG. 22D, lane 5) although it is in cardiomyocytes used as control (FIG. 22D, lane 4).

Example 22

Characterization of the Inner Zone of the Gliotic Capsule

To examine whether or not all GFAP-positive reactive astrocytes in the gliotic capsule are SUR1 positive, brains from rats that had been implanted 1 week earlier with a gelatin sponge, then perfusion-fixed and equilibrated in 40% sucrose in PBS ×2 days were studied. Cryostat sections were double labeled with anti-GFAP and anti-SUR1 antibodies and studied with immunofluorescence. For this and other immunolabeling experiments, standard control protocol included use of the appropriate immunogenic peptide when available or omission of primary antibody.

Figure 23:
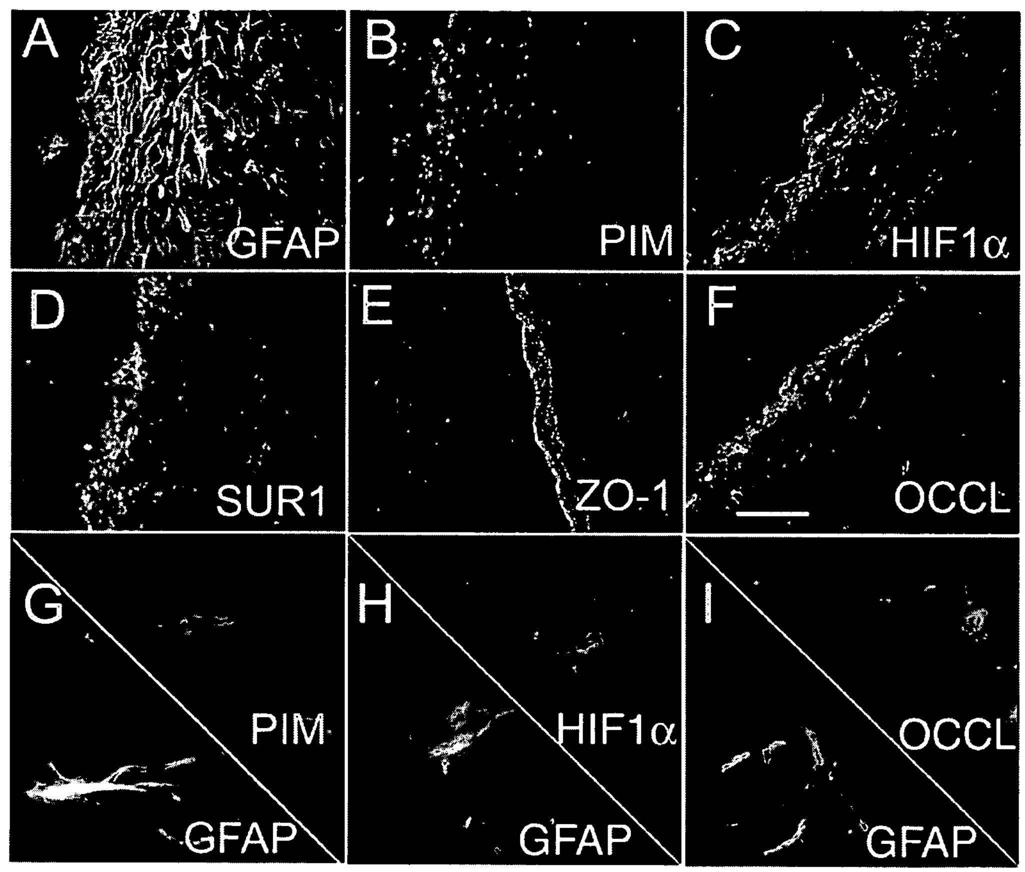
FIGS. 23A-23I show various features of the gliotic capsule. The gliotic capsule is characterized by GFAP-positive cells that are several cell-layers thick (FIG. 23A). Only the inner zone of the gliotic capsule is hypoxic, as demonstrated by pimonidozole labeling (FIG. 23B) and by immunolabeling for HIF1α (FIG. 23C). Also, only the inner zone is immunolabeled for SUR1 (FIG. 23D), and for the tight junction proteins, ZO-1 (FIG. 23E) and occludens (FIG. 23F).

Five animals were sectioned and imaged with low power images. The images invariably showed that the depth (thickness) of the GFAP response from the edge of the gelatin sponge was several-fold greater than the depth of the SUR1 response. Measurements of the depth of the GFAP response yielded values of about 400-500 μm (FIG. 23A; in FIGS. 23A-23I, the location of the gelatin sponge implant was always to the left; bar in FIG. 23F equals 100 μm). By contrast, the prominent portion of the SUR1 response extended for a depth of only 25-50 μm (FIG. 23D). Outside of the SUR1-positive zone was a wide region of GFAP-positive reactive astrocytes that were mostly SUR1 negative. The SUR1 response was always located precisely at the interface with the foreign body, in the innermost zone of the gliotic capsule. Cells that were SUR1 positive were always GFAP positive. It was evident from this experiment that cells clinging to the gelatin sponge and that were harvested with it were likeliest to express SUR1. Also, it was clear that R1 astrocytes in this innermost region comprised a unique subpopulation of reactive astrocytes. From this observation emerged the concept of the "inner zone" of the gliotic capsule as being a unique entity, distinct from the remainder of the gliotic capsule.

Example 23

Other Characteristics of the Inner Zone of the Gliotic Capsule

Other studies were performed to further evaluate the inner zone of the gliotic capsule. In previous experiments, it was found that primary culture of R1 astrocytes under normoxic culture conditions resulted in loss of the SUR1-regulated $NC_{Ca-ATP}$ channel after 3 days, whereas cultured under hypoxic conditions resulted in continued expression of the channel (Chen et al., 2003). Thus, it was determined that expression of the channel required hypoxic conditions, and thus the inner zone of the gliotic capsule where SUR1 expressing R1 astrocytes were found might also be hypoxic. To evaluate this, the histochemical marker, pimonidazole, was used which at $pO_2$<10 mm Hg, forms irreversible covalent adducts with cellular proteins that can be detected immunohistochemically (Arteel et al, 1998; Hale et al., 2002; Kennedy et al., 1997).

Briefly, rats were prepared with a stab injury and implantation of a gelatin sponge. Rats were allowed to survive 1 week. Pimonidazole was administered prior to death, and cryosections were processed for immunofluorescence study using the appropriate antibody to detect pimonidazole adducts. Cryosections were double labeled for GFAP. This experiment confirmed the presence of hypoxic conditions restricted to the SUR1-positive inner zone of the gliotic capsule, with the most prominent pimonidazole labeling extending only 20-50 μm deep (FIG. 23B; GFAP not shown but the depth of the GFAP response resembled that in FIG. 23A). High resolution imaging showed that pimonidazole labeling (FIG. 23G, upper right) was present in large GFAP-positive astrocytes (FIG. 23G, lower left).

It was reasoned that hypoxia of the inner zone might lead to up-regulation/activation of the hypoxia-responsive transcription factor, HIF-1. To examine this, immunolabeling was performed of sections with anti-HIF-1α antibodies with co-labeling for GFAP. This experiment confirmed that HIF-1α labeling was mostly restricted to the SUR1-positive inner zone of the gliotic capsule, with labeling extending only 20-50 μm deep (FIG. 23C; GFAP not shown but the depth of the GFAP response resembled that in FIG. 23A). High resolution imaging showed that HIF-1α labeling (FIG. 23H, upper right) was present in large GFAP-positive astrocytes (FIG. 23H, lower left).

Expression of tight junction proteins was also examined. Two tight junction proteins, ZO-1 and occludin-5, were studied, labeling alternate cryosections with antibodies directed against these proteins. Sections were double labeled for GFAP. Again, only the innermost layer 20-50 μm deep was labeled for either ZO-1 or occludin-5 (FIGS. 23E and 23F; GFAP not shown but the depth of the GFAP response resembled that in FIG. 23A). High resolution imaging showed that occludin-5 labeling (FIG. 23I, upper right) was present in large GFAP-positive astrocytes (FIG. 23I, lower left).

Thus, the inner zone of the gliotic capsule, with its R1 astrocytes that express SUR1-regulated $NC_{Ca-ATP}$ channels and tight junction proteins, may be acting as an important barrier between the foreign body and the brain, e.g., a foreign body-brain barrier (FbBB). If true, one would expect that breaching the barrier might significantly affect the overall response to injury.

Example 24

Manipulation of the Inner Zone

Rats were prepared with a stab injury and implantation of a gelatin sponge according to our usual protocol and were allowed to survive 1 week. At time of surgery, rats were also implanted with osmotic mini-pumps subcutaneously with the delivery catheter placed in the brain at the site of injury. Animals received pumps with either glibenclamide (1 μM at 0.5 μl/hr×7 days) or diazoxide (10 μM at 0.5 μl/hr×7 days). No systemic toxicity was observed, neurological behavior was not impaired, and animals appeared healthy and were not febrile.

Figure 24:
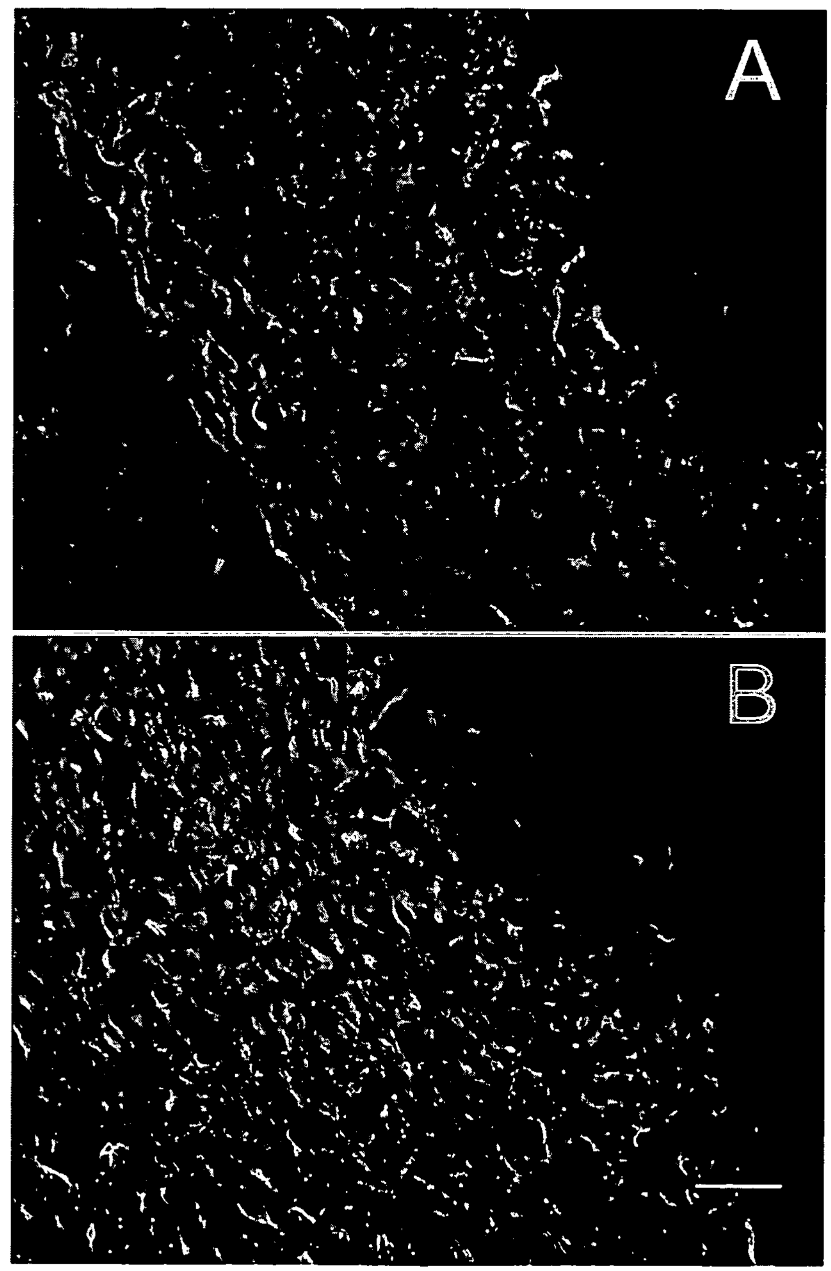
FIGS. 24A-24B show effects of $NC_{Ca\text{-}ATP}$ channel inhibition (FIG. 24A) and $NC_{Ca\text{-}ATP}$ channel activation (FIG. 24B) on the gliotic capsule. Animals with gelatin sponge implants were treated with glibenclamide infusion (FIG. 24A) or diazoxide infusion (FIG. 24B) via osmotic mini-pumps that delivered the compounds directly into the area of the gelatin sponge. Immunolabeling for GFAP showed that channel inhibition with glibenclamide resulted in formation of a well defined gliotic capsule (FIG. 24A), whereas channel activation with diazoxide resulted in formation of a broader, ill-defined capsule (FIG. 24B), due to diazoxide-induced necrotic death of inner zone cells.

Cryosections of injured brains were examined for GFAP. In animals receiving glibenclamide, a well defined gliotic capsule was visualized that was sharply demarcated from surrounding brain, with the inner zone appearing to be densely populated by GFAP-positive cells (FIG. 24A; gelatin sponge to the right). By contrast, animals receiving diazoxide showed an expanded GFAP-positive response that extended farther from the foreign body, with an outer region that was poorly demarcated, and an inner zone that was loose and not compact (FIG. 24B; gelatin sponge to the right).

Figure 25:
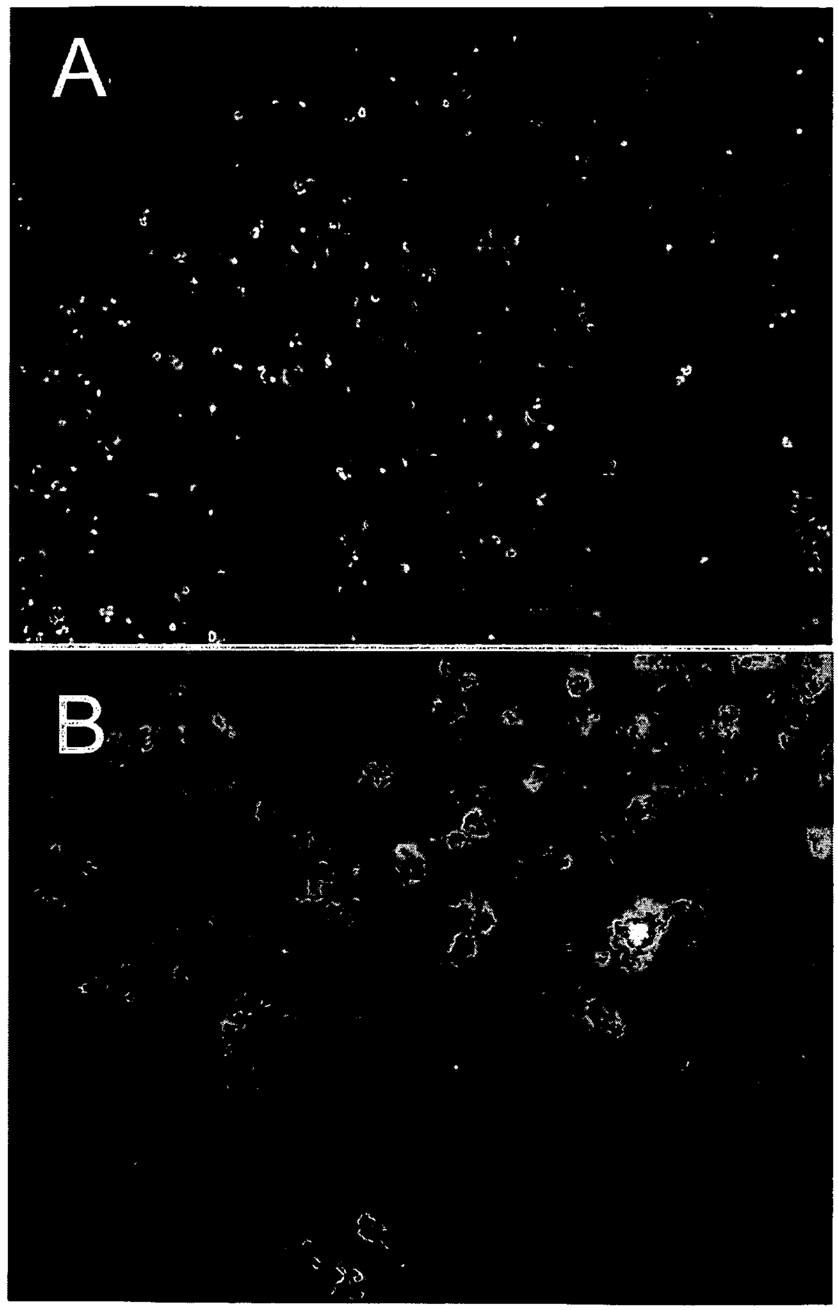
FIGS. 25A-25B show that infusion of diazoxide into the area around the gelatin sponge resulted in a heavy infiltration of polymorphonuclear leukocytes (PMNs). Nuclear labeling with DAPI showed densely packed small cells in the vicinity of the gelatin sponge (FIG. 25A), with immunolabeling using the PMN-specific marker, MMP-8, demonstrating that these cells were PMNs (FIG. 25B). It is believed that the strong inflammatory response represented by the infiltrating PMNs was due to disruption of the barrier between brain and foreign body (gelatin sponge) normally formed by the inner zone of the gliotic capsule.

Cryosections were also examined with the nuclear label, DAPI. In sections from glibenclamide-treated animals, most of the labeling was attributable to GFAP-positive astrocytes. However, in sections from diazoxide-treated animals, DAPI labeling showed "sheets" of small nucleated cells (dull spots in FIG. 25A). On inspection, these sheets of cells appeared to be polymorphonuclear leukocytes (PMNs, neutrophils). This was confirmed by labeling with MMP-8, a PMN-specific marker (FIG. 25B). It is important to note that no evidence of infection was present, and microbiological cultures of explanted materials showed no bacterial growth, including aerobic and anaerobic cultures, indicating that the inflammatory response was not due to infection.

Thus, protecting inner zone R1 astrocytes with glibenclamide appeared to have restrained the overall GFAP-response to injury, whereas killing inner zone R1 astrocytes with diazoxide appeared to have caused an expansion of the overall GFAP-response and recruitment of tremendous numbers of neutrophils. These observations strongly reinforced the concept of the "inner zone" of the gliotic capsule as being a unique entity, with a critical function in determining the overall response to injury.

Example 25

SUR1 in Multiple Brain Pathologies

Figure 26:
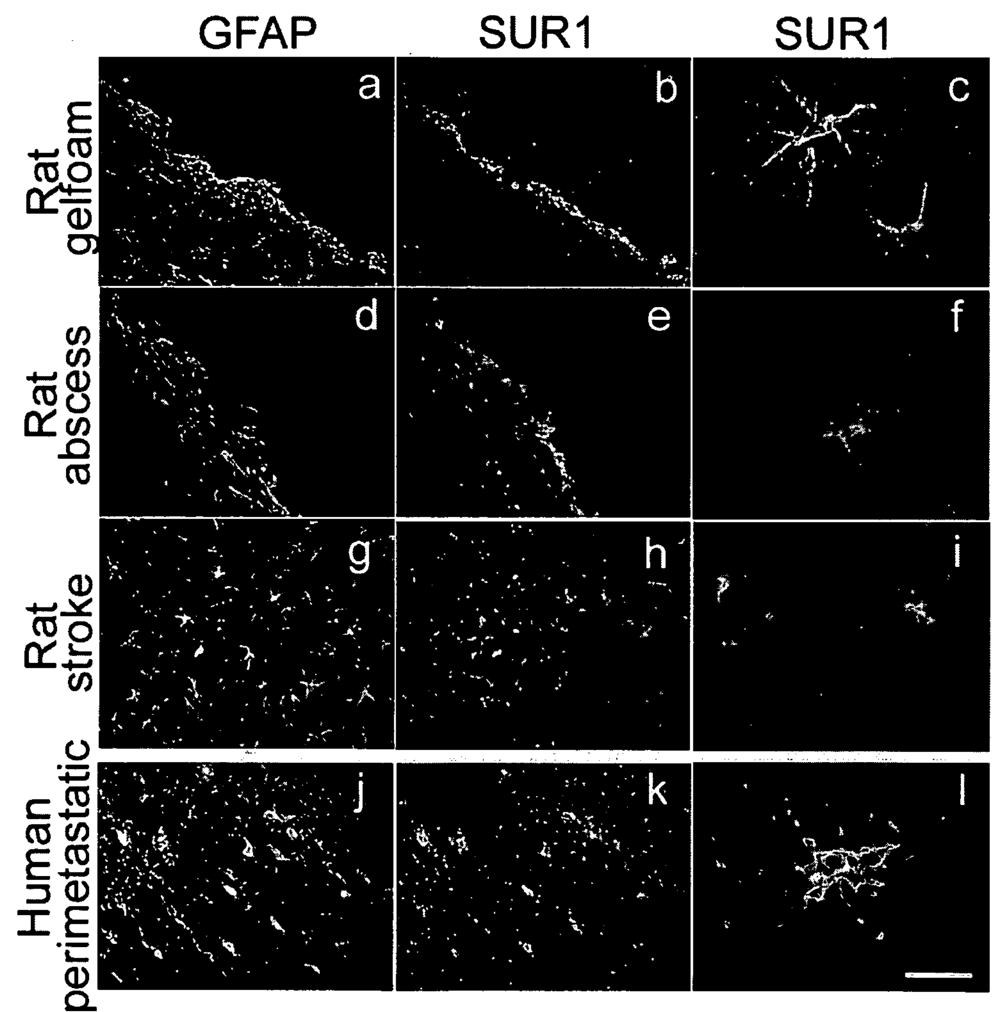
FIGS. 26A-26L show that R1 astrocytes in the inner zone of the gliotic capsule typically express SUR1, a marker for the $NC_{Ca-ATP}$ channel. The inner zones of the gliotic capsules in rats with gelatin sponge implants (FIGS. 26A-26C), in rats with cerebral abscess (FIGS. 26D-26F), and in humans with metastatic tumor (FIGS. 26J-26L) are shown. Also shown is the area of reactive gloss adjacent to a stroke in the rat (FIGS. 26G-26I) resulting from occlusion of the middle cerebral artery. In all cases, a field of cells is labeled for GFAP and co-labelled for SUR1, as indicated. Examples of single cells at high power are also shown for each condition.

Tissues were obtained from the 3 rat models (trauma, abscess and stroke) and from the gliotic capsule surrounding human metastatic tumor, and double immunolabeling was performed with antibodies directed against GFAP and SUR1. Low power views showed a layer of tissue adjacent to the gelatin sponge implant with positive immunolabeling for GFAP that coincided with positive immunolabeling for SUR1 (FIGS. 26A,B). Examination of individual cells at high power showed that the SUR1 immunolabel was present in large stellate-shaped astrocytes, confirming the presence of SUR1-positive R1 astrocytes in the inner zone of the gliotic capsule surrounding a foreign body implant (FIG. 26C).

A brain abscess model in the rat was studied. The abscess was produced by implanting an autologous fecal pellet subcortically under general anesthesia. These animals survived quite well, although they showed evidence of mild weight loss. When sacrificed 1 week after surgery, a purulent cavity was found surrounded by a gliotic capsule. Low power views of the gliotic capsule adjacent to the area of puss showed cells with positive immunolabeling for GFAP that coincided with positive immunolabeling for SUR1 (FIGS. 26D,E). Examination of individual cells at high power showed that the SUR1 immunolabel was present in large stellate-shaped astrocytes, confirming the presence of SUR1-positive R1 astrocytes in the inner zone of the gliotic capsule surrounding brain abscess (FIG. 26F).

A standard stoke model in the rat was studied. The stroke was produced by intra-carotid insertion of a thread up to the bifurcation of the internal carotid artery, placed under general anesthesia. Animals surviving the stroke were sacrificed at 1 week and the brain was examined. Low power views of tissues adjacent to the area of stroke showed cells with positive immunolabeling for GFAP that coincided with positive immunolabeling for SUR1 (FIGS. 26G,H). Examination of individual cells at high power showed that the SUR1 immunolabel was present in large stellate-shaped astrocytes, confirming the presence of SUR1-positive R1 astrocytes in the gliotic capsule surrounding stroke (FIG. 26I).

Tissue was obtained from humans undergoing surgery for resection of metastatic brain tumors. At surgery, the gliotic capsule that surrounds the metastasis is readily distinguished from the tumor itself and from edematous white matter. Low power views of the gliotic capsule adjacent to the metastasis showed cells with positive immunolabeling for GFAP that coincided with positive immunolabeling for SUR1 (FIGS. 26J,K). Examination of individual cells at high power showed that the SUR1 immunolabel was present in large stellate-shaped astrocytes with multiple well-developed processes, confirming the presence of SUR1-positive R1 astrocytes in the gliotic capsule surrounding metastatic brain tumor in humans (FIG. 26L).

These data show for the first time SUR1 up-regulation in reactive astrocytes at the site of formation of a gliotic capsule consistent with expression of SUR1-regulated $NC_{Ca\text{-}ATP}$ channels in R1 astrocytes. The data indicate that SUR1 expression in R1 astrocytes in the gliotic capsule was a common phenomenon in numerous pathological conditions that affect the brain. These data highlight a unique opportunity to manipulate R1 astrocytes of the inner zone selectively by exploiting pharmacological agents that act at SUR1 and that can therefore determine death or survival of these cells.

Overall, these observations strongly reinforced the concept of the "inner zone" of the gliotic capsule as being a unique entity, distinct from the remainder of the gliotic capsule.

Example 26

Figure 27:
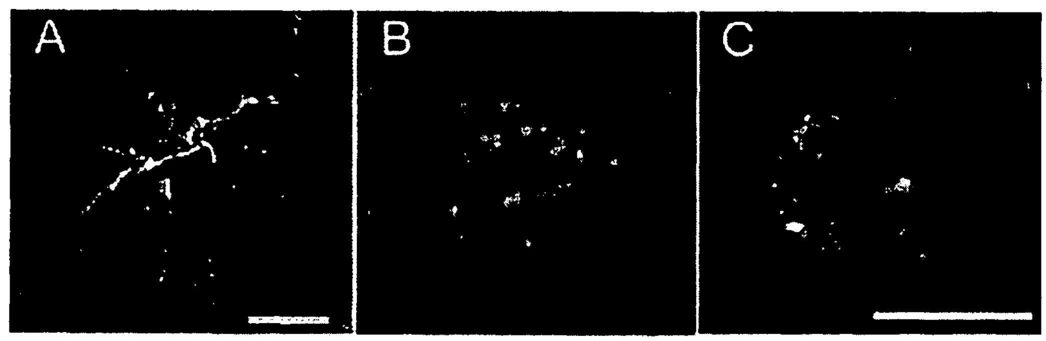
FIGS. 27A-27C shows that stellate astrocytes near the edge of a stroke up-regulate SUR1 (FIG. 27A), a marker of the $NC_{Ca-ATP}$ channel. In the middle of the stroke, cells with altered morphology including blebbing are also immunolabeled for SUR1 (FIG. 27B,27C).
Figure 28:
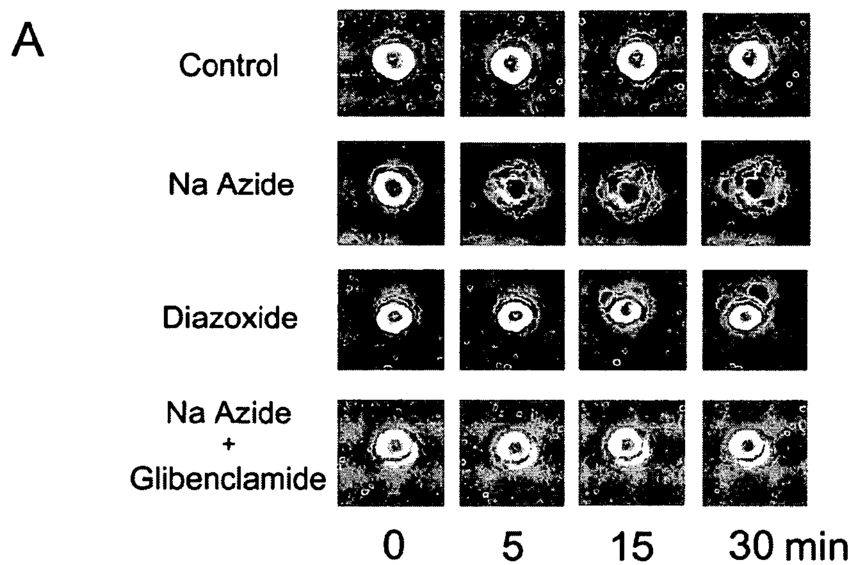
FIGS. 28A-28C show that glibenclamide protects from Na azide-induced channel opening and necrotic cell death.
Figure 28:
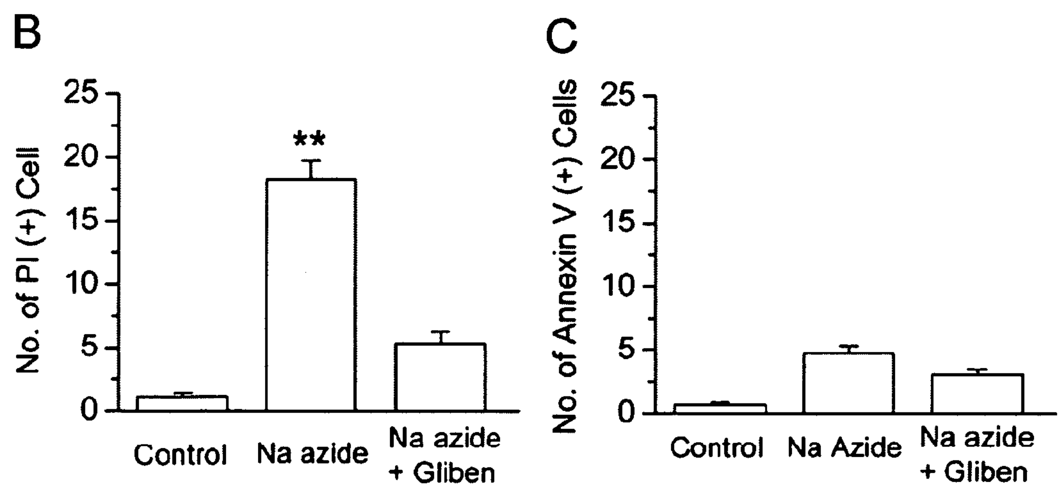

The $Nc_{ca\text{-}Atp}$ Channel and Necrotic Death $NC_{Ca\text{-}ATP}$ channels were studied in a rodent model of stroke. In the penumbra, SUR1 labeling was found in stellate-shaped cells (FIG. 27A) that were also GFAP-positive. In the middle of the stroke, stellate cells were absent, but SUR1 labeling was found in round cells exhibiting a bleb-like appearance (FIGS. 27B,C) that were also GFAP-positive (not shown). The round cells with blebbing in situ resembled reactive astrocytes in vitro undergoing necrotic death after exposure to Na azide. The effect of glibenclamide vs. saline was determined. Glibenclamide or saline was administered via subcutaneously-implanted osmotic mini-pump (1 μM at 0.5 μl/hr). In saline treated rats, 3-day mortality after stroke was 68%, whereas in glibenclamide-treated rats, 3-day mortality was reduced to 28% (n=29 in each group; $p<0.001$, by $\chi^2$). In separate animals, the stroke hemisphere in glibenclamide-treated rats contained only half as much excess water as in saline-treated rats (n=5 in each group; $p<0.01$, by t-test), confirming an important role of the $NC_{Ca-ATP}$ channel in edema formation.

SUR1 was also studied in a rodent model of trauma. The effect of direct infusion of drugs into the site of trauma was examined using an implanted osmotic mini-pump. The channel inhibitor, glibenclamide, was used to reduce death of reactive astrocytes, and the channel activator, diazoxide, to promote astrocyte death. Glibenclamide infusion reduced the overall injury response, stabilized the gliotic capsule around the foreign body implant, and minimized the inflammatory response compared to control.

Conversely, diazoxide essentially destroyed the gliotic capsule and incited a huge inflammatory response, characterized by massive influx of polymorphonuclear cells (PMNs) (FIGS. 25A, B). These data suggested that $NC_{Ca-ATP}$ channel plays a critical role in the injury response, and they strongly support the hypothesis that inflammation is closely linked to activity of the $NC_{Ca-ATP}$ channel and necrotic death of reactive astrocytes.

Example 27

Permanent MCA Models

Adult male or female Wistar rats (275-350 gm) were fasted overnight then anesthetized (Ketamine, 60 mg/kg plus Xylazine, 7.5 mg/kg, i.p.). The right femoral artery was cannulated, and physiological parameters, including temperature, pH, $pO_2$, $pCO_2$ and glucose were monitored. Using a ventral cervical incision, the right external carotid and pterygopalatine arteries were ligated. The common carotid artery was ligated proximally and catheterized to allow embolization of the internal carotid artery.

For thromboembolic (TE) stroke, 7-8 allogeneic clots, 1.5 mm long, were embolized. Allogeneic, thrombin-induced, fibrin-rich blood clots were prepared (Toomy et al., 2002).

For large MCA strokes with malignant cerebral edema (MCE), the inventors first embolized microparticles (Nakabayashi et al., 1997) [polyvinyl alcohol (PVA) particles; Target Therapeutics, Fremont Calif.; 150-250 μm diameter, 600 μg in 1.5 ml heparinized-saline], followed by standard permanent intraluminal suture occlusion (Kawamura et al., 1991) using a monofilament suture (4-0 nylon, rounded at the tip and coated with poly-L-lysine) advanced up to the ICA bifurcation and secured in place with a ligature.

After stroke, animals are given 10 ml glucose-free normal saline by dermoclysis. Rectal temperature was maintained at ≈37° C. using a servo-controlled warming blanket until animals awoke from anesthesia. Blood gases and serum glucose at the time of stroke were: $pO_2$, 94±5 mm Hg; $pCO_2$, 36±5 mm Hg; pH, 7.33±0.01; glucose 142±6 mg/dl in controls and $pO_2$, 93±3 mm Hg; $pCO_2$, 38±2 mm Hg; pH, 7.34±0.01; glucose 152±7 mg/dl in glibenclamide-treated animals.

With both models, animals awoke promptly from anesthesia and moved about, generally exhibited abnormal neurological function, typically circling behavior and hemiparesis. Mortality with the thromboembolic (TE) model was minimal, whereas with the malignant cerebral edema (MCE) model, animals exhibited delayed deterioration, often leading to death. Most deaths occurred 12-24 hr after MCA occlusion, with necropsies confirming that death was due to bland infarcts. Rarely, an animal died <6 hr after stroke and was found at necropsy to have a subarachnoid hemorrhage, in which case it was excluded from the study. Mortality in untreated animals with MCE and bland infarcts was 65%, similar to that in humans with large MCA strokes (Ayata & Ropper, 2002).

Example 28

Studies on Stroke Size, Mortality, Tissue-Water, and Drug Localization

After MCA occlusion (both TE and MCE models), mini-osmotic pumps (Alzet 2002, Durect Corporation, Cupertino, Calif.) were implanted subcutaneously that delivered either saline or glibenclamide (Sigma, St. Louis, Mo.; 300 μM or 148 μg/ml, 0.5 μl/hr subcutaneously, no loading dose). Stroke size (TE model), measured as the volume of TTC(−) tissue in consecutive 2 mm thick slices and expressed as the percent of hemisphere volume, was compared 48 after stroke in 2 treatment groups, each comprised of 10 male rats, treated with either saline or glibenclamide. Mortality (MCE model) was compared during the first week after stroke in 2 treatment groups, each comprised of 29 rats (19 female plus 10 male), treated with either saline or glibenclamide. Edema (MCE model) was compared at 8 hr after stroke in 2 treatment groups, each comprised of 11 male rats, treated with either saline or glibenclamide; rats in each of these 2 treatment groups were subdivided into 2 subgroups, with the first of these being used to analyze water in the entire involved hemisphere (no TTC processing), and the second being used to analyze water in the TTC(+) vs. TTC(−) portions of the involved hemisphere. For localization of fluorescent-tagged drug, 20 male rats were subjected to MCA stroke (MCE model) and were implanted with mini-osmotic pumps that delivered BODIPY-conjugated glibenclamide (BODIPY-FL-glyburide, Molecular Probes, Eugene, Oreg.; 300 μM or 235 μg/ml, 0.5 μl/hr subcutaneously, no loading dose). Of these, 15 rats were used for validation of drug action (mortality, tissue water and glucose) and 5 rats were used for determination of drug distribution.

Example 29

Immunolabeling

Brains were perfusion-fixed (4% paraformaldehyde) and cryoprotected (30% sucrose). Cryosections (10 μm) were prepared and immunolabeled using standard techniques (Chen et al., 2003). After permeabilizing (0.3% Triton X-100 for 10 min), sections were blocked (2% donkey serum for 1 hr; Sigma D-9663), then incubated with primary antibody directed against SUR1 (1:300; 1 hr at room temperature then 48 h at 4° C.; SC-5789; Santa Cruz Biotechnology). After washing, sections were incubated with fluorescent secondary antibody (1:400; donkey anti-goat Alexa Fluor 555; Molecular Probes, Oreg.). For co-labeling, primary antibodies directed against NeuN (1:100; MAB377; Chemicon, Calif.); GFAP (1:500; CY3 conjugated; C-9205; Sigma, St. Louis, Mo.) and vWf (1:200; F3520, Sigma) were used and tissues were processed according to manufacturers' recommendations. Species-appropriate fluorescent secondary antibodies were used as needed. Fluorescent signals were visualized using epifluorescence microscopy (Nikon Eclipse E1000).

Example 30

TTC Staining, Stroke Size

Freshly harvested brains were cut into 2-mm thick coronal sections, and slices were exposed to TTC (0.125% w/v in 62.5 mM Tris-HCl, 13 mM $MgCl_2$, 1.5% dimethylformamide) for 30 min at 37° C. For stroke size, stained sections were photographed and images were analyzed (Scion Image) to determine the percent of the involved hemisphere occupied by TTC(−) tissue; no correction for edema was performed. For some determinations of water or SUR1 protein content, individual coronal sections were divided under magnification into 3 parts: (i) the non-involved, control hemisphere; (ii) the TTC(+) portion of the involved hemisphere; (iii) the TTC(−) portion of the involved hemisphere. For each animal, pooled tissues from the 3 parts were then processed for tissue water measurements or for Western blots.

Example 31

Tissue Water Content

Tissue water was quantified by the wet/dry weight method (Hua et al., 2003). Tissue samples were blotted to remove small quantities of adsorbed fluid. Samples were weighed with a precision scale to obtain the wet weight (WW), dried to constant weight at 80° C. and low vacuum, and then reweighed to obtain the dry weight (WD). The percent $H_2O$ of each tissue sample was then calculated as (WW−WD)×100/WW.

Example 32

Immunoblots

Tissues lysates and gels were prepared (Perillan et al., 2002). Membranes were developed for SUR1 (SC-5789; Santa Cruz Biotechnology), Kir6.1 (Santa Cruz) or Kir6.2 (Santa Cruz). Membranes were stripped and re-blotted for β-actin (1:5000; Sigma, St. Louis, Mo.), which was used to normalize the primary data. Detection was carried out using the ECL system (Amersham Biosciences, Inc.) with routine imaging and quantification (Fuji LAS-3000).

Example 33

In Situ Hybridization

Non-radioactive digoxigenin-labeled probes were made according to the manufacturer's protocol (Roche) using SP6 or T7 RNA polymerase. RNA dig-labeled probes (sense and anti-sense) were generated from pGEM-T easy plasmids (Promega) with the SUR1 insert (613 bp) flanked by the primers: 5' AAGCACGTCAACGCCCT 3' (forward; SEQ ID NO: 1); 5' GAAGCTTTTCCGGCTTGTC 3' (reverse; SEQ ID NO: 2). Fresh-frozen (10 μm) or paraffin-embedded (4 μm) sections of rat brain (3, 6, 8 hours after MCA stroke) were used for in situ hybridization (Anisimov et al., 2002).

Example 34

Inner Zone of the Gliotic Capsule

To assess if other causes of hypoxia, for example arterial occlusion, resulted in up-regulation of SUR1, two rodent models of permanent focal cerebral ischemia as described in the examples were used.

The MCE model was used to evaluate SUR1 protein and mRNA, and to assess effects of SUR1 inhibition on edema and survival, while the TE model was used to measure effects of SUR1 inhibition on stroke size. Absence of perfusion (FIG. 29A), TTC staining (Mathews et al., 2000) (FIG. 29B) and GFAP immunolabeling were used to distinguish infarct from peri-infarct regions.

Figure 29:
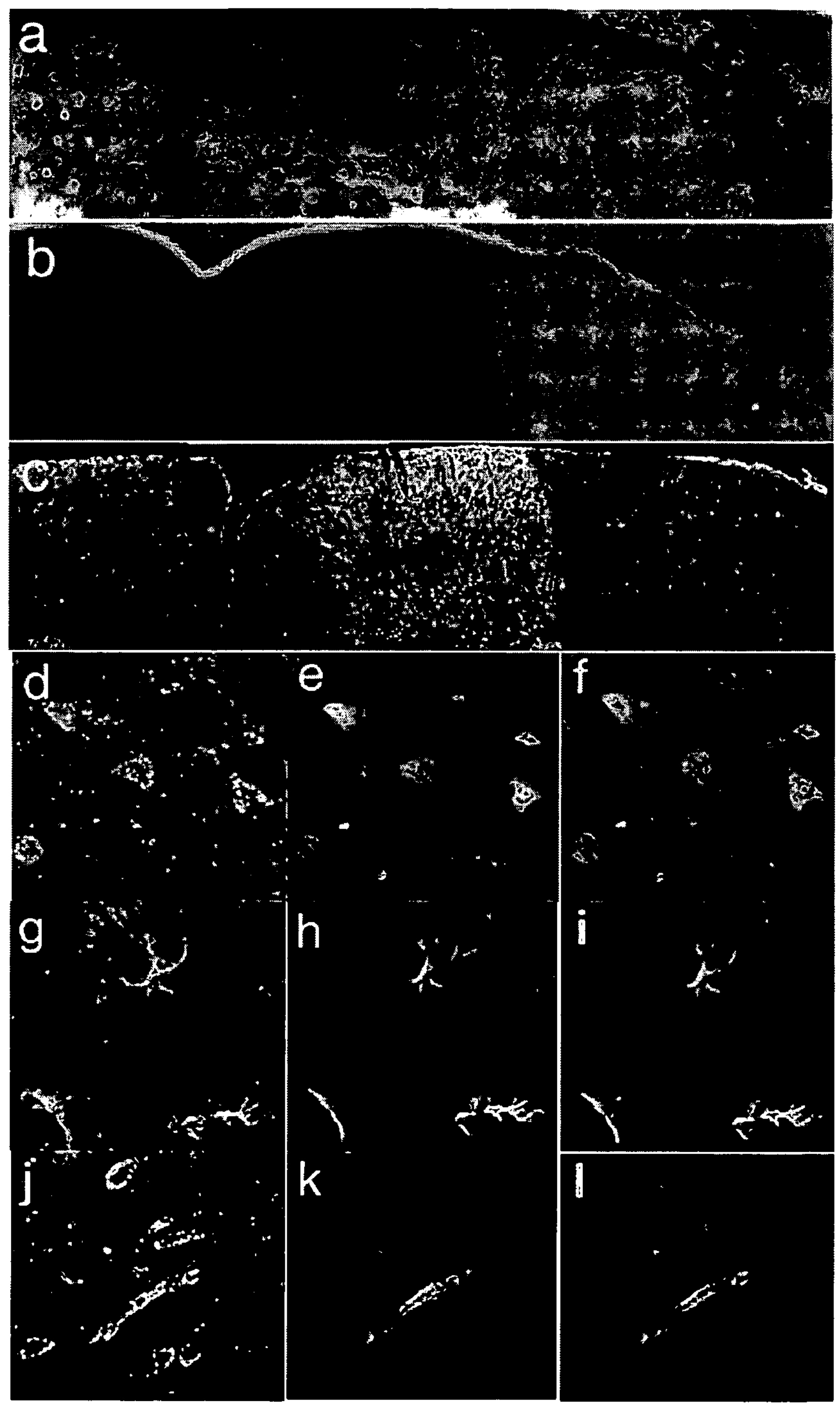
FIGS. 29A-29L shows that SUR1 is up-regulated in MCA stroke. Watershed area between MCA-ACA in 3 different animals 8-16 hr after MCA stroke, identified by pre-mortem administration of Evans blue and postmortem perfusion with India ink (FIG. 29A), by TTC staining (FIG. 29B) and by immunofluorescence imaging for SUR1 (FIG. 29C). Immunofluorescence images showing SUR1 at 3 hr in the core of the stroke in cells (FIG. 29D) double-labeled for the neuronal marker, NeuN (FIG. 29E), and showing SUR1 at 8 hr in the peri-infarct region in cells (FIGS. 14G, 14J) double-labeled for the astrocytic marker, GFAP (FIG. 29H), and the endothelial cell marker, von Willebrand factor (FIG. 29K). Superimposed images of double-labeled fields are shown (FIGS. 29F, 29I, and 29L).

SUR1 expression increased transiently in the core of the infarct. Here, an increase in SUR1 became evident as early as 2-3 hr after MCA occlusion (FIG. 29D), well before onset of necrosis, and later disappeared as necrosis set in (FIG. 29C, right side of figure). At these early times before necrosis, SUR1 was very prominent in neurons that co-labeled with NeuN (FIGS. 29D-F).

In peri-infarct regions, including the classical ischemic "watershed" zone between anterior cerebral artery (ACA) and MCA territories, SUR1 expression increased later than in the core but was sustained. By 6-12 hr, SUR1 expression sharply demarcated infarct and peri-infarct areas (FIG. 29C). Here, SUR1 expression was found in neurons, astrocytes and capillary endothelial cells, as shown by co-labeling with NeuN, GFAP (FIGS. 29G-I) and von Willebrand factor (FIGS. 29J-L), respectively. SUR1 is not normally expressed in such abundance in these cortical and subcortical areas (Treherne & Ashford, 1991; Karschin et al., 1997) as is evident in contralateral tissues (FIG. 29C, left side of figure).

Figure 30:
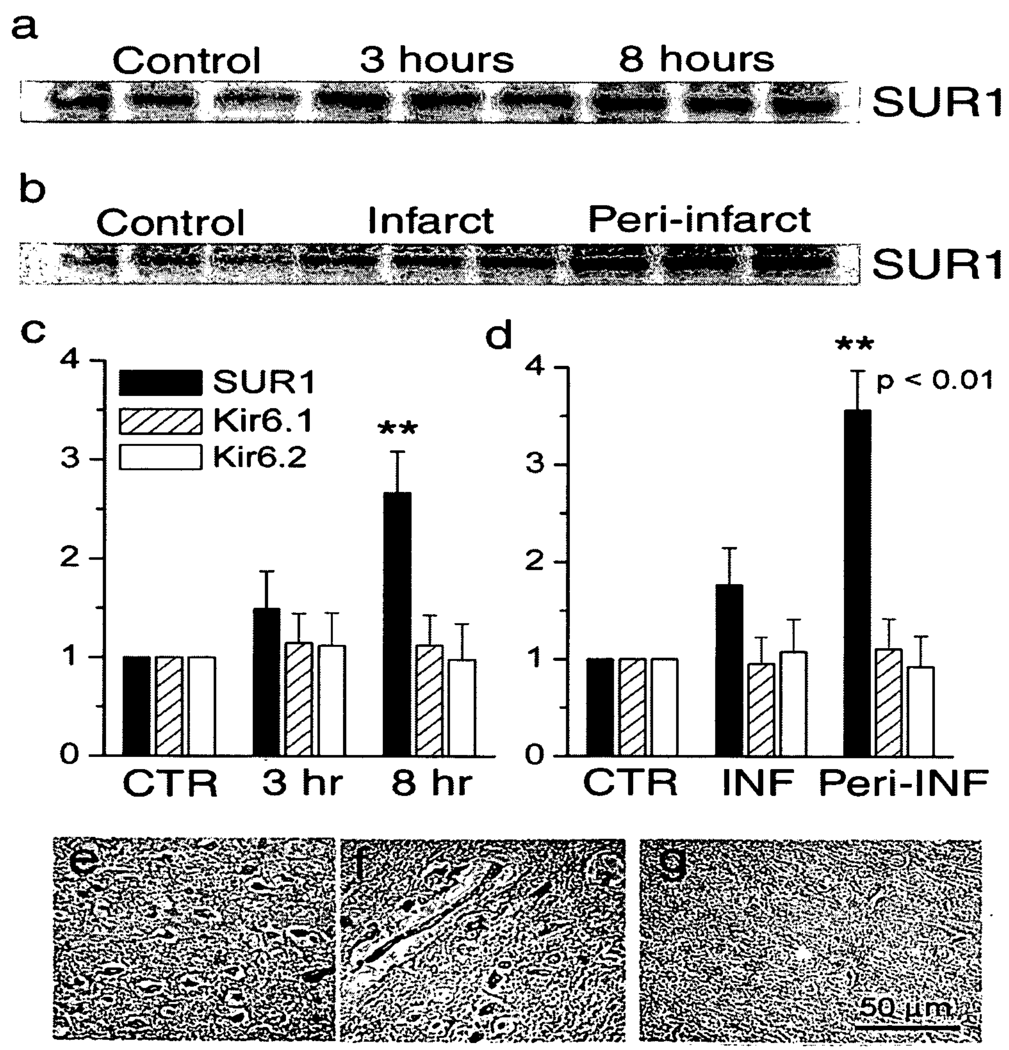
FIGS. 30A-30G show that SUR1 but not Kir6.1 or Kir6.2 is transcriptionally up-regulated in MCA stroke. Western blots for SUR1 (≈180 kDa) at different times (FIG. 30A) and in different locations (FIG. 15B) after MCA stroke; in (FIG. 30A), lysates were all from TTC(+) peri-infarct regions of the involved hemisphere, obtained at the times indicated; in (FIG. 30B), lysates were all obtained 8 hr after MCA stoke from the regions indicated; each individual lane in a and b is from a single animal. Quantification of the data from (FIG. 30A) and (FIG. 30B), respectively, combined with comparable data for Kir6.1 and Kir6.2; for each individual blot, data were normalized to values of β-actin and to the control data for that blot and analyzed separately; , $p<0.01$. In situ hybridization for SUR1, 3 hr after MCA stroke; paraffin sections showed that large neuron-like cells (FIG. 30E) and capillaries (FIG. 30F) in the ischemic zone were labeled, whereas tissues from the same areas on the control side were not (FIG. 30**G).

Western blots showed an increase in expression of SUR1 protein, most prominently in peri-infarct regions (FIGS. 30A-D). However, the pore-forming subunits of $K_{ATP}$ channels, Kir6.1 or Kir6.2, were not up-regulated (FIGS. 30C-D). In situ hybridization showed SUR1 transcripts in neurons and capillaries from regions of ischemia that were not present in control tissues (FIGS. 30E-G), suggesting that SUR1, but not $K_{ATP}$ channels, was transcriptionally up-regulated in cerebral ischemia.

Thus, these data suggest that SUR1, but not Kir6.1 or Kir6.2, is transcriptionally up-regulated in cerebral ischemia, first in regions that are destined to undergo necrosis, and later in peri-infarct regions.

Example 35

SUR1 UP-Regulation

Figure 31:
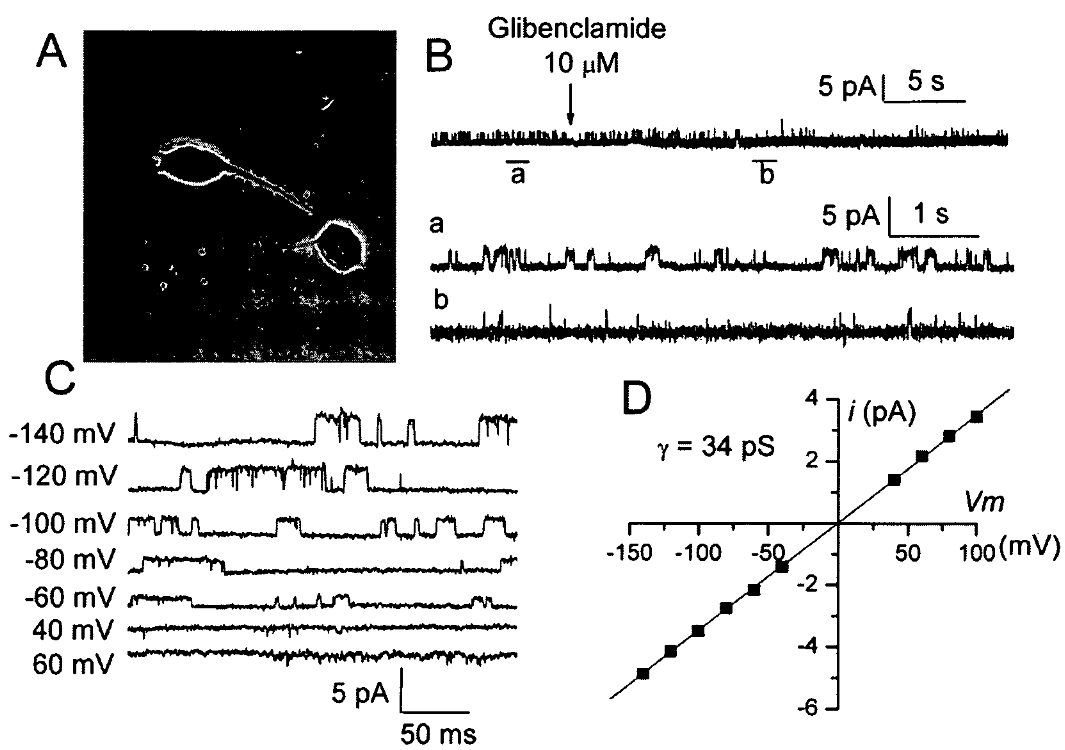
FIGS. 31A-31D show patch clamp recordings of $NC_{CaATP}$ channel in neuron-like cells in stroke.

FIGS. 30A-G discussed in Example 34 showed that SUR1 was significantly up-regulated in stroke. It also showed that the pore-forming subunits, Kir6.1 and Kir6.2, were not up-regulated in stroke, suggesting that $K_{ATP}$ channels were not involved. To prove that SUR1 up-regulation is due to $NC_{Ca-ATP}$ channels and not to $K_{ATP}$ channels, patch clamp recordings of neurons and endothelial cells from ischemic regions were performed. Large neuron-like cells were enxymatically isolated 3-hr (FIG. 31A) and 6-hr after stroke. Patch clamp study was carried out using $Cs^+$ in the bath and pipette, to block all $K^+$ channels including $K_{ATP}$ channels. These experiments showed robust cation channel activity that was blocked by glibenclamide, as predicted for the $NC_{Ca-ATP}$ channel (FIG. 31B). In addition, when channel activity was recorded with $K^+$, the slope conductance was 34 pS (FIGS. 31C,D), as previously reported in freshly isolated R1 astrocytes, and much less than the 70-75 pS reported for KATP channels.

Example 36

Function of SUR1 in Cerebral Ischemia

Figure 32:
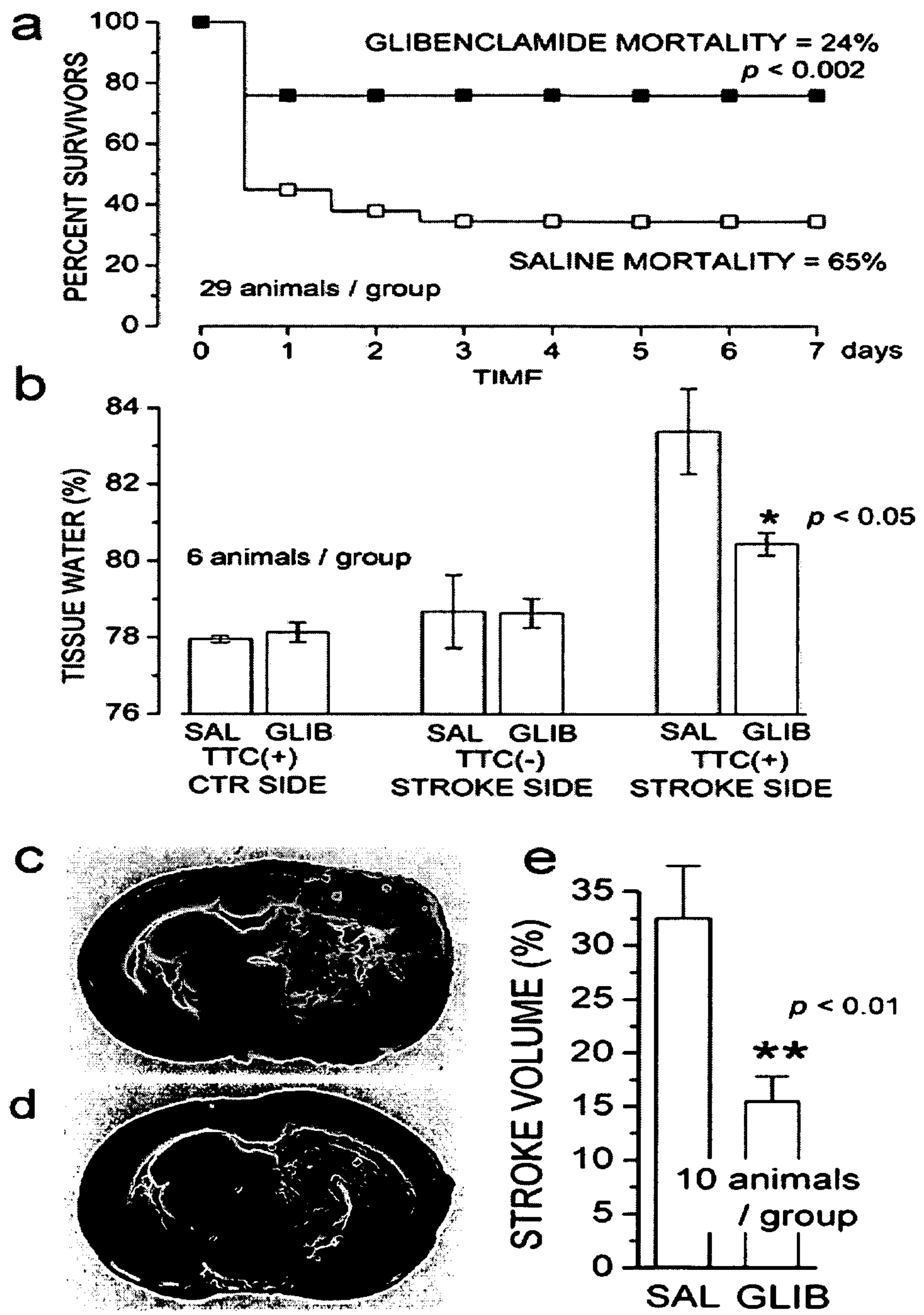
FIGS. 32A-32E show that glibenclamide reduces mortality, edema and stroke size in MCA stroke.

To determine the function of SUR1 that was newly expressed in cerebral ischemia, the effects of glibenclamide, a highly selective inhibitor of SUR1 was studied. The effect of glibenclamide on mortality (MCE model) was studied. In a large group of animals, both male and female, treatment with glibenclamide resulted in a dramatic reduction in mortality compared to saline, from 65% to 24% ($p<0.002$; FIG. 32A).

Since glibenclamide had been shown to ameliorate cytotoxic edema of astrocytes induced by energy depletion (Chen et al., 2003), it was reasoned that the beneficial effect on mortality was related to edema. The effect of glibenclamide on the formation of edema 8 hr after induction of stroke (MCE model) was examined. This is a time that preceded death of any animal in the mortality study. In the first of two experiments, water content in the involved and uninvolved hemispheres was measured using the methods described above. For the control hemisphere, water was 77.9±0.2%. For the involved hemisphere, water rose by 3.4%, to 81.3±0.5% for the group treated with saline, whereas it rose by only 2.0%, to 79.9±0.3%, for the group treated with glibenclamide. These values were significantly different ($p<0.05$), consistent with an important role of SUR1 in formation of edema.

Next, to better characterize the location of edema, the water content after dividing coronal brain sections into viable TTC (+) and non-viable TTC(−) parts was examined. Water in the uninvolved hemisphere was 78.0±0.1% (FIG. 32B), similar to the previous value of 77.9±0.2%, indicating that TTC processing had not altered water content. For the involved hemisphere, water in the TTC(+) tissue rose by 5.4%, to 83.4±1.1% for the group treated with saline, whereas it rose by only 2.5%, to 80.5±0.3%, for the group treated with glibenclamide (FIG. 32B). These values were significantly different ($p<0.05$). By contrast, values for water in TTC(−) tissues, 78.7±1.0% and 78.6±0.4% with saline and with glibenclamide, respectively, were not different ($p=0.97$), and were only slightly higher than the value for the uninvolved hemisphere (78.0%), reflecting a need for ongoing blood flow to increase tissue water (FIG. 32B) (Ayata & Ropper, 2002).

In these animals, serum glucose at 8 hr when edema was measured remained in a range unlikely to have an effect on ischemia-induced damage (Li et al., 1994; Wass & Lanier, 1996) (122±4 vs. 93±3 mg/dl for saline and glibenclamide-treated animals, respectively; 11 rats/group). Together, these data indicated that the edema was located almost entirely in viable peri-infarct (penumbral) tissue adjacent to the early core of the stroke, and that glibenclamide was highly effective in reducing it, consistent with an important role for SUR1 in formation of edema.

Thus, the data with low-dose glibenclamide, which is highly selective for SUR1 (Gribble & Reimann, 2003; Meyer et al., 1999) provided compelling evidence of a critical role for SUR1 in formation of cerebral edema.

Example 37

The Effect of Stroke Size

A non-lethal thromboembolic (TE) model was used to assess stroke size 48 hr after induction of stroke.

With the TE model, glibenclamide treatment resulted in a highly significant reduction in stroke volume, compared to saline controls (32.5±4.9% vs. 15.5±2.3%; $p<0.01$) (FIGS. 32C-E). Essentially all animals, regardless of treatment group, suffered infarctions involving the basal ganglia, which were supplied by terminal lenticulostriate arterioles. However, reduced stroke volumes in the glibenclamide group were often associated with marked sparing of the cerebral cortex (FIGS. 32C-D), a phenomenon previously reported with decompressive craniectomy (Doerfler et al., 2001). With glibenclamide, cortical sparing may reflect improved leptomeningeal collateral blood flow due to reduced cerebral edema and reduced intracranial pressure.

Example 38

MCE Model Following Stroke

The fluorescent derivative, BODIPY-glibenclamide, was used to label tissues in vivo following stroke (MCE model).

Figure 33:
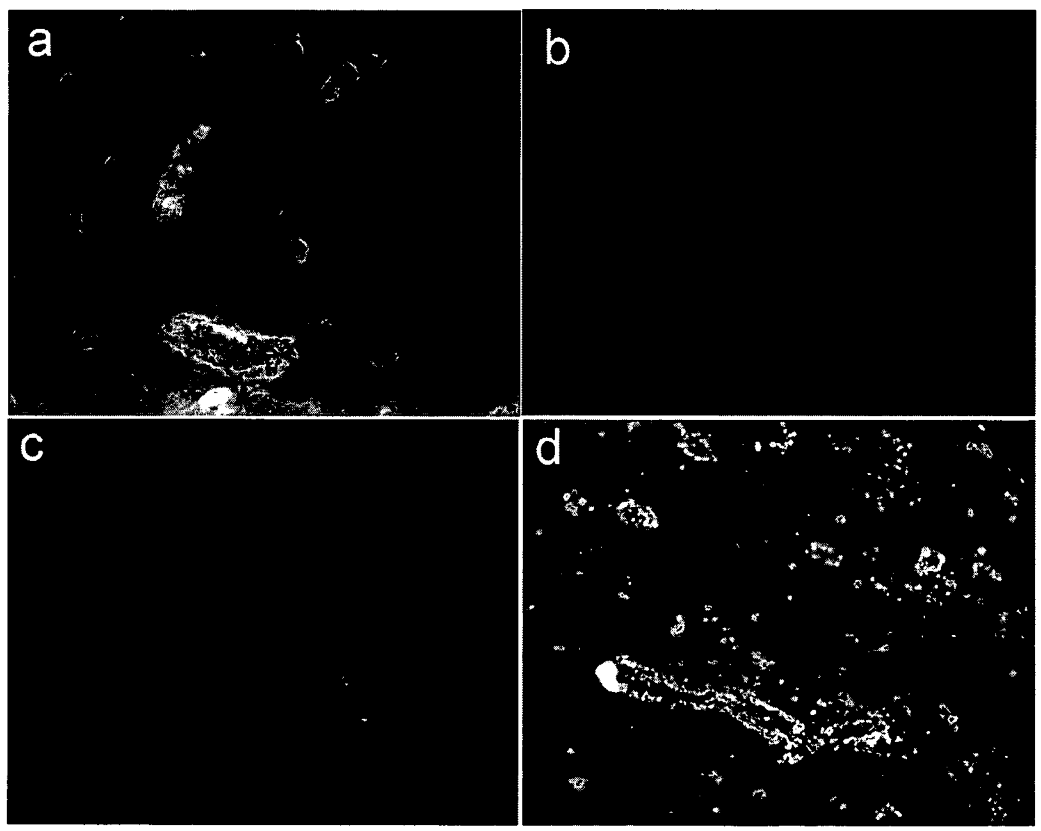
FIGS. 33A-33D show that tissue distribution of BODIPY-glibenclamide in MCA stroke. a-c, Fluorescence images of brain sections in an animal 6 hr after MCA stroke (MCE model) and administration of BODIPY-glibenclamide; fluorescent labeling was evident in cells, microvessels (FIG. 33A) and capillaries (FIG. 33C) from ischemic regions, but not in the contralateral hemisphere (FIG. 18B); the images in (FIGS. 33A, 33B) are from the same animal, taken with the same exposure time; in (FIG. 33C), the single layer of nuclei confirms that the structure brightly labeled by BODIPY-glibenclamide is a capillary.
Figure 34:
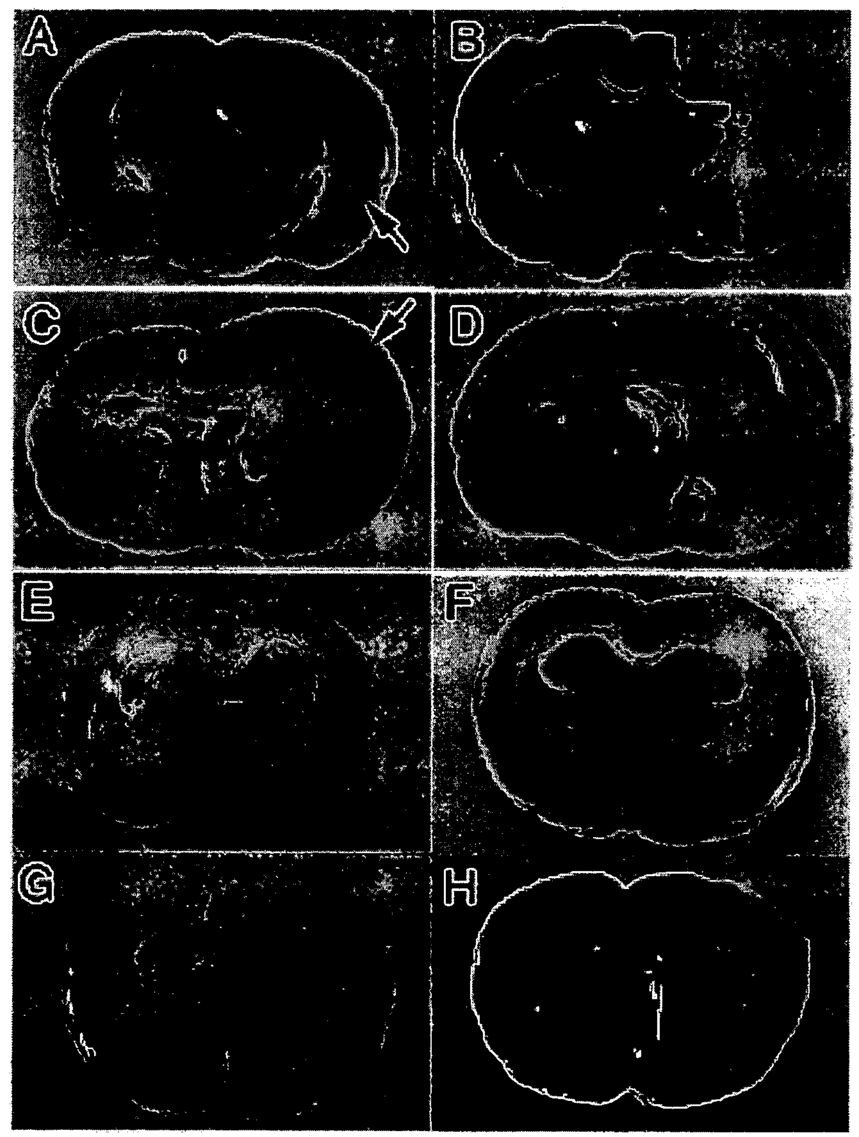
FIGS. 34A-34H show that glibenclamide reduces hemorrhagic conversion.

When delivered in the same manner as the parent compound, the fluorescent derivative exhibited similar protective effects, but was less potent [7-day mortality, 40% (n=10); water in the TTC(+) portion of the involved hemisphere at 8 hr, 82.7±1.4% (n=5); serum glucose, 109±4 mg/dl], consistent with reduced efficacy of the labeled drug (Zunkler et al., 2004). The low systemic dose of drug used yielded minimal labeling in the uninvolved hemisphere (FIG. 33B) and pancreas, and none in the unperfused core of the stroke. However, cells in peri-infarct regions were clearly labeled, with well-defined labeling of large neuron-like cells and of microvessels (FIG. 33A), including capillaries (FIG. 33C), that showed prominent expression of SUR1 (FIG. 33D). Preferential cellular labeling in ischemic brain likely reflected not only an increase in glibenclamide binding sites, but also an increase in uptake, possibly due to alteration of the blood brain barrier.

Thus, the data indicated the presence of $NC_{Ca\text{-}ATP}$ channels in capillary endothelium and neurons in addition to their previously described presence in astrocytes (Chen et al., 2001; Chen et al., 2003). Additional patch clamp experiments on neurons and microvessels isolated from ischemic cortex 1-6 hr after MCA occlusion (MCE model) confirmed the presence of $NC_{Ca\text{-}ATP}$ channels, showing a non-selective cation channel of around 30-35 pS conductance, that was easily recorded with $Cs^+$ as the charge carrier, and that was blocked by glibenclamide. This channel was not present in cells from non-ischemic cerebral tissues.

In view of the above, it is suggested that SUR1-regulated $NC_{Ca\text{-}ATP}$ channels that are opened by ATP depletion and that are newly expressed in ischemic neurons, astrocytes and endothelial cells constitute an important, heretofore unidentified pathway for $Na^+$ flux required for formation of cytotoxic and ionic edema. Together, these findings suggest a critical involvement of SUR1 in a new pathway that determines formation of edema following cerebral ischemia. Molecular therapies directed at SUR1 may provide important new avenues for treatment of many types of CNS injuries associated with ischemia.

Example 39

Co-Administration of Glibenclamide and tPA

A rodent model of thromboembolic stroke was used (Aoki et al., 2002; Kijkhuizen et al., 2001; Kano et al., 2000; Sumii et al., 2002; Tejima et al., 2001). Briefly, male spontaneously hypertensive rats that have been fasted overnight are anesthetized using halothane (1-1.5% in a 70/30 mixture of $N_2O/O_2$) with spontaneous respiration (Lee et al., 2004; Sumii et al., 2002). Rectal temperature was maintained at ≈37° C. with a thermostat-controlled heating pad. The right femoral artery was cannulated, and physiological parameters, including temperature, mean blood pressure, pH, $pO_2$, and $pCO_2$, glucose were monitored. Temporary focal ischemia was obtained with an embolic model that used allogeneic clots to occlude the MCA. Allogeneic, thrombin-induced, fibrin-rich blood clots were prepared using methods adapted from Niessen et al. (Asahi et al., 2000; Niessen et al., 2003; Sumii et al., 2002). Seven clots, 1.5 mm long, were used for embolizing.

Using a ventral cervical incision, the internal and external carotid arteries were exposed. The external carotid artery and pterygopalatine arteries were ligated. Removable surgical clips were applied to the common and internal carotid arteries. The modified PE-50 catheter containing the clots was inserted retrograde into the external carotid artery and advanced up to the internal carotid artery. The temporary clips were removed, and the clots were injected. Incisions were closed.

After stroke, animals were given glucose-free normal saline, 10 ml total, by dermoclysis. Temperature was maintained until animals were awake and were moving about.

Just prior to the time designated for treatment (reperfusion), animals were re-anesthetized and the femoral vein was cannulated. At the time designated for treatment, saline, or a loading dose of glibenclamide (1.5 μg/kg, i.v., Sigma, St. Louis) was first administered. Then, reperfusion was achieved with i.v. administration of rtPA (10 mg/kg, Alteplase, Genetech; dissolved in 2 ml distilled water, given over 30 min) (Buesseb et al., 2002). Then, using a dorsal thoracic incision, a mini-osmotic pump (Alzet 2002, Durect Corporation, Cupertino, Calif.) was implanted subcutaneously that delivered either saline or glibenclamide (300 μM or 148 μg/ml, 0.5 μl/hr s.q.). Physiological parameters, including temperature, mean blood pressure (tail cuff plethysmography), blood gases and glucose were monitored.

At the same time of 6 hr, animals were co-treated with either saline or glibenclamide (loading dose of 1.5 μg/kg i.v. plus implantation of a mini-osmotic pump containing 148 μg/ml=300 μM delivered at ½ μl/hr). Animals were euthanized 24 hr following stroke and brains were perfused to remove blood from the intravascular compartment. Coronal sections of the fresh brains were prepared and photographed, following which sections were processed for TTC staining to identify areas of infarction.

All animals (5/5) co-treated with saline showed large regions of hemorrhagic conversion in cortical and subcortical parenchymal areas of infarction, along with evidence of intraventricular hemorrhage (FIGS. 34A-D). In contrast, only ⅕ animals co-treated with glibenclamide had hemorrhagic conversion, with ⅘ showing no evidence of hemorrhage (FIGS. 34E-H).

These data suggest that there was protection from hemorrhagic conversion with the administration of glibenclamide, as well as reduction in stroke size, ionic edema, and vasogenic edema.

Example 40

Isolation of Brain Capillaries and Endothelial Cells

The method was adapted in part from Harder et al. (1994) with modifications as previously reported (Seidel, 1991). Briefly, a rat was deeply anesthetized, the descending aorta was ligated, the right atrium was opened and the left ventricle was cannulated to allow perfusion of 50 ml of a physiological solution containing a 1% suspension of iron oxide particles (particle size, 10 μm; Aldrich Chemical Co.). The brain was removed, the pia and pial vessels were stripped away and the cortical mantel is minced into pieces 1-2 $mm^3$ with razor blades. The tissue pieces were incubated with trypsin plus DNAse and then sieved through nylon mesh (210 μm). Retained microvessels were resuspended in collagenase, agitated and incubated at 37° C. for an additional 10 min. To terminate the digestion, microvessels were adhered to the side of the container with a magnet and washed repeatedly to remove enzyme and cellular debris.

Figure 36:
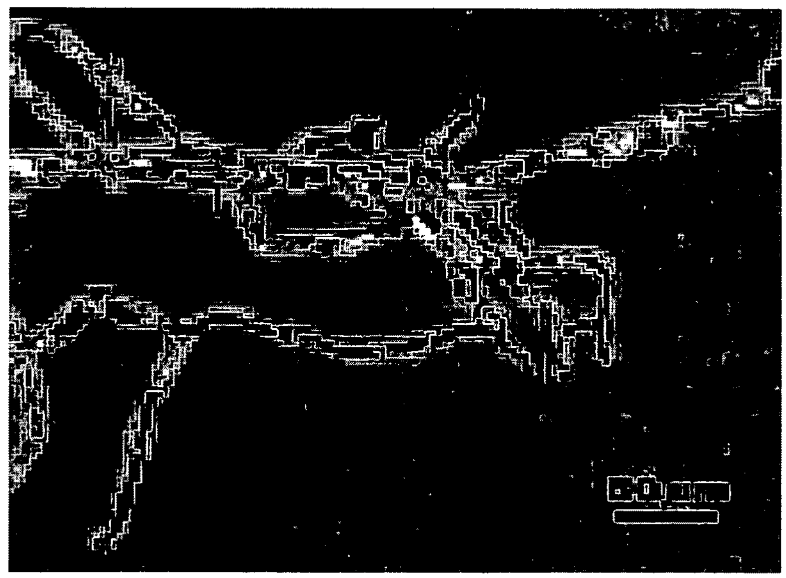
FIG. 36 shows phase contrast photomicrograph of cerebral capillaries freshly isolated from normal brain, after enzymatic cleaning in preparation for patch clamping.

Using these methods yielded healthy-appearing microvascular structures that were suitable for further digestion to obtain single cells (FIG. 36) for further experiments.

Figure 37:
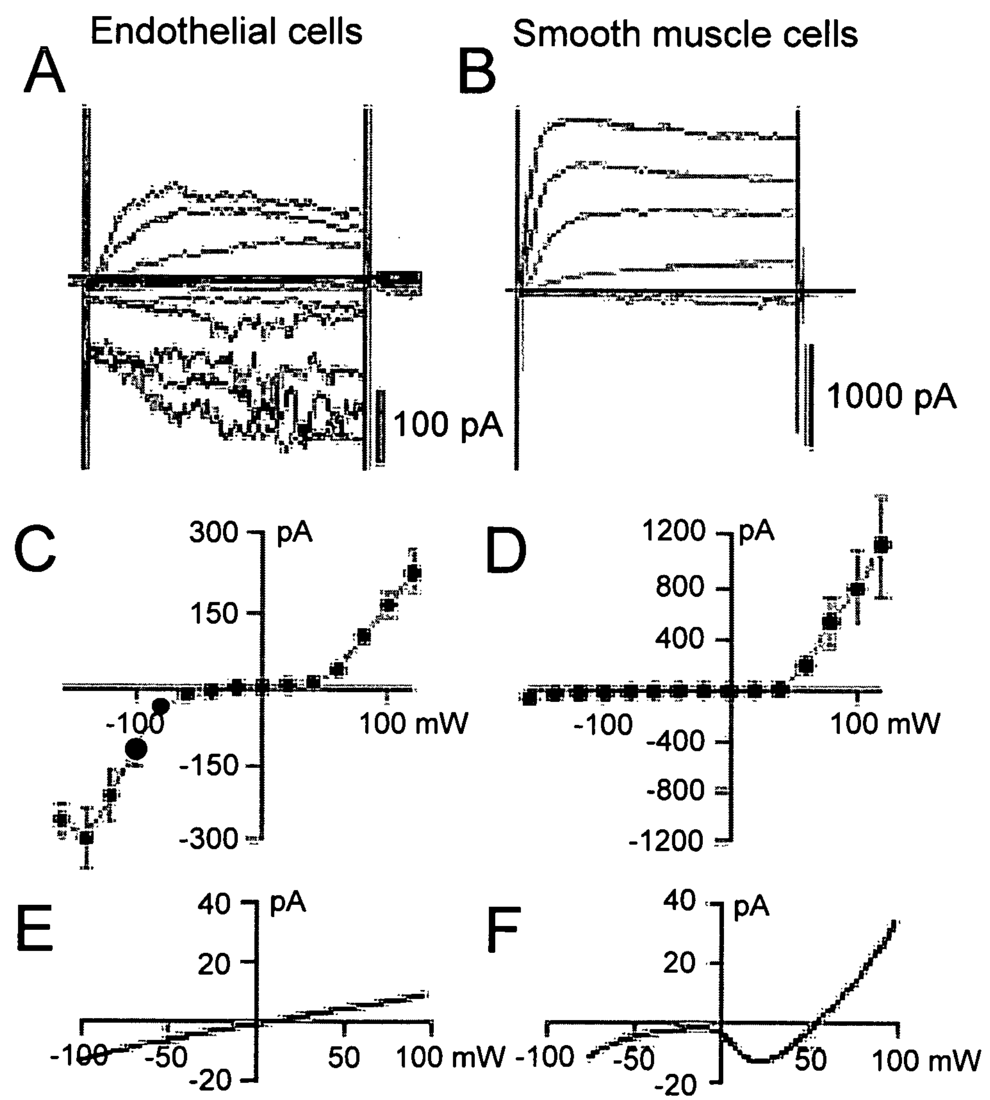
FIGS. 37A-37F show that freshly isolated cerebral endothelial and smooth muscle cells are readily distinguished electrophysiologically.

Isolated endothelial cells were studied using freshly isolated endothelial cells using a nystatin-perforated patch technique. With physiological solutions, the cells exhibited a prominent, strongly rectifying inward current at negative potentials, and a modest outward current at positive potentials (FIG. 37A), yielding a characteristic current-voltage curve with near-zero current at intermediate potentials (FIG. 37C), similar to previous observations in freshly isolated endothelial cells (Hogg et al., 2002). When $K^+$ in the pipette solution was replaced with $Cs^+$, $K^+$ channel currents were completely blocked. In endothelial cells, this yielded a current-voltage curve that was linear (FIG. 37E). These data demonstrated that voltage dependent channels in freshly isolated endothelial cells are exclusively $K^+$ channels that do not carry $Na^+$.

Example 41

Isolation of Neurons

Neurons were isolated from vibratome sections. Immunolabeling experiments indicated that ischemic NeuN-positive neurons expressed SUR1 within 2-3 hr after MCAO, before necrosis was evident. Therefore, tissues were prepared at 2-3 hr after MCAO. The brain was divided coronally at the level of the bregma, and cryosections were prepared from one half and vibratome sections were prepared from the other half. Cryosections (10 μm) were used for TTC staining (Mathews et al., 2000) or alternatively, high-contrast silver infarct staining (SIS), (Vogel et al., 1999) to identify the region of ischemia, and for immunolabeling, to verify SUR1 up-regulation in neurons double labeled for NeuN. Vibratome sections (300 μm) were processed (Hainsworth et al., 2000; Kay et al., 1986; Moyer et al., 1998) to obtain single neurons for patch clamping. Selected portions of coronal slices were incubated at 35° C. in HBSS bubbled with air. After at least 30 min, the pieces were transferred to HBSS containing 1.5 mg/ml protease XIV (Sigma). After 30-40 min of protease treatment, the pieces were rinsed in enzyme-free HBSS and mechanically triturated. For controls, cells from mirror-image cortical areas in the uninvolved hemisphere were used. Cells were allowed to settle in HBSS for 10-12 min in a plastic Petri dish mounted on the stage of an inverted microscope. Large and medium-sized pyramidal-shaped neurons were selected for recordings. At this early time of 2-3 hr, only neurons and capillaries, not astrocytes, show up-regulation of SUR1.

Once the cells were isolated patch clamp experiments using well known methods including whole-cell, inside-out, outside-out and perforated patch were used (Chen et al., 2003; Chen et al., 2001; Perillan et al., 2002; Perillan et al., 2000; Perillan et al., 1999)

Example 42

MMP Inhibition by Glibenclamide

Activation of MMP-9 & MMP-2 in stroke tissue was compared to controls. Briefly, gelatinase activity of recombinant enzyme and stroke tissue under control conditions (CTR), in presence of glibenclamide (10 μM), and in presence of MMP-inhibitor II (300 nM; Calbiochem).

Next, the supernatants underwent a gelatinase purification process with gelatin-Sepharose 4B (Pharmacia), and Zymography was performed on the purified supernatants in sodium dodecyl sulfate gels containing gelatin (Rosenberg, 1994). Dried gels were scanned with a transparency scanner, and images were analyzed by densitometry. The relative lysis of an individual sample was expressed as the integrated density value of its band and divided by the protein content of the sample.

Figure 35:
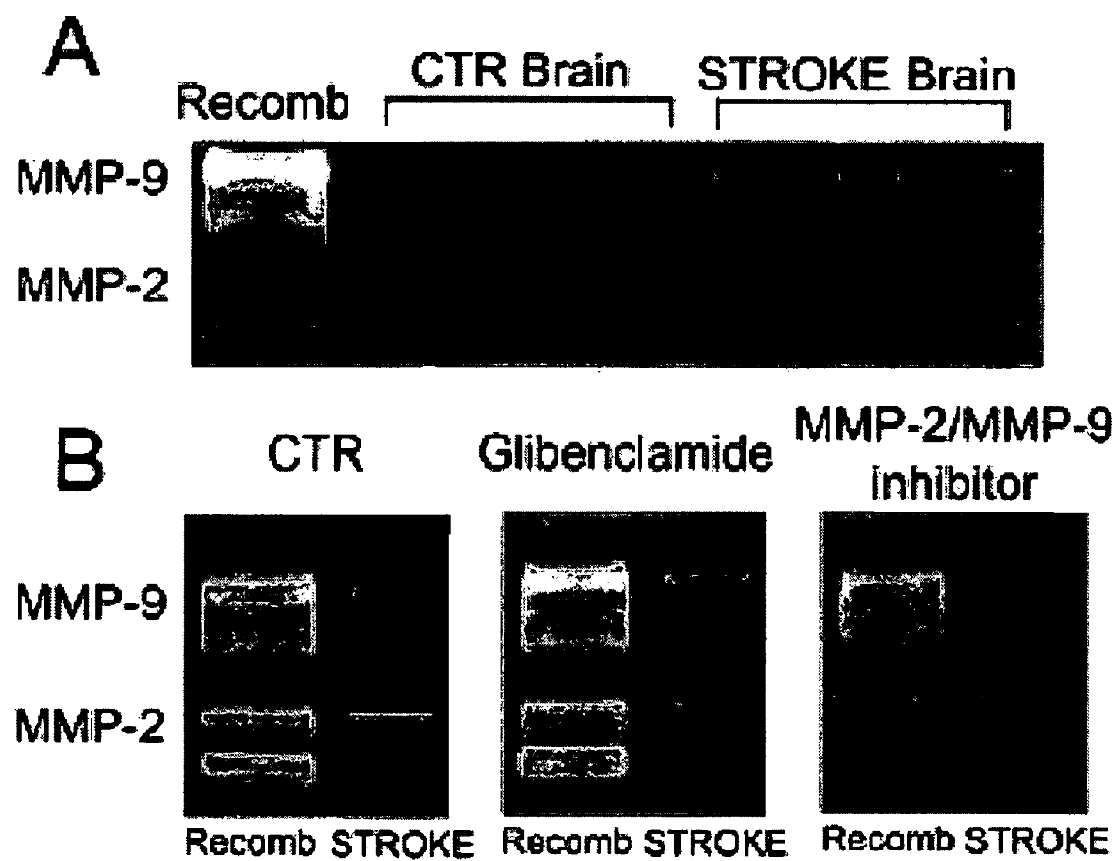
FIGS. 35A-35B show zymography showing gelatinase activity of matrix metalloproteinases (MMP's) in stroke, and absence of direct MMP inhibition by glibenclamide.

Zymography confirmed that gelatinase activity was increased after stroke (FIG. 35A), and showed that gelatinase activity assayed in the presence of glibenclamide (FIG. 35B, Glibenclamide) was the same as that assayed without (FIG. 35B, CTR), although gelatinase activity was strongly inhibited by commercially available MMP inhibitor II (FIG. 35B, MMP-2/MMP-9 inhibitor). These data demonstrated that glibenclamide did not directly inhibit gelatinase activity, and suggested that the reduction of hemorrhagic conversion observed with glibenclamide likely came about due to a beneficial, protective effect of glibenclamide on ischemic endothelial cells.

Example 43

UP-Regulation of SUR1-mRNA in Stroke

Additional molecular evidence for involvement of SUR1 in stroke was obtained using quantitative RT-PCR.

Total RNA was extracted and purified from samples of homogenized brain tissues contralateral (CTR) and ipsilateral to MCAO (STROKE) using guanidine isothyocyonatye. cDNA was synthesized with 4 μg of total RNA per 50 μl of reaction mixture using TaqMan RT kit (Applied Biosystems). Relative values of SUR1-mRNA were obtained by normalizing to H1f0 (histone 1 member 0). The following probes were used SUR1 forward: GAGTCGGACTTCTCGCCCT (SEQ ID NO: 3); SUR1 reverse: CCTTGACAGTGGCCGAACC (SEQ ID NO: 4); SUR1 TaqMan Probe: 6-FAM-TTCCACATCCTGGTCACACCGCTGTTAMRA (SEQ ID NO: 5); H1f0 forward: CGGACCACCCCAAGTATTCA (SEQ ID NO: 6); H1f0 reverse: GCCGGCACGGTTCTTCT (SEQ ID NO: 7); H1F0 TaqMan Probe: 6-FAM-CATGATCGTGGCTGCTA TCCAGGCA-TAMRA (SEQ ID NO: 8).

Figure 38:
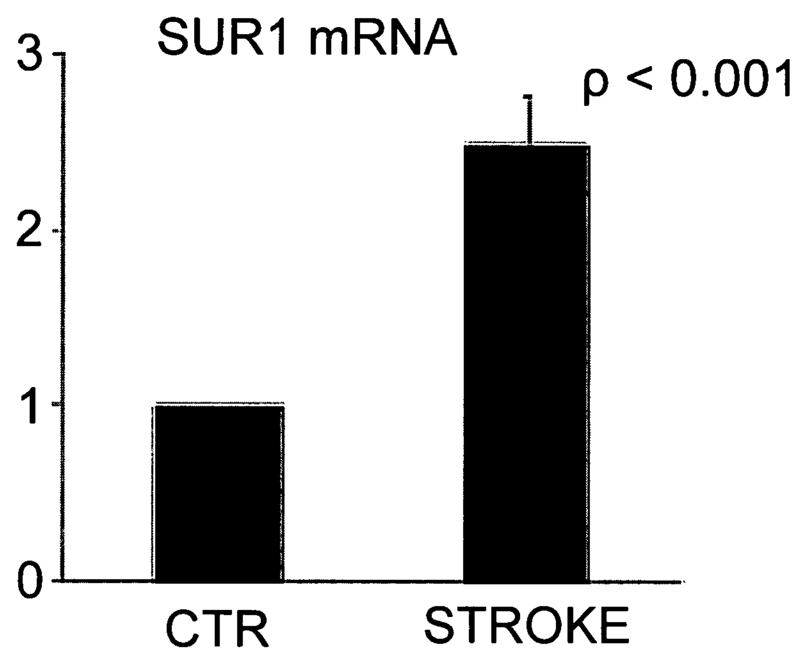
FIG. 38 shows real time RT-PCR showing up-regulation of SUR1-mRNA in stroke.

These data showed that mRNA for SUR1 was significantly increased in the core region, 3 hr after MCAO (FIG. 38).

Example 44

SUR1 Knockdown (SUR1KD) is Protective

To further test involvement of SUR1, SUR1 expression was "knocked down" in situ by infusing oligodeoxynucleotide (ODN) for 14 days using a mini-osmotic pump, with the delivery catheter placed in the gelfoam implantation site in the brain, in the otherwise standard model that the inventors use for R1 astrocyte isolation (Perillan et al., 1980, Perillan et al., 2002, Perillan et al., 2000, Perillan et al., 1999). Knockdown of SUR1 expression (SUR1KD) was achieved using antisense (AS; 5'-GGCCGAGTGGTTCTCGGT-3' (SEQ ID NO: 9)) (Yokoshiki et al., 1999) oligodeoxynucleotide (ODN), with scrambled (SCR; 5'-TGCCTGAGGCGTGGCTGT-3' (SEQ ID NO: 10)) ODN being used as control.

Figure 39:
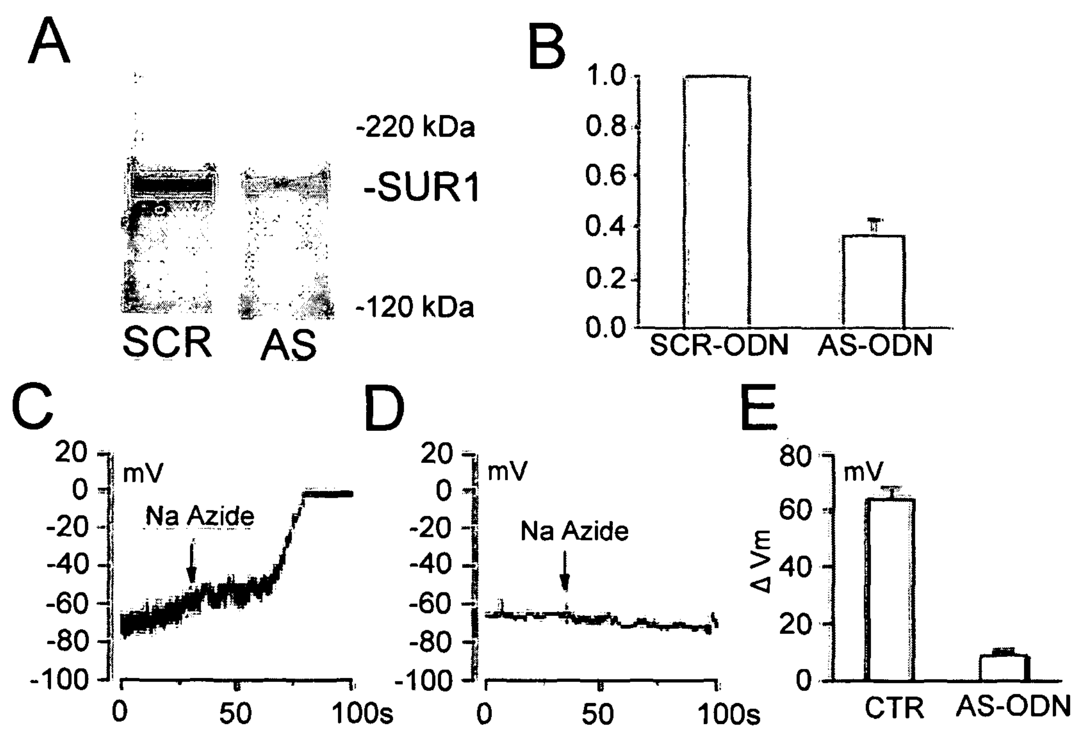
FIGS. 39A-39E show SUR1 knock down (SUR1KD) in R1 astrocytes protects from ATP-depletion-induced depolarization.

Immunoblots of gliotic capsule showed significant reduction in SUR1 expression in SUR1 knockdown (SUR1KD) tissues compared to controls receiving scrambled sequence ODN (FIGS. 39A and 39B).

The inventors enzymatically isolated single cells from SUR1KD and controls using a standard cell isolation protocols described above (Chen et al., 2003) to assess functional responses to ATP depletion induced by Na azide. In R1 astrocytes from control tissues, Na azide (1 mM) caused rapid depolarization due to $Na^+$ influx attributable to activation of $NC_{Ca\text{-}ATP}$ channels (FIG. 39C). Notably, this depolarizing response was opposite the hyperpolarizing response observed when $K_{ATP}$ channels were activated. In R1 astrocytes from SUR1KD, however, Na azide had little effect on resting membrane potential (FIG. 39D). In controls, application of Na azide resulted in depolarization of 64±3.7 mV, whereas in cells for SUR1KD, depolarization was only 8.7±1.7 mV (FIG. 39E).

In addition, membrane blebbing that typically follows exposure to Na azide was not observed in cells from SUR1KD, confirming the role for SUR1 in cytotoxic edema of R1 astrocytes.

Example 45

Molecular Factors that Regulate SUR1 Expression

Based on work in pancreatic β cells, a number of SP1 transcription factor binding sites have been identified in the proximal SUR1 promoter region that are considered to be important for activation of SUR1 transcriptional activity (Ashfield et al., 1998; Hilali et al., 2004). Notably, SP1 has essentially not been studied in stroke (Salminen et al., 1995).

Figure 40:
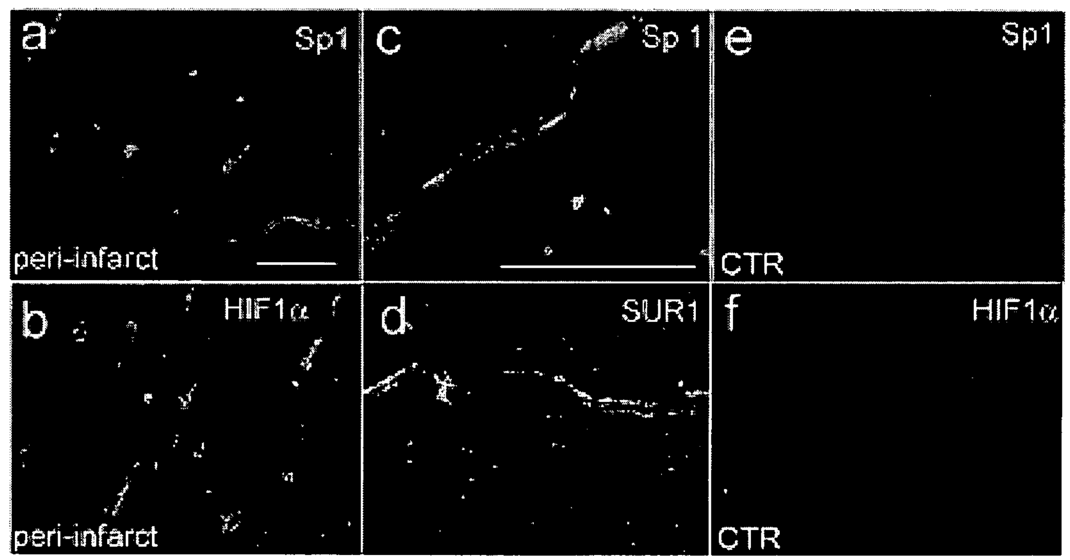
FIGS. 40A-40F show transcription factors in stroke. Immunofluorescence images of subcortical watershed region between ACA and MCA territories, from ipsilateral peri-infarct tissues 8 hr after MCAO (FIGS. 40A-D) and from contralateral control tissues (FIGS. 40E, 40F). The peri-infarct region showed up-regulation of both transcription factors, Sp1 (FIGS. 40A, 40C) and HIF1α (FIG. 40B) in neuron-like cells and capillaries, as well as SUR1 in capillaries (FIG. 40D). Control tissues showed little SP1 and no HIF1α (FIGS. 40E and 40F).

Briefly, the ischemic peri-infarct tissues was immunolabeled for SP1, which is important for SUR1 expression, for HIF1α, which is widely recognized to be up-regulated in cerebral ischemia (Semenza 2001; Sharp et al., 2000) and for SUR1 itself. SP1 was prominently expressed in large neuron-like cells and in capillaries (FIGS. 40A, 40C) in regions confirmed to be ischemic by virtue of expression of HIF1α (FIG. 40B). Notably, capillaries that expressed SP1 also showed prominent expression of SUR1 (FIGS. 40C, 40D). Contralateral control tissues showed little immunolabeling for SP1 and none for HIF1α (FIGS. 40E, 40F).

Figure 41:
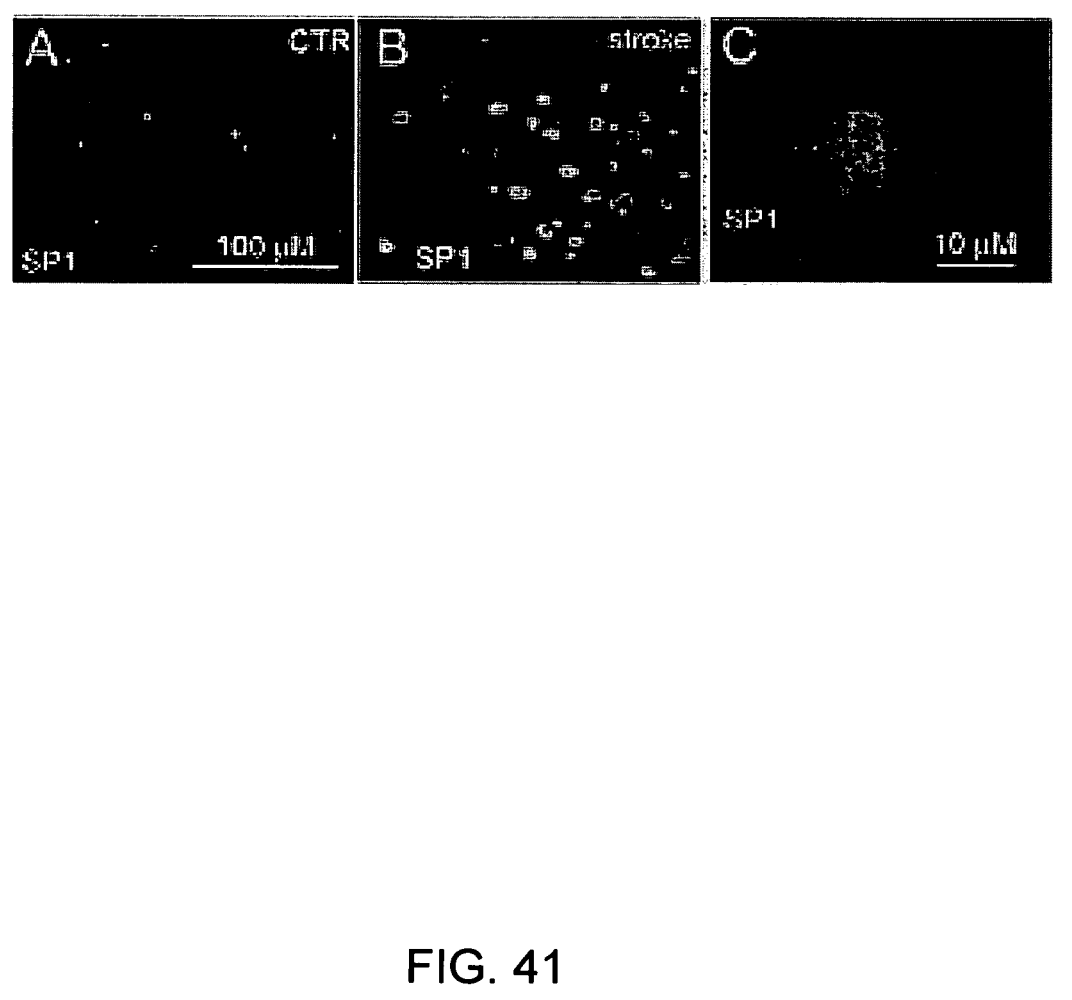

Nuclear SP1 localization was significantly augmented early-on in stroke (FIGS. 41A, 41B), and nuclear SP1 was found in large neuron-like cells that express SUR1 following MCAO (FIG. 41C).

Figure 42:
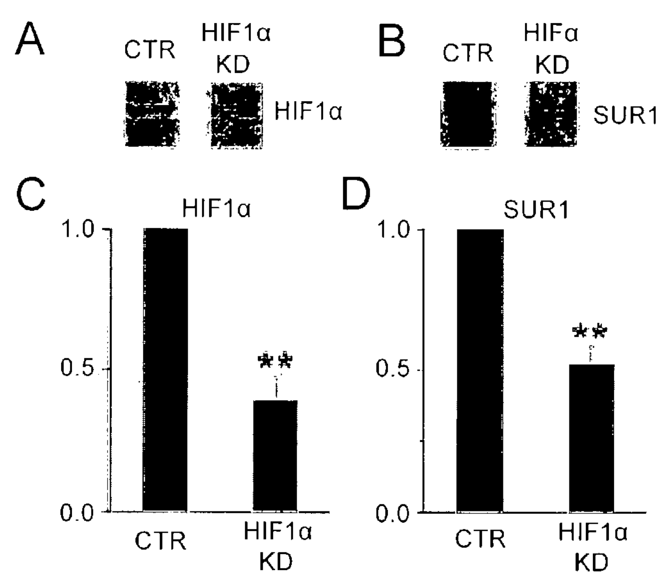
FIGS. 42A-42D show regulation of SUR1 expression by the transcription factor, HIF1α.

HIF1α knock-down animals were obtained by infusion of antisense oligodeoxynucleotide at the site of gelfoam implant. FIG. 42 confirms the HIF1α knock-down animals results in a significant decrease in SUR1 expression (FIGS. 42B, 42D), providing strong evidence that not only SP1 but also HIF1α is likely to be an important regulator of SUR1 expression.

Example 46

Blood Flow in Peri-Infarct Tissue is Protected by Treatment with $Nc_{ca\text{-}Atp}$ Channel Antagonist Block of SUR1 by systemic administration of low-dose glibenclamide reduces cerebral edema, infarct volume and mortality, with the reduction in infarct volume being associated with cortical sparing. A thromboembolic (TE) stroke model associated with non-lethal infarctions from MCAO was used to study effects on infarct volume in rats. Given the striking effects on mortality and edema, the inventors sought to determine whether glibenclamide would have a favorable effect on infarct volume. This was not feasible with the MCE model because of the high incidence of early mortality. We therefore utilized a non-lethal thromboembolic (TE) model that would allow assessment of infarct volume at 2 and 7 days after MCAO. At 2 days, glibenclamide treatment resulted in a highly significant reduction in infarct volume, compared to saline controls (35.5±4.4% vs. 16.7±2.2%; p<0.01). A similar observation was made at 7 days (15.2±1.2%; p<0.01), indicating again that the effect of treatment was durable.

All animals, regardless of treatment group, suffered infarctions involving the basal ganglia, which are supplied by terminal arterioles. However, reduced infarct volumes in the glibenclamide groups were often associated with marked sparing of the cerebral cortex, a phenomenon previously reported with decompressive craniectomy. (Doerfler, et al., (2001)). We hypothesized that cortical sparing with glibenclamide might reflect improved leptomeningeal collateral blood flow, which could be due to reduced cerebral edema. The effective dose of glibenclamide was 75 ng/hr. Direct vasodilation was not expected, since glibenclamide is normally vasoconstrictive due to block of KATP channels. (Lindauer, et al., (2003), and Tomiyama, et al., (1999)).

Figure 43:
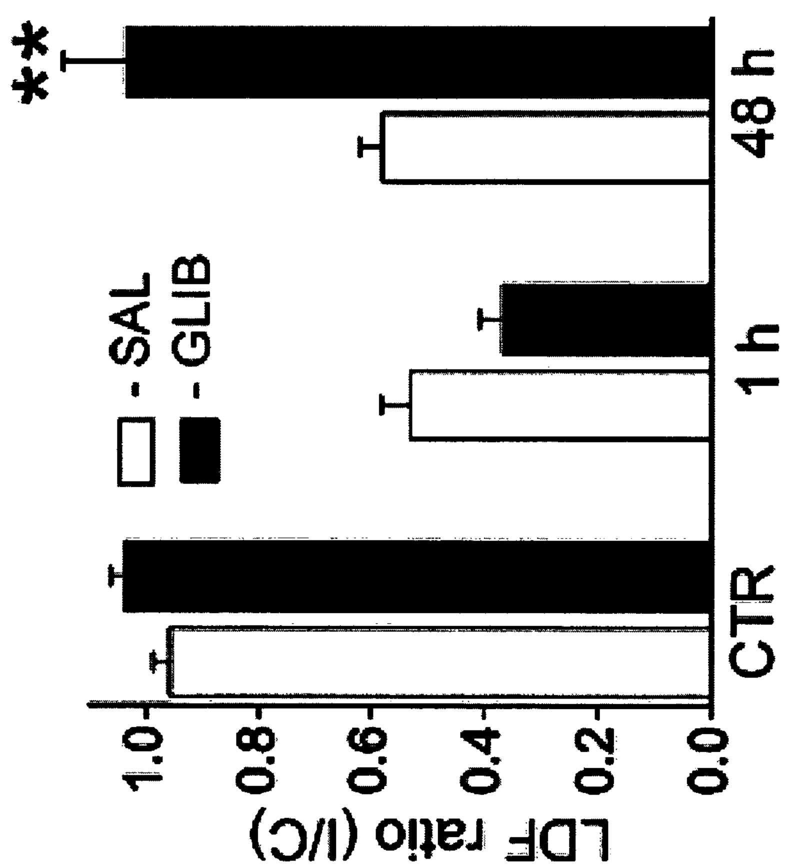
FIG. 43 shows relative cerebral blood flow, measured by Laser Doppler Flowmetry, before (CTR), 1 hr after and 48 hr after MCAO, in 2 groups, each consisting of 4 male rats, treated with either saline or glibenclamide; values at 48 hr were statistically different (by ANOVA; $p<0.01$).

Blood flow was measured using laser Doppler flowmetry in order to determine the effects of glibenclamide treatment on cerebral blood flow. Using the same TE model, measurements of relative cerebral blood flow were obtained for somatosensory cortex supplied by the middle cerebral artery (MCA). Laser Doppler flowmetry showed values in the involved hemisphere that were significantly reduced 1 hr after middle cerebral artery occlusion (MCAO) in both saline- and glibenclamide-treated groups (FIG. 43). However, flow measurements recovered completely by 48 hr in glibenclamide-treated animals but not in saline-treated animals (FIG. 43), consistent with the cortical sparing observed.

Methods

Relative cerebral blood flow (TE model) was measured using laser Doppler flowmetry (LDF) in 2 groups, each consisting of 4 male rats, treated with either saline or glibenclamide. Prior to MCAO, two 1.5-mm pits were carefully drilled halfway through the skull over the left and right somatosensory cortex (MCA territory), 3 mm posterior and 3 mm lateral to the bregma. A two-channel LDF instrument (DRT4; Moor Instruments, Axminster, UK) was used to simultaneously measure blood flow in both hemispheres. LDF readings were normalized by adjusting the depth of the pits to obtain a ratio of blood flow of ~1.0 between sides. Once this ratio had been obtained, five sets of LDF measurements were taken at 1 min intervals, values for each location were averaged and the ratio of ipsilateral to contralateral LDF values was calculated. This technique minimized effects of intra-measurement differences in probe position, angle, lighting condition, etc. Once baseline CBF had been determined, skin incisions over the pits were closed and the procedure for MCAO was initiated. Relative CBF measurements were later repeated at 1 hr and 48 hours after MCAO, using the same pits and the same method of averaging 5 bilateral measurements obtained at 1-min intervals.

Edema (MCE model) was analyzed 8 hr after MCAO in 2 series of animals. In the first series, tissue water was analyzed in the uninvolved vs. involved hemisphere of 2 groups of 11 male rats, treated with either saline or glibenclamide (no TTC processing).

In the second series, tissue water was analyzed in the uninvolved hemisphere and in the TTC(+) vs. TTC(−) portions of the involved hemisphere in 3 groups of 6 male rats treated with either saline alone, vehicle (saline plus DMSO) or glibenclamide. Tissue water was quantified by the wet/dry weight method. Tissue samples were blotted to remove small quantities of adsorbed fluid. Samples were weighed with a precision scale to obtain the wet weight ($W_W$), dried to constant weight at 80° C. and low vacuum, and then reweighed to obtain the dry weight ($W_D$). The percent $H_2O$ of each tissue sample was then calculated as $(W_W-W_D)\times100/W_W$.

Infarct volume (TE model), measured as the volume of TTC(−) tissue in consecutive 2 mm thick slices and expressed as the percent of hemisphere volume, was compared in 3 treatment groups, consisting of 9, 9 and 7 male rats, treated with saline and assessed at 2 days, or treated with glibenclamide and assessed at 2 days or 7 days after MCAO.

Permanent MCA occlusion (MCAO) models. This study was performed in accordance with the guidelines of the Institutional Animal Care and Use Committee. Adult male or female Wistar rats (275-350 gm) were fasted overnight then anesthetized (Ketamine, 60 mg/kg plus Xylazine, 7.5 mg/kg, i.p.). The right femoral artery was cannulated, and physiological parameters, including temperature, pH, $pO_2$, $pCO_2$ and glucose were monitored. Using a ventral cervical incision, the right external carotid and pterygopalatine arteries were ligated. The common carotid artery was ligated proximally and catheterized to allow embolization of the internal carotid artery. For the thromboembolic (TE) stroke model, 7-8 allogeneic clots, 1.5 mm long, were embolized. Allogeneic, thrombin-induced, fibrin-rich blood clots were prepared as described. For large MCA infarcts with malignant cerebral edema (MCE), the inventors first embolized microparticles [polyvinyl alcohol (PVA) particles; Target Therapeutics, Fremont Calif.; 150-250 μm diameter, 600 μg in 1.5 ml heparinized-saline], followed by standard permanent intraluminal suture occlusion using a monofilament suture (4-0 nylon, rounded at the tip and coated with poly-L-lysine) advanced up to the ICA bifurcation and secured in place with a ligature. After MCAO, animals were given 10 ml of glucose-free normal saline by dermoclysis. Rectal temperature was maintained at about 37° C. using a servo-controlled warming blanket until animals awoke from anesthesia. Blood gases and serum glucose at the time of MCAO were: $pO_2$, 94±5 mm Hg; $pCO_2$, 36±5 mm Hg; pH, 7.33±0.01; glucose 142±6 mg/dl in controls and $pO_2$, 93±3 mm Hg; $pCO_2$, 38±2 mm Hg; pH, 7.34±0.01; glucose 152±7 mg/dl in glibenclamide-treated animals. With both models, animals awoke promptly from anesthesia and moved about, generally exhibited abnormal neurological function, typically circling behavior and hemiparesis. Mortality with the TE model was minimal, whereas with the MCE model, animals exhibited delayed deterioration, often leading to death. Most deaths occurred 12-24 hr after MCAO, with necropsies confirming that death was due to bland infarcts. Rarely, an animal died <6 hr after MCAO and was found at necropsy to have a subarachnoid hemorrhage, in which case it was excluded from the study. Mortality in untreated animals with MCE and bland infarcts was 65%, similar to that in humans with large MCA strokes.

Within 2-3 min after MCAO (both TE and MCE models), mini-osmotic pumps (Alzet 2002, 14 day pump, 0.5 μl/hr; Durect Corporation, Cupertino, Calif.) were implanted subcutaneously that delivered either saline (0.9% NaCl), vehicle (saline plus DMSO) or glibenclamide in vehicle, subcutaneously (no loading dose). Glibenclamide (Sigma, St. Louis, Mo.) was prepared as a 10 mM stock solution in DMSO, with 15 μl stock solution diluted into 500 μl saline to give a final concentration of 148 μg/ml or 300 μM in the pump. The effective dose of glibenclamide was 75 ng/hr. The effective dose of DMSO was 15 nl/hr, which is what was delivered in vehicle-treated animals.

TTC (triphenyltetrazolium chloride) staining was measured to determine infarct volume. Freshly harvested brains were cut into 2-mm thick coronal sections, and slices were exposed to TTC (0.125% w/v in 62.5 mM Tris-HCl, 13 mM $MgCl_2$, 1.5% dimethylformamide) for 30 min at 37° C. For infarct volume, stained sections were photographed and images were analyzed (Scion Image) to determine the percent of the involved hemisphere occupied by TTC(−) tissue; no correction for edema was performed. For some determinations of water content or SUR1 protein content, individual coronal sections were divided under magnification into 3 parts: (i) the uninvolved, control hemisphere; (ii) the TTC(+) portion of the involved hemisphere; (iii) the TTC(−) portion of the involved hemisphere. For each animal, tissues from the 3 parts were then processed for tissue water measurements, or Western blots.

These findings indicate that the SUR1-regulated $NC_{Ca-ATP}$ channel is critically involved in development of cerebral edema, that modulation of the SUR1-regulated $NC_{Ca-ATP}$ channel can lead to improved blood flow in peri-infarct tissue, and that targeting SUR1 provides an important new therapeutic approach to stroke.

Example 47

$NC_{ca-Atp}$ Channel Antagonist Treatment Reduces Edema Even with Added Glucose Treatment Although the dose of glibenclamide was low, a drop in serum glucose concentration in glibenclamide-treated animals was noted in the experiments described above. The drop in glucose by glibenclamide raised the question whether the beneficial effect of glibenclamide on edema was mediated directly via $NC_{Ca-ATP}$ channels, or indirectly via reduction in serum glucose.

Tissue water as a measure of edema was measured in rats in a middle cerebral artery occlusion (MCAO) model of stroke. As in Example 46, the effective dose of glibenclamide was 75 ng/hr delivered by subcutaneously implanted Alzet mini-osmotic pump. Animals treated with glibenclamide (GLIB) alone experienced reduced serum glucose. For example, serum glucose concentration at 8 hr, when edema was measured, was 122±4 for saline-treated animals (SALINE) vs. 93±3 mg/dl for glibenclamide-treated animals (GLIB) (see FIG. 44). Administration of glucose 4 hours after occlusion resulted in serum glucose concentrations of 141±4 mg/dl at 8 hours after occlusion.

Figure 44:
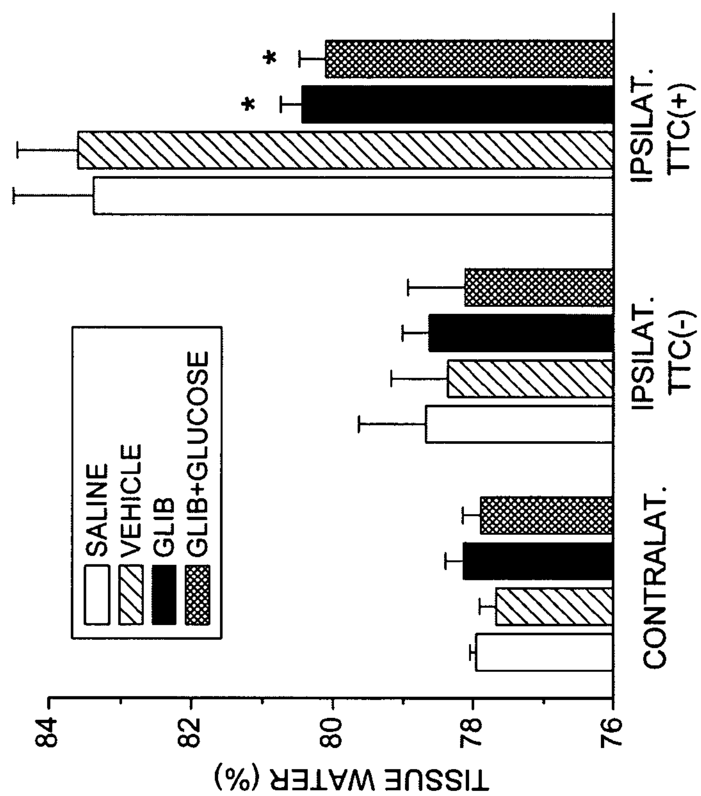
FIG. 44 Glibenclamide was just as effective in reducing edema after stroke with added glucose as without added glucose. Supplemental glucose (1 gm/kg, i.p.) was administered 4 hr after MCAO, and animals were sacrificed 8 hr after MCAO for measurements of edema.

Edema measurements in the same brain areas and at the same time in animals treated with GLIB indicated that GLIB reduced edema irrespective of the glucose concentration. In these animals, supplemental glucose (1 gm/kg, i.p.) was administered 4 hr after MCAO. This dose of glucose is reported to produce levels of hyperglycemia of 300 mg/dl, when measured shortly after administration. Animals were sacrificed 8 hr after MCAO for measurements of edema (FIG. 44, GLIB+GLUCOSE). Serum glucose 4 hr after glucose administration (i.e., at time of sacrifice, 8 hr after MCAO) was still elevated (141±4 mg/dl). However, in these animals, GLIB was just as effective in reducing edema, even in the face of hyperglycemia.

These results indicate that adding glucose does not impair the protective effect of SUR1 antagonist treatment, and may enhance the protective effect of SUR1 antagonist treatment.

Example 48

Delayed Treatment with Glibenclamide Reduces Stroke Volume in Rats Following Middle Cerebral Artery Occlusion (MCAO)

Figure 45:
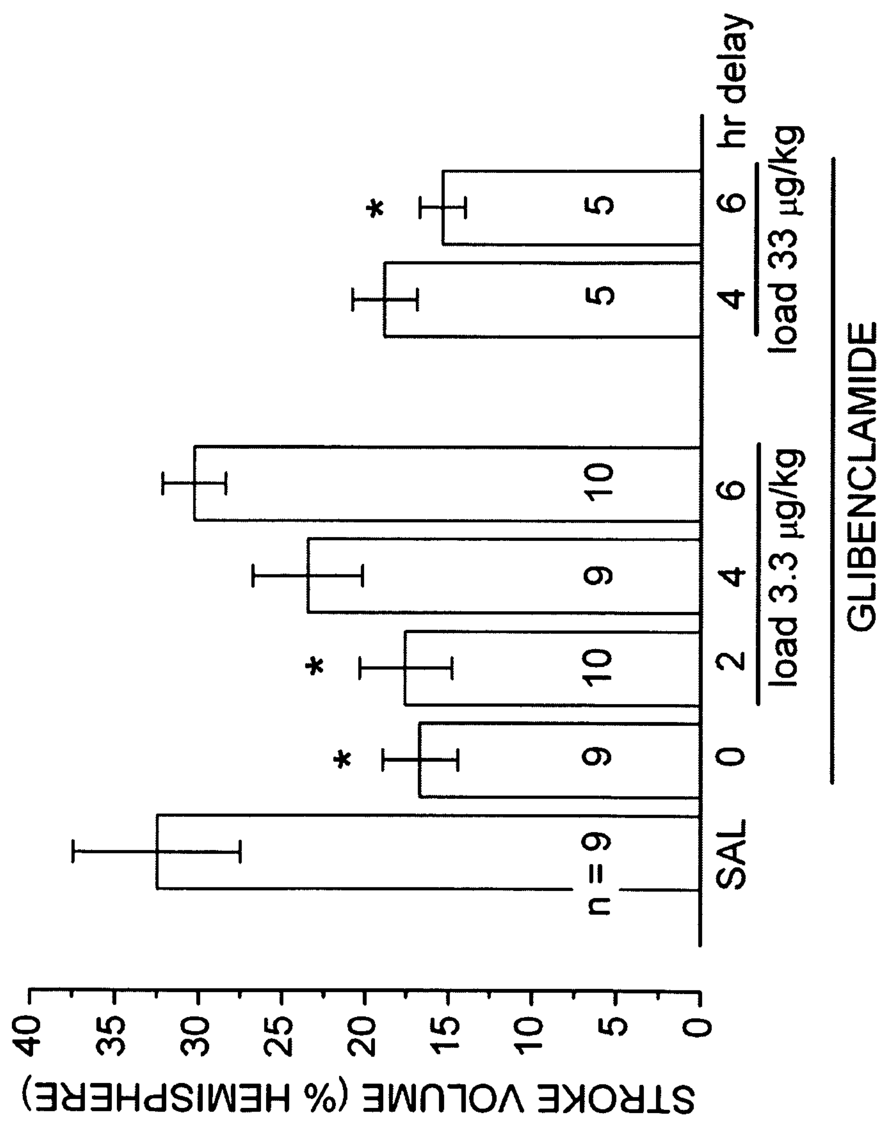
FIG. 45 Glibenclamide reduces stroke volume even when administration is delayed up to 2 hours (low dose) or up to 6 hours (higher dose) following stroke.

Stroke volume in rats was measured as discussed above. Glibenclamide (3.3 μg/kg or 33.0 μg/kg) was given as indicated in FIG. 45. Animals treated with the higher dose of glibenclamide were also given 1 gm/kg glucose in order to counteract hypoglycemia caused by the glibenclamide.

Stroke model: thromboembolic embolization of allogeneic clots via internal carotid artery in male Wistar rats, 275-325 gm. Treatment: within 2-3 min after MCAO, animals were implanted with mini-osmotic pumps fitted with catheters of a length calibrated to delay onset of drug delivery by the amount of time indicated; the pumps were filled with glibenclamide, 300 μM, that was delivered at a rate of 0.5 μl/hr, giving an effective infusion rate of 75 ng/hr for glibenclamide, and an effective delivery rate of 15 nl/hr for DMSO (used as vehicle solvent); at the designated time, animals were also injected intraperitoneally with a loading dose of glibenclamide, either 3.3 or 33 μg/kg, and in the case of the higher dose of glibenclamide, with a supplemental dose of glucose of 1 gm/kg. Stroke volume was determined at 48 after MCAO from the volume of TTC(−) tissue and is expressed as the percent of hemisphere volume in FIG. 45. Values of "n" indicate the number of rats per group; asterisks (*) indicates a statistically significant ($P<0.05$) difference in volume compared to saline (SAL) control as illustrated in FIG. 45.

A significant reduction in stroke volume was observed when glibenclamide infusion was begun: (i) immediately after stroke, with no loading dose; (ii) 2 hr after stroke, with a loading dose of 3.3 μg/kg; (iii) and up to 6 hr after stroke with a loading dose of 33 μg/kg. Thus the lower dose of glibenclamide (3.3 μg/kg) was effective at reducing stroke volume in experimental animals subjected to middle cerebral artery occlusion (MCAO) when the glibenclamide was given at 0 or 2 hours after MCAO. Although some reduction in stroke volume was seen at 4 hours after MCAO with the lower dose of glibenclamide, the difference was not statistically significant with this number of animals. However, statistically significant reductions in stroke volume (as compared to control) were observed in animals treated with the higher dose of glibenclamide (33.0 μg/kg, with co-administered glucose) given at 4 and at 6 hours after MCAO, as shown in FIG. 45. Thus, a larger dose of 33.0 μg/kg was effective up to three times as long after MCAO as was the smaller dose of glibenclamide.

These data indicate that the beneficial effect of glibenclamide can be obtained even with substantial delay in treatment, consistent with the beneficial effect being due to a reduction in edema that permits leptomeningeal collateral flow that helps salvage cortical structures. These data also demonstrate that co-adminstration of glibenclamide with glucose is effective in reducing stroke volume, that such co-administration with glucose allows treatment with higher doses of glibenclamide without the possibly deleterious effects of lowered blood glucose, and allows for effective sulfonylurea treatment with greater delay before initiating treatment after stroke than appeared possible with lower sulfonylurea doses.

Example 49

Glibenclamide Reduces Hemorrhagic Conversion

Hemorrhagic conversion is a serious condition that often follows stroke or ischemic insult, in which reperfusion to ischemic tissue causes further damage to compromised tissue as anoxic and acidic fluids which had accumulated in non-perfused tissues flows to other tissues as blood flow is restored to the region. Further, damage can come from leaky endothelial cells and blood vessels distal to the ischemic damage.

Accordingly, an outcome study was designed as indicated to determine the effect of glibenclamide on hemorrhagic conversion.

In this study, male rats of the spontaneously hypertensive (SHR) strain were subjected to a thromboembolic stroke and then treated with tissueplasminogen activator (tPA) to dissolve the clot and restore perfusion to non-perfused brain tissue. In particular, thromboembolic stroke was performed six hours after initiation of the experimental stroke, tPA was administered intravenously (10 mg/kg over 30 min), along with either saline (control) or glibenclamide. Glibenclamide-treated animals were given a loading dose of 1.5 μg/kg intravenously (i.v.) and a sub-cutaneous (s.c.) mini osmotic pump was implanted that delivered 148 μg/ml (equivalent to 300 μM at ½ μl/hr) to the animals.

Figure 46:
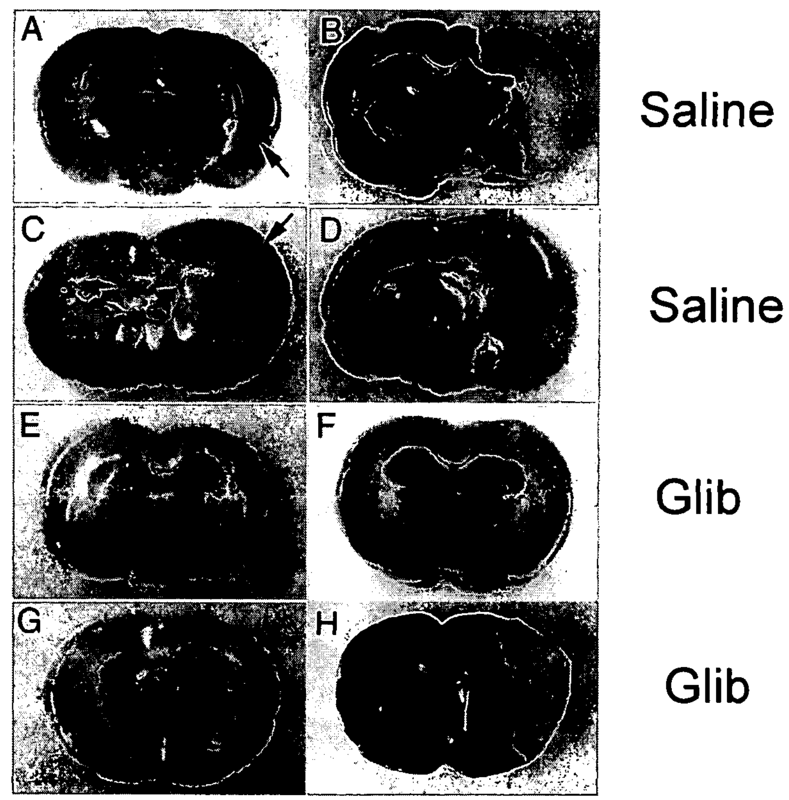
FIG. 46 Glibenclamide reduces hemorrhagic conversion. Animals treated with intravenous tPA (10 mg/kg over 30 min) following thromboembolic lesion were also treated with either saline or glibenclamide. Although 5 of 6 animals co-treated with saline showed hemorrhagic conversion, only 1 of 6 animals treated with glibenclamide showed hemorrhagic conversion, demonstrating the efficacy of glibenclamide treatment to reduce or prevent hemorrhagic conversion following thromboembolic stroke.

The internal carotid artery (ICA) of male SHR rats were embolized with allogeneic thrombi to produced MCAO. Six hours later, animals were treated with tPA (10 mg/kg i.v over 30 min) and co-treated with either saline or glibenclamide (1.5 mg/kg i.v. bolus plus implantation of a s.c. pump that delivered a 300 mM solution at 0.5 ml/hr). At 24 hr after stroke, brains were perfused to remove intravascular blood, sectioned coronally, photographed, and processed for TTC staining. Results are shown in FIG. 46. Rows 1-2 (A-D) are from animals co-treated with saline; rows 3-4 (E-H) are from animals co-treated with glibenclamide. The left column of photographs of coronal sections shows, in rows 1-2 only, intraventricular hemorrhage, plus large areas of hemorrhagic conversion in ischemic cortical/subcortical regions (red areas on the right side of pictures; arrows). The right column of photographs of TTC-processed sections from the same animals show the areas of infarction.

As shown in FIG. 46, the incidence of hemorrhage within the stroke region (measured at 24 hours) was reduced by glibenclamide treatment as compared with control. Although 5 of 6 animals co-treated with saline showed hemorrhagic conversion, only 1 of 6 animals treated with glibenclamide showed hemorrhagic conversion, demonstrating the efficacy of glibenclamide treatment to reduce or prevent hemorrhagic conversion following thromboembolic stroke. FIG. 46 thus demonstrates that glibenclamide treatment reduces hemorrhagic conversion in tPA-treated animals, and extends the time window after ischemic insult within which tPA may be administered without deleterious effects.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention. Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

Example 50

Brain Contusion Results in Up-Regulation of SUR1

Figure 47:
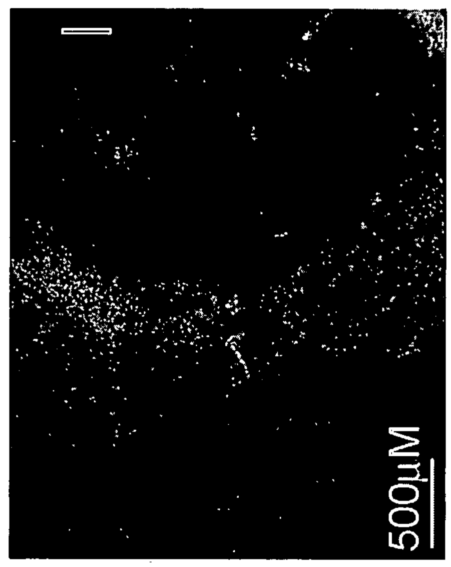
FIG. 47 shows expression of SUR1 protein in cortical brain tissues; minimal labeling was observed in control tissues (left panel), whereas prominent labeling was seen surrounding the site of the impact ("I", originating from the right side), in brain contusion (right panel); tissues were harvested 24 hr following contusion injury.
Figure 48:
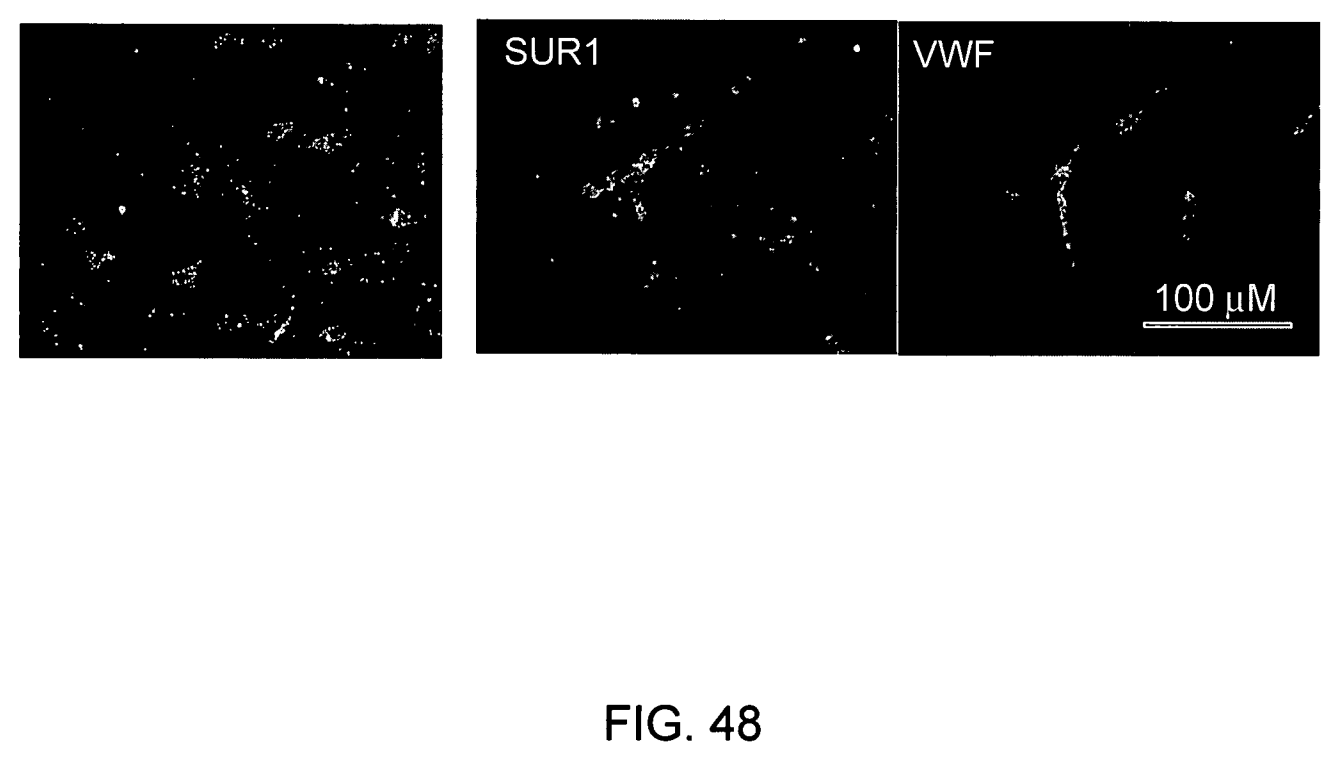

Contusion Model: Adult Wistar rats were anesthetized (Ketamine and Zylazine) and underwent aseptic surgery to create a right parietal craniectomy that exposed the dura. A contusion injury was obtained using a weight-drop device, consisting of an impactor (a thin light rod with a 5-mm polypropylene ball at the tip, guided within a glass cylinder) that was gently placed on the exposed dura and that was activated by weight drop (10-gm weight dropped from 2.5 cm). Controls underwent sham surgery that included craniectomy but no weight drop. Brains were harvested 24 hours later and cryosectioned to assess for SUR1 expression using immunohistochemistry. The antibody used for immunohistochemistry had previously been shown to be highly specific for SUR1 and to label only a single band (180 kDa) in the range between 116-290 kDa in peri-infarct brain tissues (see Simard et al., Nature Medicine, 2006). Immunolabeling showed prominent up-regulation of SUR1 in the region of contusion (see FIGS. 47 and 48), consistent with contusion-induced up-regulation of NCCa-ATP channels.

REFERENCES

All patents and publications cited herein are hereby incorporated by reference in their entirety herein. Full citations for the references cited herein are provided in the following list.

PATENTS AND PATENT APPLICATIONS

WO 03/079987
U.S. Pat. No. 5,637,085
U.S. Pat. No. 6,391,911

PUBLICATIONS

Adams et al. (1980) J Gen Physiol 75: 493-510.
Aguilar-Bryan et al. (1995) Science 268: 423-426.
Aguilar-Bryan L, et al., Science. 1995; 268:423-426.
Ammala C, et al., Nature. 1996; 379:545-548.
Anisimov, S. V., et al., Mech. Dev. 117, 25-74 (2002).
Aoki K, et al., Acta Neuropathol (Berl). 2003; 106:121-124.
Arteel G E, et al., Eur J Biochem. 1998; 253:743-750.
Ashcroft F M. Science. 1998; 282:1059-1060.
Ayata, C. & Ropper, A. H. J. Clin. Neurosci. 9, 113-124 (2002).
Babenko A P, et al., Annu Rev Physiol. 1998; 60:667-687.

Ballanyi, K. J. Exp. Biol. 207, 3201-3212 (2004).
Barclay J, et al., J Neurosci. 2002; 22:8139-8147.
Barros et al. (2001) Hepatology 33: 114-122.
Baukrowitz T, et al., Science. 1998; 282:1141-1144.
Becker J B, et al., Ann N Y Acad Sci. 2001; 937:172-187.
Beyer C, et al., J Steroid Biochem Mol Biol. 2002; 81:319-325.
Blurton-Jones M, et al., J Comp Neurol. 2001; 433:115-123.
Bordey and Sontheimer (1998) Epilepsy Res 32: 286-303.
Brismar and Collins (1993) J Physiol (Lond) 460: 365-383.
Bussink J, et al., Radiat Res. 2000; 154:547-555.
Cevolani D, et al., Brain Res Bull. 2001; 54:353-361.
Champigny et al. (1991) Biochem Biophys Res Commun 176: 1196-1203.
Chen H., et al., J. Neurol. Sci. 118, 109-6 (1993).
Chen M, et al., J Neurosci. 2003; 23:8568-8577.
Chen M, Simard J M. J Neurosci. 2001; 21:6512-6521
Choi I, et al., Mol Cell Endocrinol. 2001; 181:139-150.
Christensen and Hofbann (1992) J Membr Biol 129: 13-36.
Chuang et al. (1997) Cell 89: 1121-1132.
Cook et al. (1990) J Membr Biol 114: 37-52.
Cress A E. Biotechniques. 2000; 29:776-781.
Dalton S, et al., Glia. 2003; 42:325-339.
Dhandapani K, et al., Endocrine. 2003; 21:59-66.
Dhandapani K M, et al., Biol Reprod. 2002; 67:1379-1385.
Dhandapani K M, et al., BMC Neurosci. 2002; 3:6.
Diab A, et al., Infect Immun. 1999; 67:2590-2601.
Doerfler et al. (2001) Stroke 32, 2675-2681.
Doerfler, A., et al., Stroke 32, 2675-2681 (2001).
Drain P, et al., Proc Natl Acad Sci USA. 1998; 95:13953-13958.
Dubik D et al., Oncogene. 1992; 7:1587-1594.
El Ashry D, et al., J Steroid Biochem Mol Biol. 1996; 59:261-269.
Enkvetchakul D, et al., Biophys J. 2000; 78:2334-2348.
Falk E M, et al., Pharmacol Biochem Behav. 2002; 72:617-622.
Fischer S, et al., J Cell Physiol. 2004; 198:359-369.
Foy M R, et al., Brain Res. 1984; 321:311-314.
Fujita A, et al., Pharmacol Ther. 2000; 85:39-53.
Fujita and Kurachi (2000) Pharmacol Ther January 2000: 85 (1):39-53.
Garcia-Estrada J, et al., Brain Res. 1993; 628:271-278.
Garcia-Ovejero D, et al., J Comp Neurol. 2002; 450:256-271.
Garcia-Segura L M, et al., Prog Neurobiol. 2001; 63:29-60.
Garlid K D, et al., Circ Res. 1997; 81:1072-1082.
Giaccia A J, et al., Int J Radiat Oncol Biol Phys. 1992; 23:891-897.
Gray and Argent (1990) Biochim Biophys Acta 1029: 33-42.
Gribble, F. M. & Reimann, F. Diabetologia 46, 875-891 (2003).
Grover G J. Can J Physiol Pharmacol. 1997; 75:309-315.
Guo X Z, et al., Cell Res. 2001; 11:321-324.
Hainsworth et al., Neuropharmacology. 2001; 40:784-791.
Hale L P, et al., Am J Physiol Heart Circ Physiol. 2002; 282:H1467-H1477.
Halstead J, et al., J Biol Chem. 1995; 270:13600-13603.
Hamill et al. (1981) Pflugers Arch 391: 85-100.
Harder et al., Am J Physiol. 1994; 266:H2098-H2107. Haruna T, et al., Pflugers Arch. 2000; 441:200-207.
Harvey et al. (1999) Br J Pharmacol 126: 51-60.
Haug A, et al., Arch Toxicol. 1994; 68:1-7.
Higashijima T, et al., J Biol Chem. 1990; 265:14176-14186.
Higgins (1992) Annu Rev Cell Biol 8: 67-113.
Higgins C F. Annu Rev Cell Biol. 1992; 8:67-113.
Hiroi H, et al., J Mol Endocrinol. 1999; 22:37-44.
Hobbs M V, et al., J Immunol. 1993; 150:3602-3614.
Hogg et al., FEBS Lett. 2002; 522:125-129.
Hogg et al., Lung. 2002; 180:203-214.
Hohenegger M, et al., Proc Natl Acad Sci USA. 1998; 95:346-351.
Honda K, et al., J Neurosci Res. 2000; 60:321-327.
Horn and Marty (1988) J Gen Physiol 92:145-159.
Hossain M A, et al., J Biol Chem. 2000; 275:27874-27882.
Hua Y, et al., J Cereb Blood Flow Metab. 2003; 23:1448-1454.
Hunt R A, et al., Hypertension. 1999; 34:603-608.
Huovinen R, et al., Int J Cancer. 1993; 55:685-691.
Ignotz R A, et al., J Cell Biochem. 2000; 78:588-594.
Inagaki et al. (1996) Neuron 16:1011-1017.
Inagaki N, et al., Neuron. 1996; 16:1011-1017.
Isomoto et al. (1996) J Biol Chem 271: 24321-24324.
Isomoto S, et al., J Biol Chem. 1996; 271:24321-24324.
Jain, Sci. Amer. 271: 58-65, 1994.
Johnson et al. (1994) J Neurosci 14: 4040-4049.
Jorgensen M B, et al., Exp Neurol. 1993; 120:70-88.
Jovanovic A, et al., Lab Invest. 1998; 78:1101-1107.
Jurkowitz-Alexander et al. (1992) J Neurochem 59: 344-352.
Jurkowitz-Alexander et al. (1993) J Neurochem 61:1581-1584.
Juurlink B H, Chen Y, Hertz L (1992) Can J Physiol Pharmacol 70 Suppl: S344-S349.
Kakinuma Y, et al., Clin Sci (Lond). 2002; 103 Suppl 48:210S-214S.
Kangas L. Cancer Chemother Pharmacol. 1990; 27:8-12.
Kangas L. J Steroid Biochem. 1990; 36:191-195.
Kanthasamy A, et al., Neuroscience. 2002; 114:917-924.
Karschin, C., et al., FEBS Lett. 401, 59-64 (1997).
Kawamura, S., et al., Acta Neurochir. (Wien.) 109, 126-132 (1991).
Kay et al., J Neurosci Methods. 1986; 16:227-238.
Ke C, et al., Neurosci Lett. 2001; 301:21-24.
Kelly M J, et al., Steroids. 1999; 64:64-75.
Kempski et al. (1991). Ann N Y Acad Sci 633: 306-317.
Kennedy A S, et al., Int J Radiat Oncol Biol Phys. 1997; 37:897-905.
Kielian T, et al., J Immunol. 2001; 166:4634-4643.
Kim and Fu (1993) J Membr Biol 135: 27-37.
Kimelberg et al. (1989) Mol Chem Neuropathol 11(1): 1-31.
Kimelberg et al. (1995) J Cereb Blood Flow Metab 15: 409-416.
Kimura D. Sci Am. 1992; 267:118-125.
Kohshi K, J Neurol Sci. 2003; 209:115-117.
Kom et al. (1991) Perforated patch recording. In: Methods in Neuroscience. Electrophysiology and Microinjection. (Conn P M, ed), pp 364-373. San Diego: Academic Press.
Korbmacher et al. (1995) J Membr Biol 146: 29-45.
Koster J C, J Gen Physiol. 1999; 114:203-213.
Kucich U, et al., Arch Biochem Biophys. 2000; 374:313-324.
Kuiper G G, et al., Endocrinology. 1997; 138:863-870.
Kuiper G G, et al., Proc Natl Acad Sci USA. 1996; 93:5925-5930.
Larsson O, et al., Diabetes. 2000; 49:1409-1412.
Lawson (2000) Kidney Int March 2000: 57 (3): 838-845.
Lawson K. Kidney Int. 2000; 57:838-845.
Le Mellay V, et al., J Cell Biochem. 1999; 75:138-146.
Leaney J L, Tinker A. Proc Natl Acad Sci USA. 2000; 97:5651-5656.
Lebovitz (1985) Oral hypoglycaemic agents. Amsterdam: Elsevier.
Li, P. A., et al., Neurosci. Lett. 177, 63-65 (1994).
Lieberherr M, et al., J Cell Biochem. 1999; 74:50-60.
Lindauer et al. (2003) J. Cereb. Blood Flow Metab 23, 1227-1238.

Liss B, Roeper J. Mol Membr Biol. 2001; 18:117-127.
Liu et al. (2002) Eur. J. Pharmacol. 435: 153-160.
Liu Y, et al., Circulation. 1998; 97:2463-2469.
Lomneth and Gruenstein (1989) Am J Physiol 257: C817-C824.
Majno and Joris (1995) Am J Path 01146: 3-15.
Maruyama and Petersen (1984) J Membr Biol 81: 83-87.
Mateo J, et al., Biochem J. 2003; 376:537-544.
Mathews et al., J Neurosci Methods. 2000; 102:43-51.
McNally J G, et al., Methods. 1999; 19:373-385.
Meyer, M., et al., Br. J. Pharmacol. 128, 27-34 (1999).
Mongin et al. (1999) Am J Physiol 277: C823-C832.
Moon R C, Constantinou A I. Breast Cancer Res Treat. 1997; 46:181-189.
Moyer et al., J Neurosci Methods. 1998; 86:35-54.
Munoz A, et al, Stroke. 2003; 34:164-170.
Murayama T, et al., J Cell Physiol. 1996; 169:448-454.
Murphy K, et al., Mol Pharmacol. 2003; in press.
Nakabayashi, K. et al. AJNR Am. J. Neuroradiol. 18, 485-491 (1997).
Nichols C G, et al., Science. 1996; 272:1785-1787.
Nichols et al. (1996) Science 272: 1785-1787.
Oehmichen M, et al., Exp Toxicol Pathol. 2000; 52:348-352.
Oehmichen M, et al., Neurotoxicology. 2001; 22:99-107.
Olive P L, et al., Br J Cancer. 2000; 83:1525-1531.
Ono et al. (1994) Am J Physiol 267: F558-F565.
Paczynski R P, et al., Stroke. 2000; 31:1702-1708.
Paech K, et al., Science. 1997; 277:1508-1510.
Panten et al. (1989) Biochem Pharmacol 38: 1217-1229.
Panten U, et al., Biochem Pharmacol. 1989; 38:1217-1229.
Papadopoulos M C, et al., Mt Sinai J Med. 2002; 69:242-248.
Perillan et al. (1999) Glia 27: 213-225.
Perillan et al. (2000) Glia 31: 181-192.
Perillan et al. (2002) J. Biol. Chem. 277: 1974-1980.
Perillan P R, et al., J Biol Chem. 2002; 277:1974-1980.
Perillan P R, et al., Glia. 1999; 27:213-225.
Perillan P R, et al., Glia. 2000; 31:181-192.
Phillips M I, Zhang Y C. Methods Enzymol. 2000; 313:46-56.
Piiper A, et al., Am J Physiol. 1997; 272:G135-G140.
Pogue B W, et al., Radiat Res. 2001; 155:15-25.
Popp and Gogelein (1992) Biochim Biophys Acta 1108: 59-66.
Proks P, et al., J Physiol. 1999; 514 (Pt 1):19-25.
Qiu J, et al., J Neurosci. 2003; 23:9529-9540.
Rae et al. (1990) Exp Eye Res 50: 373-384.
Rama Rao K V, et al., J Neurosci Res. 2003; 74:891-897.
Rama Rao K V, et al., Neuroreport. 2003; 14:2379-2382.
Ramirez V D, Zheng J. Front Neuroendocrinol. 1996; 17:402-439.
Ransom and Sontheimer (1995) J Neurophysiol 73: 333-346.
Raucher D, et al., Cell. 2000; 100:221-228.
Renkin (1955) J Gen Physiol 38: 225-243.
Robinson and Stokes (1970) Electrolyte Solutions. London: Buttenvorths.
Robinson A P, et al., Immunology. 1986; 57:239-247.
Robinson S P, et al., Eur J Cancer Clin Oncol. 1988; 24:1817-1821.
Rohacs T, et al., J Biol Chem. 1999; 274:36065-36072.
Rose et al. (1998) J Neurosci 18: 3554-3562.
Rossignol F, et al., Gene. 2002; 299:135-140.
Rucker-Martin et al. (1999) Basic Res Cardiol 94: 171-179.
Ruknudin A, et al., J Biol Chem. 1998; 273:14165-14171.
Ruscher K, et al., J Neurosci. 2002; 22:10291-10301.
Russo J, et al., IARC Sci Publ. 1990; 47-78.
Russo J, Russo I H. Lab Invest. 1987; 57:112-137.
Rutledge and Kimelberg (1996) J Neurosci 16: 7803-7811.
Saadoun S, et al., Br J Cancer. 2002; 87:621-623.
Schroder et al. (1999) Glia 28: 166-174.
Schubert P, et al., Ann N Y Acad Sci. 2000; 903:24-33.
Seidel et al., Cell Tissue Res. 1991; 265:579-587.
Seino, S. Annu. Rev. Physiol 61, 337-362 (1999).
Semenza G L. Biochem Pharmacol. 2000; 59:47-53.
Shaywitz B A, et al., Nature. 1995; 373:607-609.
Shyng et al. (1997) J Gen Physiol 110: 141-153.
Shyng S, et al., J Gen Physiol. 1997; 110:643-654.
Sigworth and Sine (1987) Biophys J 52: 1047-1054.
Singer C A, et al., J Neurosci. 1999; 19:2455-2463.
Singh M, et al., J Neurosci. 1999; 19:1179-1188.
Smith S S, et al., Brain Res. 1987; 422:40-51.
Smith S S, et al., Brain Res. 1988; 475:272-282.
Sohrabji F, et al., Proc Natl Acad Sci USA. 1995; 92:11110-11114.
Staub et al. (1993) Brain Res 610: 69-74.
Stone D J, et al., J Neurosci. 1998; 18:3180-3185.
Streit W J, et al., Prog Neurobiol. 1999; 57:563-581.
Sturgess et al. (1987) Pflugers Arch 409: 607-615.
Sun M C, et al., J Neurosurg. 2003; 98:565-569.
Swanson R A (1992) Neurosci Lett 147: 143-146.
Sylvia V L, et al, J Steroid Biochem Mol Biol. 2000; 73:211-224.
Tanaka et al. (2000) J Biol Chem 275: 10388-10393.
Teixeira C, et al., Cancer Res. 1995; 55:3902-3907.
Thrash-Bingham C A, et al., J Natl Cancer Inst. 1999; 91:143-151.
Toker A. Curr Opin Cell Biol. 1998; 10:254-261.
Tomiyama, et al. (1999) Stroke 30, 1942-1947.
Toomey, J. R. et al. Stroke 33, 578-585 (2002).
Toran-Allerand C D. J Steroid Biochem Mol Biol. 1996; 56:169-178.
Tomer L, et al., J Neurosci. 2001; 21:3207-3214.
Treherne, J. M. & Ashford, M. L. Neuroscience 40, 523-531 (1991).
Tucker S J, et al., EMBO J. 1998; 17:3290-3296.
Tucker S J, et al., Nature. 1997; 387:179-183.
Ubl et al. (1988) J Membr Biol 104: 223-232.
Vogel et al., Stroke. 1999; 30:1134-1141.
Wallace W, et al., Biotechniques. 2001; 31:1076-8, 1080, 1082.
Walz et al. (1994) J Neurosci Res 38: 12-18.
Wang J Y, et al., Glia. 2000; 32:155-164.
Wang Y L. Methods Cell Biol. 1998; 56:305-315.
Wass, C. T. & Lanier, W. L. Mayo Clin. Proc. 71, 801-812 (1996).
Wiesener M S, et al., FASEB J. 2003; 17:271-273.
Woolley C S. Curr Opin Neurobiol. 1999; 9:349-354.
Xie L H, et al., Proc Natl Acad Sci USA. 1999; 96:15292-15297.
Yajima Y, et al., Endocrinology. 1997; 138:1949-1958.
Young, W. & Constantini, S. The Neurobiology of Central Nervous System Trauma. Salzman, S. K. & Faden, A. I. (eds.), pp. 123-130 (Oxford University Press, New York, 1994).
Yu et al. (2001) Glia 35: 121-130.
Zhang L, et al., Brain Res Mol Brain Res. 2002; 103:1-11.
Zhang Y, et al., J Neurosci. 2001; 21:RC176.
Zheng J, Ramirez V D. J Steroid Biochem Mol Biol. 1997; 62:327-336.
Zunkler, B. J., et al., Biochem. Pharmacol. 67, 1437-1444 (2004).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of ameliorating the effect of a reduction in blood flow in peri-infarct brain tissue in ischemic disease or injury in a subject comprising administering to a subject having a reduction in blood flow in peri-infarct brain tissue in ischemic disease or injury an amount of a compound that is effective to inhibit the activity of a $NC_{Ca-ATP}$ channel in a neuronal cell, a neuroglia cell, or a neural endothelial cell and that is effective to ameliorate the effect of a reduction in blood flow in peri-infarct brain tissue in ischemic disease or injury, wherein the compound is a sulfonylurea compound, a benzamido derivative, an imidazoline derivative, or a combination thereof, and wherein the effect of said reduction in said blood flow in peri-infarct brain tissue in said ischemic disease or said injury in the subject is ameliorated.

2. The method of claim 1, where said compound is a compound capable of effecting hypoglycemia in said subject, further comprising administration of glucose to said subject effective to at least partially ameliorate said hypoglycemic effects in said subject.

3. The method of claim 1, wherein the amelioration of the effect of a reduction in blood flow comprises a reduction in cytotoxic edema, ionic edema, vasogenic edema, or a combination thereof.

4. The method of claim 1, wherein the neuroglia cell is selected from the group consisting of astrocyte, ependymal cell, oligodentrocyte and microglia.

5. The method of claim 1, wherein the compound effective to inhibit a $NC_{Ca-ATP}$ channel is administered alimentarily, parenterally, topically, mucosally, or by injection into brain parenchema.

6. The method of claim 1, wherein said sulfonylurea compound is selected from the group consisting of glibenclamide, tolbutamide, gliclazide, and glimepiride.

7. The method of claim 1, wherein said benzamido derivative is selected from the group consisting of repaglinide, nateglinide, and meglitinide.

8. The method of claim 1, wherein said imidazoline derivative is selected from the group consisting of LY397364 and LY389382.

9. The method of claim 1, wherein the compound effective to inhibit the $NC_{Ca-ATP}$ channel is administered parenterally, topically, or mucosally.

10. The method of claim 1, further comprising administering glucose to said subject.

11. A method of inhibiting neuronal cell swelling in the brain of a subject, said method comprising administering to a subject having neuronal cell swelling in the brain a formulation comprising an amount of a compound that is effective to block a $NC_{Ca-ATP}$ channel and that is effective to inhibit neuronal cell swelling, wherein the compound is a sulfonylurea compound, a benzamido derivative, an imidazoline derivative, or a combination thereof, and a pharmaceutically acceptable carrier, and wherein said neuronal cell swelling in the brain of the subject is inhibited.

12. The method of claim 11, wherein said inhibiting neuronal cell swelling is further defined as preventing neuronal cell swelling.

13. The method of claim 11, where said formulation comprises a compound capable of effecting hypoglycemia in said subject, further comprising administration of glucose to said subject effective to at least partially ameliorate said hypoglycemic effects in said subject.

14. The method of claim 13, wherein said inhibiting neuronal cell swelling is further defined as preventing neuronal cell swelling.

15. The method of claim 11, further comprising administering glucose to said subject.

16. A method of alleviating brain swelling in a subject, comprising administering to the subject a formulation comprising an amount of a compound that is effective to block a $NC_{Ca-ATP}$ channel and that is effective to alleviate brain swelling in the subject, wherein the compound is a sulfonylurea compound, a benzamido derivative, an imidazoline derivative, or a combination thereof and a pharmaceutically acceptable carrier, and wherein said brain swelling in the subject is alleviated.

17. The method of claim 16, where said formulation is a formulation capable of effecting hypoglycemia in said subject, further comprising administration of glucose to said subject effective to at least partially ameliorate said hypoglycemic effects in said subject.

18. The method of claim 16, further comprising administering glucose to said subject.

19. A method of treating acute cerebral ischemia in a subject comprising administering to a subject having acute cerebral ischemia an amount of a compound that is effective to inhibit a $NC_{Ca-ATP}$ channel and that is effective to treat acute cerebral ischemia, wherein the compound is a sulfonylurea compound, a benzamido derivative, an imidazoline derivative, or a combination thereof, or a pharmaceutically acceptable salt thereof, and wherein said acute cerebral ischemia in the subject is treated.

20. The method of claim 19, wherein the $NC_{Ca-ATP}$ channel is expressed on neuronal cells, neuroglia cells, neural endothelial cells or a combination thereof.

21. The method of claim 19, wherein said sulfonylurea compound is selected from the group consisting of glibenclamide, tolbutamide, and glimepiride.

22. The method of claim 19, wherein the mode of administration of said $NC_{Ca-ATP}$ channel inhibitor is selected from the group of modes of administration consisting of bolus injection, infusion, and bolus injection in combination with an infusion.

23. The method of claim 19, wherein said $NC_{Ca-ATP}$ channel inhibitor is glibenclamide.

24. The method of claim 19, further comprising administering glucose to said subject.

25. The method of claim 19, wherein the compound effective to inhibit a $NC_{Ca-ATP}$ channel is administered alimentarily, parenterally, topically, mucosally, or by injection into brain parenchema.

26. The method of claim 19, wherein said benzamido derivative is selected from the group consisting of repaglinide, nateglinide, and meglitinide.

27. The method of claim 19, wherein said imidazoline derivative is selected from the group consisting of LY397364 and LY389382.

28. A method of alleviating one or more effects of traumatic brain injury or cerebral ischemia stemming from neural cell swelling in a subject, comprising administering to a subject having traumatic brain injury or cerebral ischemia stemming from neural cell swelling a formulation comprising an amount of a compound that is effective to block a $NC_{Ca-ATP}$ channel and that is effective to alleviate one or more of the effects of traumatic brain injury or cerebral ischemia, wherein the compound is a sulfonylurea compound, a benzamido derivative, an imidazoline derivative, or a combination thereof, glucose, and a pharmaceutically acceptable carrier, and wherein one or more effects of said traumatic brain injury or said cerebral ischemia stemming from said neural cell swelling in the subject is alleviated.

29. The method of claim 28, further comprising administering glucose to said subject.

30. A method of alleviating one or more effects of traumatic brain injury or cerebral ischemia in a subject, comprising administering to a subject having traumatic brain injury or cerebral ischemia a formulation comprising an amount of a sulfonylurea compound that is effective to alleviate one or more effects of traumatic brain injury or cerebral ischemia and a pharmaceutically acceptable carrier, and wherein one or more effects of said traumatic brain injury or said cerebral ischemia in the subject is alleviated.

31. A method of treating acute cerebral ischemia in a subject, comprising:

determining an appropriate amount of a compound that inhibits a $NC_{Ca-ATP}$ channel in a subject needing treatment for acute cerebral ischemia, wherein the compound is a sulfonylurea compound, a benzamido derivative, an imidazoline derivative, or a combination thereof, or a pharmaceutically acceptable salt thereof; and administering the compound to the subject, wherein said acute cerebral ischemia in the subject is treated.

32. A method of alleviating one or more effects of traumatic brain injury or cerebral ischemia in a subject, comprising:

determining an appropriate amount of a formulation for a subject, wherein the formulation comprises an effective amount of a sulfonylurea compound and a pharmaceutically acceptable carrier, and administering the formulation to the subject, wherein one or more effects of said traumatic brain injury or said cerebral ischemia in the subject is alleviated.

* * * * *

UNITED STATES PATENT AND TRADEMARK OFFICE

CERTIFICATE OF CORRECTION

PATENT NO. : 8,980,952 B2
APPLICATION NO. : 11/359946
DATED : March 17, 2015
INVENTOR(S) : Simard et al.

It is certified that error appears in the above-identified patent and that said Letters Patent is hereby corrected as shown below:

In the Specification

Beginning at col. 1, line 25, delete "This invention was made with government support under Grant No. NS048260 awarded by the National Institutes of Health, a grant awarded by the Heart Lung and Blood Institute (HL082517), and a Merit Review grant from the United States Department of Veterans Affairs. The United States Government has certain rights in the invention."

At col. 1, line 25, insert --This invention was made with government support under Grant Numbers NS048260 and HL082517 awarded by the National Institutes of Health. The government has certain rights in the invention.--

Signed and Sealed this
Sixteenth Day of June, 2015

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: Synthetic Oligonucleotide Primer

<400> SEQUENCE: 1

aagcacgtca acgccct                                                17


<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 2

gaagcttttc cggcttgtc                                              19


<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 3

gagtcggact tctcgccct                                              19


<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide Primer

<400> SEQUENCE: 4

ccttgacagt ggccgaacc                                              19


<210> SEQ ID NO 5
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 5

ttccacatcc tggtcacacc gctgt                                       25


<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide Primer
```

```
<400> SEQUENCE: 6

cggaccaccc caagtattca                                                20


<210> SEQ ID NO 7
<211> LENGTH: 17
<212> TYPE: DNA
<213> ORGANISM: Artificial Sequence
<220> FEATURE:
<223> OTHER INFORMATION: Synthetic Oligonucleotide Primer

<400> SEQUENCE: 7

gccggcacgg ttcttct                                                   17


<210> SEQ ID NO 8
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 8

catgatcgtg gctgctatcc aggca                                          25


<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide Primer

<400> SEQUENCE: 9

ggccgagtgg ttctcggt                                                  18


<210> SEQ ID NO 10
<211> LENGTH: 18
<212> TYPE: DNA
<213> ORGANISM: Artificial Sequence
<220> FEATURE:
<223> OTHER INFORMATION: Synthetic Oligonucleotide Primer

<400> SEQUENCE: 10

tgcctgaggc gtggctgt                                                  18
```